(12) United States Patent
Fu et al.

(10) Patent No.: US 10,730,868 B2
(45) Date of Patent: Aug. 4, 2020

(54) BICYCLIC HETEROARYL SUBSTITUTED COMPOUNDS

(71) Applicant: BRISTOL-MYERS SQUIBB COMPANY, Princeton, NJ (US)

(72) Inventors: Qinghong Fu, Plainsboro, NJ (US); Xiaojun Zhang, Furlong, PA (US); Eldon Scott Priestley, Yardley, PA (US); Oz Scott Halpern, Robbinsville, NJ (US); Samuel Kaye Reznik, Brookline, MA (US); Jeremy M. Richter, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/317,218

(22) PCT Filed: Jul. 13, 2017

(86) PCT No.: PCT/US2017/041868
§ 371 (c)(1),
(2) Date: Jan. 11, 2019

(87) PCT Pub. No.: WO2018/013770
PCT Pub. Date: Jan. 18, 2018

(65) Prior Publication Data
US 2019/0300520 A1 Oct. 3, 2019

Related U.S. Application Data

(60) Provisional application No. 62/362,071, filed on Jul. 14, 2016.

(51) Int. Cl.
*C07D 417/14* (2006.01)
*C07D 417/10* (2006.01)
(Continued)

(52) U.S. Cl.
CPC ......... *C07D 417/14* (2013.01); *C07D 417/04* (2013.01); *C07D 417/10* (2013.01); *C07D 513/04* (2013.01)

(58) Field of Classification Search
CPC .......................... C07D 417/04; C07D 417/14
See application file for complete search history.

(56) References Cited

U.S. PATENT DOCUMENTS 6,166,041 A 12/2000 Cavalla et al.
9,518,064 B2 12/2016 Martel et al.
(Continued)

FOREIGN PATENT DOCUMENTS

EP         1348701 A1    10/2003
WO    WO2003082839 A1    10/2003
(Continued)

OTHER PUBLICATIONS

Suresh. Tetrahedron Letters, 2016, 54, 6479-84 (Year: 2016).*
Barni, et al., "2-(Methylpyridyl or quinolinyl)benz-X-azoles, Salts and Polymethine Dyes (1)", Journal of Heterocyclic Chemistry, vol. 16, pp. 1579-1582 (1979).
Beaulieu, Pierre L. et al., Discovery of the First Thumb Pocket 1 NS5B Polymerase Inhibitor (BILB 1941) with Demonstrated Antiviral Activity in Patients Chronically Infected with Genotype 1 Hepatitis C Virus (HCV).
(Continued)

*Primary Examiner* — Noble E Jarrell
(74) *Attorney, Agent, or Firm* — Mary K. VanAtten

(57) ABSTRACT

Disclosed are compounds of Formula (I) to (IV): or a stereoisomer, tautomer, pharmaceutically acceptable salt, solvate or prodrug thereof. Also disclosed are methods of using such compounds as PAR4 inhibitors, and pharmaceutical compositions comprising such compounds. These compounds are useful in inhibiting or preventing platelet aggregation, and are useful for the treatment of a thromboembolic disorder or the primary prophylaxis of a thromboembolic disorder.

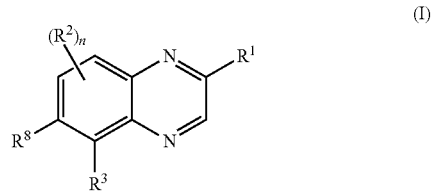

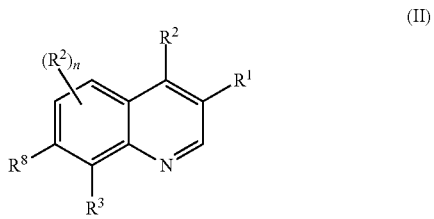

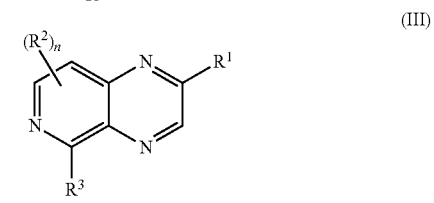

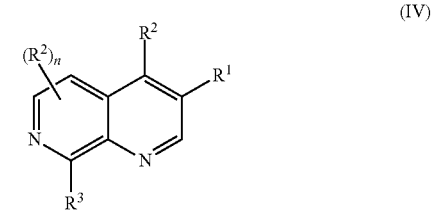

14 Claims, No Drawings

(51) Int. Cl.
*C07D 513/04* (2006.01)
*C07D 417/04* (2006.01)

(56) References Cited

U.S. PATENT DOCUMENTS

| | | |
|---|---|---|
| 9,598,419 B1 | 3/2017 | Martel et al. |
| 9,617,279 B1 | 4/2017 | Zhang |
| 9,688,695 B2 | 6/2017 | Banville et al. |
| 9,862,730 B2 | 1/2018 | Lawrence et al. |
| 10,047,103 B2 | 8/2018 | Banville et al. |
| 10,214,544 B2 | 2/2019 | Banville |
| 10,238,638 B2 | 3/2019 | Ruediger et al. |
| 2018/0214445 A1 | 8/2018 | Zhang et al. |
| 2018/0305376 A1 | 10/2018 | Banville et al. |

FOREIGN PATENT DOCUMENTS

| | | |
|---|---|---|
| WO | WO2005012288 A1 | 2/2005 |
| WO | WO2005113522 A1 | 12/2005 |
| WO | WO2006015259 A2 | 2/2006 |
| WO | WO2006076529 A1 | 7/2006 |
| WO | WO2007149395 A2 | 12/2007 |
| WO | WO2008000643 A1 | 1/2008 |
| WO | WO2008073451 A2 | 6/2008 |
| WO | WO2009073497 A2 | 6/2009 |
| WO | WO2009134973 A1 | 11/2009 |
| WO | WO2009141386 A1 | 11/2009 |
| WO | WO2010011768 A1 | 1/2010 |
| WO | WO2012154888 A1 | 11/2012 |
| WO | WO2013130660 A1 | 9/2013 |
| WO | WO2013163241 A1 | 10/2013 |
| WO | WO2013163279 A1 | 10/2013 |
| WO | WO2013163244 A8 | 4/2014 |
| WO | WO2015077550 A1 | 5/2015 |
| WO | WO2016/138199 A1 | 9/2016 |
| WO | WO2016134450 A1 | 9/2016 |
| WO | WO2017019828 A1 | 2/2017 |
| WO | WO2018/013772 | 1/2018 |
| WO | WO2018013770 A1 | 1/2018 |
| WO | WO2018013774 A1 | 1/2018 |
| WO | WO2018013776 A1 | 1/2018 |

OTHER PUBLICATIONS

Beaulieu, Pierre L. et al., "From benzimidazole to indole-5-carboxamide Thumb Pocket 1 inhibitors of HCV N55B polymerase. Part 1:Indole C-2 SAR and discovery of diamide derivatives with nanomolar potency in cell-based subgenomic replicons", Bioorganic & Medicinal Chemistry Letters, vol. 21, pp. 3658-3663 (2011).

Hao, et al., "Highly active 8-benzoxazolyl-or 8-benzothiazoly1-2-alkylquinolinylnickel(II) complexes for ethylene dimerization and vinyl polymerization of norbornene", Polyhedron, vol. 52, pp. 1138-1144 (2012).

Laroche, et al., "Direct heteroarylation of 5-bromothiophen-2-ylpyridine and of 8-bromoquinoline via palladium-catalysed C-H bond activation: simpler access to heteroarylated nitrogen-based derivatives", Catalysis Science & Technology, pp. 2072-2080 (2013).

Prakash, et al., "N-Difluoromethylation of Imidazoles and Benzimidazoles Using the Ruppert-Prakash Reagent under Neutral Conditions", Organic Letters, vol. 16, pp. 54-57 (2014).

PUBCHEM CID: 104615864, Jan. 13, 2016.

Savarino, et al., "Spectral behaviour of linked heterocyclic systems and related dyes*", Spectrochimica Acta, vol. 49A (9) pp. 1379-1393 (1993).

* cited by examiner

BICYCLIC HETEROARYL SUBSTITUTED COMPOUNDS

CROSS REFERENCE TO RELATED APPLICATIONS

This application is a 371 application of PCT/US2017/041868 filed Jul. 13, 2017 which is entitled to priority pursuant to 35 U.S.C. § 119(e) to U.S. provisional patent application No. 62/362,071, filed Jul. 14, 2016, which is incorporated herein in its entirety.

FIELD OF THE INVENTION

The present invention generally relates to bicyclic heteroaryl substituted compounds useful as inhibitors of platelet aggregation. Provided herein are bicyclic heteroaryl substituted compounds, compositions comprising such compounds, and methods of their use. The invention further pertains to pharmaceutical compositions containing at least one compound according to the invention that are useful in preventing or treating thromboembolic disorders.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S. R., Nature, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4. Inhibitors of PAR1 have been investigated extensively, and several compounds, including vorapaxar and atopaxar have advanced into late stage clinical trials. Recently, in the TRACER phase II trial in ACS patients, vorapaxar did not significantly reduce cardiovascular events, but significantly increased the risk of major bleeding (Tricoci, P. et al., N. Eng. J. Med., 366(1):20-33 (2012). Thus, there remains a need to discover new antiplatelet agents with increased efficacy and reduced bleeding side effects.

There are several early reports of preclinical studies of PAR4 inhibitors. Lee F-Y. et al., "Synthesis of 1-Benzyl-3-(5'-hydroxymethyl-2'-furyl)indazole Analogues as Novel Antiplatelet Agents", J. Med. Chem., 44(22):3746-3749 (2001) discloses in the abstract that the compound

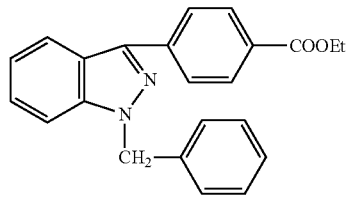

"was found to be a selective and potent inhibitor or protease-activated receptor type 4 (PAR4)-dependent platelet activation" Compound 58 is also referred to as YD-3 in Wu, C-C. et al., "Selective Inhibition of Protease-activated Receptor 4-dependent Platelet Activation by YD-3", Thromb. Haemost., 87:1026-1033 (2002). Also, see Chen, H. S. et al., "Synthesis and antiplatelet activity of ethyl 4-(1-benzyl-1H-indazol-3-yl)benzoate (YD-3) derivatives", Bioorg. Med. Chem., 16:1262-1278 (2008).

EP1166785 A1 and EP0667345 disclose various pyrazole derivatives which are useful as inhibitors of platelet aggregation.

The PCT publications WO 2013/163279, WO 2013/163244, and WO 2013/163241 disclose various PAR4 antagonists that are useful as inhibitors of platelet aggregation.

There still remains a need for compounds useful as inhibitors of platelet aggregation.

Applicants have found potent compounds that have activity as PAR4 inhibitors. These compounds are provided to be useful as pharmaceuticals with desirable potency, stability, bioavailability, therapeutic index, and toxicity values that are important to their drugability.

SUMMARY OF THE INVENTION

It has been found that bicyclic heteroaryl substituted compounds in accordance with the present invention are PAR4 antagonists which inhibit platelet aggregation in gamma-thrombin induced platelet aggregation assays.

The present invention provides compounds of formulas (I) to (IV)

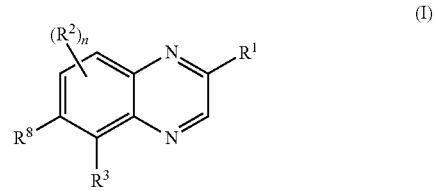

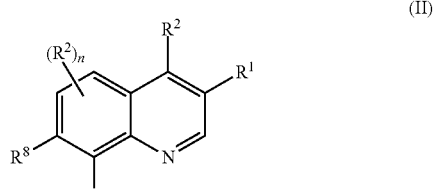

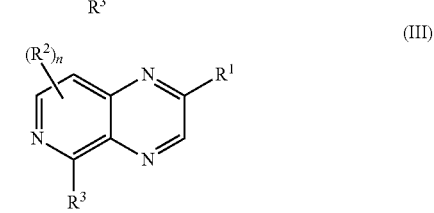

-continued

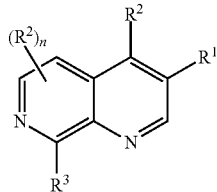
(IV)

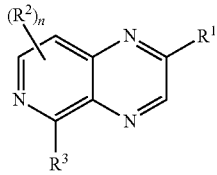
(III)

or salt, pharmaceutically acceptable salt, stereoisomers, tautomers, or prodrugs thereof, wherein the various moieties are as defined herein.

Accordingly, the present invention provides bicyclic heteroaryl substituted compounds that are PAR4 antagonists and are useful as selective inhibitors of platelet aggregation, including stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment or prophylaxis of a thromboembolic disorder.

Other features and advantages of the invention will be apparent from the following detailed description and claims.

DETAILED DESCRIPTION

The first aspect of the present invention provides at least one compound of Formulas (I), (II), (III), or (IV):

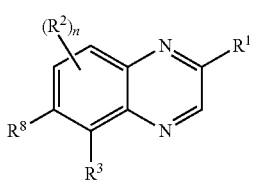
(I)

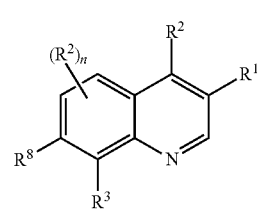
(II)

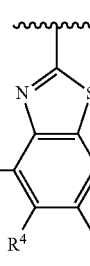
(IV)

or a salt thereof; wherein:

$R^1$ is F, Cl, —OH, $C_{1-4}$ alkyl, $C_{1-4}$ fluoroalkyl, $C_{2-4}$ alkenyl, $C_{2-4}$ alkynyl, $C_{3-7}$ cycloalkyl, $C_{3-7}$ fluorocycloalkyl, $C_{1-4}$ alkoxy, $C_{1-4}$ fluoroalkoxy, $C_{2-4}$ hydroxyalkoxy, $C_{3-6}$ cycloalkoxy, ($C_{1-3}$ alkoxy)-($C_{1-3}$ alkylene), ($C_{1-3}$ alkoxy)-($C_{1-3}$ fluoroalkylene), ($C_{1-3}$ fluoroalkoxy)-($C_{1-3}$ fluoroalkylene), ($C_{1-3}$ deuteroalkoxy)-($C_{1-3}$ deuteroalkylene), ($C_{1-3}$ fluoroalkoxy)-($C_{1-3}$ alkylene), —(CH$_2$)$_n$O(phenyl), —(CH$_2$)$_n$NR$^a$R$^a$, —C(O)O(C$_{1-6}$ alkyl), —C(O)NR$^a$R$^a$, —C(O)NR$^b$R$^b$, —NH$_2$, —NH(C$_{1-6}$ alkyl), —N(C$_{1-6}$ alkyl)$_2$, —NH(C$_{1-6}$ hydroxyalkyl), azetidinyl, pyrrolidinyl, furanyl, pyranyl, piperidinyl, morpholinyl, piperazinyl, —S(O)$_2$(C$_{1-3}$ alkyl), —S(O)$_2$NR$^a$R$^a$, $C_{1-3}$ alkylthio, or $C_{1-3}$ fluoroalkylthio;

$R^2$, at each occurrence, is independently H, F, Cl, Br, —OH—, —CN, $C_{1-4}$ alkyl, $C_{1-4}$ fluoroalkyl, $C_{1-4}$ hydroxyalkyl, $C_{1-3}$ aminoalkyl, $C_{2-4}$ alkenyl, $C_{2-4}$ alkynyl, $C_{3-7}$ cycloalkyl, $C_{3-7}$ fluorocycloalkyl, $C_{1-6}$ alkoxy, $C_{1-3}$ fluoroalkoxy, $C_{1-3}$ alkylthio, $C_{1-3}$ fluoroalkylthio, ($C_{1-3}$ alkoxy)-($C_{1-3}$ alkylene), ($C_{1-3}$ fluoroalkoxy)-($C_{1-3}$ alkylene), —C(O)NH$_2$, —C(O)NH(C$_{1-6}$ alkyl), —C(O)N(C$_{1-6}$ alkyl)$_2$, —C(O)O(C$_{1-6}$ alkyl), —C(O)NH(CH$_2$CH$_2$O(C$_{1-3}$ alkyl)), —C(O)NR$^b$R$^b$, —C(O)(piperidinyl), —CH(OH)(C$_{3-6}$ cycloalkyl), —CH(OH)(phenyl), —CH(OH)(pyridyl), —S(O)$_2$(C$_{1-3}$ alkyl), —S(O)$_2$NR$^a$R$^a$, or a cyclic group selected from phenyl, 5- to 6-membered heteroaryl, and 5- to 7-membered heterocyclyl, wherein said cyclic group is substituted with zero to 5 substituents independently selected from F, Cl, hydroxy, $C_{1-4}$ alkyl, $C_{1-4}$ fluoroalkyl, $C_{1-3}$ alkoxy, $C_{1-3}$ fluoroalkoxy, cyclopropyl, or —CN;

$R^3$ is:

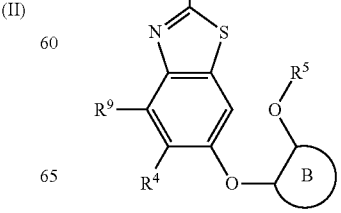 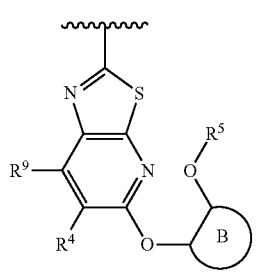

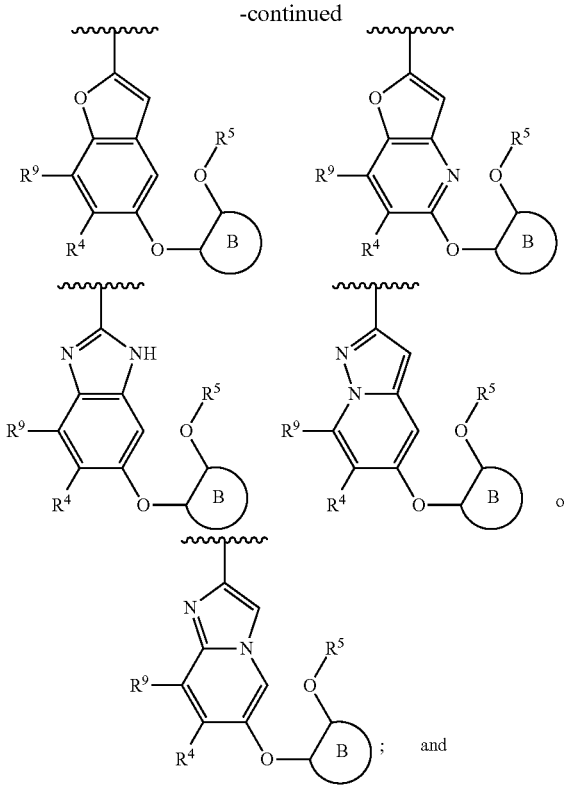

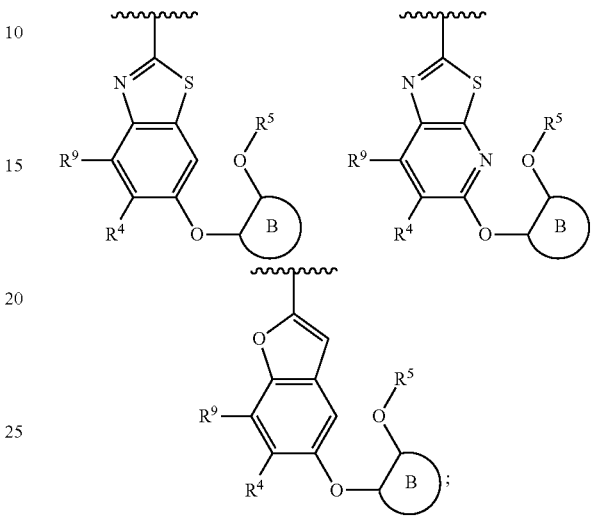

$R^4$ is H, F, Cl, hydroxy, $C_{1-4}$ alkyl, $C_{1-4}$ fluoroalkyl, $C_{1-4}$ hydroxyalkyl, $C_{1-3}$ alkoxy, $C_{1-3}$ fluoroalkoxy, $C_{1-3}$ alkylthio, cyclopropyl, or —CN:

Ring B, along with the two carbon atoms through which it is attached, is a 3 to 7 membered cycloalkyl, or a 5 to 7 membered heterocycle having 1 nitrogen, oxygen, or sulphur atom, wherein the cycloalkyl and heterocycle are substituted with 0-4 $R^d$;

$R^5$ is —H, or $C(O)NR^aR^6$;

$R^6$ is H, $C_{1-4}$ alkyl, phenyl, or a 5 or 6 membered heteroaryl, containing 1 to 3 nitrogen atoms and 0-1 oxygen or sulphur atoms, the phenyl or heteroaryl being substituted with 0-2 $R^7$, or phenyl substituted with 0-2 $R^7$;

$R^7$ is CN, hydroxy, $NR^aR^a$, halogen, $C_{1-4}$alkyl, $C_{1-4}$fluoroalkyl, $C_{1-4}$-hydroxyalkyl, $C_{1-4}$-hydroxyfluoroalkyl, $C(O)R^a$, $C(O)OR^a$, $C(O)NR^aR^c$, $S(O)_2NR^aR^c$, and $S(O)_2R^a$, —O—$C_{1-4}$alkyl, —S—$C_{1-4}$alkyl, —O—$C_{1-4}$-hydroxyalkyl, —O—$C_{1-4}$-aminoalkyl, —O—$C_{1-4}$-hydroxyfluoroalkyl, O—$C_{1-4}$fluoroalkyl, O—$PO_3^{-2}$, —$C_{1-4}$alkyl-O—$PO_3^{-2}$, —$C_{1-4}$fluoroalkyl-O—$PO_3^{-2}$, —O—$C_{1-4}$alkyl-O—$PO_3^{-2}$, —O—$C_{1-4}$fluoroalkyl-O—$PO_3^{-2}$, —N($R^a$)—$C_{1-4}$hydroxyalkyl, or —N($R^a$)—$C_{1-4}$hydroxyfluoroalkyl;

$R^8$ is H, F, Cl, or $CH_3$;

$R^9$ is H, CN, hydroxyl, $C_{1-4}$alkyl, $C_{1-4}$fluoroalkyl, cyclopropyl, or halogen.

$R^a$ is H, or $C_{1-4}$alkyl, or $C_{1-4}$fluoroalkyl;

two $R^b$s, along with the nitrogen atom to which they are attached, form a 4- to 7-membered heterocyclo ring, having 1 to 2 nitrogen atoms and 0-1 oxygen or sulfur atoms;

$R^c$ is H, $C_{1-4}$alkyl, or $C_{1-4}$hydroxyalkyl;

$R^d$ is F, Cl, hydroxy, $C_{1-4}$ alkyl, $C_{1-4}$ fluoroalkyl, $C_{1-4}$ hydroxyalkl, $C_{1-3}$ alkoxy, $C_{1-3}$ fluoroalkoxy, $C_{1-3}$ alkylthio, cyclopropyl, —CN, $C(O)R^a$, $C(O)OR^a$, $C(O)NR^aR^c$, $S(O)_2NR^aR^c$, or $S(O)_2R^a$; and n is 1 to 3.

In a second aspect of the present invention provides at least one compound of Formulas (I), (II), (III), or (IV), salt thereof; wherein $R^1$ is methyl, methoxy, ethoxy, $OCHF_2$, or —$CH_2OCH_3$;

$R^2$ is F, Cl, CN, methyl, hydroxymethyl, methoxy, or difluoromethyl;

$R^3$ is $R^4$ is H or F;

Ring B, along with the two carbon atoms through which it is attached, is cyclobutyl, cyclopentyl, cyclohexyl, or tetrahydrofuranyl, pyrrolidinyl, tetrahydropyranyl, or piperadinyl, each of these being substituted with 0-3 $R^d$;

$R^5$ is $C(O)NHR^6$;

$R^6$ is phenyl, pyridinyl, pyrimidinyl, pyridazinyl, or pyrazinyl, each of these being substituted with 0-2 $R^7$;

$R^7$ is F, Cl, CN, hydroxy, $C_{1-4}$alkyl, $C_{1-4}$fluoroalkyl $C_{1-4}$-hydroxyalkyl, $C(O)OR^a$, $C(O)NR^aR^c$, —O—$C_{1-4}$alkyl, —S—$C_{1-4}$alkyl, —O—$C_{1-4}$-hydroxyalkyl, O—$C_{1-4}$-fluoroalkyl, —O—$PO_3$, —$C_{1-4}$alkyl-O—$PO_3$, or —O—$C_{1-4}$alkyl-O—$PO_3$;

$R^8$ is H or F;

$R^9$ is H, F, Cl, $CH_3$, or $CHF_2$;

$R^a$ is H, or $C_{1-4}$alkyl;

$R^c$ is H, $C_{1-4}$alkyl, or $C_{1-4}$hydroxyalkyl; and $R^d$ is F, $C_{1-4}$ alkyl, $C(O)O$—$C_{1-4}$alkyl, $C_{1-4}$ fluoroalkyl, $C_{1-3}$ alkoxy, or $C_{1-3}$ fluoroalkoxy.

In a third aspect of the present invention provides a compound of Formulas (I), (II), (III), or (IV), or any proceeding aspect, or salt thereof; wherein $R^1$ is methoxy, or ethoxy;

$R^2$ is F, Cl, CN, or methyl;

$R^3$ is

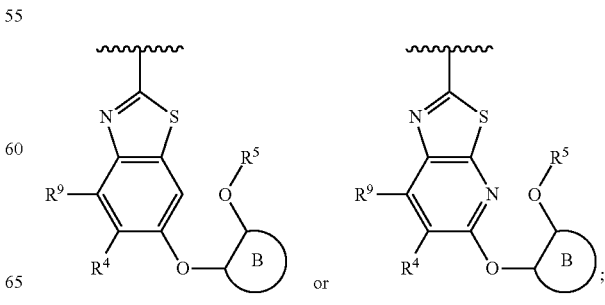

R⁴ is H or F;

Ring B, along with the two carbon atoms through which it is attached, is a cyclobutyl, cyclopentyl, or cyclohexyl, each of these being substituted with 0-2 R$^d$;

R⁵ is C(O)NHR⁶;

R⁶ is pyridinyl, or pyrimidinyl, each of these being substituted with 0-2 R⁷;

R⁷ is F, Cl, CN, hydroxy, methyl, $CF_3$, $CHF_2$, $CH_2OH$, $CH_2CH_2OH$, —$OCH_2CH_2OH$, —$OCH_3$, —$OCF_3$—$OCHF_2$, —$CH_2CH(CH_3)OH$, —O—CH—$CH(CH_3)OH$, —O—$PO_3^{-2}$, $CH_2O$—$PO_3^{-2}$, $CH_2CH_2O$—$PO_3^{-2}$, —$OCH_2CH_2O$—$PO_3^{-2}$, $CH_2CH(CH_3)O$—$PO_3^-$, or —O—$CH_2CH(CH_3)O$—$PO_3^{-2}$;

R⁸ is H or F;

R⁹ is H; and

R$^d$ is F, or methyl.

In a fourth aspect of the present invention provides a compound of Formulas (I), (I), (III), or (IV), or any proceeding aspect, or salt thereof; wherein R³ is

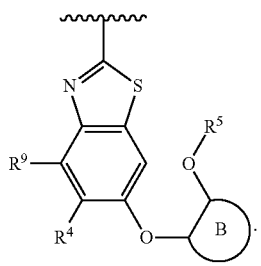

In a fifth aspect of the present invention provides a compound of Formula (I), or any proceeding aspect, or salt thereof; wherein

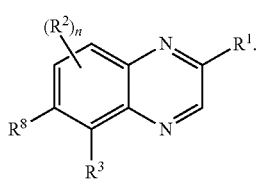

(I)

In a sixth aspect of the present invention provides a compound of Formulas (I), or any proceeding aspect, or salt thereof; wherein the compound of Formula (I) is:

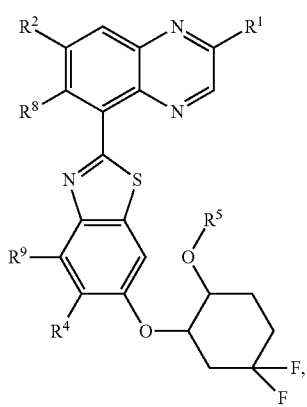

-continued

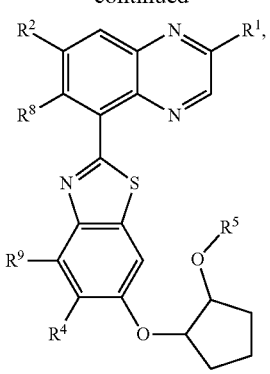

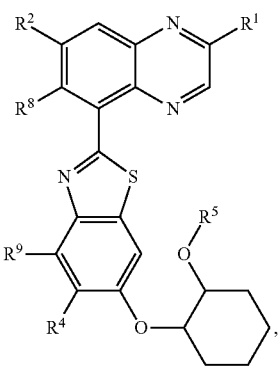

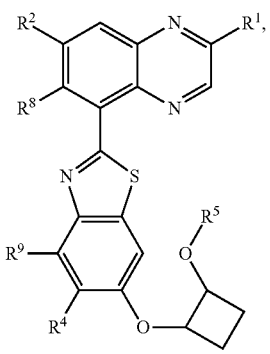

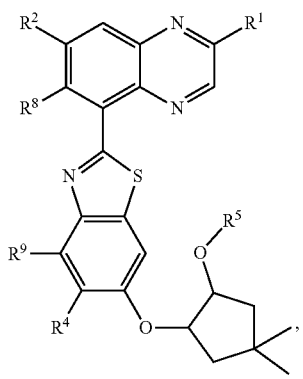

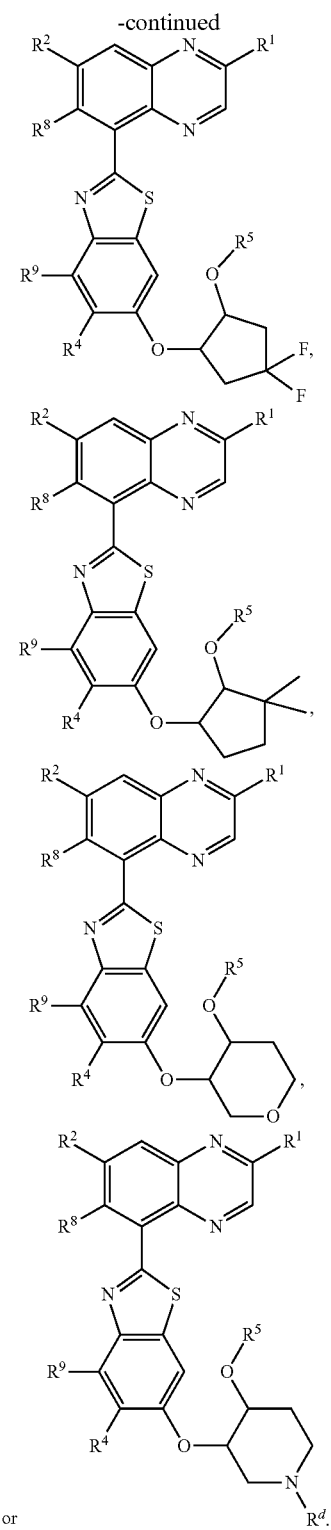

or

In a seventh aspect of the present invention provides a compound of Formulas (I), (II), (III), or (IV), or any proceeding aspect, or any of the compounds of the sixth aspect, or salt thereof; wherein R¹ is methoxy, or ethoxy;
R² is F, Cl, CN, or methyl;
R⁴ is F;

Ring B, along with the two carbon atoms through which it is attached, is a cyclobutyl, cyclopentyl, or cyclohexyl, each of these being substituted with 0-2 R$^d$;
R⁵ is C(O)NHR⁶;
R⁶ is pyridinyl, or pyrimidinyl, each of these being substituted with 0-2 R⁷;
R⁷ is F, Cl, CN, hydroxy, methyl, CF₃, CHF₂, CH₂OH, CH₂CH₂OH, —OCH₂CH₂H, —OCH₃, —OCF₃—OCHF₂, —CH₂CH(CH₃)OH, or —O—CH₂CH(CH₃)OH;
R⁸ is H;
R⁹ is H;
R$^d$ is H, methyl, or C(O)O—C₁₋₄alkyl.

In a eighth aspect of the present invention provides a compound of Formulas (I), (II), (III), or (IV), or any proceeding aspect, or any of the compounds of the sixth aspect, or salt thereof wherein R³ is

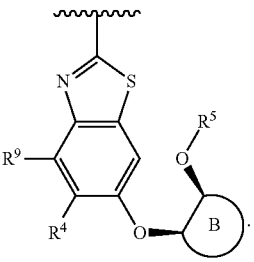

In a ninth aspect of the present invention provides a compound of Formulas (I), (II), (III), or (IV), or any proceeding aspect, or any of the compounds of the sixth aspect, or salt thereof; wherein
R⁷ is F, Cl, CN, hydroxy, methyl, CF₃, CHF₂, CH₂OH, CH₂CH₂OH, —OCH₂CH₂OH, —OCH₃, —OCF₃—OCHF₂, —CH₂CH(CH₃)OH, or —O—CH₂CH(CH₃)OH.

In a tenth aspect of the present invention provides a compound of examples I-104, or salt thereof.

In a eleventh aspect of the present invention provides a compound of Formula (I), or any proceeding aspect, or salt thereof;

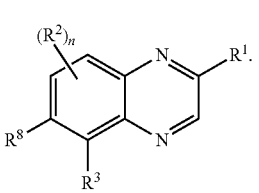

In a twelfth aspect of the present invention provides a compound of Formula (II), or any proceeding aspect, or salt thereof;

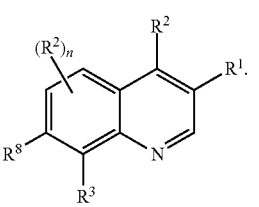

In a thirteenth aspect of the present invention provides a compound of Formula (III), or any proceeding aspect, or salt thereof;

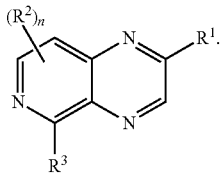
(III)

In a fourteenth aspect of the present invention provides a compound of Formula (IV), or any proceeding aspect, or salt thereof;

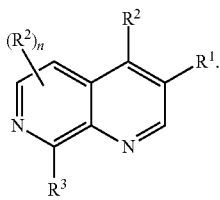
(IV)

In a fifteenth aspect of the present invention provides a compound of Formulas (I), (II), (III), or (IV), or any proceeding aspect, or salt thereof wherein $R^3$ is

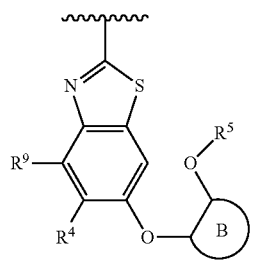 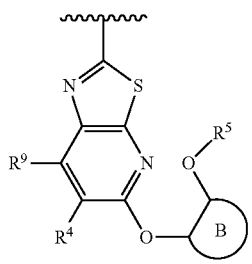

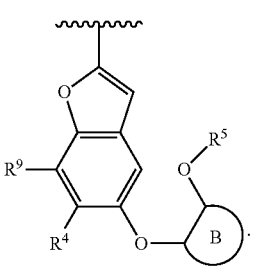

In a sixteenth aspect of the present invention provides a compound of Formulas (I), (II), (III), or (IV), or any proceeding aspect, or salt thereof; wherein $R^3$ is

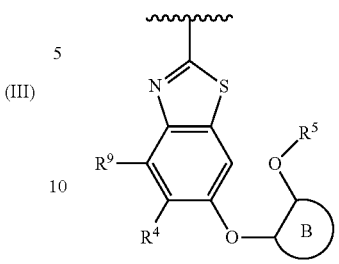 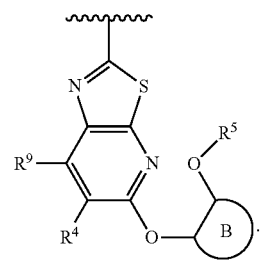

In a seventeenth aspect of the present invention provides a compound of Formulas (I), (II), (III), or (IV), or any proceeding aspect, or any of the compounds of the sixth aspect, or salt thereof; wherein Ring B, along with the two carbon atoms to which it is attached, is a cyclobutyl, cyclopentyl, or cyclohexyl, each of which is substituted with 0-2 $R^d$.

In a eighteenth aspect of the present invention provides a compound of Formulas (I), (II), (III), or (IV), or any proceeding aspect, or any of the compounds of the sixth aspect, or salt thereof; wherein $R^6$ is pyridinyl, or pyrimindinyl, each of which is substituted with 0-2 $R^7$.

In a nineteenth aspect of the present invention provides a compound of Formulas (I), (II), (III), or (IV), or any proceeding aspect, or any of the compounds of the sixth aspect, or salt thereof; wherein $R^6$ is pyrimidinyl, which is substituted with 0-2 $R^7$.

In a twentieth aspect of the present invention provides a compound of Formulas (I), (II), (III), or (IV), or any proceeding aspect, or any of the compounds of the sixth aspect, or salt thereof; wherein $R^6$ is pyridinyl, which is substituted with 0-2 $R^7$.

The present invention may be embodied in other specific forms without departing from the spirit or essential attributes thereof. This invention encompasses all combinations of the aspects and/or embodiments of the invention noted herein. It is understood that any and all aspects and/or embodiments of the present invention may be taken in conjunction with any other aspect and/or embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "aminoalkyl" as used herein is intended to include both branched and straight-chain saturated aliphatic hydrocarbon groups substituted with one or more amino groups. For example, "$C_{1-4}$ aminoalkyl" is intended to include $C_1$, $C_2$, $C_3$, and $C_4$ alkyl groups substituted with one or more amino groups. Representative examples of aminoalkyl groups include, but are not limited to, —CH$_2$NH$_2$, —CH$_2$CH$_2$NH$_2$, and —CH$_2$CH(NH$_2$)CH$_3$.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and $C_{1-4}$ hydroxyalkyl.

The term "hydroxy-deuteroalkyl" includes both branched and straight-chain saturated alkyl groups substituted with one or more hydroxyl groups and one or more deuterium atoms. Representative examples of hydroxy-deuteroalkyl groups include, but are not limited to, —CD$_2$OH and —CH(CD$_3$)$_2$OH.

The term "hydroxy-fluoroalkyl" includes both branched and straight-chain saturated alkyl groups substituted with one or more hydroxyl groups and one or more fluorine atoms. Representative examples of hydroxy-fluoroalkyl groups include, but are not limited to, —CF$_2$OH and —CF$_2$CH$_2$OH.

As used herein, "alkylene" refers to a bivalent alkyl radical having the general formula —(CH$_2$)$_n$—, where n is 1 to 10. Non-limiting examples include methylene, dimethylene, trimethylene, tetramethylene, pentamethylene, and hexamethylene. For example, "$C_{1-6}$ alkylene" denotes straight and branched chain alkylene groups with one to six carbon atoms. Further, for example, "$C_{0-4}$ alkylene" denotes a bond and straight and branched chain alkylene groups with one to four carbon atoms.

As used herein, "deuteroalkylene" refers to an alkylene group in which one or more hydrogen atoms have been replaced with deuterium atoms. For example, "$C_{1-6}$ deuteroalkylene" denotes straight and branched chain deuteroalkylene groups with one to six carbon atoms.

As used herein, "fluoroalkylene" refers to an alkylene group substituted with one or more fluorine atoms. For example, "$C_{1-6}$ fluoroalkylene" denotes straight and branched chain fluoroalkylene groups with one to six carbon atoms.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "fluorocycloalkyl" refers to a cycloalkyl group in which one or more hydrogen atoms are replaced by fluoro group(s).

The term "cycloalkylalkylene" refers to a cycloalkyl group attached through an alkylene group to the patent molecular moiety. For example, "($C_{3-6}$ cycloalkyl)-($C_{0-2}$ alkylene)" denotes a $C_{3-6}$ cycloalkyl group attached through a bond or a $C_{1-2}$ alkylene to the parent molecular moiety.

The term "alkoxy," as used herein, refers to an alkyl group attached to the parent molecular moiety through an oxygen atom, for example, methoxy group (—OCH$_3$). For example, "C$_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "C$_{1-4}$ fluoroalkoxy" is intended to include C$_1$, C$_2$, C$_3$, and C$_4$ fluoroalkoxy groups.

The term "hydroxyalkoxy" represent a hydroxyalkyl group as defined above attached through an oxygen linkage (—O—). For example, "C$_{1-4}$ hydroxyalkoxy" is intended to include C$_1$, C$_2$, C$_3$, and C$_4$ hydroxyalkoxy groups.

The term "cycloalkoxy," as used herein, refers to a cycloalkyl group attached to the parent molecular moiety through an oxygen atom, for example, cyclopropoxy group (—O(cyclopropyl)).

The term "alkoxyalkoxy" as used herein, refers to an alkoxy group attached through an alkoxy group to the patent molecular moiety. For example, "(C$_{1-3}$ alkoxy)-(C$_{1-6}$ alkoxy)" denotes a C$_{1-3}$ alkoxy group attached through a C$_{1-6}$ alkoxy group to the parent molecular moiety.

The term "alkoxyalkylene" as used herein, refers to an alkoxy group attached through an alkylene group to the patent molecular moiety. For example, "(C$_{1-3}$ alkoxy)-(C$_{1-3}$ alkylene)" denotes a C$_{1-3}$ alkoxy group attached through a C$_{1-3}$ alkylene to the parent molecular moiety.

The term "fluoroalkoxyalkylene" as used herein, refers to a fluoroalkoxy group attached through an alkylene group. For example, "(C$_{1-2}$ fluoroalkoxy)-(C$_{1-2}$ alkylene)" denotes a C$_{1-2}$ fluoroalkoxy group attached through a C$_{1-2}$ alkylene to the parent molecular moiety.

The term "alkoxy-fluoroalkylene" as used herein, refers to an alkoxy group attached through a fluoroalkylene group to the patent molecular moiety. For example, "(C$_{1-3}$ alkoxy)-(C$_{1-3}$ fluoroalkylene)" denotes a C$_{1-3}$ alkoxy group attached through a C$_{1-3}$ fluoroalkylene to the parent molecular moiety.

The term "deuteroalkoxy-deuteroalkylene" as used herein, refers to a deuteroalkoxy group attached through a deuteroalkylene group to the patent molecular moiety. For example, "(C$_{1-3}$ deuteroalkoxy)-(C$_{1-3}$ deuteroalkylene)" denotes a C$_{1-3}$ deuteroalkoxy group attached through a C$_{1-3}$ deuteroalkylene to the parent molecular moiety.

The term "alkylthio," as used herein, refers to an alkyl group attached to the parent molecular moiety through a sulfur atom, for example, methylthio group (—SCH$_3$). For example, "C$_{1-3}$ alkylthio" denotes alkylthio groups with one to three carbon atoms.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl. The amyl ring may be unsubstituted or may contain one or more substituents as valence allows.

The term "benzyl," as used herein, refers to a methyl group in which one of the hydrogen atoms is replaced by a phenyl group. The phenyl ring may be unsubstituted or may contain one or more substituents as valence allows.

The term "aryloxy," as used herein, refers to an aryl group attached through an oxygen group.

The term "phenoxy," as used herein, refers to a phenyl group attached through an oxygen group (—O-phenyl). The phenyl ring may be unsubstituted or may contain one or more substituents as valence allows.

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom. The heterocyclo ring may be unsubstituted or may contain one or more substituents as valence allows.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

The term "heteroaryloxy," as used herein, refers to a heteroaryl group attached through an oxygen group to the patent molecular moiety.

The term "arylalkylene" refers to an aryl group attached through an alkylene group to the patent molecular moiety. For example, "aryl($C_{1-2}$ alkylene)" refers to an aryl group attached through a $C_{1-2}$ alkylene to the parent molecular moiety.

The term "heteroarylalkylene" refers to a heteroaryl group attached through an alkylene group to the patent molecular moiety. For example, "heteroaryl($C_{1-2}$ alkylene)" refers to a heteroaryl group attached through a $C_{1-2}$ alkylene to the parent molecular moiety.

The term "aryloxyalkylene" refers to an aryloxy group attached through an alkylene group to the patent molecular moiety. For example, "aryloxy-($C_{1-2}$ alkylene)" refers to an aryloxy group attached through a $C_{1-2}$ alkylene to the parent molecular moiety.

The term "heteroaryloxyalkylene" refers to a heteroaryloxy group attached through an alkylene group to the patent molecular moiety. For example, "heteroaryloxy-($C_{1-2}$ alkylene)" refers to a heteroaryloxy group attached through a $C_{1-2}$ alkylene to the parent molecular moiety.

The compounds of the present invention can be provided as amorphous solids or crystalline solids. Lyophilization can be employed to provide the compounds as amorphous solids.

It should further be understood that solvates (e.g., hydrates) of the Compounds of the invention are also within the scope of the present invention. The term "solvate" means a physical association of a compound of Formulas (I) to (IV) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and insoluble solvates. Exemplary solvates include hydrates, ethanolates, methanolates, isopropanolates, acetonitrile solvates, and ethyl acetate solvates. Methods of solvation are known in the art.

In addition, compounds of Formulas (I) to (IV), subsequent to their preparation, can be isolated and purified to obtain a composition containing an amount by weight equal to or greater than 99% of a compound of Formulas (I) to (IV) ("substantially pure"), which is then used or formulated as described herein. Such "substantially pure" compounds of Formulas (I) to (IV) are also contemplated herein as part of the present invention.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Compounds of Formulas (I) to (IV) may be an acid or base salt thereof. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like. Other non pharmaceutically acceptable salt forms may be utilized in the preparation and/or purification of the compounds.

The salts and pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two: generally, nonaqueous media like ether, ethyl acetate, ethanol, isopropanol, or acetonitrile are preferred. Lists of suitable salts are found in Allen, L. V., Jr., ed., Remington: The Science and Practice of Pharmacy, 22nd Edition, Pharmaceutical Press, London, UK (2012), the disclosure of which is hereby incorporated by reference.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as—$CD_3$.

Biology

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%, 20%, 30%, 40%, 50%, 60%, 70%, 80%, 90%, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, P-selectin or CD40L release, or thrombosis and hemostasis models). In certain embodiments, platelet activation is measured by changes in the platelet cytoplasm, by changes of the platelet membrane, by changes in the levels of analytes released by platelets, by the changes in the morphology of the platelet, by the ability of platelets to form thrombi or platelet aggregates in flowing or stirred whole blood, by the ability of platelets to adhere to a static surface which is derivatized with relevant ligands (e.g., von Willebrand Factor, collagen, fibrinogen, other extracellular matrix proteins, synthetic fragments of any of the proteins, or any combination thereof), by changes in the shape of the platelets, or any combinations thereof. In one embodiment, platelet activation is measured by changes in the levels of one or more analytes released by platelets. For example, the one or more analytes released by platelets can be P-selectin (CD62p), CD63, ATP, or any combination thereof. In a particular embodiment, platelet activation is measured by the level of binding of fibrinogen or GPIIbIIIa antibodies to platelets. In other embodiments, platelet activation is measured by the degree of phosphorylation of vasodilator-stimulated phosphoprotein (VASP) upon platelet activation. In yet other embodiments, platelet activation is measured by the level of platelet-leukocyte aggregates. In certain embodiments, platelet activation is measured by proteomics profiling. The term "PAR4 antagonist" also includes a compound that inhibits both PAR1 and PAR4.

Preferably, compounds of the invention have $IC_{50S}$ in the PAR4 FLIPR Assay (described hereinafter) of about 10 µM, preferably 1 µM or less, more preferably 100 nM or less, and even more preferably 10 nM or less. PAR4 FLIPR assay data for compounds of the present invention is presented in the Table.

In some embodiments, the present invention provides a pharmaceutical composition, which includes a pharmaceutically acceptable carrier and a therapeutically effective amount of a compound of Formula I- to (IV), preferably, a compound selected from one of the examples, more preferably, Examples 1 to 104, or stereoisomers, tautomers, pharmaceutically acceptable salts, or solvates thereof, alone or in combination with another therapeutic agent.

In some embodiments, the present invention provides a pharmaceutical composition which further includes another therapeutic agent(s). In a preferred embodiment, the present invention provides a pharmaceutical composition, wherein the additional therapeutic agent(s) are an anti-platelet agent or a combination thereof. Preferably, the anti-platelet agent(s) are P2Y12 antagonists and/or aspirin. Preferably, the P2Y12 antagonists are clopidogrel, ticagrelor, or prasugrel. In another preferred embodiment, the present invention provides a pharmaceutical composition, wherein the additional therapeutic agent(s) are an anticoagulant or a combination thereof. Preferably, the anticoagulant agent(s) are a FXa inhibitor, a thrombin inhibitor, or a FXIa inhibitor. Preferably, the FXa inhibitors are apixaban, rivaroxaban, or edoxaban. Preferably, the thrombin inhibitor is dabigatran.

It is desirable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; (h) improved therapeutic index with less propensity for bleeding; and (h) factors that improve manufacturing costs or feasibility.

As used herein, the term "patient" encompasses all mammalian species.

As used herein, the term "subject" refers to any human or nonhuman organism that could potentially benefit from treatment with a PAR4 antagonist. Exemplary subjects include human beings of any age with risk factors for cardiovascular disease, or patients that have already experienced one episode of cardiovascular disease. Common risk factors include, but are not limited to, age, male sex, hypertension, smoking or smoking history, elevation of triglycerides, elevation of total cholesterol or LDL cholesterol.

In some embodiments, the subject is a species having a dual PAR1/PAR4 platelet receptor repertoire. As used herein, the term "dual PAR1/PAR4 platelet receptor repertoire" means that a subject expresses PAR1 and PAR4 in platelets or their precursors. Exemplary subjects having a dual PAR1/PAR4 platelet receptor repertoire include human beings, non-human primates, and guinea pigs.

In other embodiments, the subject is a species having a dual PAR3/PAR4 platelet receptor repertoire. As used herein, the term "dual PAR3/PAR4 platelet receptor repertoire" means that a subject expresses PAR3 and PAR4 in platelets or their precursors. Exemplary subjects having a dual PAR3/PAR4 platelet receptor repertoire include rodents and rabbits.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005).) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular weight heparin preparations have been approved by the FDA for these indications.

The term "pharmaceutical composition," as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy*, 20th Edition, Mack Publishing Co., Easton, Pa. (2000).

The invention includes administering to a subject a pharmaceutical composition that includes a compound that binds to PAR4 and inhibits PAR4 cleavage and/or signaling (referred to herein as a "PAR4 antagonist" or "therapeutic compound").

The pharmaceutical composition is administered using methods known in the art. Preferably, the compound is administered orally, rectally, nasally, by inhalation, topically or parenterally, e.g., subcutaneously, intraperitoneally, intramuscularly, and intravenously. The compound is optionally formulated as a component of a cocktail of therapeutic drugs to treat a thromboembolic disorder. In one embodiment, the pharmaceutical composition is administered orally.

The therapeutic compounds described herein are formulated into pharmaceutical compositions utilizing conventional methods. For example, a PAR4 antagonist is formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant.

Examples of solid carriers include starch and sugar bentonite. The compound is administered in the form of a hard shell tablet or a capsule containing a binder, e.g., lactose or mannitol, a conventional filler, and a tableting agent. Other formulations include an ointment, suppository, paste, spray, patch, cream, gel, resorbable sponge, or foam. Such formulations are produced using methods well known in the art. The compositions of the invention are also useful for parenteral administration, such as intravenous, subcutaneous, intramuscular, and intraperitoneal. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The preferred dose of the PAR4 antagonist is a biologically active dose. A biologically active dose is a dose that will inhibit cleavage and/or signaling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS), Western blot or ELISA analysis using PAR4 cleavage sensitive antibodies. Alternatively, the biological activity of PAR4 is measured by assessing cellular signaling elicited by PAR4 (e.g., calcium mobilization or other second messenger assays).

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

The activity of the PAR4 antagonists of the present invention can be measured in a variety of in vitro assays. Exemplary assays are shown below.

The Fluorometric Imaging Plate Reader (FLIPR) assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored.

AYPGKF is a known PAR4 agonist. An alternative PAR4 agonist is H-Ala-Phe(4-F)-Pro-Gly-Trp-Leu-Val-Lys-Asn-Gly-NH$_2$. As shown in Example B of WO2013/163279, H-Ala-Phe(4-F)-Pro-Gly-Trp-Leu-Val-Lys-Asn-Gly-NH$_2$ was validated as a PAR4 agonist in the FLIPR assay. A side-by-side comparison of the IC$_{50}$ values of ~180 compounds were performed using AYPGKF versus H-Ala-Phe(4-F)-Pro-Gly-Trp-Leu-Val-Lys-Asn-Gly-NH$_2$. The results demonstrated a strong correlation between the two assays. Additionally, H-Ala-Phe(4-F)-Pro-Gly-Trp-Leu-Val-Lys-Asn-Gly-NH$_2$ has improved agonist activity as compared to AYPGKF with an EC$_{50}$ that is 10 fold lower than the EC$_{50}$ for AYPGKF in the FLIPR assay. H-Ala-Phe(4-F)-Pro-Gly-Trp-Leu-Val-Lys-Asn-Gly-NH$_2$ can be synthesized using methods well known to those of skill in the art.

The FLIPR assay can also be used as a counterscreen to test agonist activity or PAR1 antagonist activity in a cell line that expresses both PAR1 and PAR4. The PAR1 antagonist activity can be tested by the ability of the compound to inhibit calcium mobilization induced by the PAR1 agonist peptide SFLLRN or other PAR1 agonist peptides.

The compounds of the current invention can be tested in vitro for their ability to inhibit platelet aggregation induced by gamma-thrombin as shown below.

Gamma-thrombin, a proteolytic product of alpha-thrombin which no longer interacts with PAR1, selectively cleaves and activates PAR4 (Soslau, G. et al., "Unique pathway of thrombin-induced platelet aggregation mediated by glycoprotein Ib", *J. Biol. Chem.*, 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, PAR1 agonist peptide, ADP, or thromboxane analogue U46619.

The compounds of the current invention can be tested in vitro for their ability to inhibit platelet aggregation induced by alpha-thrombin as shown below. Alpha-thrombin activates both PAR1 and PAR4. The ability of a selective PAR4 antagonist of the present invention to inhibit platelet aggregation can be measured using a standard optical aggregometer.

The compounds of the current invention can be tested in vitro for their ability to inhibit platelet aggregation induced by tissue factor as shown below. The conditions in this assay mimic the physiological events during thrombus formation. In this assay, platelet aggregation in human platelet rich plasma (PRP) is initiated by the addition of tissue factor and CaCl$_2$. Tissue factor, the initiator of the extrinsic coagulation cascade, is highly elevated in human atherosclerotic plaque. Exposure of blood to tissue factor at the atherosclerotic site triggers a robust generation of thrombin and induces the formation of obstructive thrombi.

The activity of the PAR4 antagonists of the present invention can also be measured in a variety of in vivo assays. Exemplary mammals that can provide models of thrombosis and hemostasis to test the effectiveness of the PAR4 antagonists of the present invention as antithrombotic agents include, but are not limited to, guinea pigs and primates. Relevant efficacy models include, but are not limited to, electrically-induced carotid arterial thrombosis, $FeCl_3$-induced carotid artery thrombosis and arteriovenous-shunt thrombosis. Models of kidney bleeding time, renal bleeding time and other bleeding time measurements can be used to assess the bleeding risk of the antithrombotic agents described in the current invention.

Assays

Materials
1) PAR1 and PAR4 Agonist Peptides

SFFLRR is a known high affinity PAR1 selective agonist peptide. (Reference: Seiler, S. M., "Thrombin receptor antagonists", *Seminars in Thrombosis and Hemostasis*, 22(3):223-232 (1996).) The PARA agonist peptides AYPGKF and H-Ala-Phe(4-F)-Pro-Gly-Trp-Leu-Val-Lys-Asn-Gly-$NH_2$ were synthesized. H-Ala-Phe(4-F)-Pro-Gly-Trp-Leu-Val-Lys-Asn-Gly-$NH_2$ showed improved PAR4 agonist activity over AYPGKF in the FLIPR assay ($EC_{50}$ value of 8 μM for H-Ala-Phe(4-F)-Pro-Gly-Trp-Leu-Val-Lys-Asn-Gly-$NH_2$ and 60 μM for AYPGKF) and in washed platelet aggregation assay ($EC_{50}$ value of 0.9 μM for H-Ala-Phe(4-F)-Pro-Gly-Trp-Leu-Val-Lys-Asn-Gly-$NH_2$ and 12 μM for AYPGKF).

2) PARA Expressing Cells

HEK293 cells stably expressing PAR4 were generated by a standard method of transfection of human PAR4 (F2R23) cDNA expression vector and selected based on PAR4 protein expression or mRNA expression. Those cells demonstrated functional responses to PAR4 agonist peptide-induced intracellular calcium elevation using FLIPR® (Fluorometric Imaging Plate Reader; Molecular Devices Corp.). These cells also express endogenous PAR1 and can elicit calcium signal upon stimulation with PAR1 agonist peptide. Therefore, the same cells were also used to determine selectivity against PAR1 and agonist activity for both receptors. Cells from HEK293 PAR4 Clone 1.2A (BMS Arctic ID 383940) were propagated and used for calcium mobilization studies.

3) Preparation of Platelet Rich Plasma (PRP)

Human blood was collected in 3.8% sodium citrate at a ratio of 1 ml per 9 ml blood and centrifuged in a Sorvall® RT6000B centrifuge at 900 revolution per minute (rpm) at room temperature (RT) for 15 minutes. PRP was collected and used for aggregation assay. Refludan (Berlex Labs, Wayne, N.J.), a recombinant hirudin, at a final concentration of 1 unit/mL was added to the sample to selectively prevent PAR1 activation induced by residual alpha-thrombin contamination. The remaining blood sample was centrifuged at 2500 rpm at room temperature for 5 minutes to collect platelet-poor plasma (PPP).

4) Preparation of Washed Platelets (WP)

Human blood was collected in ACD (85 mM tri-sodium citrate, 78 mM citric acid, 110 mM D-glucose, pH1–4.4) at a ratio of 1.4 ml per 10 ml blood. PRP was isolated by centrifugation at 170 g for 14 minutes and platelets were further pelleted by centrifugation at 1300 g for 6 minutes. Platelets were washed once with 10 ml ACD containing 1 mg/ml bovine serum albumin. Platelets were resuspended at $\sim 2.5 \times 10^8$/ml in Tyrode's Buffer (137 mM NaCl, 2 mM KCl, 1.0 mM $MgCl_2$, 1 mM $CaCl_2$, 5 mM glucose, 20 mM HEPES pH 7.4).

FLIPR Assay in PAR4-Expressing HEK293 Cells

FLIPR-based calcium mobilization assay in HEK293 cells was used to measure PAR4 antagonism agonism, and selectivity against PAR1. The activity of the PAR4 antagonists of the present invention were tested in PAR4 expressing cells by monitoring H-Ala-Phe(4-F)-Pro-Gly-Trp-Leu-Val-Lys-Asn-Gly-$NH_2$-induced intracellular calcium mobilization. Counter screens for agonist activity and PAR1 antagonist activity were also performed. Briefly, PAR/PAR4-expressing HEK293 cells were grown in DMEM (Life Technology, Grand Island, N.Y.) containing 10% heat-inactivated FBS, 1% Penicillin-Streptomycin, 10 μg/mL blasticidin, and 100 μg/mL Zeocin at 37° C. with 5% $CO_2$. Cells were plated overnight prior to the experiment in a black 384-well Purecoat Amine clear bottom plate (Becton Dickinson Biosciences, San Jose, Calif.) at 10,000 cells/well in 30 μL growth medium and incubated in a humidified chamber at 37° C. with 5% $CO_2$ overnight. Prior to compound addition, the cell medium was replaced with 40 μL of 1× calcium and magnesium-containing Hank's Balanced Saline Solution (HBSS) (with 20 mM HEPES) and 1:1000 diluted fluorescent calcium indicator (Codex Biosolutions, Gaithersburg, Md.). After a 30 minute incubation period at 37° C. and a further 30 minute incubation and equilibration period at room temperature, 20 μL test compound (diluted in 1×HBSS buffer) was added at various concentrations at 0.17% dimethyl sulfoxide (DMSO) final concentration. Changes in fluorescence intensity were measured using a Functional Drug Screening System (FDSS, Hamamatsu, Japan) to determine agonist activities. The cells were then incubated for 30 minutes at room temperature followed by addition of 20 μL of agonist peptide for antagonist activity measurement. The PAR4 agonist peptide (H-Ala-Phe(4-F)-Pro-Gly-Trp-Leu-V al-Lys-Asn-Gly-$NH_2$) and the PAR1 agonist peptide (SFFLRR) were routinely tested to ensure a proper response at the $EC_{50}$ value in the assay (~5 μM for PAR4 agonist peptide and ~2 μM for PAR1 agonist peptide). Compound potency was derived from 11-point concentration-response curves.

Gamma Thrombin Induced Platelet Aggregation Assays

The ability of the compounds of the current invention to inhibit platelet aggregation induced by gamma-thrombin was tested in a 96-well microplate aggregation assay format. Briefly, 90 μL of PRP or washed platelets were pre-incubated for 5 minutes at 37° C. with 3-fold serially diluted test compound, which was prepared as a 100-fold stock solution in dimethyl sulfoxide (DMSO). Aggregation was initiated by addition of 10 μL of gamma-thrombin (Haematologic Technologies, Inc. Essex Junction, Vt.) at 50-100 nM final concentration, which was titrated daily to achieve 80% platelet aggregation. The plate was then placed into a SpectraMax® Plus Plate Reader (Molecular Devices) at 37° C. Platelet aggregation was monitored at a wavelength of 405 nm using a kinetic analysis mode. Prior to the first data collection time point, the plate was shaken for 10 seconds to allow thorough mixing. Data was subsequently collected every 10 seconds for up to 7 minutes total. Data was collected using SoftMax® 5.4.1 software and exported to Microsoft Excel for analysis. The optical density (OD) values at the time point that achieved 75% platelet activation by agonist alone were used for analysis. The OD value from a PRP sample without any treatment served as ODmaximum, and the OD value from a PPP sample containing no platelets served as the ODminimum. Inhibition of platelet aggregation (IPA) was calculated based on the formula: % IPA=(100-100*[ODcompound−ODminimum]/[ODmaximum−ODminimum]), The $IC_{50}$ value of the test compound was calculated by fitting the % IPA values to the one-site concentration response equation: Y=A+(B-A)/{1+(C/X)^D}, using XLfit for 32 bit Excel® Version 2 Build 30 (ID Business Solutions Limited).

The aggregation assays were also employed to test the selectivity of the compound against other platelet receptors by using SFFLRR for PAR1, collagen (Chrono-Log, Havertown, Pa.) for collagen receptors, ADP for P2Y1 and P2Y12 and U46619 (Cayman Chemical, Ann Arbor, Mich.) for thromboxane receptors.

Alpha-Thrombin Induced Platelet Aggregation Assays

The ability of PAR4 antagonists to inhibit platelet aggregation induced by alpha-thrombin can be tested using human washed platelets. The antagonists are pre-incubated with washed platelets for 20 min. Aggregation is initiated by addition of 1.5 nM alpha-thrombin (Haematologic Technologies, Essex Junction, Vt.) to 300 µl of washed platelets at stirring speed of 1000 rpm. Platelet aggregation is monitored using an Optical Aggregometer (Chrono-Log, Havertown, Pa.) and the area under the curve (AUC) at 6 min was measured. $IC_{50}$ values are calculated using vehicle control as 0% inhibition.

Tissue Factor-Induced Platelet Aggregation Assay

The ability of PAR1 or PAR4 antagonists to inhibit platelet aggregation induced by endogenous thrombin can be tested in a tissue factor driven aggregation assay. Aggregation is initiated by addition of $CaCl_2$ and recombinant human tissue factor, which results in the generation of thrombin through activation of the coagulation pathway in the plasma. Anticoagulant agents such as corn trypsin inhibitor (Haematologic Technologies, Essex Junction, Vt.) at 50 µg/ml and PEFABLOC® FG (Centerchem, Norwalk, Conn.) are also added to the sample to prevent fibrin clot formation during the time of the study. Platelet aggregation is monitored using standard instrumentation including optical aggregometer or impedance aggregometer.

Cynomolgus Monkey Electrolytic Injury-induced Carotid Artery Thrombosis Model

Healthy cynomolgus monkeys are used in the study. These monkeys are retired from other pharmacokinetic and pharmacodynamic studies and have at least a 4-week washout period. On the day of the study, compounds or vehicles are administered orally at 1 to 2 hours before the experiment. Monkeys are then sedated by intramuscular administration of 0.2 mg/kg atropine, 5 mg/kg TELAZOL (tiletamine/zolazepam) and 0.1 mg/kg hydromorphone to facilitate placement of an endotracheal tube. An intravenous catheter is placed in the left cephalic vein for fluid administration to prevent dehydration. Animals are then administered with an inhalant anesthetic, isoflurane (1-5% to effect) and oxygen, ventilated, and placed on a thermostatically controlled heating pad to maintain the body temperature at 37° C. General anesthesia is maintained at a surgical plane using inhaled isoflurane and oxygen. The left brachial artery is cannulated to record blood pressure and heart rate. Blood pressure and heart rate are monitored to maintain normal vital signs. The carotid arterial thrombosis model in monkeys was based on a rabbit arterial thrombosis model, as described by Wong et al. (Wong, P. C. et al., "Nonpeptide factor Xa inhibitors: II. Antithrombotic evaluation in a rabbit model of electrically induced carotid artery thrombosis", J. Pharmacol. Exp. Ther., 295:212-218 (2002)) The monkey thrombosis model has recently been described by Wong et al. (Wong, P. C. et al., "The $P2Y_1$ receptor antagonist MRS2500 prevents carotid artery thrombosis in cynomolgus monkeys", J. Thromb. Thrombolysis, 41:514-521 (2016)) Thrombosis is induced by electrical stimulation of the carotid artery for 5 min at 10 mA using an external stainless-steel bipolar electrode. Carotid blood flow is measured with an appropriately sized TRANSONIC flow probe and a TRANSONIC perivascular flowmeter (TS420 Model, Transonic Systems Inc., Ithaca, N.Y.). It is continuously recorded over a 90-min period to monitor thrombosis-induced occlusion. Integrated carotid blood flow is measured by the area under the flow-time curve. It is expressed as percent of total control carotid blood flow, which would result if control blood flow had been maintained continuously for 90 min. In addition, thrombus from the injured artery is removed, blotted twice on a weighing paper to remove residual fluid, and weighed.

The following table sets out the results obtained employing various compounds of the invention tested in the PAR4 FLIPR assay.

TABLE

| Ex. No. | PAR4 FLTPR assay ($IC_{50}$, nM) |
|---|---|
| 1 | 1.6 |
| 2 | 0.46 |
| 3 | 0.82 |
| 4 | 1.9 |
| 5 | 6.8 |
| 6 | 0.76 |
| 7 | 0.67 |
| 8 | 1.2 |
| 9 | 12 |
| 10 | 23 |
| 11 | 2.8 |
| 12 | 5.7 |
| 13 | 110 |
| 14 | 2.4 |
| 15 | 0.77 |
| 16 | 1.3 |
| 17 | 4.1 |
| 18 | 3.9 |
| 19 | 1.0 |
| 20 | 1.8 |
| 21 | 470 |
| 22 | 2.4 |
| 23 | 30 |
| 24 | 7.8 |
| 25 | 1.3 |
| 26 | 83 |
| 27 | 58 |
| 28 | 96 |
| 29 | 12 |
| 30 | 2.6 |
| 31 | 1.1 |
| 32 | 2.6 |
| 33 | 3.1 |
| 34 | 1.6 |
| 35 | 2.5 |
| 36 | 2.4 |
| 37 | 4.0 |
| 38 | 9.4 |
| 39 | 400 |
| 40 | 83 |
| 41 | 180 |
| 42 | 320 |
| 43 | 22 |
| 44 | 25 |
| 45 | 2.2 |
| 46 | 2.0 |
| 47 | 4.2 |
| 48 | 2.4 |
| 49 | 3.6 |
| 50 | 3.4 |
| 51 | 6.8 |

TABLE-continued

| Ex. No. | PAR4 FLTPR assay (IC$_{50}$, nM) |
|---|---|
| 52 | 2.5 |
| 53 | 94 |
| 54 | 13 |
| 55 | 1.4 |
| 56 | 1.8 |
| 57 | 6.1 |
| 58 | 1.4 |
| 59 | 77 |
| 60 | 9.8 |
| 61 | 1.3 |
| 62 | 6.9 |
| 63 | 7.4 |
| 64 | 1.9 |
| 65 | 3.7 |
| 66 | 0.79 |
| 67 | 0.99 |
| 68 | 0.75 |
| 69 | 1.2 |
| 70 | 9.0 |
| 71 | 1.6 |
| 72 | 1.1 |
| 73 | 0.50 |
| 74 | 8.9 |
| 75 | 5.9 |
| 76 | 10 |
| 77 | 9.2 |
| 78 | 9.7 |
| 79 | 0.90 |
| 80 | 7.0 |
| 81 | 9.2 |
| 82 | 1.1 |
| 83 | 6.8 |
| 84 | 5.4 |
| 85 | 41 |
| 86 | 2.7 |
| 87 | 6.2 |
| 88 | 21 |
| 89 | 3.8 |
| 90 | 330 |
| 91 | 3.8 |
| 92 | 12 |
| 93 | 980 |
| 94 | 2300 |
| 95 | 72 |
| 96 | 44 |
| 97 | 9.2 |
| 98 | 14 |
| 99 | 32 |
| 100 | 1.3 |
| 101 | 20 |
| 102 | 0.75 |
| 103 | 20 |
| 104 | 2.4 |

The data values in the Table are reported with two significant digits.

Methods of Preparation

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reaction mixtures are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (*Greene's Protective Groups In Organic Synthesis,* 4th Edition, Wiley-Interscience (2006).

Compounds of Formula I can be prepared from palladium catalyzed cross coupling of arylboronic acids of Formula Ib with halides R$_3$—X shown in Scheme 1.

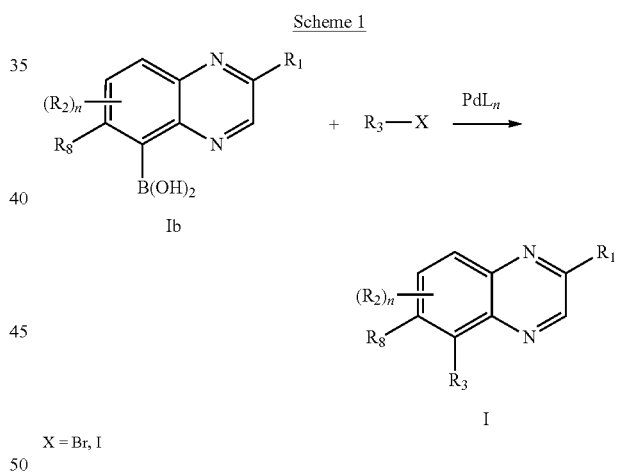

A regiospecific synthesis of quinoxalines of Formula Ia and Ib is shown in Scheme 2. A protected ortho-nitro aniline Ie is alkylated with methyl bromoacetate to yield compound If. Deprotection of compound If and reduction of compound Ig initiates cyclization to give rise to compound Ih. Compound Ih can be oxidized to quinoxaline-2-one of Formula Ii, which can be converted to the intermediate Ij with oxophosphorus halides. The halide in compound Ij can be displaced with a nucleophile containing an R$_1$ group to compound Ia, and compounds of Formula Ia can be converted to corresponding boronic acids of Formula Ib via Suzuki-Miyaura reaction. Intermediate Ii could also be converted to Ik by condensation reaction with sodium chlorodifluoroacetate in the presence of a base such as K$_2$CO$_3$. The difluoroalkoxy group may be displaced with a nucleophile containing an R$_1$ group to compound Ia.

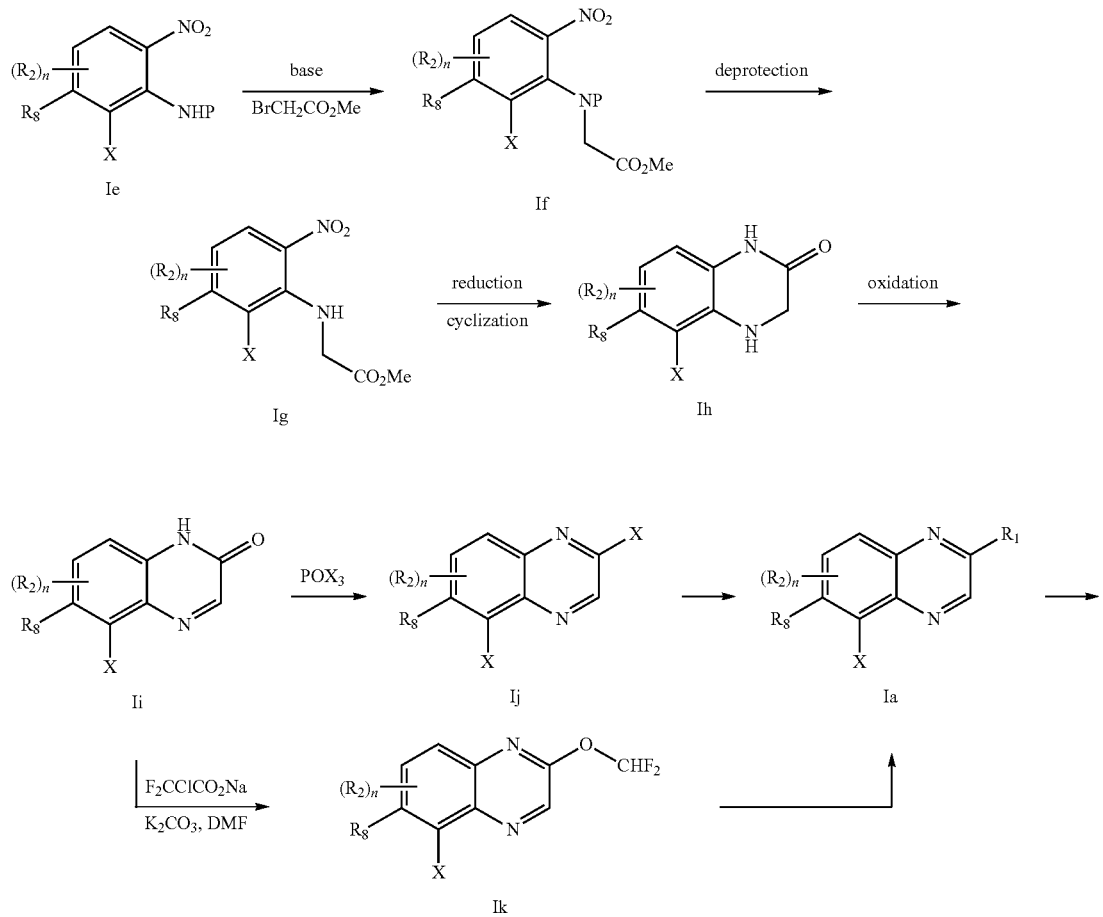

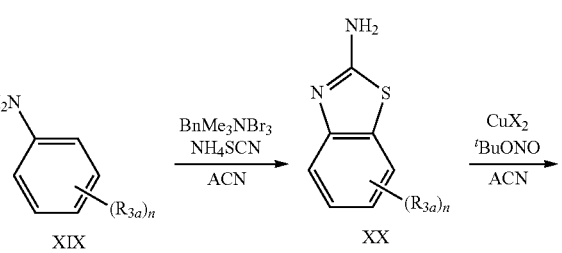

A synthesis of 2-halo benzothiazoles XXI is shown in Scheme 3. Beginning with the appropriately substituted aniline XIX, the 2-amino benzothiazole XX is formed via addition and oxidative cyclization of a thiocyanate. Subsequent Sandmeyer chemistry is employed to generate the desired 2-halo benzothiazole XXI. With XXI in hand, various compounds of Formula I with structure YXXIIa are prepared with boronic acid Ib via Suzuki cross-coupling. Intermediates for preparation of compounds containing bicyclic $R_3$ groups other than benzothiazole are commercially available or can be prepared by one skilled in the art, and can be incorporated via cross coupling chemistry as shown in Scheme 3.

-continued

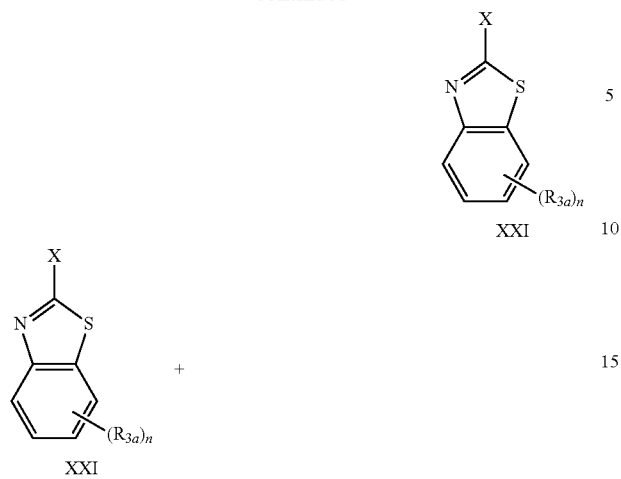

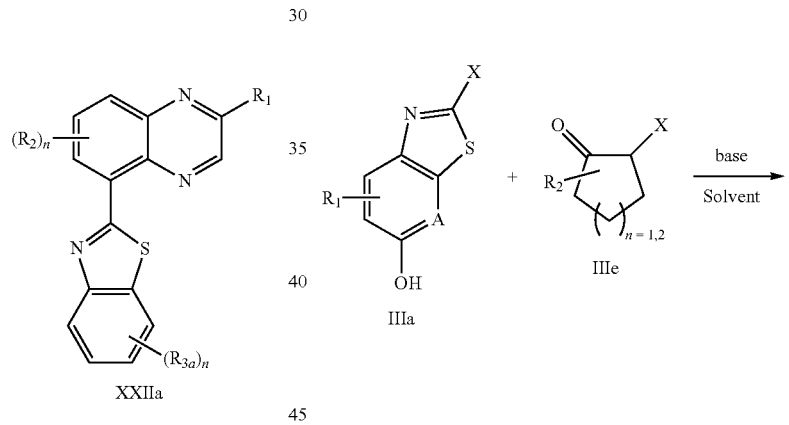

A synthesis of cis-2-halo benzothiazole cyclic diol intermediates is shown in Scheme 3. Beginning with the appropriately substituted 2-halobenzothiazole reacting with cyclic alpha-halo ketones, cyclic ketones are formed, which are reduced to cis-hydroxy cyclic ether intermediates by L-Selectride.

Scheme 3

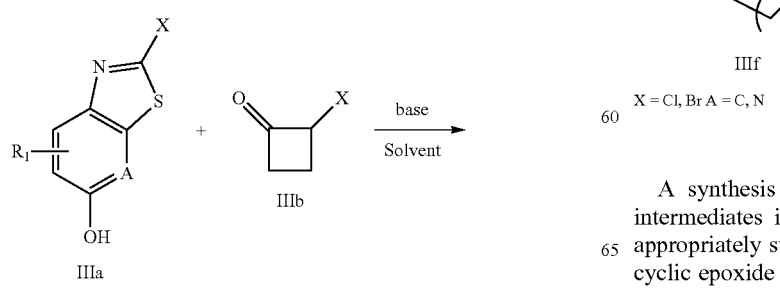

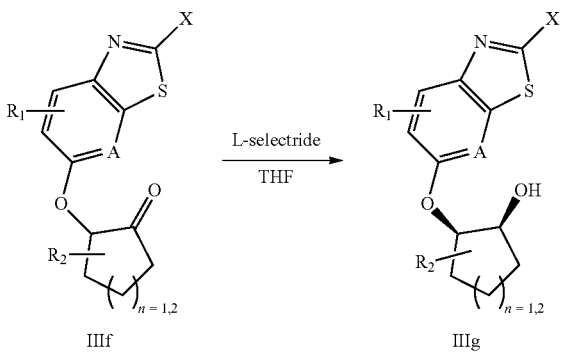

X = Cl, Br  A = C, N

A synthesis of trans-2-halo benzothiazole cyclic diol intermediates is shown in Scheme 4 Beginning with the appropriately substituted 2-halobenzothiazole reacting with cyclic epoxide IVb, to form trans-hydroxy ether intermediate IVc.

Scheme 4

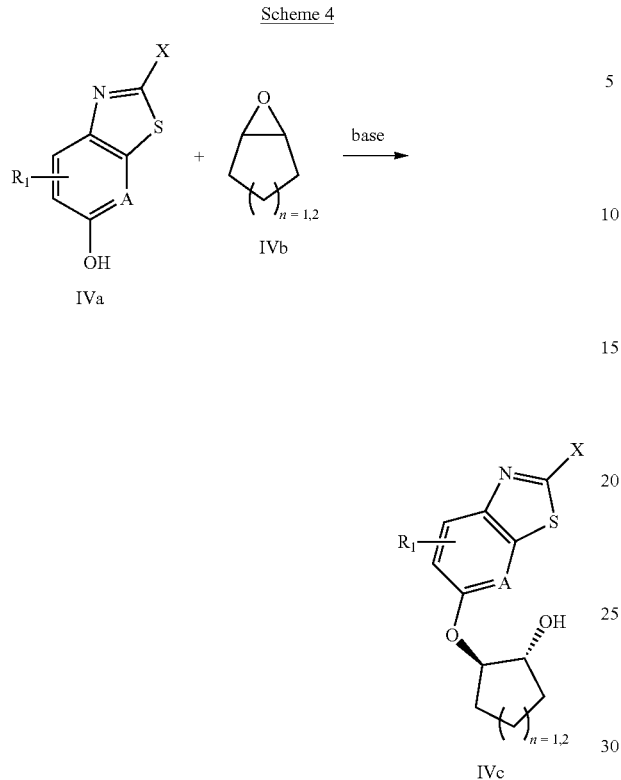

X = Cl, Br, A = C, N

A synthesis of some example compounds is shown in Scheme 5. Beginning with the appropriately cyclic diol intermediates Va and boron intermediates Yb, Pd catalyzed cross-coupling forms bi-aryl intermediates Vc. These compounds react with phosgene to form chloroformates Vd, which are converted to carbamates Ve by reacting with amines.

Scheme 5

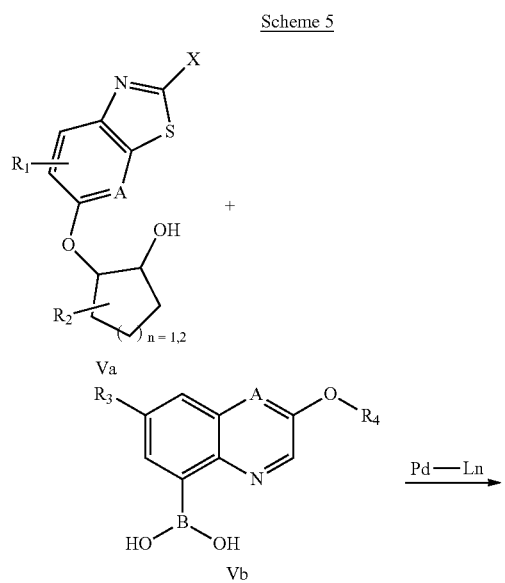

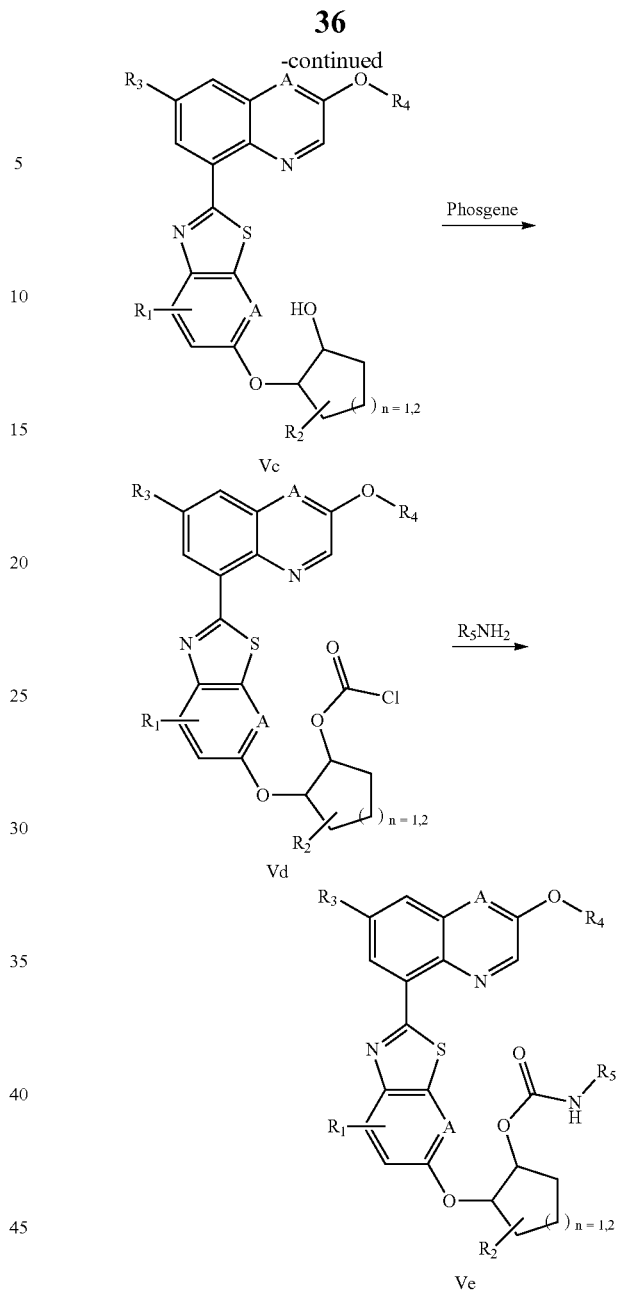

X = Cl, Br
A = C, N

The "R" groups described in the above schemes are for illustrative purposes, and do not necessarily correspond to the "R" groups described and claimed elsewhere.

General Methods

The following methods were used in the exemplified Examples, except where noted otherwise.

Products were analyzed by reverse phase analytical HPLC carried out on a Shimadzu Analytical HPLC system running Discovery VP software using one of the following methods:

Method A: PHENOMENEX® Luna C18 column (4.6×50 mm or 4.6×75 mm) eluted at 4 nm/min with 2, 4 or 8 min gradient from 100% A to 100% B (A: 10% methanol, 89.9% water, 0.1% TFA; B: 10% water, 89.9% methanol, 0.1% TFA, UV 220 nm).

Method B: PHENOMENEX® Luna C18 column (4.6×50 mm) eluted at 4 mL/min with a 4 min gradient from 100%

A to 100% B (A: 10% acetonitrile, 89.9% water, 0.1% TFA; B: 10% water, 89.9% acetonitrile, 0.1% TFA, UV 220 nm).

Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm).

Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $NH_4OAc$; B: 10% water, 89.9% methanol, 0.1% $NH_4OAc$, UV 220 nm).

Method E: BEH C18 2.1×50 mm; A: water+0.05% TFA; B: acetonitrile+0.05% TFA; wavelength 220 nm; flow rate 0.8 mL/min; 0% B to 100% B in 1 minute, gradient time 1.5 min.

Method F: BEH C18 2.1×50 mm; A: water+0.05% TFA; B: acetonitrile+0.05% TFA; wavelength 220 nm; flow rate 0.8 mL/min; 0% B to 50% B in 1 minute, gradient time 1.5 min.

Method G: BEH C18 2.1×50 mm; A: water+0.05% TFA; B: acetonitrile+0.05% TFA; wavelength 220 nm; flow rate 0.8 mL/min; 50% B to 100% B in 1 minute, gradient time 1.5 min.

Reverse phase preparative HPLC was carried out using a Shimadzu Preparative HPLC system running Discovery VP software using one of the following methods.

Method A: PHENOMENEX® Axia Luna 5 μM C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm).

Method B: YMC Sunfire 5 μM C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm).

Method C: XBridge C18, 19×200 mm column, 5-μm particles; Mobile Phase A: 5:95 acetonitrile:water with 0.1% trifluoroacetic acid; Mobile Phase B: 95:5 acetonitrile:water with 0.1% trifluoroacetic acid; Flow: 20 mL/min.

Method D: Waters XBridge C18, 19×100 mm column, 5-μm particles; Mobile Phase A: 5:95 acetonitrile:water with 10-mM ammonium acetate; Mobile Phase B: 95:5 acetonitrile:water with 10-mM ammonium acetate; Flow: 20 mL/min.

Method E: PHENOMENEX® Luna 5 μM C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm).

Method F: PHENOMENEX® Luna 5 μM C18 30×100 mm column with a 10 min gradient at 40 mL/min from 100% A to 100% B (A: 10)% methanol, 89.9% water, 0.1% TFA; B: 10% water, 89.9% methanol, 0.1% TFA, UV 220 nm).

Method G: Waters XBridge C18, 19×200 mm, 5-μm particles; Mobile Phase A: 5:95 acetonitrile:water with 0.1% formic acid; Mobile Phase B: 95:5 acetonitrile:water with 0.1% formic acid: Flow: 20 mL/min.

LCMS chromatograms were obtained on a Shimadzu HPLC system running Discovery VP software, coupled with a Waters ZQ mass spectrometer running MassLynx version 3.5 software using:

Method A: A linear gradient using solvent A (10% acetonitrile, 90% water, 0.1% of TFA) and solvent B (90% acetonitrile, 10% water, 0.1% of TFA); 0-100% of solvent B over 2 min and then 100% of solvent B over 1 min. Column: PHENOMENEX® Luna 3u C18(2) (2.0×30 mm). Flow rate was 5 ml/min. And UV detection was set to 220 nm. The LC column was maintained at room temperature.

Method B: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHENOMENEX® Luna 5u C18 (4.5×30 mm). Flow rate was 4 ml/min. And UV detection was set to 220 nm. The LC column was maintained at room temperature.

Method C: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 3u C18(2) (2.0×30 mm) Flow rate was 1 ml/min. And UV detection was set to 220 nm. The LC column was maintained at room temperature.

Method D: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 3u C18(2) (4.5×30 mm). Flow rate was 5 ml/min. And UV detection was set to 220 nm. The LC column was maintained at room temperature.

Method E: 30-95% acetonitrile in water with 0.1% TFA in 8 min run, Waters Xbridge 4.6×50 mm 5 um C18, flow rate 1.2 mL/min and UV detection was set to 220 nm. The LC column was maintained at room temperature.

Method F: 10-95% methanol in water, 0.1% TFA in a 10 min run, PHENOMENEX® Onyx Monolithic 4.6×100 mm 5 um C18, flow rate 2.0 mL/mL and UV detection was set to 220 nm. The LC column was maintained at room temperature.

Method G: 5-95% acetonitrile in water, 10 mM of modifier in 6 min run, Waters Xbridge 2.1×50 mm 5 um C18, flow rate 1.0 mL/min and UV detection was set to 220 nm. The LC column was maintained at room temperature.

Method H: BEH C18 2.1×50 mm: A: water+0.05% TFA; B: acetonitrile+0.05% TFA; wavelength 220 nm: flow rate 0.8 mL/min; gradient time 1.5 min; 2 to 98% B.

Method I: BEH C18 2.1×50 mm; A: water+0.05% TFA: B: acetonitrile+0.05% TFA; wavelength 220 nm; flow rate 0.8 mL/min; gradient time 1.5 min; 2 to 52% B.

Method J: BEH C18 2.1×50 mm; A: water+0.05% TFA; B: acetonitrile+0.05% TFA; wavelength 220 nm: flow rate 0.8 mL/min; gradient time 1.5 min; 48 to 98% B.

Method K: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm, Method L: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

In addition, the following orthogonal HPLC conditions were used to check the purity of the compounds:

Method A: Two analytical LC/MS injections were used to determine the final purity. Injection 1 condition: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 um (4.6×150 mm). Flow rate was 2 ml/min. And UV detection was set to 220 nm. The LC column was maintained at room temperature. Injection 2 conditions: A linear gradient using solvent A (5% acetonitrile, 95% water, 0.05% TFA) and solvent B (95% acetonitrile, 5% water, 0.05% TFA): 10-100% of solvent B over 10 min and then 100% of solvent B over 5 min. Column: Xbridge Phenyl 3.5 um (4.6×150 mm). Flow rate was 2 ml/min. And UV detection was set to 220 nm. The LC column was maintained at room temperature.

Method B: Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min: Detection: UV at 220 nm.

Methods of Preparation

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reaction mixtures are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (*Greene's Protective Groups In Organic Synthesis,* 4th Edition, Wiley-Interscience (2006).

Intermediate I-01 rac-cis-2-((2-bromo-5-fluorobenzo[d]thiazol-6-yl)oxy)cyclopentanol

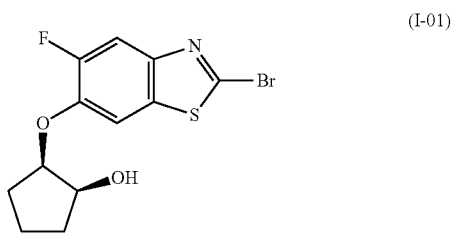 [SMILES: O[C@H]1CCC[C@H]1Oc1cc2sc(Br)nc2cc1F]

(I-01)

Intermediate I-01A: 2-((2-bromo-5-fluorobenzo[d]thiazol-6-yl)oxy)cyclopentanone

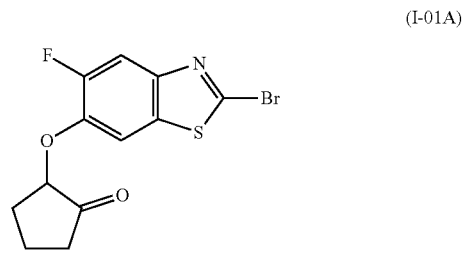 [SMILES: O=C1CCCC1Oc1cc2sc(Br)nc2cc1F]

(I-01A)

A mixture of 2-bromo-5-fluorobenzo[d]thiazol-6-ol (168 mg, 0.677 mmol) (Intermediate I-19), 2-chlorocyclopentanone (120 mg, 1.016 mmol), and potassium carbonate (187 mg, 1.354 mmol) in DMF (2 mL) was stirred for 1 h at 60° C. After cooling to room temperature, the reaction mixture was loaded on a silica gel column (24 g) and eluted with 0-100% EtOAc/hexane gradient. Collecting the desired fractions and removing solvent gave 2-((2-bromo-5-fluorobenzo[d]thiazol-6-yl)oxy)cyclopentanone (208 mg, 0.630 mmol, 93% yield) as a colorless oil. $^1$H NMR (400 MHz, CDCl$_3$) δ 7.69 (d, J=11.0 Hz, 1H), 7.55 (d, 3=7.5 Hz, 1H), 4.67-4.60 (m, 1H), 2.50 (m, 1H), 2.45-2.36 (m, 2H), 2.27-2.10 (m, 2H), 2.01-1.89 (m, 1H); $^{19}$F NMR (376 MHz, CDCl$_3$) δ −131.79 (s, 1F); LC-MS: method H, RT=0.90 min, MS (ESI) m/z: 330.0 and 332.0 (M+H)$^+$.

Intermediate I-01

Intermediate I-01A (578 mg, 1.751 mmol) was dissolved in THF (10 mL) and cooled to −78° C. under N$_2$. To this solution was added L-Selectride (2.101 mL, 2.101 mmol) at −78° C. dropwise. After 3 h of stirring, the mixture was warmed to room temperature and 14 drops of aq. sodium hydroxide (aq., 2N) and 10 drops of 35% hydrogen peroxide were added to the mixture, and the mixture was extracted with ethyl acetate (40 mL×2). The combined organic layers were washed with brine, dried over sodium sulfate, filtered and concentrated in vacuo to give an oil. The residual oil was purified by silica gel chromatography (12 g size column, 0-100% EtOAc/hexane) to give the title compound as white solid. $^1$H NMR (400 MHz, CDCl$_3$) δ 7.73 (d, J=11.0 Hz, 1H), 7.45 (d, J=7.5 Hz, 1H), 4.45-4.38 (m, 1H), 3.99 (d, J=7.5 Hz, 1H), 2.23 (d, J=5.9 Hz, 1H), 2.11-1.91 (m, 2H), 1.84-1.64 (m, 4H), 1.50-1.34 (m, 2H); $^{19}$F NMR (376 MHz, CDCl$_3$) δ -131.68 (s, 1F); LC-MS: method H, RT=0.94 min, MS (ESI) m/z: 332.0 and 334.1 (M+H)+.

Intermediate I-02 rac-cis-2-((2-bromo-5-fluorobenzo[d]thiazol-6-yl)oxy)cyclohexanol

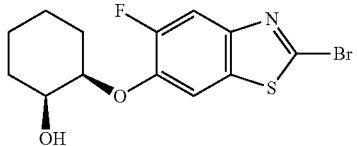

(I-02)

Intermediate I-02A: 2-((2-bromo-5-fluorobenzo[d]thiazol-6-yl)oxy)cyclohexanone

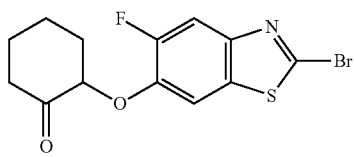

(I-02A)

Intermediate I-02A (1.1 g, 3.2 mmol, 80% yield) was made from 2-bromo-5-fluorobenzo[d]thiazol-6-ol (1.0 g, 4.03 mmol) (I-19) and 2-chlorocyclohexanone (1.069 g, 8.06 mmol) via the procedure described for I-01A. $^1$H NMR (400 MHz, CDCl$_3$) δ ppm 7.70 (1H, d, J=11.00 Hz), 7.31 (1H, d, J=7.70 Hz), 4.67 (1H, dd, J=9.68, 5.28 Hz), 2.59-2.72 (1H, m), 2.41 (2H, dd, J=10.56, 4.84 Hz), 1.98-2.23 (3H, m), 1.68-1.93 (2H, m); $^{19}$F NMR (376 MHz, CDCl$_3$) δ ppm -131.73 (1F, s); LC-MS: method H, RT=1.04 min, MS (ESI) m/z: 343.9 and 345.9 (M+H)$^+$.

Intermediate I-02

Intermediate I-02 (201 mg, 0.581 mmol, 95% yield) was made as a yellow solid from I-02A via same procedure described for I-01. $^1$H-NMR (400 MHz, CDCl$_3$) δ 7.71 (d, 1=10.8 Hz, 1H), 7.43 (d, J=7.5 Hz, 1H), 4.44-4.35 (m, 1H), 3.97 (d, J=7.5 Hz, 1H), 2.21 (d, J=5.9 Hz, 1H), 2.10-1.87 (m, 2H), 1.81-1.62 (m, 4H), 1.49-1.32 (m, 2H); $^{19}$F NMR (376 MHz, CDCl$_3$) δ -131.68 (s, 1F). LC-MS: method H, RT=0.94 min, MS (ESI) m/z: 346.0 and 348.1 (M+H)$^+$.

Intermediate I-03 rac-trans-2-((2-bromo-5-fluorobenzo[d]thiazol-6-yl)oxy)cyclopentanol

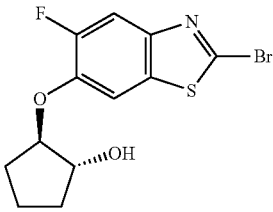

(I-03)

I-19 (100 mg, 0.403 mmol) and 6-oxabicyclo[3.1.0]hexane (1 mL, 0.403 mmol) were mixed in a vial. K$_2$CO$_3$ (55.7 mg, 0.403 mmol) was added, and the mixture was stirred at 100° C. for overnight. On the next day, the reaction was diluted by adding 30 mL of EtOAc and 20 mL of water. After separation, the aq. layer was extracted with EtOAc (15 mL×2). Organic layers were combined and washed with brine, dried over anhydrous Na$_2$SO$_4$, filtered and concentrated. The crude product was purified by silica gel chromatography (24 g silica gel column, 0-100% EtOAc/hexane gradient). Removing solvent gave I-03 (48.5 mg, 0.146 mmol, 36.2% yield) as a white solid. $^1$H NMR (400 MHz, CDCl$_3$) δ 7.69 (d, J=11.0 Hz, 1H), 7.43 (d, J=7.7 Hz, 1H), 4.61-4.54 (m, 1H), 4.40 (m, 1H), 2.30-2.09 (m, 2H), 1.95-1.80 (m, 3H), 1.76-1.63 (m, 2H); $^{19}$F NMR (376 MHz, CDCl$_3$) δ -132.68 (s, 1F); LC-MS: method H, RT=0.98 min, MS (ESI) m/z: 332.0 and 334.0 (M+H)$^+$.

Intermediate I-04 rac-cis-2-((2-bromo-5-fluorobenzo[d]thiazol-6-yl)oxy)-4,4-difluorocyclohexanol

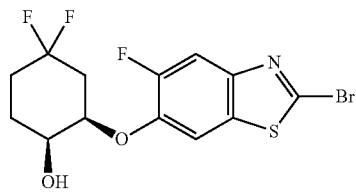

(I-04)

Intermediate I-04A: 2-bromo-4,4-difluorocyclohexanone

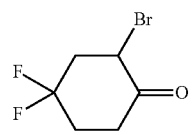

(I-04A)

4,4-difluorocyclohexanone (5 g, 37.3 mmol) was dissolved in CHCl$_3$ (60 ml) and cooled to 0° C. Br$_2$ (2.017 ml, 39.1 mmol) in CHCl$_3$ (30 mL) was added into the reaction solution dropwise. The mixture was stirred at room temperature for 2 hours. The reaction was followed by TLC (in 10 minutes, the color of bromine disappeared and the reaction turned to a clear yellow solution). Then saturated NaHCO$_3$ (aq.) solution was added into reaction slowly with stirring until no bubbles were generated. The layers were separated, and the organic phase was washed with brine, dried over anhydrous Na$_2$SO$_4$, filtered and concentrated to I-04A (8.40 g, 39.4 mmol, 106% yield) as yellow oil. $^1$H NMR (400 MHz, CDCl$_3$) δ 4.70 (dd, J=11.1, 6.3 Hz, 1H), 3.09-2.94 (m, 1H), 2.87 (m, 1H), 2.74-2.55 (m, 2H), 2.52-2.22 (m, 2H); $^{19}$F NMR (376 MHz, CDCl$_3$) δ ppm −101.01-94.88 (2F, m)

Intermediate I-04B 2-((2-bromo-5-fluorobenzo[d]thiazol-6-yl)oxy)-4,4-difluorocyclohexanone

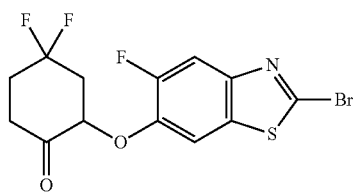

(I-04B)

I-04A (2.061 g, 9.67 mmol) was mixed with 2-bromo-5-fluorobenzo[d]thiazol-6-ol (1.2 g, 4.84 mmol) (Intermediate I-19) in anhydrous DMF (10 mL). K$_2$CO$_3$ (1.003 g, 7.26 mmol) was added. The mixture was stirred at 50° C. for 6 hours. LC/MS showed a small amount of starting material remained. Another 0.4 eq. of 2-bromo-4,4-difluorocyclohexanone (0.412 g, 1.935 mmol) was added. The mixture was stirred at 50° C. for additional 1 hour. The reaction was diluted by adding 50 mL of EtOAc and 30 mL of water. After separation, the aq. layer was extracted by 30 mL of EtOAc. The combined organic phases were washed by brine, dried over anhydrous Na$_2$SO$_4$, filtered and concentrated. The crude product was added to a silica gel (80) column and was eluted with 0-100% EtOAc/hexane. The solvent was removed from the desired fractions to give I-04B (1.81 g, 4.76 mmol, 98% yield) as the product. LC-MS: method H, RT=1.02 min, MS (ESI) m/z: 380.0 and 382.0 (M+H)$^+$.

Intermediate I-04

I-04B was dissolved in anhydrous THF (100 mL) and cooled to −78° C. under N$_2$. L-Selectride (16.79 mL, 16.79 mmol in THF) was added dropwise. The mixture was stirred at −78° C. for 3 hours, and then the reaction was slowly warmed up to room temperature. At the same time, 40 drops of NaOH (aq., 2N) was added to the reaction dropwise, followed by 20 drops of 35% H$_2$O$_2$ (aq.). Then 100 mL of EtOAc, and 50 mL of sat. NH$_4$Cl (aq.) were added to the reaction. After separation, the aq. layer was extracted with EtOAc (50 mL×2). The organic phases were combined and washed with brine, dried over anhydrous Na$_2$SO$_4$, filtered and concentrated. The crude product was added to a silica gel (220 g) column and was eluted with a 0-100% EtOAc/hexane gradient. Solvent was removed from the desired fractions to give I-04 (4.8 g, 12.56 mmol, 79% yield) as a white solid. $^1$H NMR (400 MHz, CDCl$_3$) δ ppm 7.74 (1H, d, J=10.78 Hz), 7.45 (1 Hd, d, J=7.48 Hz), 4.41 (1H, m), 4.21-4.28 (1H, m), 4.05-4.18 (1H, m), 2.36-2.52 (2H, m), 2.13 (2H, s), 1.85-2.04 (1H, m), 1.64-1.81 (1H, m); $^{19}$F NMR (376 MHz, CDCl$_3$) δ ppm −108.38 to −84.16 (2F, m), −131.47 (1F, s); LC-MS: method H, RT=0.99 min, MS (ESI) m/z: 381.9 and 384.0 (M+H)$^+$.

Intermediate I-05

(1R,2S)-2-((2-bromo-5-fluorobenzo[d]thiazol-6-yl)oxy)-4,4-difluorocyclohexanol

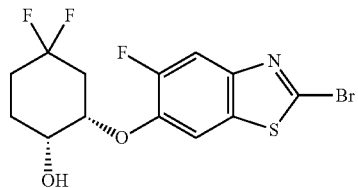

(I-05)

Intermediate I-06

(1S,2R)-2-((2-bromo-5-fluorobenzo[d]thiazol-6-yl)oxy)-4,4-difluorocyclohexanol

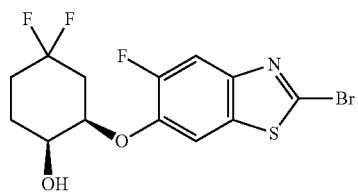

(I-06)

Intermediate I-04 (686 mg, 1.8 mmol) was separated by chiral SFC (supercritical fluid chromatography) to afford I-05 (170 mg, 24.8%, peak 2, retention time: 9.53 min, >99% ee) and I-06 (165 mg, 24%, peak 1, retention time: 7.96 min, >99% ee): Column: Chiralcel OJ-H, 30×250 mm, 5 micron; Mobile Phase: 20% MeOH/80% CO2; Flow Conditions: 100 mL/min, 150 Bar, 40° C., Detector Wavelength: 220 nm; Injection Details: 0.6 mL of −27 mg/ml in MeOH. The absolute stereochemistry of I-06 was assigned by x-ray crystallography, from the anomalous dispersion signal using the Flack method.

Intermediate I-07 rac-cis-2-((2-bromo-5-fluorobenzo[d]thiazol-6-yl)oxy)cyclobutanol

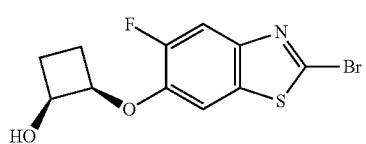

(I-07)

Intermediate I-07A: 2-bromocyclobutanone

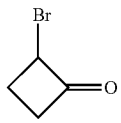
(I-07A)

Cyclobutanone (3.0 g, 42.8 mmol) was dissolved in CHCl₃ (60 mL) and cooled to 0° C., Br₂ (2.205 mL, 42.8 mmol) in CHCl₃ (40 mL) was added dropwise. After addition, the reaction was warmed to room temperature and stirred at room temperature overnight. On the next day, 30 mL of sat. NaHCO₃ was added slowly and the mixture was stirred for 10 minutes, and then layers were separated. The organic layer was washed with brine, dried over anhydrous Na₂SO₄, filtered and concentrated. The crude product was used in the next step without purification (5.9 g, 39.5 mmol, 95% yield). $^1$H NMR (400 MHz, CDCl₃) δ 5.07-4.94 (m, 1H), 3.29-3.13 (m, 2H), 2.74 (m, 1H), 2.31-2.19 (m, 1H).

Intermediate I-07B: 2-((2-bromo-5-fluorobenzo[d]thiazol-6-yl)oxy)cyclobutanone

(I-07B)

I-07B (0.810 g, 2.56 mmol, 63.6% yield) was made from I-07A and I-19 via the procedure described for I-04B. $^1$H NMR (400 MHz, CDCl₃) δ 7.70 (d, J=1.0 Hz, 1H), 7.54 (d, J=7.5 Hz, 1H), 5.47-5.19 (m, 1H), 2.99 (d, J=10.3 Hz, 2H) 2.75-2.60 (m, 1H), 2.39-2.28 (m, 1H); $^{19}$F NMR (376 MHz, CDCl₃) δ −132.29 (s, 1F); LC-MS: method H, RT=0.97 min, MS (ESI) m/z: 316.0 and 317.8 (M+H)⁺.

Intermediate I-07

Intermediate I-07 (0.54 g, 1.697 mmol, 66.2% yield) was made from I-07B (0.81 g, 2.56 mmol) as a white solid via the procedure described for I-04. $^1$H NMR (400 MHz, CDCl₃) δ 7.71 (d, J=11.0 Hz, 1H), 7.25 (d, J=7.7 Hz, 1H), 4.86-4.75 (m, 1H), 4.61-4.49 (m, 1H), 2.66 (d, J=8.6 Hz, 1H), 2.40-2.27 (m, 2H), 2.25-2.10 (m, 2H); $^{19}$F NMR (376 MHz, CDCl₃) δ −132.86 (s, 1F); LC-MS: method H, RT=0.90 min, MS (ESI) m/z: 318.0 and 320.0 (M+H)⁺.

Intermediate I-08 cis-2-((2-bromo-5-fluorobenzo[d]thiazol-6-yl)oxy)cyclobutanol enantiomer 1

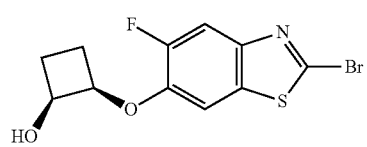
(I-08)

Intermediate I-09 cis-2-((2-bromo-5-fluorobenzo[d]thiazol-6-yl)oxy)cyclobutanol enantiomer 2

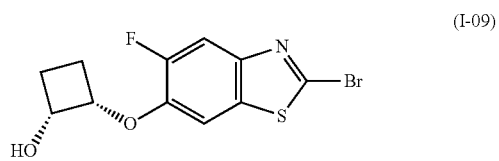 [SMILES: O[C@@H]1CC[C@@H]1Oc1cc2sc(Br)nc2cc1F]
(I-09)

I-07 (740 mg, 1.8 mmol) was separated by chiral SFC to afford I-08 (peak 1, 243 mg, 33%, retention time: 8.38 min, >99% ee) and I-09 (peak 2, 261 mg, 35%, retention time: 13.14 min, >99% ee): Column: Chiralcel AD-H, 30×250 mm, 5 micron; Mobile Phase: 20% MeOH/80% CO2; Flow Conditions: 85 mL/min, 150 Bar, 40° C.; Detector Wavelength: 220 nm; Injection Details: 1 mL of 35 mg/mL in MeOH/ACN 4:1.

Intermediate I-10 rac-cis-2-((2-bromo-5-fluorobenzo[d]thiazol-6-yl)oxy)-4,4-difluorocyclopentanol

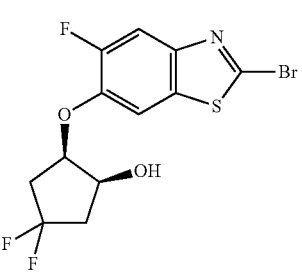
(I-10)

Intermediate I-10A: (cyclopent-3-en-1-yloxy)triisopropylsilane

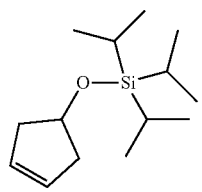
(I-10A)

Cyclopent-3-enol (2.1 g, 24.97 mmol) was dissolved in CH₂Cl₂ (30 mL). TIPS-Cl (10.58 mL, 49.9 mmol) was added, followed by imidazole (3.40 g, 49.9 mmol). The mixture was stirred at room temperature for 2 days. White solid was filtered out and washed with small amount of DCM, The organic solution was evaporated and the residue was purified by silica gel chromatography (80 g silica gel column, 0-50% EtOAc/hexane gradient). Removing solvent gave (cyclopent-3-en-1-yloxy)triisopropylsilane (4.92 g, 20.46 mmol, 82% yield) as a colorless oil. $^1$H NMR (400

MHz, CDCl₃): δ ppm 5.67 (2H, s), 4.63 (1H, t, J=3.63 Hz), 2.62 (2H, dd, J=14.97, 6.82 Hz), 2.20-2.45 (2H, m), 1.00-1.13 (21-1, m).

Intermediate I-10B: cis-4-((triisopropylsilyl)oxy)cyclopentane-1,2-diol

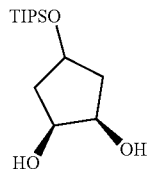

(I-10B)

(Cyclopent-3-en-1-yloxy)triisopropylsilane (4.9 g, 20.46 mmol) was dissolved in THF (50 ml) water (6 ml). NMO (2.88 g, 24.55 mmol) was added, followed by osmium tetroxide (1.605 ml, 0.205 mmol). The mixture was stirred at room temperature overnight (TLC was used to follow the reaction). On the next day, the reaction was diluted by adding 50 mL of EtOAc and 40 mL of sat. Na₂S₂O₃ (aq.) solution. After stirring for 5 minutes, the layers were separated, and the organic phase was washed with brine, dried on anhydrous Na₂SO₄, filtered and concentrated in vacuo (attention: product sublimes). The crude product was purified by silica gel chromatography (80 g, 0-100% EtOAc/hexane gradient). Removing solvent gave cis-4-((triisopropylsilyl)oxy)cyclopentane-1,2-diol (4.86 g, 17.71 mmol, 87% yield) as a white solid. ¹H NMR (400 MHz, CDCl₃): δ ppm 4.53 (1H, dt, J=6.77, 3.33 Hz), 4.30 (2H, br s), 2.20 (2H, s), 1.98-2.10 (2H, m), 1.85-1.98 (2H, m), 0.96-1.14 (21H, m)

Intermediate I-10C triisopropyl((cis-(3a,6a)-2-phenyltetrahydro-3aH-cyclopenta[d][1,3]dioxol-5-yl)oxy)silane

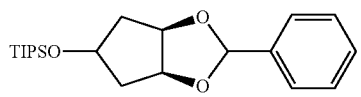

(I-10C)

To a stirred solution of I-10B (2.18 g, 7.94 mmol) in DCM (35 mL) at room temperature was added (dimethoxymethyl)benzene (1.788 mL, 11.91 mmol) and pyridine 4-methylbenzenesulfonate (PPTS) (0.794 mmol). The solution was stirred at room temperature for 4 hours. Then reaction mixture was washed with brine, dried over anhydrous Na₂SO₄, filtered and concentrated. The crude product was purified by silica gel chromatography (120 g silica gel column, 0-50% EtOAc/hexane gradient). Removing solvent gave triisopropyl((cis-(3a,6a)-2-phenyltetrahydro-3aH-cyclopenta[d][1,3]dioxol-5-yl)oxy)silane (3.03 g, 8.36 mmol, 105% yield) as an oil. ¹H NMR (400 MHz, CDCl₃): δ 7.50-7.42 (m, 2H), 7.42-7.37 (m, 3H), 5.61 (s, 1H), 4.76-4.65 (m, 3H), 2.32 (dd, J=14.2, 6.1 Hz, 2H), 1.73-1.62 (m, 2H), 1.12-1.01 (m, 21H)

Intermediate I-10D cis-(3a,6a)-2-phenyltetrahydro-3aH-cyclopenta[d][1,3]dioxol-5-ol

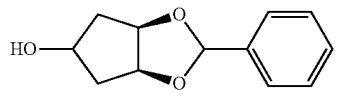

(I-10D)

I-10C (3.0 g, 8.27 mmol) was dissolved in THF (30 mL). TBAF (12.41 mL, 12.41 mmol) solution was added. The mixture was heated at reflux for 1 hour. After cooling to room temperature, the solvent was removed and the crude product was added to a silica gel (80 g) column and was eluted with 0-100% EtOAc/hexane. The desired fractions were collected and evaporated to give cis-(3a,6a)-2-phenyltetrahydro-3aH-cyclopenta[d][1,3]dioxol-5-ol (1.46 g, 7.08 mmol, 86% yield) as the product. ¹H NMR (400 MHz, CDCl₃) δ ppm 7.45-7.51 (2H, min), 7.35-7.44 (3H, m), 562 (1H, s), 4.71-474 (2H, m), 4.68 (1H s) 238 (2H, dd, J=14.31, 5.94 Hz), 1.60-1.75 (3H, m).

Intermediate I-10E cis-(3a,6a)-2-phenyldihydro-3 aH-cyclopenta[d][1,3]dioxol-5(4H)-one

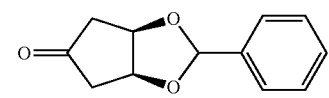

(I-10E)

I-10D (1.46 g, 7.08 mmol) was dissolved in DCM (30 mL) cooled to 0° C., and sodium hydrogen carbonate (1.784 g, 21.24 mmol) was added, followed by Dess-Martin periodinane (3.60 g, 8.50 mmol). The mixture was stirred at room temperature for 2 hours, then the reaction was diluted by adding 30 mL of DCM and 30 mL of sat. NaS₂O₃ (aq.) solution. After stirring for 10 minutes, the layers were separated, and aq. layer was extracted with DCM (30 mL×2). The combined organic phases were washed with brine, dried over anhydrous Na₂SO₄, filtered and concentrated. The crude product was added to a silica gel (80 g) column and was eluted with 0-50% EtOAc/hexane. The desired fractions were collected and solvent was removed to give cis-(3a,6a)-2-phenyldihydro-3aH-cyclopenta[d][1,3]dioxol-5(4H)-one (1.10 g, 5.39 mmol, 76% yield) as oil. ¹H NMR (400 MHz, CDCl₃) δ ppm 7.46 (2H, d, J=3.74 Hz), 7.38-7.42 (3H, m), 5.88 (1H, s), 4.97 (2H, d, J=0.88 Hz), 2.63-2.68 (4H, m).

Intermediate I-10F cis-(3a,6a)-5,5-difluoro-2-phenyltetrahydro-3aH-cyclopenta[d][1,3]dioxole

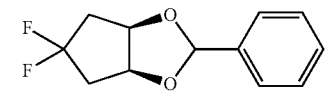

(I-10F)

To a solution of I-10E (1.29 g, 6.32 mmol) in DCM (20 mL) was added deoxofluor (3.49 mL, 18.95 mmol), and the reaction mixture was stirred at room temperature for 42 h. Then 5 mL of water was added slowly and the mixture was stirred for 5 minutes. The reaction was diluted by adding 30 mL of DCM and 30 mL of water. After separation, the aqueous layer was extracted by DCM (30 mL×2). The combined organic phases were washed with sat. NaHCO$_3$, brine, dried over anhydrous Na$_2$SO$_4$, filtered and concentrated. The crude product was purified by silica gel chromatography (40 g, 0-50% EtOAc/hexane gradient). Removing the solvent gave cis-(3a,6a)-5,5-difluoro-2-phenyltetrahydro-3aH-cyclopenta[d][1,3]dioxole (1.04 g, 4.60 mmol, 72.8% yield) as a white solid. $^1$H NMR (400 MHz, CDCl$_3$): δ ppm 7.50-7.58 (2H, m), 7.37-7.45 (3H, m), 5.70 (1H, d, J=0.66 Hz), 4.73-4.85 (2H, m), 2.49-2.66 (2H, m), 2.23-2.44 (2H, m): $^{19}$F NMR (376 MHz, CDCl$_3$): −86.87 to −90.15 (m, 1F), −92.38 to −97.06 (m, 1F).

Intermediate I-10G:
cis-4,4-difluorocyclopentane-1,2-diol

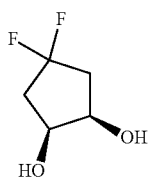

(I-10G)

To a solution of I-10F (1.04 g, 4.60 mmol) in MeOH (30 mL) was added Pd—C(0.489 g, 0.460 mmol). After degassing, the reaction mixture was treated with H$_2$ (1 atm.) at room temperature for 18 hours. On the next day, the catalyst was filtered with a celite pad. The filter cake was washed with MeOH. The filtrate was evaporated to give cis-4,4-difluorocyclopentane-1,2-diol (628 mg, 4.55 mmol, 99% yield) as a white solid. $^1$H NMR (400 MHz, CDCl$_3$): δ ppm 4.12-4.36 (2H, m), 224-2.53 (4H, m), 1.39-2.07 (2H, br); $^{19}$F NMR (376 MHz, CDCl$_3$): −81.58 to −87.32 (dd, 2F).

Intermediate I-10H: cis-4,4-difluoro-2-(2-fluoro-4-nitrophenoxy)cyclopentanol

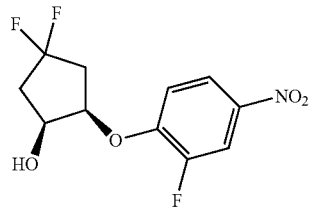

(I-10H)

I-10G (242 mg, 1.752 mmol) was dissolved in anhydrous THF (10 mL) and cooled to 0° C. Potassium tert-butoxide (177 mg, 1.577 mmol) was added in several parts. After stirring for 30 minutes, 1,2-difluoro-4-nitrobenzene (251 mg, 1.577 mmol) in 3 mL of THF (3 ml) was added dropwise. The mixture was stirred at room temperature for 24 hours. On the next day, the solvent was removed on the rotary evaporator. The residue was dissolved in EtOAc and washed with water, brine, dried over anhydrous Na$_2$SO$_4$, filtered and concentrated. The crude product was added to a silica gel column (24 g) and was eluted with 0-100% EtOAc/hexane gradient. The desired fractions were evaporated to give cis-4,4-difluoro-2-(2-fluoro-4-nitrophenoxy)cyclopentanol (291 mg, 1.050 mmol, 59.9% yield) as the product. $^1$H NMR (400 MHz, CDCl$_3$) δ ppm 7.89-8.17 (2H, m), 7.02-7.16 (1H, m), 5.14 (1H, t, J=4.84 Hz), 4.86 (1H, d. J=5.06 Hz), 4.42-4.62 (1H, m), 2.49-2.92 (4H, m); $^{19}$F NMR (376 MHz, CDCl$_3$) δ ppm −89.30 to −81.35 (2F, m), −127.76 (1F, s).

Intermediate I-101: cis-2-(4-amino-2-fluorophenoxy)-4,4-difluorocyclopentanol

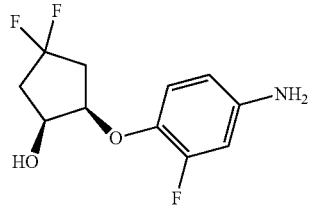

(I-10I)

I-10H (290 rig, 1.046 mmol) was dissolved in MeOH (20 mL). After degassing, the mixture was treated with 1H$_2$ (1 atm) for 3 hours, which was catalyzed by Pd—C(55.7 mg, 0.052 mmol). Then the catalyst was filtered on celite. The filter cake was washed with a small amount of MeOH—, and the solution was evaporated to give cis-2-(4-amino-2-fluorophenoxy)-4,4-difluorocyclopentanol (259 mg, 1.046 mmol, 100% yield) as a crude product, used in next step without purification. LC-MS: method H, RT=0.55 min, MS (ESI) m/z: 248.1 (M+H)$^+$.

Intermediate I-10J cis-2-((2-amino-5-fluorobenzo[d]thiazol-6-yl)oxy)-4,4-difluorocyclopentanol

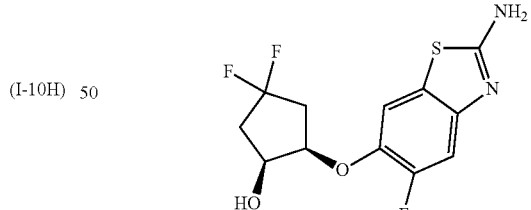

(I-10J)

To a solution of I-101 (53 mg, 0.214 mmol) in acetonitrile (5 mL) was added ammonium thiocyanate (19.58 mg, 0.257 mmol). The mixture was stirred at room temperature for 10 min until all of the NH$_4$SCN dissolved, followed by the addition of benzyltrimethylammonium tribromide (100 mg, 0.257 mmol) in 1 ml of ACN. The solution turned yellow and deposited lots of solids, then gradually turned white over time. The mixture was stirred at room temperature overnight. On the next day, the mixture was diluted with sat. NaHCO$_3$ (aq., 10 mL) and EtOAc (20 mL), and the aq. layer was extracted with EtOAc (10 mL). The combined organic layers were washed with brine and dried with anhydrous Na₂SO₄, filtered and concentrated. The crude product was added to a silica gel (12 g) column and was eluted with 0-100% EtOAc/hexane. Solvent was removed from the desired fractions to give cis-2-((2-amino-5-fluorobenzo[d]thiazol-6-yl)oxy)-4,4-difluorocyclopentanol (23 mg, 0.076 mmol, 35% yield). LC-MS: method H, RT=0.62 min, MS (ESI) m/z: 305.1 (M+H)⁺.

Intermediate I-10

Tert-butyl nitrite (11.69 mg, 0.113 mmol) was added to copper(II) bromide (25.3 mg, 0.113 mmol) in dry acetonitrile (2 mL) under N₂. The mixture was stirred at room temperature for 10 min. A suspension of cis-2-((2-amino-5-fluorobenzo[d]thiazol-6-yl)oxy)-4,4-difluorocyclopentanol (23 mg, 0.076 mmol) in acetonitrile (2 mL) was added to the reaction slowly by a pipette. The reaction mixture was stirred at room temperature for 1 h. The reaction mixture was diluted with EtOAc (20 mL) and 10 mL of 0.5M HCl (aq.). After separation, the organic layer was washed with 0.5 N HCl (10 mL), sat. brine (10 mL) and dried over sodium sulfate, filtered and concentrated on rotary evaporator to give the crude product. The crude product was added to a silica gel (12 g) column and was eluted with 0-100% EtOAc/hexane. Solvent was removed from the desired fractions to give cis-2-((2-bromo-5-fluorobenzo[d]thiazol-6-yl)oxy)-4,4-difluorocyclopentanol (12 mg, 0.033 mmol, 43.1% yield) as the product. ¹H NMR (400 MHz, CDCl₃): δ ppm 7.75 (1H, d, J=10.78 Hz), 7.41 (1H, d, 1=7.70 Hz), 4.74 (1H, d, J=4.84 Hz), 4.45-4.55 (1H, m), 2.40-2.71 (5H, m); F NMR (376 MHz, CDCl₃): δ ppm −88.86 to −80.22 (255° F., m), −131.58 (165° F., s); LC-MS: method H, RT=0.93 min, MS (ESI) m/z: 367.9 and 369.9 (M+H)⁺.

Intermediate I-11

(cis)-2-((2-bromo-5-fluorobenzo[d]thiazol-6-yl)oxy)-4,4-difluorocyclopentanol enantiomer 1

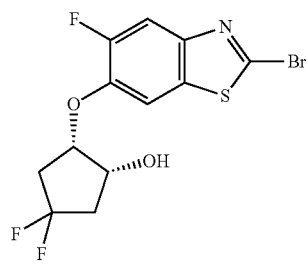

(I-11)

Intermediate I-12

(cis)-2-((2-bromo-5-fluorobenzo[d]thiazol-6-yl)oxy)-4,4-difluorocyclopentanol enantiomer 2

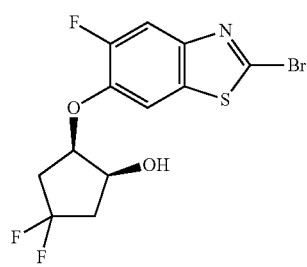

(I-12)

I-10 (82 mg, 0.22 mmol) was separated by chiral SFC to afford I-11 (peak 1, retention time 8.00 min, 16 mg, 20%, >99% ee) and I-12 (peak 2, retention time 9.46 min, 18 mg, 24%, >99% ee): Column: Chiralpak ID, 20×250 mm, 5 micron; Mobile Phase: 15% MeOH/85% CO2; Flow Conditions: 45 mL/min, 150 Bar, 40° C.; Detector Wavelength: 220 nm; Injection Details: 0.5 mL of 11 mg/mL in MeOH.

Intermediate I-13 rac-cis-2-((2-bromo-5-fluorobenzo[d]thiazol-6-yl)oxy)-4,4-dimethylcyclopentanol

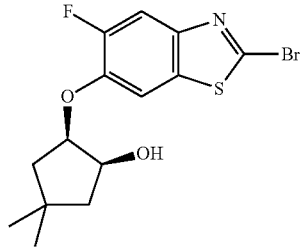

(I-13)

Intermediate I-13A: dimethyl 3,3-dimethylpentanedioate

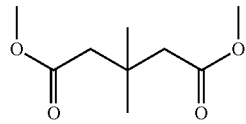

(I-13A)

3,3-dimethylpentanedioic acid (4 g, 24.97 mmol) was dissolved in MeOH (40 mL) cooled at −5° C. Thionyl chloride (4 nm, 54.8 mmol) was added dropwise. After addition, the reaction mixture was stirred at room temperature for 4 hours. Then methanol was removed in vacuo at room temperature and the residue was dissolved in 50 mL of EtOAc. 50 mL of NaHCO₃ (aq.) solution was added with stirring. After stirring for 5 minutes, the layers were separated. The organic phase was washed with brine, dried over anhydrous Na₂SO₄, filtered and concentrated to give dimethyl 3,3-dimethylpentanedioate (4.5 g, 23.91 mmol, 96% yield) as a colorless oil. ¹H NMR (400 MHz, CDCl₃): δ ppm 3.66 (6H, s), 2.43 (4H, s), 1.12 (6H, s)

Intermediate I-13B ((4,4-dimethylcyclopent-1-ene-1,2-diyl)bis(oxy))bis(trimethylsilane)

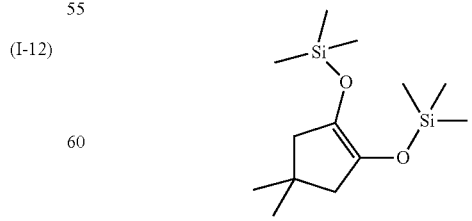

(I-13B)

Sodium (0.660 g, 28.7 mmol, precut as small pieces) was dispersed in anhydrous toluene (50 mL) in a pre-dried 500 mL, 3 neck round bottom flask. At reflux, TMS-Cl (4.07 mL, 31.9 mmol) was added by syringe rapidly. Then I-13A (1 g, 5.31 mmol) in 10 mL of anhydrous toluene was added to the reaction over a period of 15 minutes. The mixture was refluxed overnight. On the next day, after cooling to RT, the reaction mixture was passed through a celite pad. The filter cake was washed with EtOAc several times. Then the combined organic solution was evaporated on the rotary evaporator, and the residue was loaded on an 80 gram silica gel column. The product was eluted with 0-100% EtOAc/hexane. The desired fractions were collected and evaporated to give ((4,4-dimethylcyclopent-1-ene-1,2-diyl)bis(oxy))bis(trimethylsilane) (1.04 g, 3.82 mmol, 71.8% yield) as a colorless oil. $^1$H NMR (400 MHz, CDCl$_3$) δ ppm 2.07 (5H, s), 1.09 (7H, s), 0.19 (18H, s).

Intermediate I-13C: 2-hydroxy-4,4-dimethylcyclopentanone

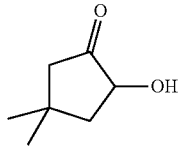

(I-13C)

I-13B (1.04 g, 3.82 mmol) was dissolved in THF (10 mL) and 1HCl (0.382 mL, 1M) aqueous solution was added. The mixture was refluxed for 3 hours. 1 eq. of Na$_2$CO$_3$ solid was added and the mixture was stirred at room temperature for 5 minutes. Then the reaction was diluted by adding 30 mL of DCM and 20 mL of water. After separation, the organic phase was washed with brine, dried over anhydrous Na$_2$SO$_4$, filtered and concentrated to give 2-hydroxy-4,4-dimethylcyclopentanone (199 mg, 1.553 mmol, 40.7% yield) as a colorless oil. $^1$H NMR (400 MHz, CDCl$_3$) δ ppm 4.22-4.34 (1H, m), 2.27 (2H, dt, J=3.36, 1.51 Hz), 2.10 (1H, s), 2.05 (1H, s), 1.20 (3H, s), 1.17 (3H, s).

Intermediate I-13D: 4,4-dimethyl-2-oxocyclopentyl methanesulfonate

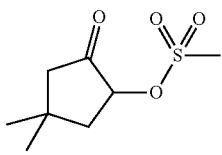

(I-13D)

Mesyl-Cl (0.288 mL, 3.70 mmol) was added dropwise into the solution of 2-hydroxy-4,4-dimethylcyclopentanone (237 mg, 1.849 mmol) in anhydrous pyridine (4 mL) cooled to 0° C. under N$_2$. The mixture was stirred at 0° C. for 3 hours. Then the reaction was diluted by adding 30 mL of DCM and was washed with water, 1N HCl (15 mL×2), brine, dried over anhydrous Na$_2$SO$_4$, filtered and concentrated to give 4,4-dimethyl-2-oxocyclopentyl methanesulfonate (322 mg, 1.561 mmol, 84% yield) as a colorless oil. $^1$H NMR (400 MHz, CDCl$_3$) δ ppm 5.09 (1H, dd, J=9.68, 9.02 Hz), 3.21 (3H, s), 2.39 (1H, ddd, J=13.15, 8.75, 1.87 Hz), 2.16-2.33 (2H, m), 1.95 (1H, dd, J=12.98, 10.12 Hz), 1.24 (3H, s), 1.16 (3H, s)

Intermediate I-13E: 2-chloro-4,4-dimethylcyclopentanone

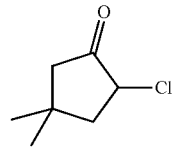

(I-13E)

4,4-dimethyl-2-oxocyclopentyl methanesulfonate (241 mg, 1.168 mmol) was dissolved in ether (4 mL). Tetrabutylammonium chloride hydrate (1383 mg, 4.67 mmol) was added. The mixture was stirred at 25° C. overnight. On the next day, the reaction was diluted by adding 20 mL of Et$_2$O and 15 mL of water. After separation, organic phase was washed with brine, dried over anhydrous Na$_2$SO$_4$, filtered and concentrated to give 2-chloro-4,4-dimethylcyclopentanone (101 mg, 0.689 mmol, 59.0% yield). $^1$H NMR (400 MHz, CDCl$_3$): δ ppm 4.10-4.20 (1H, m), 2.23-2.32 (1H, m), 2.10 (2H, d, J=3.30 Hz), 1.80 (1H, dd, J=13.42, 10.12 Hz), 1.09 (3H, s), 0.96 (3H, s)

Intermediate I-13F 2-((2-bromo-5-fluorobenzo[d]thiazol-6-yl)oxy)-4,4-dimethylcyclopentanone

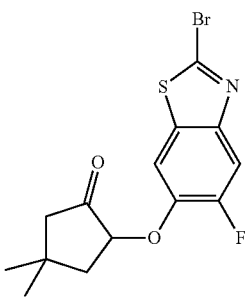

(I-13F)

2-Bromo-5-fluorobenzo[d]thiazol-6-ol (50 mg, 0.202 mmol) was mixed with 2-chloro-4,4-dimethylcyclopentanone (100 mg, 0.682 mmol) in anhydrous DMF (2 mL). K$_2$CO$_3$ (111 mg, 0.806 mmol) was added. The mixture was stirred at 60° C. for 5 hours. After cooling to RT, the reaction mixture was diluted by adding 20 mL of EtOAc and washed by 15 mL of water, brine, dried over anhydrous Na$_2$SO$_4$, filtered and concentrated. The crude product was purified by silica gel chromatography (24 g column, 0-100% EtOAc/hexane). Desired fractions were collected and evaporated to give 2-((2-bromo-5-fluorobenzo[d]thiazol-6-yl)oxy)-4,4-dimethylcyclopentanone (20 mg, 0.056 mmol, 27.7% yield) as a white solid. $^1$H NMR (400 MHz, CDCl$_3$) δ ppm 7.69 (1H, d, J=10.78 Hz), 7.56 (1H, d, J=7.70 Hz), 4.78 (1H, t, J=8.69 Hz), 2.38 (1H, dd, J=13.31, 8.47 Hz), 2.32 (2H, s), 2.04 (1H, dd, J=13.20, 9.02 Hz), 1.28 (3H, s), 1.19 (3H, s), $^{19}$F NMR (376 MHz, CDCl$_3$) δ ppm−131.80 (1F, s); LC-MS method H, RT=1.13 min, MS (ESI) m/z: 358.0 and 360.0 (M+H)$^+$.

Intermediate I-13

Intermediate I-13 (20 mg, 0.056 mmol, 100% yield) was obtained from Intermediate I-13F (20 mg, 0.056 mmol) via same procedure described for I-04. LC-MS: method H, RT=1.13 min, MS (ESI) m/z: 360.0 and 362.0 (M+H)+.

Intermediate I-14 rac-cis-5-((2-bromo-5-fluorobenzo[d]thiazol-6-yl)oxy)-2,2-dimethylcyclopentanol

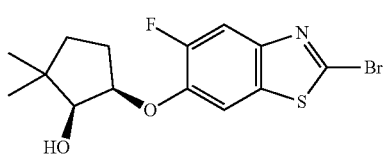 [SMILES: CC1(C)CC[C@@H](Oc2cc3sc(Br)nc3cc2F)[C@H]1O]

Intermediate I-14A:
5-chloro-2,2-dimethylcyclopentanone

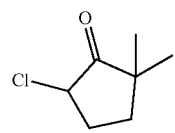
(I-14A)

To a solution of 2,2-dimethylcyclopentanone (1.0 g, 8.92 mmol) in DCM (20 mL) at 0° C., sulfuryl chloride (0.797 mL, 9.81 mmol) was added slowly. After addition, the reaction mixture was stirred at room temperature overnight. On the next day, the reaction mixture was diluted by adding 20 mL of DCM and poured into 30 mL of sat. NaHCO$_3$ (aq.) solution/ice. After stirring for 10 minutes, the mixture was transferred into a separation funnel. Layers were separated, and organic phase was washed with 20 mL of sat. NaHCO$_3$ (aq.) solution, brine, dried over anhydrous Na$_2$SO$_4$, filtered and concentrated to give 5-chloro-2,2-dimethylcyclopentanone (1.46 g, 9.96 mmol, 112% yield) used in the next step without purification.

Intermediate I-14B 5-((2-bromo-5-fluorobenzo[d]thiazol-6-yl)oxy)-2,2-dimethylcyclopentanone

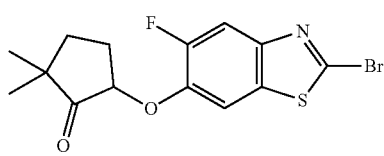
(I-14B)

I-14B (78 mg, 0.218 mmol, 40.6% yield) was made from I-19 (133 mg, 0.536 mmol) and I-14A (1.4 g, 9.55 mmol) via the procedure described for I-01A. $^1$H NMR (400 MHz, CDCl$_3$) δ 7.69 (d, =11.0 Hz, 1H), 7.57 (d, J=7.5 Hz, 1H), 4.72 (dd, =9.2, 8.1 Hz, 1H), 2.46 (m, 1H), 2.21-2.08 (m, 1H), 208-1.98 (m, 1H), 1.79 (ddd, J=13.1, 10.7, 6.7 Hz, 1H), 1.18 (d, J=4.4 Hz, 6H); $^{19}$F NMR (376 MHz, CDCl$_3$) δ −131.71 (s, 1F); LC-MS: method H, RT=1.12 min, MS (ESI) m/z: 358.0 and 360.0 (M+H)+.

Intermediate I-14

I-14 (36 mg, 0.100 mmol, 49.7% yield) was made from I-14B (0.072 g, 0.201 mmol) by following the same procedure in I-01. $^1$H NMR (400 MHz, DMSO-d$_6$) δ ppm 7.95 (1H, d, J=8.36 Hz), 7.86 (1H, d, J=11.66 Hz), 4.77-4.84 (1H, m), 4.64 (1H, d, J=5.94 Hz), 3.70 (1H, t, J=5.28 Hz), 2.09-223 (1H, m), 1.72-1.85 (1H, m), 1.58-1.71 (1H, m), 1.34 (1H, ddd, J=12.54, 9.24, 6.38 Hz), 1.01 (6H, d, 1=2.42 Hz); $^{19}$F NMR (376 MHz, DMSO-d$_6$) δ ppm −132.99 (1F, s); LC-MS: method H, RT=1.12 min, MS (ESI) m/z: 360.0 and 362.0 (M+H)+.

Intermediate I-15 rac-cis-4-((2-bromo-5-fluorobenzo[d]thiazol-6-yl)oxy)tetrahydrofuran-3-ol

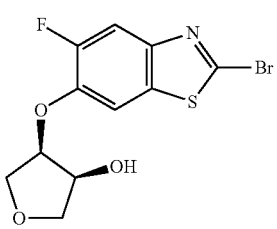
(I-15)

Intermediate I-15A trans-4-((2-bromo-5-fluorobenzo[d]thiazol-6-yl)oxy)tetrahydrofuran-3-ol

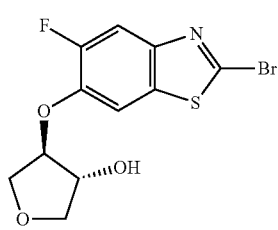
(I-15A)

In a vial charged with a stirring bar, I-19 (300 mg, 1.209 mmol) was mixed with potassium carbonate (251 mg, 1.814 mmol) in 3,6-dioxabicyclo[3.1.0]hexane (2 mL, 1.209 mmol)/DMF (1 mL). The mixture was stirred at 100° C. for 1 hours. The reaction was diluted by adding 30 mL of EtOAc and 20 mL of water. After separation, aqueous layer was extracted with EtOAc (20 mL×3). Organic phases were combined and washed with brine, and concentrated. The crude product was purified by silica gel chromatography (24 g column, 0-100% EtOAc/hexane gradient). Collecting the desired fractions and removing solvent gave trans-4-((2-bromo-5-fluorobenzo[d]thiazol-6-yl)oxy)tetrahydrofuran-3-ol (207 mg, 0.619 mmol, 51.2% yield) as a white solid. $^{19}$F NMR (376 MHz, DMSO-d$_6$) δ −133.27 (s, 1F);

$^1$H NMR (400 MHz, DMSO-d$_6$) δ 7.97 (d, J=1.5 Hz, 1H), 7.97 (d, J=18.0 Hz, 1H), 5.53 (d, J=4.0 Hz, 1H), 4.77 (d, J=4.0 Hz, 1H), 4.30 (br s, 1H), 4.07 (d, J=4.2 Hz, 1H), 3.95

(d, J=4.6 Hz, 1H), 3.62 (dd, J=9.5, 2.0 Hz, 1H); LC-MS: method H, RT=0.80 min, MS (ESI) m/z: 334.0 and 335.9 (M+H)$^+$.

Intermediate I-15B 4-((2-bromo-5-fluorobenzo[d]thiazol-6-yl)oxy)dihydrofuran-3(2H)-one

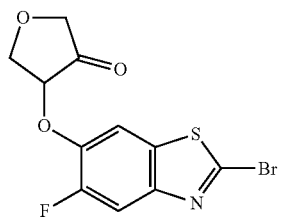

(I-15B)

I-15A (202 mg, 0.604 mmol) was suspended in CH$_2$Cl$_2$ (5 mL) and was treated with Dess-Martin periodinane (385 mg, 0.907 mmol) at room temperature for 18 hours. Then the reaction was diluted by adding 15 mL of DCM and was washed with sat. Na$_2$SO$_3$ (aq., 10 mL×2) solution, brine, dried over anhydrous Na$_2$SO$_4$, filtered and concentrated. The crude product was purified by silica gel chromatography (40 g column, 0-100% EtOAc/hexane). The desired fractions were collected and the solvent was removed to give 4-((2-bromo-5-fluorobenzo[d]thiazol-6-yl)oxy)dihydrofuran-3(2H)-one (183 mg, 0.551 mmol, 91% yield) as the product. $^1$H NMR (400 MHz, DMSO-d$_6$) δ 8.09 (d, J=8.1 Hz, 1H), 7.98 (d, J=11.4 Hz, 1H), 5.25 (t, J=7.4 Hz, 1H), 4.66 (dd, J=9.9, 7.3 Hz, 1H), 4.24-4.08 (m, 2H), 4.03 (dd, J=9.8, 7.4 Hz, 1H); $^{19}$F NMR (376 MHz, DMSO-d$_6$) δ −133.15 (s, 1F); LC-MS: method H, RT=0.89 min, MS (EST) m/z: 331.9 and 3340 (M+H)$^+$.

Intermediate I-15

I-15 (178 mg, 0.533 mmol, 97% yield) was made from I-15B (182 mg, 0.55 mmol) as a white solid, by following the same procedure described for I-01. $^1$H NMR (400 MHz, DMSO-d$_6$) δ 8.01 (d, J=8.4 Hz, 1H), 7.92 (d, J=11.4 Hz, 1H), 5.18 (d, J=5.9 Hz, 1H), 4.86 (d, J=5.3 Hz, 1H), 4.54-4.44 (m, 1H), 4.09 (dd, J=9.6, 5.6 Hz, 1H), 3.93 (dd, J=8.7, 5.8 Hz, 1H), 3.82 (dd, J=9.6, 4.5 Hz, 1H), 3.62 (dd, J=8.8, 5.5 Hz, 1H); $^{19}$F NMR (376 MHz, DMSO-d$_6$) δ −132.88 (s, 1F); LC-MS: method H, RT=0.76 min, MS (ESI) m/z: 334.0 and 335.9 (M+H)$^+$.

Intermediate I-16 rac-cis-3-((2-bromo-5-fluorobenzo[d]thiazol-6-yl)oxy)tetrahydro-2H-pyran-4-ol

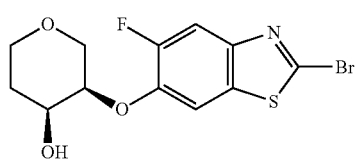

(I-16)

Intermediate I-16

I-16 was made from commercial available dihydro-2H-pyran-4(3H)-one by following the same procedure described for I-14 to give a white solid. $^1$H NMR (400 MHz, CDCl$_3$) δ 7.73 (d, J=10.8 Hz, 1H), 7.49 (d, J=7.5 Hz, 1H), 4.37 (dt, J=6.6, 3.3 Hz, 1H), 4.18 (br s, 1H), 4.03-3.88 (m, 2H), 3.71 (dd, J=1=11.9, 3.3 Hz, 1H), 3.65-3.55 (m, 1H), 2.37 (d, J=5.5 Hz, 1H), 2.13-2.02 (m, 1H), 1.97-1.85 (m, 1H); $^{19}$F NMR (376 MHz, CDCl$_3$) δ −131.18 (s, 1F); LC-MS: method H, RT=0.78 min, MS (ESI) m/z: 348.0 and 349.8 (M+H)$^+$.

Intermediate I-17 rac-cis-tert-butyl 3-((2-bromo-5-fluorobenzo[d]thiazol-6-yl)oxy)-4-hydroxypiperidine-1-carboxylate

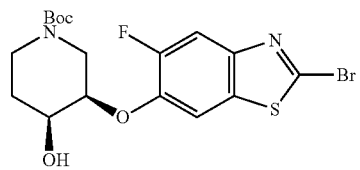

(I-17)

Intermediate I-17A: tert-butyl 3-((2-bromo-5-fluorobenzo[d]thiazol-6-yl)oxy)-4-oxopiperidine-1-carboxylate

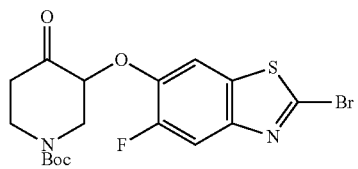

(I-17A)

The commercial available tert-butyl 3-chloro-4-oxopiperidine-1-carboxylate (565 mg, 2.419 mmol) was mixed with I-19 (500 mg, 2.016 mmol) in DMF (10 mL). K$_2$CO$_3$ (836 mg, 6.05 mmol) was added to the reaction. The mixture was stirred at 60° C. for 4 hours. After cooling to RT, the reaction was diluted by adding 50 mL of EtOAc and 30 mL of water. After separation, the aqueous layer was extracted with 20 mL of EtOAc twice. The combined organic phases were washed with brine, dried over anhydrous Na$_2$SO$_4$, filtered and concentrated. The crude product was purified by silica gel chromatography (40 g column, 0-100% EtOAc/hexane gradient). The desired fractions were collected and the solvent was removed to give tert-butyl 3-((2-bromo-5-fluorobenzo[d]thiazol-6-yl)oxy)-4-oxopiperidine-1-carboxylate (779 mg, 1.749 mmol, 87% yield). LC-MS: method H, RT=1.1 min, MS (ESI) m/z: 445.0 and 447.0 (M+H)$^+$.

Intermediate I-17

I-17A (779 mg, 1.749 mmol) was dissolved in anhydrous THF (10 mL) and cooled to −78° C. under N$_2$. L-Selectride (1749 mL, 1.749 mmol) was added dropwise. The reaction was stirred at −78° C. for 2 hours. Then the reaction was warmed to RT. At the same time, the reaction was quenched by adding sat. NH₄Cl (aq.) solution slowly and diluted by adding 30 mL of EtOAc. After separation, the organic phase was washed with brine, dried over anhydrous Na₂SO₄, filtered and concentrated. Crude product (634 mg, 1.4 mmol, 81% yield) was used without purification. LC-MS: method H, RT=1.1 min, MS (ESI) m/z: 447.0 and 449.1 (M+H)⁺.

Intermediate I-18 trans-2-((2-bromo-5-fluorobenzo[d]thiazol-6-yl)oxy)cyclohexanol

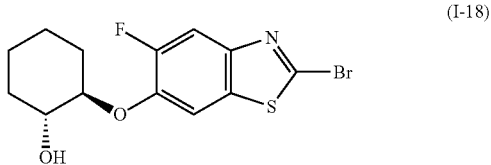 [SMILES: O[C@@H]1CCCC[C@H]1Oc1cc2sc(Br)nc2cc1F]

(I-18)

In DMF (1 mL), I-19 (200 mg, 0.806 mmol) was mixed with 7-oxabicyclo[4.1.0]heptane (1 mL, 0.806 mmol) and Cs₂CO₃ (315 mg, 0.967 mmol). The mixture was stirred at 100° C. for 1 hour. After cooling to RT, the reaction was diluted by adding 20 mL of EtOAc, and 20 mL of Water. After separation, the aq. layer was extracted with EtOAc (1 mL×2). The combined organic phases were washed with brine, dried over Na₂SO₄, filtered and concentrated. The crude product was purified by silica gel chromatography (24 g, 0-100% EtOAc/hexane). Removing the solvent gave I-18 (35 mg, 0.101 mmol, 12.54% yield) as a white solid. LC-MS: method H, RT=1.00 min, MS (ESI) m/z 345.9 and 348.0 (M+H)⁺.

Intermediate I-19

2-bromo-5-fluorobenzo[d]thiazol-6-ol

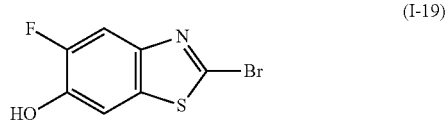 [SMILES: Oc1cc2sc(Br)nc2cc1F]

(I-19)

Intermediate I-19A: 5-fluoro-6-methoxybenzo[d]thiazol-2-amine

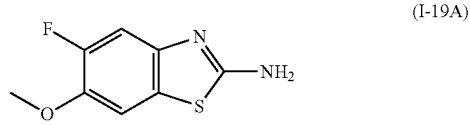

(I-19A)

To a solution of 3-fluoro-4-methoxyaniline (2.1 g, 14.88 mmol) in acetonitrile (50 mL) was added ammonium thiocyanate (1.472 g, 19.34 mmol). The mixture was stirred at room temperature for 10 minutes until all of the NH₄SCN dissolved, followed by the addition of benzyltrimethylammonium tribromide (5.80 g, 14.88 mmol). The reaction solution turned yellow immediately and deposited lots of solids, and gradually turned white over time. The reaction was stirred over two nights. Then most of the solvent was removed on rotary evaporator, 100 mL sat. NaHCO₃ was added to the mixture and stirred vigorously for 30 minutes. The solid was filtered and washed with water. The collected solid was coevaporated two times with toluene to remove residual water. Then the solid was dried on HVAC (high vacuum) to give intermediate I-19A (3.16 g, 15.94 mmol, 107% yield) as a white solid. ¹H NMR (400 MHz, DMSO-d₆) δ 7.51 (d, J=8.6 Hz, 1H), 7.35 (s, 2H), 7.17 (d, J=12.3 Hz, 1H), 3.80 (s, 3H); ¹⁹F NMR (376 MHz. DMSO-d₆) δ −137.92 (s, 1F); LC-MS: method H, RT=0.55 min, MS (ESI) m/z: 1991 (M+H)⁺.

Intermediate I-19B: 2-bromo-5-fluoro-6-methoxy-benzo[d]thiazole

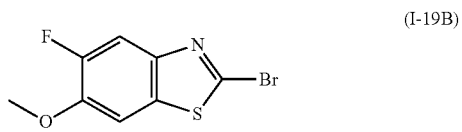

(I-19B)

tert-Butyl nitrite (1.686 g, 16.35 mmol) was added to copper(II) bromide (3.65 g, 16.35 mmol) in dry acetonitrile (50 mL) under N₂. The mixture was stirred at room temperature for 10 min A suspension of I-19A (2.16 g, 10.9 mmol) in acetonitrile (40 mL) was added dropwise. The reaction mixture was stirred at room temperature for 6 hours. LC/MS indicated a clean reaction. The reaction was concentrated to almost dryness under vacuum, and was diluted with EtOAc (100 mL) and 50 mL of 0.5M HCl (aq.). After separation, the organic layer was washed with 0.5 N HCl (40 mL×2), sat. brine (30 mL) and dried over sodium sulfate, filtered and concentrated on rotary evaporator to give crude product. This was dissolved in EtOAc (40 mL) and dry-loaded onto silica gel, and purified (80 g silica gel column, 0-100% EtOAc/hexane gradient). Removing solvent gave I-19B (1.42 g, 5.42 mmol, 49.7% yield) as a white solid. LC-MS: method H, RT=0.97 min, MS (ESI) m/z: 262.0, 264.0 (M+H)⁺.

Intermediate I-19

In a round bottom flask charged with a stirring bar, I-19B (502 mg, 1.915 mmol) was dissolved in anhydrous CH₂Cl₂ (10 mL) at 0° C. Boron tribromide (5.75 mL, 5.75 mmol) solution was added dropwise at 0° C. carefully over 5 minutes. Lots of white solid precipitated during addition. The reaction was allowed to warm to room temperature then stir overnight. On the next day, the reaction was poured into ice and 30 mL of EtOAc was used to wash the flask. The mixture was stirred for 10 minutes, then layers were separated and the aq. layer was extracted with EtOAc (30 mL×2). Organic phases were combined and washed with brine, dried over Na₂SO₄, filtered and concentrated to give I-19 (468 mg, 1.887 mmol, 98% yield) as an off-white solid. ¹H NMR (400 MHz, DMSO-d₆) δ 10.48 (s, 1H), 7.84 (d, J=11.4 Hz, 1H), 7.62 (d, J=8.4 Hz, 1H); ¹⁹F NMR (376 MHz, DMSO-d₆) δ −135.05 (s, 1F); LC-MS: method H, RT=0.85 min, MS (ESI) m/z: 248.0, 249.9 (M+H)⁺.

Intermediate I-20

(2-methoxy-7-methylquinoxalin-5-yl)boronic acid

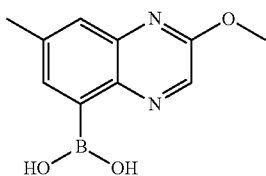
(I-20)

Intermediate I-20A: tert-butyl N-(2-bromo-4-methyl-6-nitrophenyl)-N-[(tert-butoxy) carbonyl] carbamate

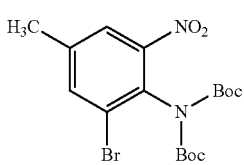
(I-20A)

To a solution of 2-bromo-4-methyl-6-nitroaniline (9.6 g, 41.6 mmol) in THF (60 mL) was added DMAP (0.508 g, 4.16 mmol), followed by Boc₂O (22.67 g, 104 mmol) as a solid. The mixture was stirred at room temperature overnight. Solvent was removed by vacuum. The crude product was dissolved in a small amount of chloroform and charged to a 120 g silica gel cartridge (2 separate columns) which was eluted with 5% EtOAc in hexanes for 4 min., then a 12 min gradient from 5% to 30% EtOAc in hexanes. The desired fractions were combined and concentrated to give Intermediate I-20A (17.12 g, 39.7 mmol, 96% yield) as a white solid. $^1$H NMR (500 MHz, CDCl$_3$) δ 7.80-7.79 (m, 1H), 7.73 (dd, J=1.9, 0.8 Hz, 1H), 2.48 (s, 3H), 1.42 (s, 18H); LC-MS: method A, RT=1.90 min, MS (ESI) m/z: 230.0 and 232.0 (M-2 Boc)⁺.

Intermediate I-20B: tert-butyl (2-bromo-4-methyl-6-nitrophenyl)carbamate

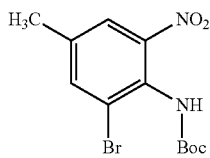
(I-20B)

To a solution of Intermediate I-20A (17.1 g, 39.6 mmol) in dichloromethane (60 mL) was added TFA (6.11 mL, 79 mmol) and the mixture was stirred at room temperature for 1.0 h. The reaction mixture was quenched by addition of saturated sodium bicarbonate, extracted with dichloromethane (3×), dried over sodium sulfate. After evaporation of solvent, Intermediate I-20B was obtained as a yellow solid (12.88 g, 88% yield): $^1$H NMR (500 MHz, CDCl$_3$) δ 7.71 (d, J=1.1 Hz, 1H), 7.68 (dd, J=1.9, 0.8 Hz, 1H), 2.42 (s, 3H), 1.51 (s, 9H); LC-MS: method A, RT=1.53 min, MS (ESI) m/z: 231.0 and 233.0 (M-Boc)⁺.

Intermediate I-20C: methyl 2-((2-bromo-4-methyl-6-nitrophenyl)(tert-butoxycarbonyl) amino)acetate

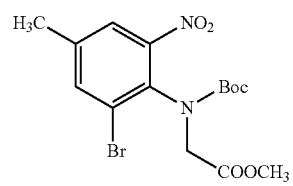
(I-20C)

Intermediate I-20B (12 g, 26.3 mmol) was dissolved in DMF (80 mL), cooled with a water bath. Cs$_2$CO$_3$ (25.8 g, 79 mmol) was added. The dark brown solution was stirred at room temperature for 10 min, then methyl 2-bromoacetate (4.37 mL, 47.6 mmol) was added dropwise. After addition of methyl bromoacetate, the brown color faded to yellow. The mixture was stirred at room temperature for 1.0 h, diluted with EtOAc, quenched with water. The organic layer was collected, washed with brine, dried over sodium sulfate. After evaporation of solvent, the crude product was dissolved in a small amount of chloroform and charged to a 330 g silica gel cartridge which was eluted with 5% EtOAc in hexanes for 5 min., then a 12 min gradient from 5% to 50% EtOAc in hexanes. The desired fractions were combined and concentrated to give Intermediate I-20C (15.2 g, 37.7 mmol, 95% yield) as a yellow oil. $^1$H NMR (500 MHz, CDCl$_3$) indicated a mixture of rotamers: δ 7.75-7.67 (m, 2H), 4.61-3.97 (m, 2H), 3.76 and 3.69 (s, 3H), 2.48 and 2.43 (s, 3H), 1.55 and 1.37 (s, 9H); LC-MS: method A, RT=1.70 min, MS (ESI) m/z: 303.0 and 305.0 (M-Boc)⁺.

Intermediate I-20D: methyl 2-((2-bromo-4-methyl-6-nitrophenyl)amino)acetate

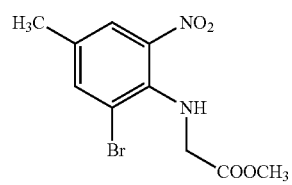
(I-20D)

To Intermediate I-20C (15.2 g, 37.7 mmol) was added 4.0 N HCl in dioxane (47.1 ml, 188 mmol) and the mixture was stirred at room temperature overnight. Solvent was removed under vacuum, chased with EtOAc (2×) to give Intermediate I-20D (13.6 g, 40.1 mmol, 106% yield) as a yellow solid. $^1$H NMR (500 MHz, CD$_3$OD) δ 7.88 (dd, J=1.9, 0.6 Hz, 1H), 7.80 (dd, =1.9, 0.6 Hz, 1H) 4.47 (d, J=17.3 Hz, 1H), 4.08 (d, J=17.1 Hz, 1H), 3.69 (s, 3H), 2.46 (s, 3H); LC-MS: Method A, RT=1.94 min, MS (ESI) m/z: 303.1 and 305.1 (M+H)⁺.

Intermediate I-20E:
5-bromo-7-methyl-3,4-dihydroquinoxalin-2(1H)-one

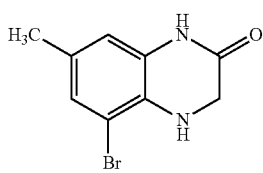

(I-20E)

To a solution of Intermediate I-20D (13.6 g, 40.1 mmol) in MeOH (100 mL) in a 1 L flask cooled with water bath was added concentrated HCl (13.35 mL, 160 mmol), followed by tin(II) chloride dihydrate (36.1 g, 160 mmol). The mixture was stirred at 68° C. for 2.5 h. MeOH was removed by vacuum. The crude was partitioned in water (100 mL)/EtOAc (200 mL), and the pH was adjusted to neutral with 4.0 N NaOH (ca 90 mL). The white precipitate formed was very fine particle that was very hard to remove by filtration. The mixture was transferred to a separatory funnel. The organic layer was collected. The aqueous was further extracted (2×200 mL) with EtOAc. The combined organic layer was washed with water (2×) and brine (2×), dried over sodium sulfate. After evaporation of solvent, Intermediate I-20E (8.36 g, 34.7 mmol, 87% yield) was obtained as a pale yellow solid. $^1$H NMR (500 MHz, DMSO-d$_6$) δ 10.37 (s, 1H), 6.87 (dd, J=1.8, 0.7 Hz, 1H), 6.56 (dd, J=1.1, 0.6 Hz, 1H), 5.46 (s, 1H), 376 (d, J=2.2 Hz, 2H), 2.14 (s, 3H); LC-MS: method A, RT=1.66 min, MS (ESI) m/n: 241.0 and 243.0 (M+H)$^+$.

Intermediate I-20F:
5-bromo-7-methylquinoxalin-2-ol

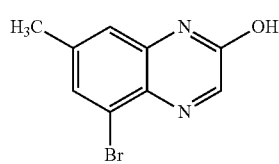

(I-20F)

To a suspension of Intermediate I-20E (6.7 g, 27.8 mmol) in MeOH (50 mL) in a 1L flask was added 30% hydrogen peroxide (28.4 mL, 278 mmol), followed by 4.0 N NaOH (20.84 mL, 83 mmol). The mixture was stirred at room temperature for 5 min, then gently heated at 60° C. After 15 min heating, the reaction mixture turned strongly exothermic, suggesting an initiation of the reaction mixture. The heating bath was removed and stirring continued for 30 min until the mixture turned completely clear. After cooling to room temperature with a water bath, MeOH was removed by vacuum. The mixture was then neutralized with 2.0 N HCl (to pH 2-3) and ice cooling. The precipitate formed was collected by filtration, washed with water, dried under vacuum in the air for 1.0 h and then at vacuum at 60° C. for 2.0 hi, and under high vacuum to give Intermediate I-20F (6.55 g, 27.4 mmol, 99% yield) as an off-white solid. $^1$H NMR (500 MHz, DMSO-d$_6$) δ 12.52 (br s, 1H), 8.17 (s, 1H), 7.49 (d, J=1.1 Hz, 1H), 7.08 (s, 1H), 2.40 (s, 3H; LC-MS: method A, RT=1.62 min, MS (ESI) m/z: 239.0 and 241.0 (M+H)$^+$.

Intermediate I-20G:
5-bromo-2-(difluoromethoxy)-7-methylquinoxaline

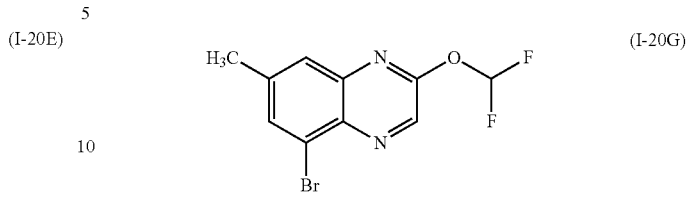

(I-20G)

A mixture of Intermediate I-20F (7.4 g, 26.9 mmol) and potassium carbonate (18.56 g, 134 mmol) in DMF (120 mL) was heated at 100° C. for 5 min. Sodium 2-chloro-2,2-difluoroacetate (16.40 g, 107.6 mmol) was added in one portion, and the mixture was stirred at 100° C. for 10 min. The mixture turned from yellow slurry to brown. The mixture was cooled to room temperature, diluted with EtOAc and water, extracted with EtOAc (3×). The combined organic layer was washed with brine, dried over sodium sulfate. After evaporation of solvent, the crude product was dissolved in a small amount of chloroform/toluene and purified with a 330 g ISCO column eluted with 5% dichloromethane in hexanes for 3 min, then 5-70% DCM/hexanes for 40 min (12 min gradient time). The desired fractions were combined, concentrated to give Intermediate I-20G (6.0 g, 20.76 mmol, 77% yield) as a slightly yellow solid. $^1$H NMR (500 MHz, CDCl$_3$) δ 8.64 (s, 1H), 7.89 (d, J=1.7 Hz, 1H), 7.68 (dd, J=1.8, 1.0 Hz, 1H), 7.63 (t, J$_{HF}$=71.80 Hz, 1H), 2.59 (s, 3H); $^{19}$F NMR (471 MHz, CDCl$_3$) δ −89.82 (s, 2F); LC-MS: method A, RT=2.09 min, MS (ESI) m/z: 289.0 and 291.0 (M+H)$^+$.

Intermediate I-20H:
5-bromo-2-methoxy-7-methylquinoxaline

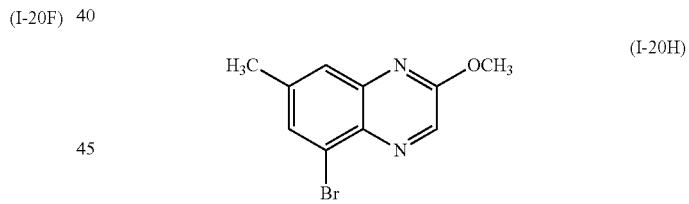

(I-20H)

To Intermediate I-20G (3.13 g, 10.83 mmol) dissolved in THF (20 mL) and MeOH (15 mL) at room temperature was added 4.3 M sodium methoxide in MeOH (7.55 mL, 32.5 mmol). The reaction mixture was stirred at room temperature overnight. Methanol was removed under vacuum. The reaction mixture was diluted with EtOAc, quenched with 0.5 N HCl (30.0 mL). The organic layer was washed with saturated sodium bicarbonate, brine, dried and concentrated to give Intermediate I-20H (2.7 g, 10.67 mmol, 99% yield) as a slightly yellow solid. $^1$H NMR (500 MHz, CDCl$_3$) δ 8.48 (s, 1H), 7.72 (d, J=1.7 Hz, 1H), 7.60 (dd, J=0.8, 1.0 Hz, 1H), 4.10 (s, 3H), 2.53 (s, 3H); LC-MS: Method A, 30 to 100% B. RT 1.71 min, MS (ESI) m/z: 253.0 and 255.0 (M+H)$^+$.

Intermediate I-20

In a sealed tube charged with a stirring bar, I-20H (2.54 g, 10.04 mmol), 4,4,4',4',5,5,5',5'-octamethyl-2,2'-bi(1,3,2- dioxaborolane) (5.10 g, 20.07 mmol), and potassium acetate (1.970 g, 20.07 mmol) were mixed in 1,4-dioxane (20 mL). After degassing with bubbling N₂ for 10 minutes, PdCl₂(dppf)-CH₂Cl₂ adduct (0.410 g, 0.502 mol) was added. The tube was sealed and was heated at 120° C. for 120 minutes. After cooling to room temperature, the reaction was diluted by adding 20 mL of EtOAc, followed by 100 mL of sat. NH₄Cl (aq.) solution. After stirring at room temperature for 15 minutes, the precipitated solid was filtered and washed with a small amount of water. Then the filter cake was collected and freeze-dried to give I-20 (1.85 g, 8.49 mmol, 85% yield) as a grey solid. ¹H NMR (500 MHz, CD₃OD) δ 8.41 (s, 1H), 7.69 (br s, 1H), 7.49 (br s, 1H), 4.10 (s, 31H), 2.56 (s, 31H). LC-MS: method H, RT=0.88 min, MS (ESI) m/z: 218.8 (M+H)⁺.

Intermediate I-21

2-bromo-6-fluoro-5-methoxythiazolo[5,4-b]pyridine

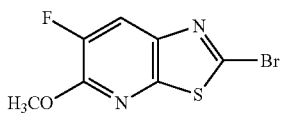

(I-21)

Intermediate I-21A: N-((5-fluoro-6-methoxypyridin-3-yl)carbamothioyl)benzamide

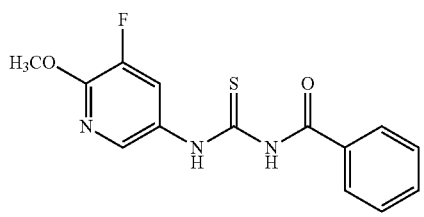

(I-21A)

To a solution of 5-fluoro-6-methoxypyridin-3-amine (0.100 g, 0.704 mmol) in acetone (1 mL) was added dropwise benzoyl isothiocyanate (0.104 mL, 0.774 mmol). The reaction mixture was allowed to stir at room temperature for 3 h. The reaction mixture was diluted with water and EtOAc. The layers were separated and the organic layer was washed with brine, dried with sodium sulfate, and concentrated under reduced pressure to yield Intermediate I-21A (0.215 g, 0.704 mmol, 100% yield): ¹H NMR (400 MHz, CDCl₃) δ 12.48 (br s, 1H), 9.12 (br s, 1H), 8.06 (d, J=2.0 Hz, 1H), 8.01 (dd, J=10.8, 2.2 Hz, 1H), 7.91 (d, J=1.1 Hz, 1H), 7.89 (d, J=1.5 Hz, 1H), 7.71-7.65 (m, 1H), 7.60-7.54 (nm, 2H), 4.06 (s, 3H). LC-MS: method H, RT=1.18 min, MS (ESI) m/z: 306.1 (M+H)⁺.

Intermediate I-21B: 1-(5-fluoro-6-methoxypyridin-3-yl)thiourea

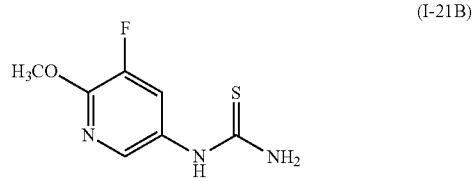 [SMILES: COc1ncc(NC(N)=S)cc1F]

(I-21B)

To a solution of Intermediate I-21A (0.215 g, 0.704 mmol) in tetrahydrofuran (1 mL) was added dropwise sodium methoxide (0.5 M in MeOH) (2.112 mL, 1.056 mmol). The reaction mixture was allowed to stir at room temperature for 18 h. The reaction mixture was diluted with water and EtOAc. The layers were separated and the organic layer was washed with brine, dried with sodium sulfate, and concentrated under reduced pressure. The residue was triturated with Et₂O, and the solid was collected to yield Intermediate I-21B (0.09 g, 0.447 mmol, 63.5% yield) as a pale yellow solid. LC-MS: method H, RT=0.81 min, MS (ESI) m/z: 202.1 (M+H)⁺. ¹H NMR (400 MHz, CDCl₃) δ 7.86 (d, J=2.2 Hz, 1H), 7.63 (br s, 2H), 7.32 (s, 1H), 4.03 (s, 3H).

Intermediate I-21C: 6-fluoro-5-methoxythiazolo[5,4-b]pyridin-2-amine

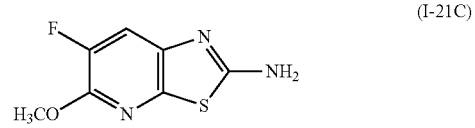 [SMILES: COc1nc2sc(N)nc2cc1F]

(I-21C)

To a solution of Intermediate I-21B (0.078 g, 0.338 mmol) in tetrahydrofuran (1 mL) was added benzyltrimethylammonium tribromide (0.151 g, 0.388 mmol). The reaction mixture was allowed to stir at room temperature for 2 hours. The reaction mixture was diluted with water and EtOAc. The layers were separated and the organic layer was washed with saturated aqueous NaHCO₃, washed with brine, dried with sodium sulfate, and concentrated under reduced pressure. The reaction mixture was purified by preparative HPLC using Method A to yield Intermediate I-21C (0.028 g, 0.141 mmol, 36.3% yield) as a white solid. ¹H NMR (400 MHz, CDCl₃) δ 7.87 (br s, 2H), 7.59 (d, J=9.7 Hz, 1H), 4.05 (s, 3H) LC-MS: method H, RT=0.84 min, MS (ESI) m/z: 200.1 (M+H)⁺.

Intermediate I-21

Copper (II) bromide (0.055 g, 0.247 mmol) and t-butyl nitrite (0.029 mL, 0.247 mmol) were dissolved in MeCN (0.582 mL) and allowed to stir 10 minutes. Intermediate I-21C (0.029 g, 0.146 mmol) was dissolved in MeCN (0.873 mL) and the copper solution was added. The reaction mixture was diluted with EtOAc, washed with 1 N HCl, saturated aqueous NaHCO₃, then brine, dried with sodium sulfate, filtered, and concentrated in vacuo to yield Intermediate I-21 (0.035 g, 0.133 mmol, 91% yield). ¹H NMR (400 MHz, CDCl₃) δ 7.86 (d, J=9.9 Hz, 1H), 4.09 (s, 3H). LC-MS: method H, RT=1.23 ruin, MS (EST) m/z: 263.0 (M+H)⁺.

Intermediate I-22

2-amino-6-fluorothiazolo[5,4-b]pyridin-5-ol, 2 hydrobromide

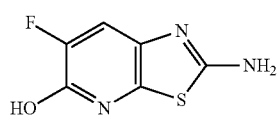
(I-22)

Intermediate I-21C (0.500 g, 2.510 mmol) was dissolved in HBr in acetic acid (1.704 mL, 15.06 mmol), and the reaction was stirred at 130° C. for 3 h. The reaction was concentrated under reduced pressure to yield Intermediate I-22 (0.422 g, 1.216 mmol, 48.5% yield) as a tan solid. $^1$H NMR (400 MHz, CD$_3$OD) δ 7.67 (d, J=9.7 Hz, 1H). LC-MS: method H, RT=0.44 min, MS (EST) m/z: 186.1 (M+H)$^+$.

Intermediate I-23

(2-(difluoromethoxy)-7-methylquinoxalin-5-yl)boronic acid

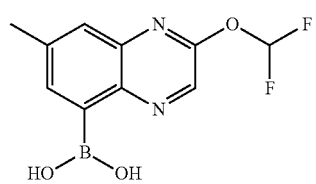
(I-23)

A mixture of Intermediate I-20G (385 g, 13.32 mmol), 4,4,4',4',5,5,5',5'-octamethyl-2,2'-bi(1,3,2-dioxaborolane) (5.07 g, 19.98 mmol), potassium acetate (3.27 g, 33.3 mmol) and [1,1'-Bis(diphenyl phosphino)ferrocene]dichloropalladium (II) complex with dichloromethane (1:1) (0.435 g, 0.533 mmol) in dioxane (60 mL) was degassed by bubbling argon for 10 min in a pressure vessel. The pressure vessel was sealed and heated at 90° C. overnight. After cooling to room temperature, the reaction mixture was poured into water, diluted with EtOAc, stirred at room temperature for 10 min. The mixture was filtered through a pad of wet celite. The organic layer was washed with brine, dried over sodium sulfate and concentrated. The crude product was purified by flash chromatography (loading in toluene, 5% to 100% EtOAc (containing 1% MeOH) in hexane over 20 min using a 120 g silica gel cartridge). The desired fractions were combined and concentrated to yield 2.5 g of crude product. The crude product was triturated with acetonitrile. The precipitate was collected by filtration to give 1.0 g of desired product. The filtrate was evaporated and purified by preparative HPLC equipped with a C18 Phenomenex Luna AXIA column (30 mm×75 cm, 5m) with the UV detector set at 220 nm. The separation was performed by using a gradient method: 30-100% B in 10 mins: then 100% B in 2 mins with a flow rate of 40 mL/min. Solvent B is 90% acetonitrile-10% water-0.1% TFA and solvent A is 10% acetonitrile-90% water-0.1% TFA. RT=6 min. The desired fractions were placed in a speedvac overnight to remove solvent, then lyophilized to give additional product 1.0 g. The product was combined to give Intermediate I-23 (2.0 g, 7.87 mmol, 59.1% yield) as a solid. $^1$H NMR (500 MHz, DMSO-d$_6$) δ 8.88 (s, 2H), 8.81 (s, 1H), 8.04 (d, J=1.9 Hz, 1H), 7.86 (t, J$_{HF}$=71.6 Hz, 1H), 7.83-7.79 (m, 1H), 2.57 (s, 3H); LC-MS: method H, RT=0.80 min, MS (ESI) m/z: 225.00 (M+H)$^+$.

Intermediate I-24

7-chloro-2-methoxy-5-(4,4,5,5-tetramethyl-1,3,2-dioxaborolan-2-yl)quinoxaline

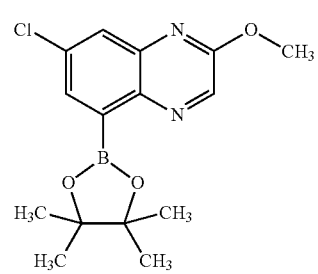
(I-24)

Intermediate I-24A: 2-bromo-4-chloro-6-nitroaniline

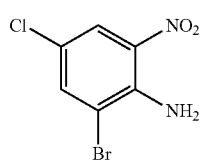
(I-24A)

A solution of 4-chloro-2-nitroaniline (10 g, 57.9 mmol) in acetic acid (50 mL) was cooled to 0° C. with an ice bath. Bromine (3.28 mL, 63.7 mmol) was added dropwise, and the mixture was stirred at room temperature for 1 hr, and then poured into ice water. The precipitated solid was filtered and was washed with water several times. The filter cake was re-dissolved in EtOAc, dried over sodium sulfate, filtered and concentrated in vacuo to give the title compound as a yellow solid (14.66 g, 100%). $^1$H NMR (400 MHz, DMSO-d$_6$) δ 8.08 (d, J=2.4 Hz, 1H), 8.02 (d, J=2.6 Hz, 1H), 7.27 (br s, 2H); LC-MS: method H, RT=1.15 min, MS (ESI) m/z: 250.9 and 252.9 (M+H)$^+$.

Intermediate I-24B: tert-butyl

N-(2-bromo-4-chloro-6-nitrophenyl)-N-[(tert-butoxy)carbonyl]carbamate

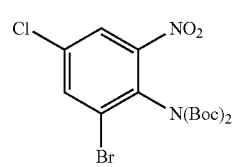
(I-24B)

In a round bottom flask charged with a stirring bar, Intermediate I-24A (5 g, 19.88 mmol) was dissolved in THF (30 mL). DMAP (0.243 g, 1.988 mmol) was added, followed by di-tert-butyl dicarbonate (11.54 mL, 49.7 mmol). The reaction mixture was stirred at room temperature for 1 hour, and then solvent was removed on a rotary evaporator. The residue was purified by flash chromatography (120 g silica gel column eluted with 0-100% EtOAc/hexane) to give the title compound as a white solid (8.2 g, 18.1 mmol, 91%). $^1$H NMR (400 MHz, CDCl$_3$): 7.97 (d, J=2.4 Hz, 1H), 7.90 (d, J=2.4 Hz, 1H), 1.42 (s, 18H); LC-MS: method H, RT=1.04 min, MS (ESI) m/z: 250.9 and 252.9 (M+H-2Boc)$^+$.

Intermediate I-24C: tert-butyl (2-bromo-4-chloro-6-nitrophenyl)carbamate

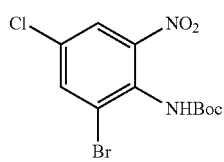

(I-24C)

To a solution of Intermediate I-24B (8.2 g, 18.15 mmol) in DCM (50 mL) was added TFA (2.80 mL, 36.3 mmol) and the mixture was stirred at room temperature for 1 hour. Saturated NaHCO$_3$ (aq. 30 mL) was added to the mixture. After stirring at room temperature for 10 minutes, the layers were separated and the aqueous layer was extracted by DCM (30 mL×2), The combined organic solution was washed with brine, dried over Na$_2$SO$_4$ and concentrated to give the title compound as a yellow solid (6.32 g, 18.0 mmol, 99%). $^1$H NMR (400 MHz, DMSO-d$_6$) δ 9.45 (br s, 1H), 8.24 (d, J=2.4 Hz, 1H), 8.12 (d, J=2.4 Hz, 1H), 1.43 (br s, 9H): LC-MS: method H, RT=0.82 min, MS (ESI) m/z: 250.9 and 252.9 (M+H-Boc)$^+$.

Intermediate I-24D: methyl 2-((2-bromo-4-methyl-6-nitrophenyl)amino)acetate

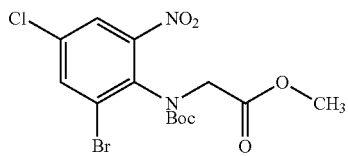

(I-24D)

To a solution of Intermediate I-24C (6.32 g, 18.0 mmol) in DMF (30 mL) was added Cs$_2$CO$_3$ (14.64 g, 44.9 mmol. Methyl 2-bromoacetate (5.50 g, 36.0 mmol) was added dropwise and the mixture was stirred at room temperature for 30 minutes. The reaction mixture was diluted with 100 mL of EtOAc and 50 mL of water. After separation, the aqueous layer was extracted by EtOAc (50 mL), and the combined organic layers were washed with brine and concentrated. The residue was purified by flash chromatography (120 g silica gel column, eluted with 0-50% EtOAc/Hex) to give the title compound (7.55 g, 17.8 mmol, 99%) as a yellow oil. $^1$H NMR (400 MHz, CDCl$_3$) δ 7.92-7.81 (m, 2H), 4.58 (d, J=17.6 Hz, 1H), 3.99 (d, J=17.4 Hz, 1H), 3.69 (s, 3H), 1.38 (s, 9H): LC-MS: method H, RT=1.23 min, MS (ESI) m/z: 366.9 and 368.9 (M+H−56)$^+$.

Intermediate I-24E: methyl 2-((2-bromo-4-chloro-6-nitrophenyl)amino)acetate, TFA salt

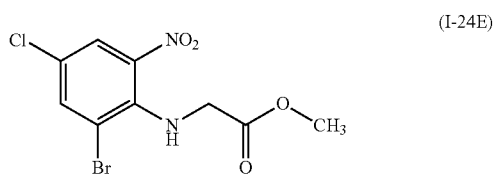 [SMILES: COC(=O)CNc1c(Br)cc(Cl)cc1[N+](=O)[O-]]

(I-24E)

Intermediate I-24D (5.6 g, 13.22 mmol) was dissolved in DCM (30 mL) and was treated with TFA (10.18 mL, 132 mmol) at room temperature overnight. On the next day, the solvent was removed and the crude product was used in the next step without purification. LC-MS: method H, RT=1.22 min, MS (ESI) m/z: 323.0 and 324.9 (M+H)$^+$.

Intermediate I-24F: 5-bromo-7-chloro-3,4-dihydroquinoxalin-2(1H)-one

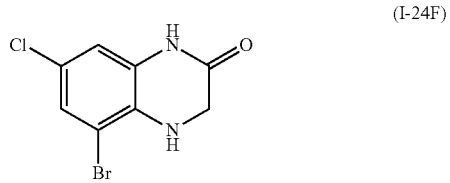 [SMILES: O=C1CNc2c(Br)cc(Cl)cc2N1]

(I-24F)

In a round bottom flask charged with a stirring bar, Intermediate I-24E (6.0 g, 18.55 mmol) was dissolved in MeOH (60 mL), and concentrated HCl (4.64 mL, 55.6 mmol) was added, followed by SnCl$_2$ (14.07 g, 74.2 mmol). The reaction mixture was stirred at 60° C. overnight. On the next day, after cooling to room temperature, another 2 equivalents of SnCl$_2$ was added to the reaction mixture. After 2 h at 60° C., the reaction mixture was cooled to room temperature; the precipitate was filtered, washed with small amount of MeOH, and dried to give a white solid as desired product. The filtrate was concentrated on a rotary evaporator and then partitioned between 150 mL of EtOAc and 30 mL of water. Next, 4M NaOH (aq.) was added to adjust the pH to 12. The solid was filtered on a Celite pad and the filter cake was washed with EtOAc. The layers were separated and the aqueous phase was extracted twice with EtOAc. The combined organic phases were washed with saturated NaHCO$_3$ (aq.), brine, dried over Na$_2$SO$_4$, filtered, and concentrated in vacuo to give additional product. Combining material gave 5-bromo-7-chloro-3,4-dihydroquinoxalin-2 (1H)-one (3.55 g, 13.58 mmol, 73.2% yield) as a white solid. $^1$H NMR (400 MHz, DMSO-d$_6$) δ 10.53 (s, 1H), 7.12 (d, 3J=2.2 Hz, 1H), 6.85-6.66 (m, 1H), 5.83 (s, 1H), 3.82 (d, J=2.0 Hz, 2H); LC-MS: method H, RT=1.02 min, MS (ESI) m/z: 261.0 and 263.0 (M+H)$^+$.

Intermediate I-24G:
5-bromo-7-chloroquinoxalin-2-ol

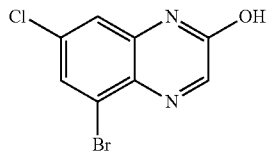

(I-24G)

In 1 L round bottom flask charged with a stirring bar, Intermediate I-24F (3.84 g, 14.7 mmol) was suspended in MeOH (50 mL), and $H_2O_2$ (15.00 mL, 147 mmol, 30% in water) was added, followed by 4N NaOH (11.01 mL, 44.1 mmol). The mixture was stirred at room temperature for 5 minutes, and then heated at 60° C. for 15 minutes. Heating was removed and the reaction mixture was stirred at room temperature over the weekend. Another 5 mL of $H_2O_2$ was added and the mixture was stirred at room temperature for 2 h. The reaction mixture was concentrated on a rotary evaporator. The residual mixture was cooled in an ice bath, and 6 N HCl was added to adjust the pH value to 2-3, followed by 200 mL of EtOAc. After shaking and separation, the aqueous layer was extracted with EtOAc (50 mL×2). The combined organic phases were combined and dried over $Na_2SO_4$. Removing solvent in vacuo gave the title compound as a brown solid. (2.51 g, 9.70 mmol, 66%). $^1$H NMR (400 MHz, DMSO-$d_6$): 12.63 (br s, 1H), 8.23 (s, 1H), 773 (d, J=2.0 Hz, 1H), 7.31 (d, J=2.0 Hz, 1H); LC-MS: method H, RT=1.01 min, MS (ESI) m/z: 258.9 and 260.9 $(M+H)^+$.

Intermediate I-24H:
5-bromo-7-chloro-2-methoxyquinoxaline

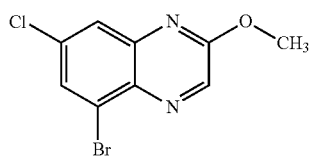

(I-24H)

In a round bottom flask charged with a stirring bar, Intermediate I-24G (1.60 g, 6.17 mmol) was suspended in $POCl_3$ (10 mL, 107 mmol), and the mixture was refluxed for 2 h. Excess $POCl_3$ was removed on a rotary evaporator and the residue was dried in vacuo for 30 minutes to give a brown solid. This brown solid was suspended in MeOH (30 mL), and anhydrous $K_2CO_3$ (1.704 g, 12.33 mmol) was added. The mixture was stirred at room temperature for 10 minutes, and then refluxed for 2 h. After cooling to room temperature, the solvent was removed on a rotary evaporator. The residue was dissolved in 100 ml of EtOAc, washed with water, brine, dried over $Na_2SO_4$, filtered, and concentrated to give the crude product. The crude product was purified by flash chromatography (80 g silica gel column, 0-50% EtOAc/hexane) to give Intermediate I-24-H (1.02 g, 3.73 mmol, 60.5% yield) as a yellow solid. $^1$H NMR (400 MHz, CDCl$_3$): 8.53 (s, 1H), 7.87-7.83 (m, 2H), 4.12 (s, 3H); LC-MS: method J, RT=0.96 min, MS (ESI) m/z: 273.0 and 275.0 $(M+H)^+$.

Intermediate I-24

In a microwave vial charged with a stirring bar, Intermediate I-24H (330 mg, 1.207 mmol), 4,4,4',4',5,5,5',5'-octamethyl-2,2'-bi(1,3,2-dioxaborolane) (460 mg, 1.810 mmol), and potassium acetate (296 mg, 3.02 mmol) were mixed with 1,4-dioxane (10 mL). After degassing with bubbling $N_2$ for 10 minutes, $PdCl_2$(dppf)-$CH_2Cl_2$ adduct (49.3 mg, 0.060 mmol) was added. The vial was sealed and was heated by microwave to 120° C. for 60 minutes. After cooling to room temperature, the reaction mixture was diluted by adding 40 mL of EtOAc and 30 mL of water. After separation, the aqueous layer was extracted with EtOAc (20 mL×2). The combined organic layers were dried over $Na_2SO_4$ and concentrated on a rotary evaporator. The residue was purified by flash chromatography (40 g silica gel column, 0-100% EtOAc/hexane gradient in 10 minutes, 100% EtOAc for 10 minutes) to give Intermediate I-24 as a yellow solid. (293 mg, 76%). $^1$H NMR (400 MHz, CDCl$_3$): 8.53 (s, 1H), 7.92-7.85 (m, 2H), 4.08 (s, 3H), 1.45 (s, 12H): LC-MS: method H, RT=1.09 min, MS (ESI) m/z: 239.1 $(M+Ht-82)^+$.

Intermediate I-25

3-methoxy-8-(4,4,5,5-tetramethyl-1,3,2-dioxaborolan-2-yl)quinoxaline-6-carbonitrile

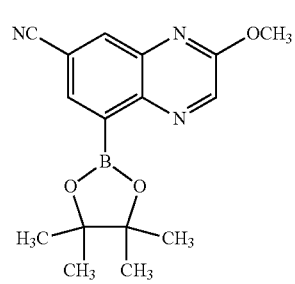

(I-25)

Intermediate I-25A: 8-bromo-3-oxo-1,2,3,4-tetrahydroquinoxaline-6-carbonitrile

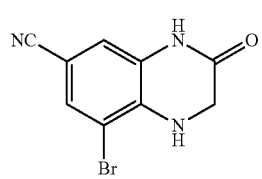

(I-25A)

Intermediate I-25A was synthesized from 4-amino-3-nitrobenzonitrile via the route described for Intermediate I-24. LC-MS: method I, RT=0.94 min, MS (ESI) m/z: 252.0 and 253.9 $(M+H)^+$.

Intermediate I-25B: 8-bromo-3-oxo-3,4-dihydroquinoxaline-6-carbonitrile

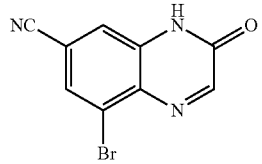
(I-25B)

In a round bottom flask charged with a stirring bar, Intermediate I-25A (394 mg, 1.563 mmol) was suspended in DMF (10 mL), and manganese dioxide (1359 mg, 15.63 mmol) was added. The mixture was stirred at room temperature for 60 minutes. LC/MS showed starting material remained. Another 10 equivalents of manganese dioxide (1359 mg, 15.63 mmol) was added, and the mixture was stirred at room temperature overnight. The next day, the solid was filtered and solvent was removed on a rotary evaporator and dried on HVAC to give the title compound (100 mg, 0.400 mmol, 25.6% yield) as a yellow solid. $^1$H NMR (400 MHz, DMSO-d$_6$) δ 8.32 (s, 1H), 7.95 (d, J=2.6 Hz, 1H), 7.65 (s, 1H); LC-MS: method A, RT=2.42 min, MS (ESI) m/z: 248.0 and 250.0 (M+H)$^+$.

Intermediate I-25

Intermediate I-25 was synthesized in two steps from Intermediate I-25B via the route described for Intermediate I-24. LC-MS: method A, RT=0.97 min, MS (ESI) m/z: 230.1 (M+H)$^+$ of boronic acid.

Intermediate I-26

(7-(hydroxymethyl)-2-methoxyquinoxalin-5-yl)boronic acid

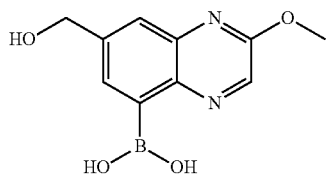
(I-26)

Intermediate I-26A: 4-bromo-2-chloro-6-nitroaniline

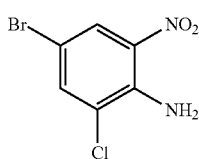
(I-26A)

A mixture of 4-bromo-2-nitroaniline (10.82 g, 49.9 mmol) and NCS (8.32 g, 62.3 mmol) in DMF (100 mL) was heated to 100° C. for 1H. After cooling to room temperature, the solution was poured into ice water. The yellow precipitate was collected by filtration and was washed with water. The solid was dissolved in dichloromethane (100 mL) and the organic phase was washed with water and brine, dried (Na$_2$SO$_4$), filtered, and concentrated to yield the title compound (11.54 g, 45.9 mmol, 92% yield) as a yellow solid. $^1$H NMR (400 MHz, CDCl$_3$) δ 8.26 (d, J=2.2 Hz, 1H), 7.67 (d, J=2.2 Hz, 1H), 6.57 (br s, 2H).

Intermediate I-26B: tert-butyl N-(4-bromo-2-chloro-6-nitrophenyl)-N-[(tert-butoxy)carbonyl]carbamate

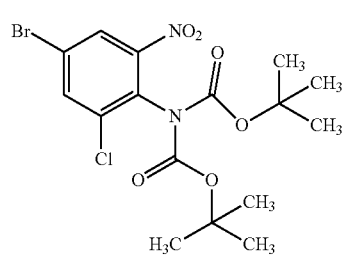
(I-26B)

Intermediate I-26B (11.75 g, 87%/o) was made as a yellow solid from Intermediate I-26A (7.52 g, 29.9 mmol) via the same procedure as Intermediate I-20A. $^1$H NMR (400 MHz, CDCl$_3$) δ 8.08 (d, J=2.2 Hz, 1H), 7.89 (d. J=2.2 Hz, 1H), 1.42 (s, 18H).

Intermediate I-26C: tert-butyl (4-bromo-2-chloro-6-nitrophenyl)carbamate

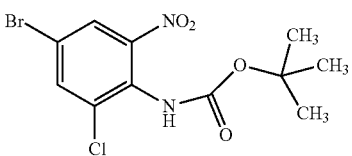
(I-26C)

Intermediate I-26C (5.2 g, 14.8 mmol, 98%) was made as a brown waxy solid from Intermediate I-26B (6.8 g, 15.0 mmol) via the same procedure as Intermediate I-20B. $^1$H NMR (400 MHz, CDCl$_3$) δ 8.00 (d, J=2.2 Hz, 1H), 7.81 (d, J=2.2 Hz, 1H), 6.92 (br s, 1H), 1.50 (s, 9H)

Intermediate I-26D: methyl 2-((4-bromo-2-chloro-6-nitrophenyl)(tert-butoxycarbonyl)amino)acetate

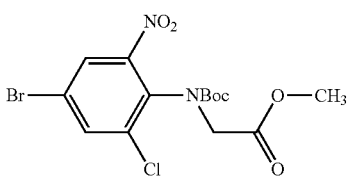
(I-26D)

Intermediate I-26D (5.4 g, 12.8 mmol, 87%) was made as a yellow oil from Intermediate I-26C (5.2 g, 14.8 mmol) via the same procedure as Intermediate I-20C. $^1$H NMR (400 MHz, CDCl$_3$) δ 7.99 (d, J=2.2 Hz, 1H), 7.88-7.85 (m, 1H), 4.49 (d, J=17.4 Hz, 1H), 4.07 (d, J=17.4 Hz, 1H), 3.71-3.67 (m, 3H), 1.37 (s, 9H): LC-MI: method H, RT=1.04 min, MS (ESI) m/z: 323.0 and 325.0 (M-+H-100).

Intermediate I-26E: methyl 2-((4-bromo-2-chloro-6-nitrophenyl)amino)acetate

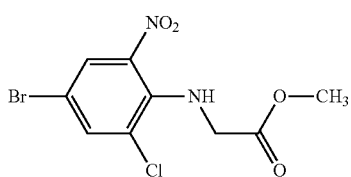

Intermediate I-26E (4.15 g, 12.8 mmol, 100%) was made as a brown oil from Intermediate I-26D (5.44 g, 12.8 mmol) via the same procedure as Intermediate I-20D. LC-MS: method H, RT=1.0 min, MS (EST) m/z: 323.1 and 325.0 (M+H)$^+$.

Intermediate I-26F:
7-bromo-5-chloro-3,4-dihydroquinoxalin-2(1H)-one

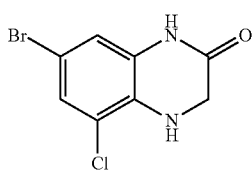

Intermediate I-26F (3.02 g, 11.55 mmol, 73%) was made as a white solid from Intermediate I-26E (5.1 g, 15.8 mmol) via the same procedure as Intermediate I-20E. $^1$H NMR (400 MHz, DMSO-d$_6$) δ 10.54 (s, 1H), 7.10 (d, J=2.0 Hz, 1H), 6.83 (d, J=2.2 Hz, 1H), 6.02 (s, 1H), 3.82 (d, J=1.8 Hz, 2H); LC-MS: method H, RT=0.84 min, MS (ESI) m/z: 261.0 and 263.0 (M+H)$^+$.

Intermediate I-26G:
7-bromo-5-chloroquinoxalin-2(1H)-one

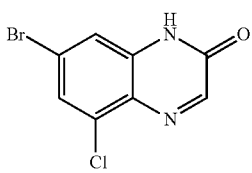

Intermediate I-26G (3.40 g, 13.10 mmol, 70%) was made as an off-white solid from Intermediate I-26F (4.85 g, 18.5 mmol) via the same procedure as Intermediate I-20E. $^1$H NMR (400 MHz, DMSO-d$_6$) δ 7.76 (s, 1H), 7.21 (d, J=2.2 Hz, 1H), 7.11 (d, J=2.2 Hz, 1H); LCMS: method H, RT=1.08 min, MS (ESI) m/z: 259.1 and 261.1 (M+H)$^+$.

Intermediate I-26H:
7-bromo-5-chloro-2-methoxyquinoxaline

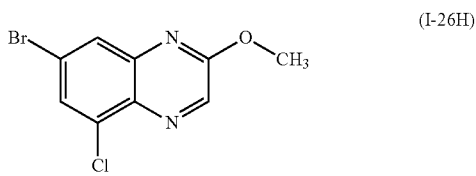

Intermediate I-26H (2.13 g, 7.79 mmol, 86%) was made as a yellow solid from Intermediate I-26G (2.34 g, 9.02 mmol) via the same procedure as Intermediate I-20H. $^1$H NMR (400 MHz, CDCl$_3$) δ 8.55 (s, 1H), 7.98 (d, J=2.2 Hz, 1H), 7.80 (d, J=2.0 Hz, 1H), 4.12 (s, 3H); LC-MS: method H, RT=1.07 min., MS (ESI) m/z: 273.1 and 275.1 (M+H)$^+$.

Intermediate I-26I:
5-chloro-2-methoxy-7-vinylquinoxaline

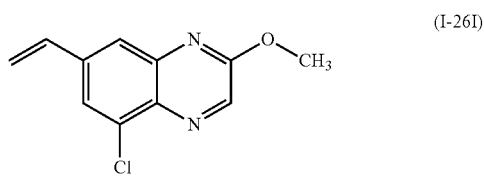

To a vial charged with a stirring bar was added Intermediate I-26H (0.7 g, 2.56 mmol), potassium vinyltrifluoroborate (0.377 g, 2.82 mmol), cesium carbonate (1.668 g, 5.12 mmol), (s)-2,2'-bis(diphenylphosphino)-1,1'-binaphthalene (0.159 g, 0.256 mmol) and diacetoxypalladium (0.029 g, 0.128 mmol). After applying vacuum and refilling with N$_2$ 3 times, DMF (10 mL) was added and N$_2$ was bubbled through the solution for 10 minutes. The vial was sealed, stirred at room temperature for 10 minutes, and then heated at 80° C. for 3 h. After cooling to room temperature, the reaction mixture was diluted with 60 mL of EtOAc, washed with water and brine, dried over Na$_2$SO$_4$, filtered and concentrated. The crude product was purified by flash chromatography (0-50% EtOAc/hexane in 12 minutes, 50-100% EtOAc/hexane in 6 minutes, 40 g silica gel column) to give the title compound (470 mg, 2.130 mmol, 83% yield) as an off-white solid. $^1$H NMR (4001 MHz, CDCl$_3$) δ 8.51 (s, 1H), 7.79 (d, J=2.0 Hz, 1H), 7.73 (d, J=1.8 Hz, 1H), 6.83 (dd, J=17.5, 10.9 Hz, 1H), 5.96 (d, J=17.4 Hz, 1H), 5.48 (d, J=1.0 Hz, 1H), 4.12 (s, 3H): LC-MS: method H, RT=1.02 min, MS (EST) m/z: 221.1.

Intermediate I-26J: 8-chloro-3-methoxyquinoxaline-6-carbaldehyde

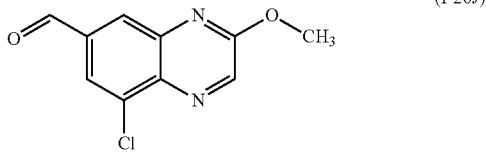
(I-26J)

In a round bottom flask charged with a stirring bar, Intermediate I-26I (470 mg, 2.130 mmol) was dissolved in THF (20 mL)/water (6 mL), and treated with sodium periodate (1367 mg, 6.39 mmol) and osmium tetroxide (4% by wt in water) (0.271 mL, 0.043 mmol). The mixture was stirred at room temperature for 4 h, and then reaction mixture was diluted by adding 40 mL of EtOAc and 20 mL of water. The organic phase was washed with saturated $Na_2S_2O_3$ (aq., 3×) and brine, dried over $Na_2SO_4$, and filtered. The filtrate was concentrated on a rotary evaporator to give the title compound (457 mg, 2.053 mmol, 96% yield) as a yellow solid. $^1$H NMR (400 MHz, $CDCl_3$) δ 10.17 (s, 1H), 8.67 (s, 1H), 8.27 (d, J=1.8 Hz, 1H), 8.16 (d, J=1.8 Hz, 1H), 4.17 (s, 3H); LC-MS: method H, RT=0.88 min, MS (ESI) m/z: 223.2.

Intermediate I-26K: (8-chloro-3-methoxyquinoxalin-6-yl)methanol

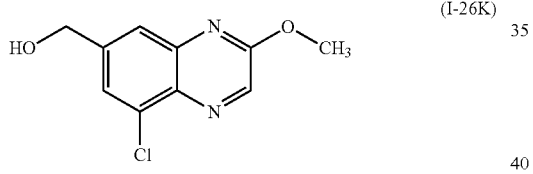
(I-26K)

In a round bottom flask charged with a stirring bar, Intermediate I-26J (421 mg, 1.89 mmol) was dissolved in toluene (10 mL) and mixed with sodium triacetoxyborohydride (882 mg, 4.16 mmol). The mixture was stirred at 60° C. for 4 h. After cooling to room temperature, the solvent was removed on a rotary evaporator. The residue was dissolved in 30 mL of EtOAc and 20 mL of water. The organic phase was washed with brine, dried over $Na_2SO_4$, filtered and concentrated on a rotary evaporator to give the title compound (0.415 g, 1.847 mmol, 98% yield) as an off-white solid. $^1$H NMR (400 MHz, $CDCl_3$) δ 8.55 (s, 1H), 7.79-7.75 (m, 1H), 7.70 (d, J=1.8 Hz, 1H), 4.89 (s, 2H), 4.12 (s, 3H), 1.94 (br s, 1H); LC-MS: method H, RT=0.75 min, MS (ESI) m/z: 225.2.

Intermediate I-26

A microwave tube was charged with $Pd_2(dba)_3$ (48.9 mg, 0.053 mmol), X-Phos (102 mg, 0.214 mmol), 4,4,4,4',5,5,5',5'-octamethyl-2,2'-bi(1,3,2-dioxaborolane) (814 mg, 3.21 mmol), and potassium acetate (315 mg, 3.21 mmol). The tube was capped and then evacuated and backfilled with argon 3 times. Intermediate I-26K (240 mg, 1.068 mmol) in 1,4-dioxane (10 mL) was added via syringe, followed by flushing the reaction mixture with $N_2$ for 10 minutes. The reaction mixture was heated at 110° C. in a microwave reactor for 30 minutes. After cooling to room temperature, the reaction mixture was concentrated in vacuo and the residue was purified by flash chromatography (40 g silica gel, 0-100% EtOAc, then 0-10% MeOH/DCM) to give Intermediate I-26 (121 mg, 0.517 mmol, 48.4% yield) as a grey solid. LC-MS: method H, RT=0.75 min, MS (ESI) m/z: 235.2.

Intermediate I-27

5-fluoro-2-(2-methoxy-7-methyl quinoxalin-5-yl) benzo[d]thiazol-6-ol

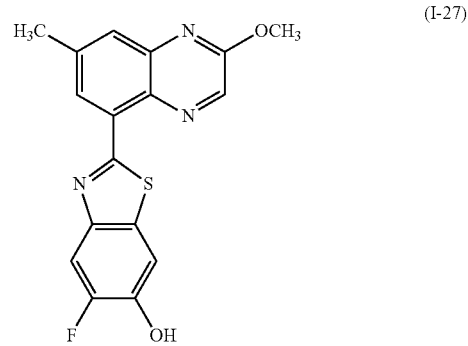 [SMILES: COc1cnc2c(-c3nc4cc(F)c(O)cc4s3)cc(C)cc2n1]
(I-27)

Intermediate I-27A 2-(2-(difluoromethoxy)-7-methylquinoxalin-5-yl)-5-fluorobenzo[d]thiazol-6-ol

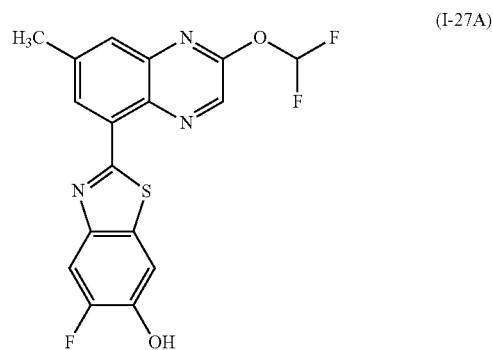 [SMILES: Cc1cc(-c2nc3cc(F)c(O)cc3s2)c2ncc(OC(F)F)nc2c1]
(I-27A)

A microwave vial was charged with Intermediate I-23 (80 mg, 0.314 mmol), Intermediate I-19 (65 mg, 0.262 mmol) and [1,1'-bis(diphenylphosphino)ferrocene]dichloropalladium (II) complex with dichloromethane (1:1) (17.12 mg, 0.021 mmol). A solvent mixture of toluene (1638 µl), EtOH (546 µl) and 2.0 M $Na_2CO_3$ (197 µl, 0.393 mmol) was then added, and the resulting solution was sparged with argon for 10 min before being sealed and then heated in the microwave at 130° C. for 30 min. The crude reaction mixture was diluted with EtOAc and filtered over celite before being concentrated and purified by ISCO (24 g 0-100% EtOAc/hexanes, 16 min) to afford Intermediate I-27A (95 mg, 0.252 mmol, 96% yield) as a dark yellow solid. $^1$H NMR (400 MHz, CHLOROFORM-d) δ 8.76 (d, J=2.0 Hz, 1H), 8.69 (s, 1H), 7.84 (d, J=10.8 Hz, 1H), 7.80 (s, 1H), 7.66 (t, J=71.8

Hz, 1H), 7.55 (d, J=8.4 Hz, 1H), 5.30 (d, J=5.1 Hz, 1H), 2.68 (s, 3H). LC-MS: Method H, RT=1.06 min, MS (ESI) m/z: 378.2 (M+H)+.

Intermediate I-27

To a solution of Intermediate I-27A (20 mg, 0.053 mmol) in THF (1 mL) was added a 0.5 M NaOMe solution in MeOH (0.530 mL, 0.265 mmol). After 1 h, the reaction mixture was diluted with EtOAc and quenched with 1.0 N HCl. The organic phase was extracted, dried over MgSO4, filtered and concentrated in vacuo to afford Intermediate I-27 (18 mg, 0.053 mmol, 99% yield) as a yellow solid. This material was used without further purification. LC-MS: Method H, RT=1.08 min, MS (ESI) m/z: 342.2 (M+H)+. 1H NMR (400 MHz, THF) δ 8.95 (br. s., 1H), 8.70 (d, J=1.3 Hz, 1H), 8.54 (s, 1H), 7.80-7.67 (m, 2H), 7.46 (d, J=8.6 Hz, 1H), 4.10 (s, 3H), 2.63 (s, 3H).

Intermediate I-28

3-methoxy-6-methyl-8-(4,4,5,5-tetramethyl-1,3,2-dioxaborolan-2-yl)quinolin e

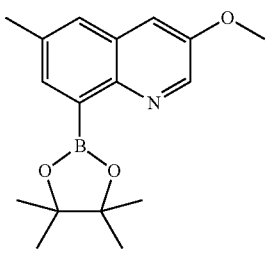
(I-28)

Intermediate I-28A: methyl 2-amino-3-bromo-5-methylbenzoate

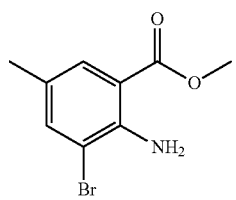

2-Amino-3-bromo-5-methylbenzoic acid (3.8 g, 16.5 mmol) was dissolved in MeOH (33.0 mL). Thionyl chloride (3.62 mL, 49.6 mmol) was added carefully dropwise and the reaction was heated to 65° C. After stirring for 8 days, the reaction was concentrated in vacuo. The crude material was redissolved in EtOAc, washed with 1 N NaOH, water, then brine, dried (Na2SO4), filtered, and concentrated in vacuo to give Intermediate I-28A (3.38 g, 13.9 mmol, 84%) as an orange oil: 1H NMR (400 MHz, CHLOROFORM-d) δ 7.66 (d, J=1.1 Hz, 1H), 7.43 (d, J=1.8 Hz, 1H), 6.14 (br. s., 2H), 3.88 (s, 3H), 2.22 (s, 3H); LC-MS: Method H, RT=1.18 min, MS (ESI) m/z: 244/246 (M+H)+

Intermediate I-28B: (2-amino-3-bromo-5-methylphenyl)methanol

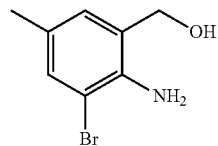

Intermediate I-28A (3.38 g, 13.8 mmol) was dissolved in THF (46.2 mL). Lithium borohydride (0.603 g, 27.7 mmol) was added and the reaction was heated to 50° C. After 1 hour, the reaction was diluted with water and stirred for 30 minutes. All of the lithium borohydride had not dissolved, so concentrated HCl was added carefully to speed up the quenching process. The reaction was then extracted thrice with EtOAc. The combined organic layers were washed with brine, dried (Na2SO4), filtered, and concentrated in vacuo to give Intermediate I-28B (2.85 g, 13.2 mmol, 95%) as a white solid: 1H NMR (400 MHz, CHLOROFORM-d) δ 7.23 (d, J=1.1 Hz, 1H), 6.84 (d, J=1.3 Hz, 1H), 4.65 (s, 2H), 4.53 (br. s., 2H), 2.22 (s, 3H); LC-MS: Method H, RT=1.00 inn, MS (ESI) n/z: 216/218 (M+H)+.

Intermediate I-28C: 2-amino-3-bromo-5-methylbenzaldehyde

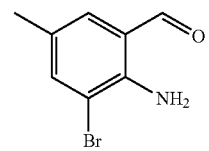

Intermediate I-28B (2.85 g, 13.2 mmol) was dissolved in CHCl3 (88 mL). Manganese dioxide (6.88 g, 79 mmol) was added and the reaction was heated to 40° C. After heating overnight, the reaction was filtered through celite and concentrated in vacuo to give Intermediate I-28C (2.72 g, 12.7 mmol, 96%) as a yellow solid: 1H NMR (400 MHz, CHLOROFORM-d) δ 9.78 (s, 1H), 7.47 (d, J=1.5 Hz, 1H), 7.28-7.26 (m, 1H), 6.49 (br. s., 2H), 2.28 (s, 3H); LC-MS: Method H, RT=1.26 min, MS (ESI) m/z: 214/216 (M+H)+

Intermediate I-28D: 3-(benzyloxy)-8-bromo-6-methylquinoline

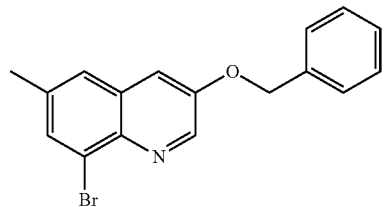 [SMILES: Cc1cc(Br)c2ncc(OCc3ccccc3)cc2c1]

Intermediate I-28C (2.72 g, 12.7 mmol), 2-(benzyloxy) acetaldehyde (1.91 g, 12.7 mmol), and sodium methoxide (0.5 M in MeOH, 28.0 mL, 13.98 mmol) were dissolved in MeOH (50.8 mL) and heated to reflux. After heating overnight, the reaction was diluted with saturated NH₄Cl, partially concentrated in vacuo and diluted with EtOAc. The layers were separated and the organic layer was washed with brine, dried (Na₂SO₄), filtered, and concentrated in vacuo. The crude material was purified by silica gel chromatography (ISCO, 220 g silica gel column, 41 minute gradient from 0 to 40% EtOAc in hexanes) to give Intermediate I-28D (1.86 g, 5.67 mmol, 45%) as a yellow solid: ¹H NMR (400 MHz, CHLOROFORM-d) δ 8.79 (d, J=2.9 Hz, 1H), 7.74 (d, J=1.5 Hz, 1H), 7.51-7.46 (m, 2H), 7.45-7.40 (m, 3H), 7.39-7.33 (m, 2H), 5.20 (s, 2H), 2.49 (s, 3H); LC-MS: Method H, RT=1.22 min, MS (ESI) m/z: 328/330 (M+H)⁺

Intermediate I-28E: 8-bromo-6-methylquinolin-3-ol

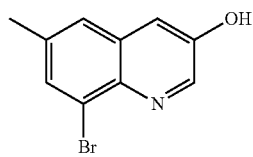

Intermediate I-28D (1.86 g, 5.67 mmol) and pentamethylbenzene (5.88 g, 39.7 mmol) were dissolved in DCM (113 mL) and cooled to −78° C. Boron trichloride (1 M in heptane, 14.7 mL, 14.7 mmol) was added and the reaction was allowed to warm slowly to ambient temperature. After stirring overnight, the reaction was diluted with hexanes and 1 N HCl and allowed to stir for 1 hour. The aqueous layer still contained product by LC/MS. The aqueous layer was neutralized with NaOH until approximately pH 7 and copious amounts of precipitates were formed. The precipitate was collected by suction filtration to give Intermediate I-28E (829 mg, 3.48 mmol, 62%) as an off-white solid: ¹H NMR (400 MHz, METHANOL-d₄) δ 8.50 (d, J=2.6 Hz, 1H), 7.72 (s, 1H), 7.51 (s, 1H), 7.43 (d, J=1.8 Hz, 1H), 2.47 (s, 3H); LC-MS: Method H, RT=0.82 min, MS (ESI) m/z: 238/240 (M+H)⁺

Intermediate I-28F:
8-bromo-3-methoxy-6-methylquinoline

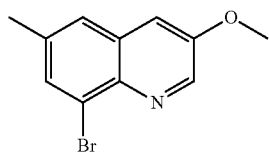

Intermediate I-28E (200 mg, 0.728 mmol), K₂CO₃ (302 mg, 2.18 mmol), and methyl iodide (91 μl, 1.46 mmol) were dissolved in acetone (7.29 mL) and heated to 50° C. in a sealed tube. After heating overnight, the reaction was diluted with EtOAc, washed with water, then brine, dried (Na₂SO₄), filtered, and concentrated in vacuo to give Intermediate I-28F (207 mg, 0.82 mmol, 100%) as a yellow solid: ¹H NMR (400 MHz, CHLOROFORM-d) δ 8.71 (d, J=2.9 Hz, 1H), 7.74 (d, J=1.8 Hz, 1H), 7.46 (s, 1H), 7.29 (d, J=2.9 Hz, 1H), 3.95 (s, 3H), 250 (s, 3H): LC-MS: Method H, RT=1.06 min, MS (ESI) m/z: 252/254 (M+H)⁺

Intermediate I-28

Intermediate I-28F (183 mg, 0.726 mmol), bispinacolatodiboron (369 mg, 1.45 mmol), potassium acetate (178 mg, 1.82 mmol), and PdCl₂(dppf)-CH₂Cl₂ adduct (47.4 mg, 0.058 mmol) were stored on HIVAC for 15 minutes then were dissolved in dry 1,4-dioxane (7.26 mL) and degassed for 15 minutes by bubbling with argon. The reaction was heated to 130° C. in the microwave for 40 minutes. The reaction was diluted with EtOAc and washed with water then brine, dried (Na₂SO₄), filtered, and concentrated in vacuo. The crude material was purified by silica gel chromatography (ISCO, 24 g silica gel column, 19 minute gradient from 0 to 100% EtOAc in DCM then 0 to 20% MeOH in DCM) to give Intermediate I-28 (108 mg, 0.36 mmol, 50%) as a brown solid: LC-MS: Method H, RT=0.80 min, MS (ESI) m/z: 218.0 (boronic acid observed, M+H)⁺

Intermediate I-29

6-chloro-3-methoxy-8-(4,4,5,5-tetramethyl-1,3,2-dioxaborolan-2-yl)quinoline

Intermediate I-29 was made from methyl 2-amino-5-chlorobenzoate via the procedure described for Intermediate I-28. LC-MS: Method H, RT=0.84 min, MS (ESI) m/z: 238.0 (boronic acid observed, M+H)⁺

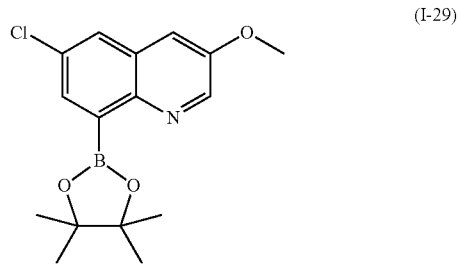 [SMILES: COc1cnc2c(B3OC(C)(C)C(C)(C)O3)cc(Cl)cc2c1]

Intermediate I-30

2-(2-((tert-butyldimethyl silyl)oxy)ethoxy)pyrimidin-5-amine

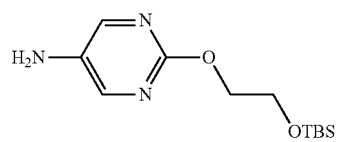

Intermediate I-30A:
2-((5-nitropyrimidin-2-yl)oxy)ethanol

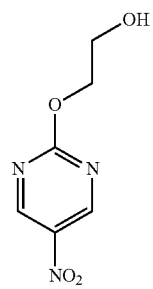

2-chloro-5-nitropyrimidine (1 g, 6.27 mmol) was mixed with ethylene glycol (8 ml, 143 mmol) and DIEA (3.28 ml, 18.81 mmol) was added. The mixture was stirred at 80° C. for 20 minutes and was then poured into 30 mL of ice water. 40 mL of EtOAc was added to the mixture followed by 20 mL of 1N aq. HCl. EtOAc (30 mL×3) was used to extract the aq. layer. The combined organic layer was washed with brine, dried with sodium sulfate, filtered and concentrated to give I-30A in quantitative yield as a yellow oil. The product was brought forward without further purification. $^1$H NMR (400 MHz, CDCl$_3$) δ 9.33 (s, 2H), 4.73-4.51 (m, 2H), 4.08-3.96 (m, 2H), 2.41 (br. s., 1H).

Intermediate I-30B: 2-(2-((tert-butyldimethylsilyl)oxy)ethoxy)-5-nitropyrimidine

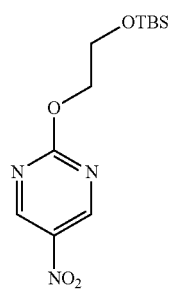

(I-30B)

I-30A, (1.23 g, 6.64 mmol), was mixed with tert-butylchlorodimethylsilane (2.003 g, 13.29 mmol) in DCM (20 ml). Imidazole (0.905 g, 13.29 mmol) was added to the reaction mixture and the reaction mixture stirred at room temperature for 30 minutes. The solid was filtered off and the filter cake was washed with a small amount of DCM. The filtrate was mixed with 30 g of silica gel, evaporated to dryness, and purified by silica gel chromatography (80 g column, 0-50% EtOAc/hexane) for purification. The fractions containing desired product were collected and concentrated to give I-30B, (1.73 g, 5.78 mmol, 87% yield), as a light yellow solid. $^1$H NMR (400 MHz, CDCl3) δ ppm 9.30 (2H, s), 4.61 (2H, dd, J=5.50, 4.62 Hz), 4.02 (2H, dd, J=5.61, 4.73 Hz), 0.88 (9H, s), 0.09 (6H, s). LC-MS: Method H, MS (ESI) m/z: 300.0 (M+H)$^+$.

Intermediate I-30

I-30B, (1.73 g, 5.78 mmol) was dissolved in THF (40 ml). Wet Pd—C(0.307 g, 0.289 mmol, 10% by wt) was then added to the solution. The mixture was then evacuated and backfilled with hydrogen 3×, and the mixture was stirred under 1 atm H$_2$ for 7 hours at rt. The catalyst was filtered off over a pad of celite which was washed with a small amount of EtOAc. The filtrate was concentrated to yield I-30, (1.53 g, 5.68 mmol, 98% yield), as a gray solid. $^1$H NMR (400 MHz, CDCl$_3$) δ ppm 8.05 (2H, s), 4.35 (2H, t, J=5.50 Hz), 3.97 (2H, t, J=5.61 Hz), 1.69 (2H, d, J=5.06 Hz), 0.89 (9H, s), 0.08 (6H, s). LC-MS: Method H, MS (ESI) m/z: 270.1 (M+H)$^+$.

Intermediate I-31

(R)-2-(2-((tert-butyldimethylsilyl)oxy)propoxy)pyrimidin-5-amine

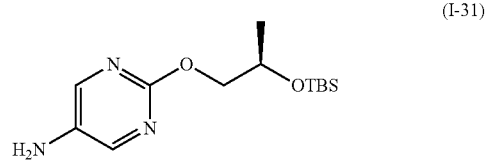 [SMILES: C[C@H](COc1ncc(N)cn1)O[Si](C)(C)C(C)(C)C]

(I-31)

This intermediate was prepared from (R)-ethyl 2-hydroxypropanoate in the same manner as described for I-32 below. $^1$H NMR (400 MHz, CDCl$_3$) δ 7.97 (s, 2H), 4.20-4.06 (m, 2H), 4.01-3.93 (m, 1H), 3.29 (br. s., 2H), 1.17 (d, J=6.2 Hz, 3H), 0.81 (s, 9H), 0.01 (d, J=6.2 Hz, 61H LC-MS: Method H, MS (ESI) m/z: 284.2 (M+H)$^+$.

Intermediate I-32

(S)-2-(2-((tert-butyldimethylsilyl)oxy)propoxy)pyrimidin-5-amine

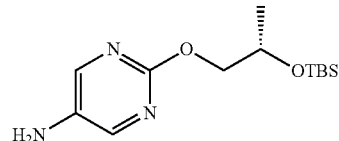

(I-32)

Intermediate I-32A: (S)-ethyl 2-((tert-butyldimethylsilyl)oxy)propanoate

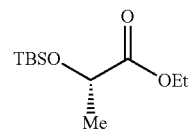

(I-32A)

Ethyl (S)-2-hydroxypropanoate (1.50 g, 12.70 mmol), imidazole (2.2 equiv.) and TBS-Cl (2.0 equiv.) were dissolved in DCM (0.1 M). The reaction was allowed to stir at room temperature for 18 h. The reaction mixture was then diluted with 1.5 M dipotassium phosphate solution and extracted with EtOAc (3×). The combined organic layer was washed with brine (1×), dried with sodium sulfate, filtered and concentrated. The resulting residue was dissolved in a small amount of methylene chloride and purified by silica gel chromatography to yield I-32A (2.3 g, 9.90 mmol, 78% yield) as a clear oil. $^1$H NMR (400 MHz, CDCl3) δ 4.35-4.28 (m, 1H), 4.18 (t, J=7.5 Hz, 2H), 0.40 (d, J=6.8 Hz, 3H), 1.28 (t, J=7.2 Hz, 31H), 0.91 (s, 9H), 0.10 (s, 3H), 0.07 (s, 3H).

Intermediate I-32B: (S)-2-((tert-butyldimethylsilyl)oxy)propan-1-ol

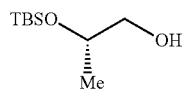

(I-32B)

I-32A (2.2 g, 9.47 mmol) was dissolved in THF (100 ml) and the solution was cooled to −78° C. To the reaction mixture was added DIBAL-H (23.67 n-ml, 23.67 mmol) and the reaction mixture was allowed to warm to room temperature and stirred for 3 h at room temperature before being quenched with saturated Rochelle's salt. The quenched reaction mixture was stirred for 18 h at room temperature and then extracted with EtOAc (3×). The combined organic layer was washed with brine, dried with sodium sulfate, filtered and concentrated under reduced pressure to yield I-32B in quantitative yield. $^1$H NMR (400 MHz, CDCl3) δ 3.87-3.77 (m, J=2.6 Hz, 1H), 3.46-3.37 (m, 1H), 3.32-3.21 (m, 1H), 1.03 (d, J=6.4 Hz, 3H), 0.82 (s, 9H), 0.00 (s, 6H).

Intermediate I-32C (S)-5-bromo-2-(2-((tert-butyldimethylsilyl)oxy)propoxy)pyrimidine

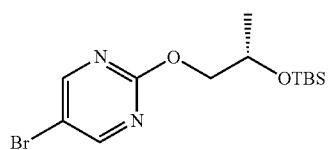

(I-32C)

Triphenylphosphine (2.88 g, 10.98 mmol) was dissolved in THF (143 ml) and the solution was cooled to 0° C. DIAD (1.941 ml, 9.98 mmol) was added and reaction mixture was allowed to stir for 5 minutes at 0° C. I-32B (1.9 g, 9.98 mmol) was added to the reaction mixture and the reaction mixture was allowed to stir for 10 minutes at 0° C. 5-bromopyrimidin-2-ol (1.5 g, 8.57 mmol) was then added to the reaction mixture which was allowed to warm to room temperature slowly and stirred for 72 hours at rt. The reaction mixture was then diluted with water and extracted with EtOAc (3×). The combined organic layer was washed with brine (1×), dried with sodium sulfate, filtered and concentrated. The resulting residue was dissolved in a small amount of methylene chloride before being charged to an 80 g silica gel cartridge which was eluted with a 30 min gradient from 0-100% EtOAc in hexane. Fractions containing desired product were collected and concentrated to yield I-32C (1.9 g, 5.47 mmol, 55% yield). $^1$H NMR (400 MHz, CDCl3) δ 8.52 (s, 2H), 4.34-4.26 (m, 1H), 4.18 (s, 1H), 4.15-4.05 (m, 1H), 1.24 (d, J=6.2 Hz, 3H), 0.87 (s, 9H), 0.07 (d, J=8.1 Hz, 5H). LC-MS: Method H. MS (ESI) 3/z: 349.1 (M+H)$^+$.

Intermediate I-32D (S)-2-(2((tert-butyldimethylsilyl)oxy)propoxy)-N-(diphenylmethylene)pyrimidin-5-amine

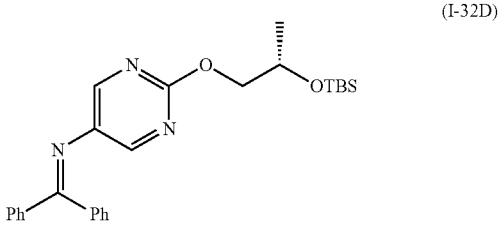 [SMILES: C[C@@H](COc1ncc(N=C(c2ccccc2)c2ccccc2)cn1)O[Si](C)(C)C(C)(C)C]

(I-32D)

To a vial containing I-32 C (1.0 equiv.), palladium(11) acetate (0.1 equiv.), BINAP (0.2 equiv.), cesium carbonate (1.2 equiv.) and diphenylmethanimine (1.1 equiv.) was added toluene (0.5 M). The vial was sealed, evacuated and backfilled with Ar 3×, and the reaction mixture was heated to 105° C. for 18 hours. The reaction mixture was then diluted with EtOAc and washed with 1M aq. NaOH (1×) and brine (1×). The organic layer was dried with sodium sulfate, filtered and concentrated. The resulting residue was dissolved in methylene chloride before being purified by silica gel chromatography to provide I-32 D (78% yield). $^1$H NMR (400 MHz, CDCl$_3$) δ 7.95 (s, 2H), 7.78-7.71 (m, 2H), 7.53-7.30 (m, 6H), 716-7.06 (m, 2H), 4.31-4.11 (m, 2H), 4.08-4.01 (m, 1H), 1.22 (d, J=5.9 Hz, 3H), 0.87 (s, 9H), 0.05 (d, J=9.9 Hz, 6H). LC-MS: Method H, MS (ESI) m/z: 448.2 (M+H)$^+$.

Intermediate I-32

I-32D (1.9 g, 4.24 mmol) was dissolved in 90:10:0.1 MeOH/water/TFA (14 ml) and the solution stirred for 15 minutes at room temperature then basified with 1.5 M dipotassium phosphate solution and extracted with EtOAc (3×). The combined organic layer was washed with brine (1×), dried with sodium sulfate, filtered and concentrated. The resulting residue was dissolved in methylene chloride and charged to an 80 g silica gel cartridge which was eluted with a 30 min gradient from 0-15% MeOH in methylene chloride. Fractions containing the desired product were concentrated to yield I-32 (210 mg, 0.741 mmol, 17% yield). $^1$H NMR (400 MHz, DMSO-d$_6$) δ 7.92 (s, 2H), 4.93 (s, 2H), 4.16-3.83 (m, J=7.4, 5.6 Hz, 3H), 1.12 (d, J=6.2 Hz, 3H). LC-MS: RT=1.01 min, LC-MS: Method H, MS (ESI) m/z: 284.2 (M+H)$^+$.

Example 001

(1R,2S)-4,4-difluoro-2-((5-fluoro-2-(2-methoxy-7-methylquinoxalin-5-yl)benzo[d]thiazol-6-yl)oxy)cyclohexyl (2(2-(2-hydroxy ethoxy)pyrimidin-5-yl)carbamate

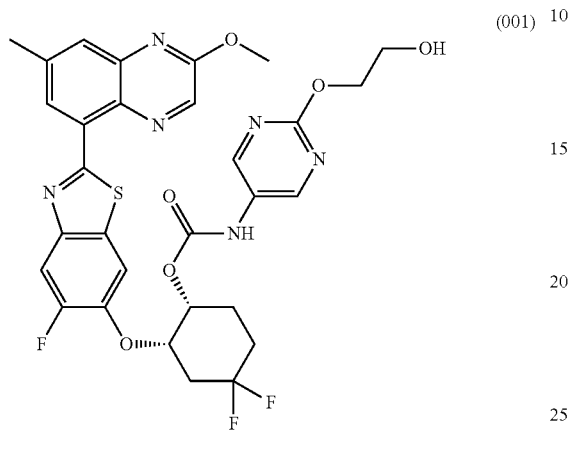

(001)

Example 001A (1R,2S)-4,4-difluoro-2-((5-fluoro-2-(2-methoxy-7-methylquinoxalin-5-yl)benzo[d]thiazol-6-yl)oxy)cyclohexanol

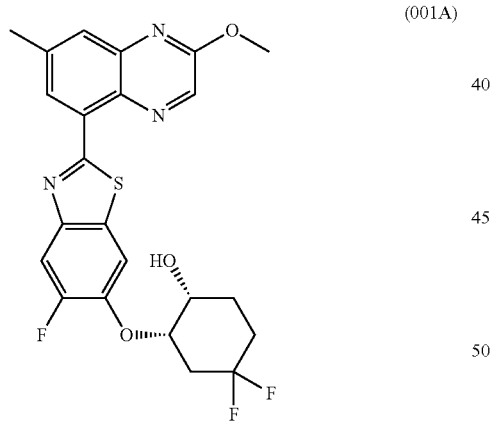

(001A)

In a round bottom flask charged with a stirring bar, I-05 (183 mg, 0.479 mmol) was mixed with I-20 (157 mg, 0.718 mmol) in 1,4-dioxane (2.5 mL). Na$_2$CO$_3$ solution (aq., 1.5 mL, 2M) was added, followed by PdCl$_2$(dppf)-CH$_2$Cl$_2$ adduct (19.55 mg, 0.024 mmol). The mixture was stirred at 90° C. for 30 minutes. After cooling to RT, the reaction mixture was diluted by adding 30 mL of EtOAc and 20 mL of water. After separation, the aqueous layer was extracted with 20 mL of EtOAc. The combined organic phases were washed with brine, dried over Na$_2$SO$_4$, filtered and concentrated. The crude product was purified by silica gel chromatography (SiO$_2$, 0-100% EtOAc/hexane gradient). Removing solvent gave Example 001A (163 mg, 0.343 mmol, 71.6% yield) as a yellow solid. LC-MS: method H, RT=1.25 min, MS (ESI) m/z: 476.1 (M+H)$^+$.

Example 001B (1R,2S)-4,4-difluoro-2-((5-fluoro-2-(2-methoxy-7-methylquinoxalin-5-yl)benzo[d]thiazol-6-yl)oxy)cyclohexyl carbonochloridate

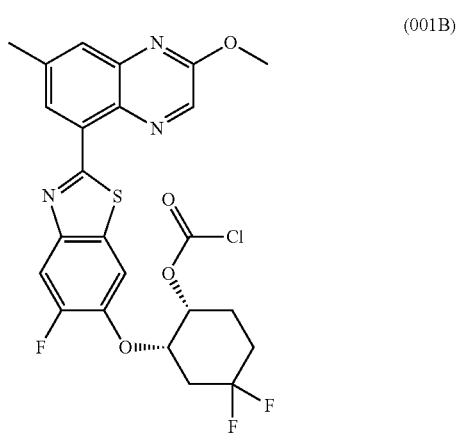 [SMILES: COc1cnc2c(-c3nc4cc(F)c(O[C@H]5CC(F)(F)CC[C@H]5OC(=O)Cl)cc4s3)cc(C)cc2n1]

(001B)

Example 001A (163 mg, 0.343 mmol) was dissolved in anhydrous THF (5 ml) and was treated with phosgene solution in Toluene (2.447 ml, 3.43 mmol), catalyzed by pyridine (27.1 mg, 0.343 mmol). The reaction was stirred at room temperature overnight. On the next day, the solvent was removed. The residue was dried on HVAC and used as crude in the next step. LC-MS: method J, RT=1.17 min, MS (ESI) m/z: 538.0 (M+H)$^+$.

Example 001C (1R,2S)-4,4-difluoro-2-((5-fluoro-2-(2-methoxy-7-methylquinoxalin-5-yl)benzo[d]thiazol-6-yl)oxy)cyclohexyl (2-(2-((tert-butyldimethylsilyl)oxy)ethoxy)pyrimidin-5-yl)carbamate

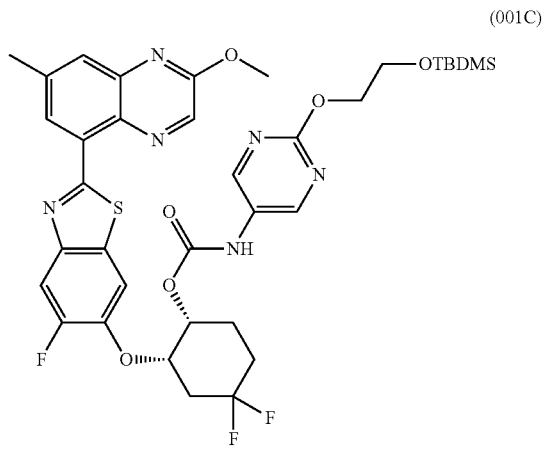 [SMILES: COc1cnc2c(-c3nc4cc(F)c(O[C@H]5CC(F)(F)CC[C@H]5OC(=O)Nc5cnc(OCCO[Si](C)(C)C(C)(C)C)nc5)cc4s3)cc(C)cc2n1]

(001C)

Example 001B (18.83 mg, 0.035 mmol) in anhydrous DCM (1 mL) was added dropwise into the solution of Intermediate I-30 (14.14 mg, 0.053 mmol) and pyridine (5.66 µl, 0.070 mmol) in anhydrous DCM (1 mL). The mixture was stirred at room temperature for 3 hours. Then the reaction mixture was loaded on a silica gel column (12 g silica) and eluted with 0-100% EtOAc/hexane gradient. The desired fractions were collected and evaporated to give cis-4,4-difluoro-2-((5-fluoro-22-(2-methoxy-7-methylquinoxalin-5-yl)benzo[d]thiazol-6-yl)oxy)cyclohexyl (2-(2-((tert-butyldimethylsilyl)oxy)ethoxy)pyrimidin-5-yl)carbamate (18 mg, 0.023 mmol, 66.7% yield) as the title compound. LC-MS: method J, RT=1.36 min, MS (ESI) m/z: 771.0 (M+H)$^+$.

Example 001

Example 001C (18 mg, 0.023 mmol) was dissolved in THF (1 mL) and treated with TBAF solution in TI-HF (0.467 ml, 0.467 mmol) at room temperature for 30 minutes. Then reaction was diluted by adding 20 mL of EtOAc and 10 mL of water. After separation, the organic layer was dried over Na$_2$SO$_4$, filtered and concentrated. The crude product was purified via preparative LC/MS with the following conditions: Column: Waters XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 40-100% B over 20 minutes, then a 5-minute hold at 100% B; Flow: 20 mL/min. Fractions containing the desired product were combined and dried via centrifugal evaporation to give the title compound (8.2 mg, 0.012 mmol, 51% yield). $^1$H NMR (400 MHz, CDCl$_3$) δ ppm 8.65 (2H, s), 8.62 (1H, d, J=1.98 Hz), 8.56 (1H, s), 7.84 (1H, d, J=11.44 Hz), 7.78 (1H, dd, J=1.98, 0.88 Hz), 7.60 (1H, d, J=7.70 Hz), 6.79 (1H, br s), 5.44 (1H, br s), 4.57 (1H, d, J=10.12 Hz), 4.50 (2H, dd, J=5.17, 3.63 Hz), 4.14 (3H, s), 3.96-4.04 (2H, m), 2.66 (3H, s), 2.58 (2H, br s), 2.24-2.36 (1H, m), 2.02-2.19 (2H, m), 1.81-1.94 (1H, m), 1.27 (1H, 1, J=7.15 Hz); $^{19}$F NMR (376 MHz, CDCl$_3$) ppm −95.90 to −80.92 (2F, m), −132.44 (1F, s): LC-MS: method H, RT=1.10 min, MS (ESI) m/z: 657.2 (M+H)$^+$.

Example 002 to 014

The following additional examples have been prepared, isolated and characterized using the methods described for Example 001 and the examples above, from corresponding cyclic diol and aniline intermediates.

| Ex. No. | Structure | Chirality | LCMS [M + H]$^+$ m/z | LCMS RT(Min)/ Method | NMR |
|---|---|---|---|---|---|
| 002 | 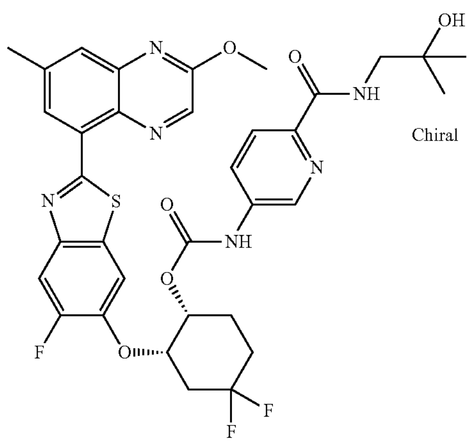 [SMILES: COc1cnc2c(-c3nc4cc(F)c(O[C@H]5CC(F)(F)CC[C@H]5OC(=O)Nc5ccc(C(=O)NCC(C)(C)O)nc5)cc4s3)cc(C)cc2n1] | Chiral (1R,2S) | 711.3 | 2.43/L | $^1$H NMR (500 MHz, DMSO-d$_6$) δ ppm 10.24 (1 H, br s), 8.59 (1 H, s), 8.56 (1 H, s), 8.42 (1 H, s), 8.27 (1 H, t, J = 5.95 Hz), 7.94-8.07 (2 H, m), 7.88-7.94 (1 H, m), 7.84 (1 H, d = 11.29 Hz), 7.71 (1H, s), 5.33 (1 H, br s), 4.89 (1 H, br s), 4.02 (3 H, s), 3.21 (2 H, d, J = 6.41 Hz), 2.55 (3 H, s), 2.45-2.50 (3 H, m), 2.11 (3 H, d, J = 19.53 Hz), 1.93 (1 H, m.), 1.06 (6 H, s); $^{19}$F NMR (471 MHz, DMSO-d$_6$) δ ppm −88.41 (2 F, m), −133.09 (1 F, br s) |
| 003 | 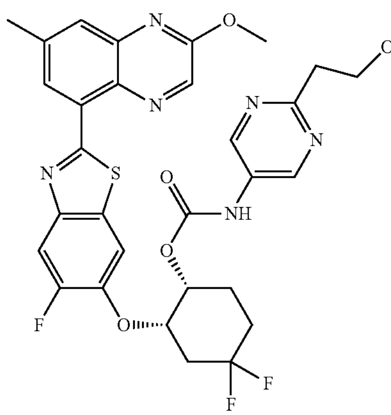 | Chiral (1R,2S) | 641.1 | 1.13/H | $^1$H NMR (400 MHz, dioxane-d$_8$) δ ppm 10.76 (1 H, s), 8.72 (2 H, s), 8,70 (1H, d, J = 1.98 Hz), 8.59 (1 H, s), 7.87 (1 H, d, J = 11.44 Hz), 7.79 (1 H, dd, J = 1.98, 0.88 Hz), 7.73 (1 H, d, J = 8.14 Hz), 5.36 (1 H, br s), 4.73 (1 H, br s), 4.09 (3 H, s), 3.89 (3 H, q, J = 6.16 Hz), 3.43 (1 H, t, J = 5.94 Hz), 3.01 (2 H, t, J = 6.38 Hz), 2.63 (3 H, s), 2.24-2.36 (1 H, m), 1.99-2.23 (2 H, m), 1.75-1.94 (1 H, m); $^{19}$F NMR (376 MHz, dioxane-d$_8$) δ ppm −101.89 to −86.66 (2 F, m), −134.17 (1 F, br s) |

-continued

| Ex. No. | Structure | Chirality | LCMS [M + H]+ m/z | LCMS RT(Min)/ Method | NMR |
|---|---|---|---|---|---|
| 004 | 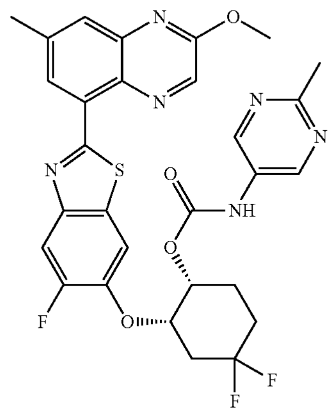 | (1R,2S) | 611.3 | 1.18/H | ¹H NMR (400 MHz CDCl₃) δ ppm 8.80 (2 H, s), 8.63 (1 H, d, J = 1.76 Hz), 8.56 (1 H, s), 7.75-7.88 (2 H, m), 7.61 (1 H, d = 7.70 Hz), 6.73 (1 H, br s), 5.46 (1 H, br s), 4.57 (1 H, d, J = 10.34 Hz), 4.14 (3 H, s), 2.73 (3 H, s), 2.66 (3 H, s), 2.59 (1 H, br s), 2.37-2.54 (1 H, m), 2.23-2.37 (1 H, m), 2.09 (2 H, br s), 1.90 (1 H, d, J = 15.85 Hz); ¹⁹F NMR (376 MHz, CDCl₃) δ ppm −94.40 to −84.41 (2 F, m), −132.34 (1 F, s) |
| 005 | 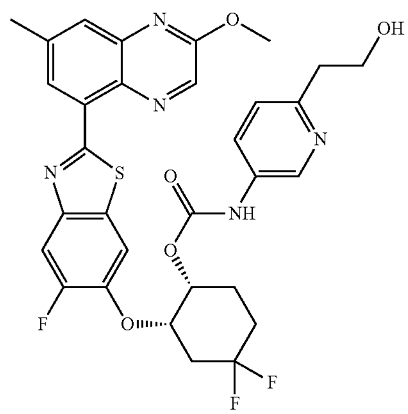 [SMILES: COc1cnc2c(-c3nc4cc(F)c(O[C@H]5CC(F)(F)CC[C@H]5OC(=O)Nc5ccc(CCO)nc5)cc4s3)cc(C)cc2n1] | (1R,2S) | 640.15 | 2.06/L | ¹H NMR (500 MHz, DMSO-d₆) δ ppm 10.30 (1 H, br s), 8.60-8.68 (2 H, m), 8.49 (1 H, s), 8.09 (1H, d, J = 8.24 Hz), 8.02 (1 H, d, J = 8.54 Hz), 7.90 (1 H, d, J = 11.29 Hz), 7.77 (1 H, s), 7.54 (1 H, d, J = 8.54 Hz), 5.36 (1 H, br s), 4.88 (1 H, br s), 4.05 (3 H, s), 3.70 (2 H, t, J = 6.26 Hz), 2.89 (2 H, t, J = 6.26 Hz), 2.59 (3 H, s), 2.54 (3 H. s), 2.01-2.20 (3 H, m), 1.95 (1 H, m); ¹⁹F NMR (471 MHz, DMSO-d₆) δ ppm −87.3 (2F, m), −133.22 (1F, br s) |
| 006 | 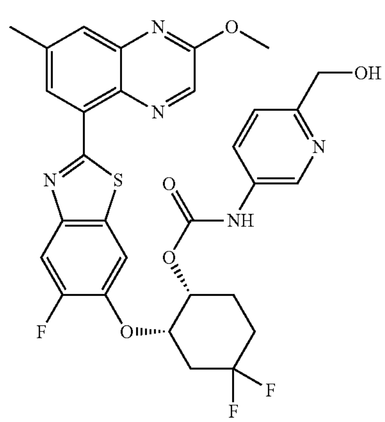 [SMILES: COc1cnc2c(-c3nc4cc(F)c(O[C@H]5CC(F)(F)CC[C@H]5OC(=O)Nc5ccc(CO)nc5)cc4s3)cc(C)cc2n1] | (1R,2S) | 626.15 | 2.124/L | ¹H NMR (500 MHz, DMSO-d₆) δ ppm 9.95 (1 H, br s), 8.58 (1 H, s), 8.49 (1 H, br s), 8.43 (1 H, s), 8.02 (1 H, d, J = 8.24 Hz), 7.80-7.88 (2 H, m), 7.72 (1 H, s), 7.38 (1H, d, J = 8.54 Hz), 5.33 (1 H, br s), 4.84 (1 H, br s), 4.46 (2 H, s), 4.02 (3 H, s), 2.55 (3 H, s), 2.54 (3 H, m), 2.09 (3 H, m), 1.92 (1 H, m); ¹⁹F NMR (471 MHz, DMSO-d₆) δ ppm −87.42 (2 F, m), −133.14 (1 F, br s) |

-continued

| Ex. No. | Structure | Chirality | LCMS [M + H]+ m/z | LCMS RT(Min)/ Method | NMR |
|---|---|---|---|---|---|
| 007 | 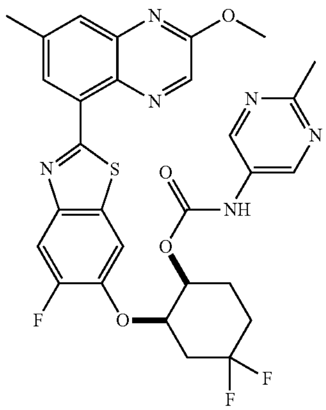 | racemic (from I-04) | 611.1 | 1.23/H | ¹H NMR (400 MHz, CDCl₃) δ 8.80 (s, 2H), 8.62 (d, J = 1.8 Hz, 1 H), 8.55 (s, 1 H), 7.83 (d, J = 11.2 Hz, 1 H), 7.78 (s, 1 H), 7.60 (d, J = 7.7 Hz, 1 H), 6.77 (br s, 1 H), 5.45 (br s, 1 H), 4.56 (d, J = 9.9 Hz, 1 H), 4.14 (s, 3H), 2.73 (s, 3H), 2.66 (s, 3H), 2.59 (d, J = 9.7 Hz, 1 H), 2.40 (br s, 1 H), 2.35-2.22 (m, 1 H), 2.09 (d, J = 8.4 Hz, 2H), 1.94-1.80 (m, 1H); ¹⁹F NMR (376 MHz, CDCl₃) δ −83.85 to −94.63 (d, 2F), −132.35 (s, 1 F) |
| 008 | 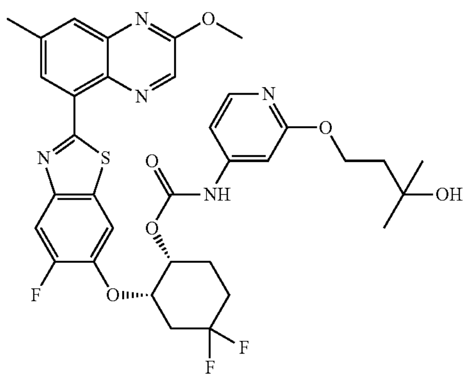 [SMILES: COc1cnc2c(-c3nc4cc(F)c(O[C@H]5CC(F)(F)CC[C@H]5OC(=O)Nc5ccnc(OCCC(C)(C)O)c5)cc4s3)cc(C)cc2n1] | (1R,2S) | 698.30 | 2.24/L | ¹H NMR (500 MHz, DMSO-d₆) δ ppm 10.14 (1 H, br s), 8.72 (1 H, s), 8.56 (1 H, d, J = 1.65 Hz), 8.13 (1 H, d, J = 8.25 Hz), 7.90-7.99 (2 H, m), 7.82 (1 H, d, J = 0.83 Hz), 6.95 (1 H, dd, J = 5.78, 1.65 Hz), 6.84 (1 H, d, J = 1.38 Hz), 5.36 (1 H, br s), 4.89 (1 H, d, J = 4.68 Hz), 4.27 (3 H, t, J = 7.29 Hz), 4.07 (3 H, s), 2.62 (3 H, s), 2.54 (2 H, s), 2.04-2.23 (3 H, m), 1.88-2.00 (1 H, m), 1.74-1.79 (2 H, m), 1.12 (6 H, s); ¹⁹F NMR (471 MHz, DMSO-d₆) δ ppm −88.93 to −87.12 (2 F, m), −133.13 (1 F, s) |
| 009 | 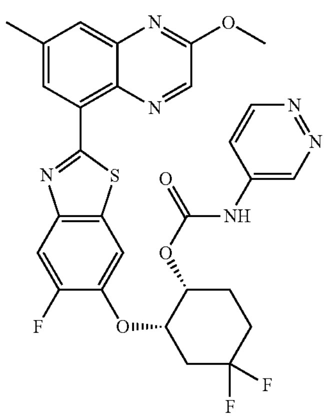 [SMILES: COc1cnc2c(-c3nc4cc(F)c(O[C@H]5CC(F)(F)CC[C@H]5OC(=O)Nc5ccnnc5)cc4s3)cc(C)cc2n1] | (1R,2S) | 597.15 | 2.11/L | ¹H NMR (500 MHz, DMS-d₆) δ ppm 9.17 (1 H, s), 9.01 (1 H, d, J = 6.10 Hz), 8.67 (1 H, s), 8.51 (1 H, s), 8.10 (1 H, d, J = 7.93 Hz), 7.91 (1 H, d, J = 11 .60 Hz), 7.79 (2 H, br s), 5.39 (1 H, br s), 4.90 (1 H, br s), 4.05 (3 H, s), 2.59 (3 H, s), 2.54 (3 H, s), 2.14 (3 H, br s), 1.96 (1 H, br s) |

-continued

| Ex. No. | Structure | Chirality | LCMS [M + H]+ m/z | LCMS RT(Min)/ Method | NMR |
|---|---|---|---|---|---|
| 010 | 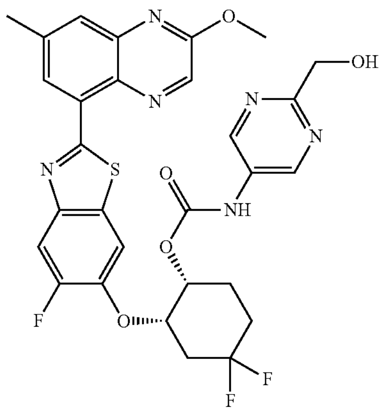 [SMILES: COc1cnc2c(-c3nc4cc(F)c(O[C@H]5CC(F)(F)CC[C@H]5OC(=O)Nc5cnc(CO)nc5)cc4s3)cc(C)cc2n1] | (1R,2S) | 627.15 | 2.28/L | ¹H NMR (500 MHz DMSO-d₆) δ ppm 10.14 (1 H, br s), 8.80 (2 H, s), 8.73 (1 H, s), 8.57 (1 H, d, J = 1.93 Hz), 8.15 (1 H, d, J = 7.98 Hz), 7.95 (1 H, d, J = 11.55 Hz), 7.84 (1 H, dd, J = 1.93, 0.83 Hz), 5.37 (1 H, br s), 5.21 (1 H, t, J = 6.19 Hz), 4.85-4.97 (1 H, m), 4.51 (2 H, d, J = 6.33 Hz), 4.08 (3 H, s), 2.63 (3 H, s), 2.55-2.60 (2 H, m), 2.02-2.21 (3 H, m) 1.91-2.00 (1 H, m) ¹⁹F NMR (471 MHz, DMSO-d₆) δ ppm −88.7 (2 F, m), −133.23 (1 F, s) |
| 011 | 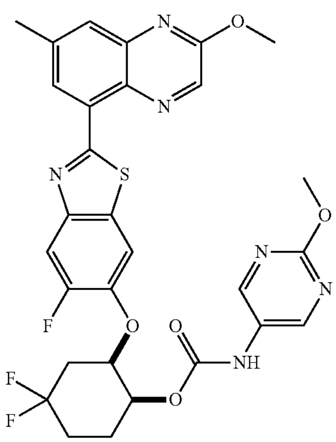 | racemic (from I-04) | 627.30 | 2.52/L | ¹H NMR (500 MHz, DMSO-d₆) δ ppm 9.75-10.00 (1 H, m), 8.69 (1H, s), 8.59 (2 H, br s), 8.54 (1 H, s), 8.11 (1 H, d, J = 7.93 Hz), 7.94 (1 H, d, J = 11.60 Hz), 7.80 (1 H, s), 5.33 (1 H, br s), 4.90 (1 H, br s), 4.07 (3 H, s), 3.83 (3 H, s), 2.61 (3 H, s), 2.02-2.23 (3 H, m), 1.94 (1 H, d, J = 8.54 Hz); ¹⁹F NMR (471 MHz, DMSO-d₆) δ ppm −87.98 (2 F, m), −133.18 (1 F, br s) |
| 012 | 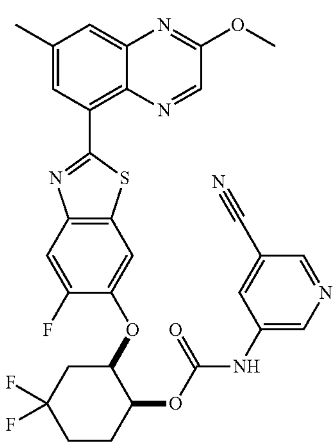 | racemic (from I-04) | 621.30 | 2.57/L | ¹H NMR (500 MHz, DMSO-d₆) δ ppm 10.36 (1 H, br s), 8.70 (2 H, s), 8.54 (1 H, s), 8.21 (1 H, br s), 8.12 (1 H, d, J = 7.93 Hz), 7.93 (1 H, d, J = 11.29 Hz), 7.81 (1 H, s), 5.36 (1 H, br s), 4.93 (1 H, br s), 4.07 (3 H, s), 3.36 (1 H, d, J = 3.66 Hz), 2.61 (3 H, s), 2.15 (3 H, br s), 1.95 (1 H, br s); ¹⁹F NMR (471 MHz, DMSO-d₆) δ ppm −84.8 (2 F, m), −133.15 (1 F, br s) |

-continued

| Ex. No. | Structure | Chirality | LCMS [M + H]+ m/z | LCMS RT(Min)/ Method | NMR |
|---|---|---|---|---|---|
| 013 | 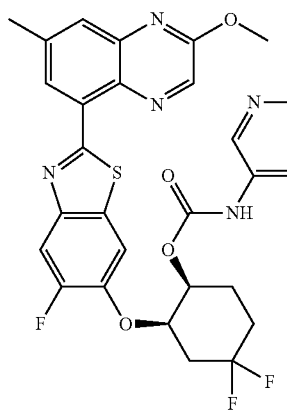 | Chiral (1S,2R) | 611.2 | 1.18/H | ¹H NMR (400 MHz, CDCl₃) δ ppm 8.80 (2 H, s), 8.63 (1 H, d, J = 1.54 Hz), 8.56 (1 H, s), 7.75-7.87 (2 H, m), 7.61 (1 H, d, J = 7.70 Hz), 6.71 (1 H, br s), 5.46 (1 H, br s), 4.56 (1 H, br s), 4.14 (3 H, s), 2.73 (3 H, s), 2.66 (3 H, s), 2.37-2.63 (2 H, m), 2.28 (1 H, br s), 2.09 (2 H, br s), 1.80-1.95 (1 H, m); ¹⁹F NMR (376 MHz, CDCl₃) δ ppm −90.12 (2 F, br s), −132.33 (1 F, s) |
| 014 | 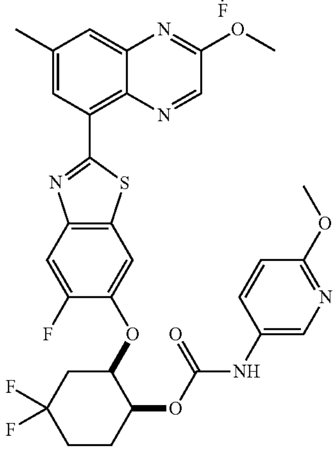 | racemic (from I-104) | 626.25 | 2.57/L | ¹H NMR (500 MHz, DMSO-d₆) δ ppm 9.70 (1 H, br s), 8.70 (1 H, s), 8.54 (1 H, s), 8.17 (1 H, br s), 8.11 (1 H, d, J = 8.24 Hz), 7.94 (1 H, d, J = 11.60 Hz), 7.81 (1 H, s), 7.73 (1 H, d, J = 7.63 Hz), 6.75 (1 H, d, J = 8.85 Hz), 5.33 (1 H, br s), 4.88 (1 H, br s), 4.07 (3 H, s), 3.76 (3 H, s), 3.35 (1 H, d, J = 11.29 Hz), 2.61 (3 H, s), 2.02-2.19 (3 H, m), 1.92 (1 H, br s); ¹⁹F NMR (471 MHz, DMSO-d₆) δ ppm −88.0 (2 F, m), −133.14 (1 F, br s) |

Example 015

(1R, 2S)-4,4-difluoro-2-((5-fluoro-2-(3-methoxy-6-methylquinolin-8-yl)benzo[d]thiazol-6-yl)oxy)cyclohexyl (2-(2-hydroxyethoxy)pyrimidin-5-yl)carbamate

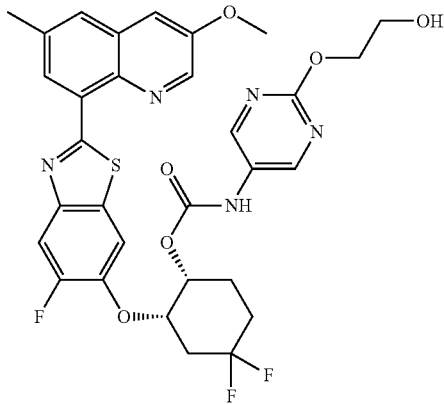 [SMILES: COc1cnc2c(-c3nc4cc(F)c(O[C@H]5CC(F)(F)CC[C@H]5OC(=O)Nc5cnc(OCCO)nc5)cc4s3)cc(C)cc2c1]

Example 015 was prepared, isolated and characterized using the methods described for Example 001 and the examples above, from Intermediate I-28 instead of I-20, ¹H NMR (500 MHz, DMSO-d₆) ppm 9.77-1.01 (1H, m), 8.78 (1H, br s), 8.59 (3H, m), 8.12 (1H, d, J=1.63 Hz), 7.93 (1H, d, J=11.29 Hz) 7.86 (2H, d, J=3.36 Hz), 5.34 (1H, m), 4.89 (1H, m.), 4.23 (2H, m.), 3.98 (3H, s), 3.67 (2H, m), 2.60 (3H, s), 2.54 (3H, m), 2.13 (3H, m.), 1.94 (1H, m.); ¹⁹F NMR (471 MHz, DMSO-d₆) ppm −96.82 to −85.75 (2F, m), −133.46 (1F, s); LC-MS: method L, RT=1.92 min, MS (ESI) m/z: 656.25 (M+H)⁺.

Example 016

(1R,2S)-2-((2-(6-chloro-3-methoxyquinolin-8-yl)-5-fluorobenzo[d]thiazol-6-yl)oxy)-4,4-difluorocyclohexyl (2-(2-hydroxyethoxy)pyrimidin-5-yl)carbamate

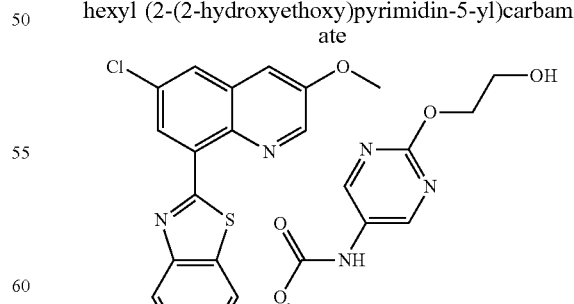

Example 016 was prepared, isolated and characterized using the methods described for Example 001 and the examples above, from Intermediate I-29 instead of I-20. $^1$H NMR (400 MHz, DMSO-d$_6$) ppm 9.86-9.99 (1H, m), 8.90 (1H, d, J=2.86 Hz), 8.64 (1H, d, J=2.42 Hz), 8.58 (2H, s), 8.22 (1H, d, J=2.42 Hz), 8.17 (1H, d, J=8.14 Hz), 7.93-8.06 (2H, m), 5.34 (1H, br s), 4.92 (1H, br s), 4.86 (1H, t, J=5.61 Hz), 4.21 (2H, t, J=4.95 Hz), 4.00 (3H, s), 3.62-3.71 (2H, m), 2.55 (2H, d, J=1.98 Hz), 2.03-2.21 (3H, m), 1.84-2.00 (1H, m); $^{19}$F NMR (376 MHz, DMSO-d$_6$) ppm −88.51 to −90.36 (2F, m), −133.05 (1F, br s); LC-MS: method H, RT=1.14 min, MS (ESI) m/z: 676.1 (M+H)$^+$.

Example 017

(1R,2S)-2-((2-(6-chloro-3-methoxyquinolin-8-yl)-5-fluorobenzo[d]thiazol-6-yl)oxy)-4,4-difluorocyclohexyl (2-methylpyrimidin-5-yl)carbamate

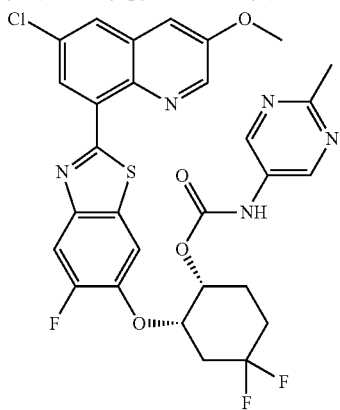 [SMILES: COc1cnc2c(-c3nc4cc(F)c(O[C@H]5CC(F)(F)CC[C@H]5OC(=O)Nc5cnc(C)nc5)cc4s3)cc(Cl)cc2c1]

Example 017 was prepared, isolated and characterized using the methods described for Example 001 and the examples above, from Intermediate I-29 instead of I-20. $^1$H NMR (500 MHz, DMSO-d$_6$) δ 10.03 (br s, 1H), 8.87 (br s, 1H), 8.70 (br s, 2H), 8.62 (s, 1H), 8.19 (s, 1H), 8.15 (d, J=7.9 Hz, 1H), 8.02-7.89 (m, 2H), 5.35 (br s, 1H), 4.92 (br s, 1H), 3.99 (s, 3H), 2.62-2.56 (min, 2H), 2.54 (s, 3H), 2.15 (br s, 3H), 1.95 (d, J=6.7 Hz, 1H); $^{19}$F NMR (471 MHz, DMSO-d$_6$) δ ppm −89.30 to −86.27 (1F, m), −96.31 to −92.88 (1F, m), −133.04 (1F, br s); LC-MS: method L, RT=2.38 min, MS (ESI) m/z: 630.1 (M+H)$^+$.

Example 018

(1R,2S)-2-((2-(2-ethoxy-7-methylquinoxalin-5-yl)-5-fluorobenzo[d]thiazol-6-yl)oxy)-4,4-difluorocyclohexyl (2-methylpyrimidin-5-yl)carbamate

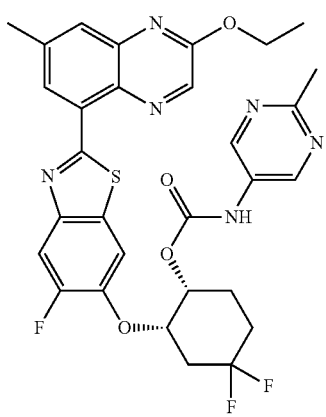

Example 018A (1R,2S)-2-((2-(2-(difluoromethoxy)-7-methylquinoxalin-5-yl)-5-fluorobenzo[d]thiazol-6-yl)oxy)-4,4-difluorocyclohexanol

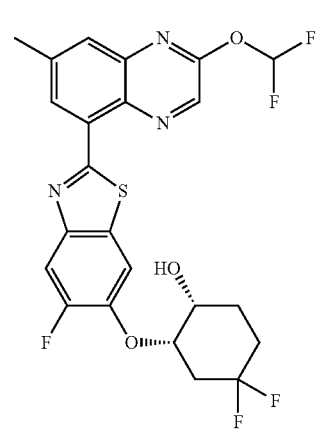

In a vial charged with a stirring bar, I-05 (25 mg, 0.065 mmol) was mixed with I-23 (19.94 mg, 0.078 mmol) in 1,4-dioxane (1 mL). Na$_2$CO$_3$ (0.5 ml, 1.000 mmol) aq. solution was added, followed by PdCl$_2$(dppf)-CH$_2$Cl$_2$ adduct (5.34 mg, 6.54 µmol). The mixture was stirred at 90° C. for 1 hour. After cooling to RT, the organic phase was taken out and evaporated. The residue was purified by flash chromatography (12 g silica column, 0-100% EtOAc/hexane). The desired fractions were evaporated to give 018A (28 mg, 0.055 mmol, 84% yield) as a yellow solid. LC-MS: method H, RT=1.21 min, MS (ESI) m/z: 512.1 (M+H)$^+$.

Example 018B (1R,2S)-2-((2-(2-ethoxy-7-methylquinoxalin-5-yl)-5-fluorobenzo[d]thiazol-6-yl)oxy)-4,4-difluorocyclohexanol

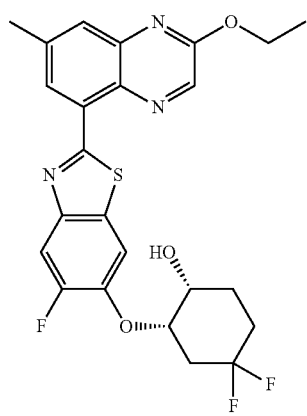

To THF (2 mL)/ethanol (2 mL) was added NaH (5.32 mg, 0.133 mmol, 60%) slowly. After bubbling stopped, intermediate 018A (34 mg, 0.066 mmol) in THF (1 mL) was added. The mixture was stirred at room temperature for 3 hours.

Example 018C (1R,2S)-2-((2-(2-ethoxy-7-methylquinoxalin-5-yl)-5-fluorobenzo[d]thiazol-6-yl)oxy)-4,4-difluorocyclohexyl carbonochloridate

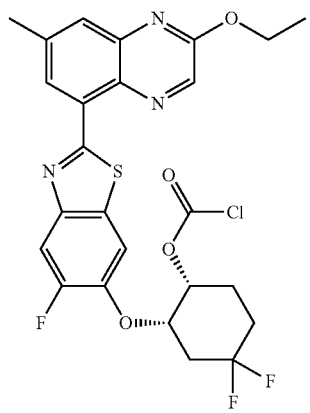

(018C)

In a vial charged with a stirring bar, Intermediate 018B (25 mg, 0.051 mmol) was dissolved in anhydrous THF (2 mL) and treated with phosgene (0.364 mL, 0.511 mmol) in toluene. Pyridine (8.26 µl, 0.102 mmol) was added. The mixture was stirred at room temperature for 18 hours. On the next day, the solvent was removed and the crude product was used without purification in the next step. LC-MS: method J, RT=1.25 min, MS (ESI) m/z: 552.1 (M+H)⁺.

Example 018

In a vial charged with a stirring bar, Intermediate 018C (22.5 mg, 0.041 mmol) was dissolved in DCM (2 mL). 2-methylpyrimidin-5-amine (17.79 mg, 0.163 mmol) was added, followed by pyridine (0.016 mL, 0.204 mmol). The mixture was stirred at room temperature for 1 hour. The crude material was purified via preparative LC/MS Method C: Fractions containing the desired product were combined and dried via centrifugal evaporation to give Example 018 (8.0 mg, 0.013 mmol, 31.4% yield) as the title compound. $^1$H NMR (500 MHz, CDCl$_3$) δ ppm 8.83 (2H, s), 8.57 (1H, d, J=1.65 Hz), 8.49 (1H, s), 7.80 (2H, d, J=11.28 Hz), 7.71 (1H, s), 7.57 (1H, d, J=7.70 Hz), 5.42 (1H, br s), 4.56 (3H, q, J=6.97 Hz), 2.71 (3H, s), 2.62-2.63 (3H, m), 2.51-2.59 (1H, m), 2.36-2.51 (1H, m), 2.29 (1H, d, J=14.31 Hz), 2.06 (2H, br s), 1.85 (1H, br s), 1.50 (3H, t, J=7.02 Hz); $^{19}$F NMR (471 MHz, CDCl$_3$) δ ppm −100.34 to −72.99 (2F, m), −132.45 (1F, d, J=8.58 Hz); LC-MS: method L, RT=2.53 min, MS (ESI) m/z: 625.15 (M+H)⁺.

Example 019

(1R,2S)-4,4-difluoro-2-((5-fluoro-2-(2-methoxy-7-methylquinoxalin-5-yl)benzo[d]thiazol-6-yl)oxy)cyclohexyl (2-(2-(phosphonooxy)ethoxy)pyrimidin-5-yl)carbamate

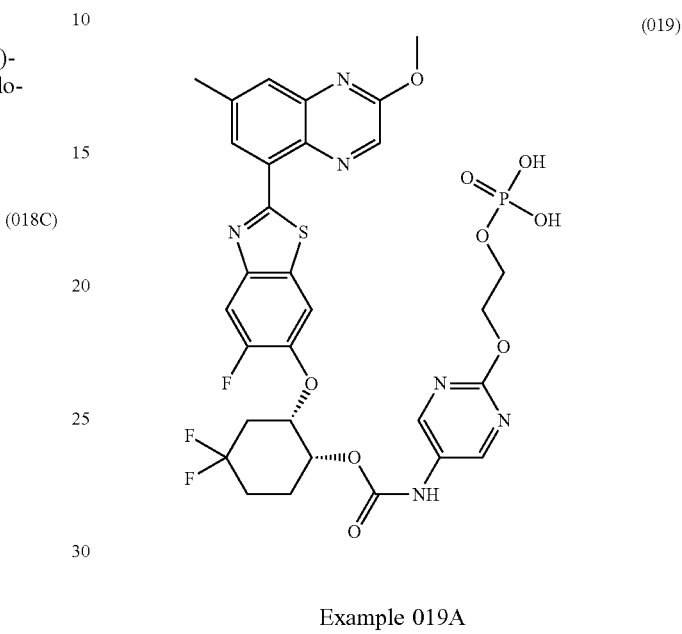

(019)

Example 019A (1R,2S)-4,4-difluoro-2-((5-fluoro-2-(2-methoxy-7-methylquinoxalin-5-yl)benzo[d]thiazol-6-yl)oxy)cyclohexyl (2-(2-((bis(2-(trimethylsilyl)ethoxy)phosphoryl)oxy)ethoxy) pyrimidin-5-yl)carbamate

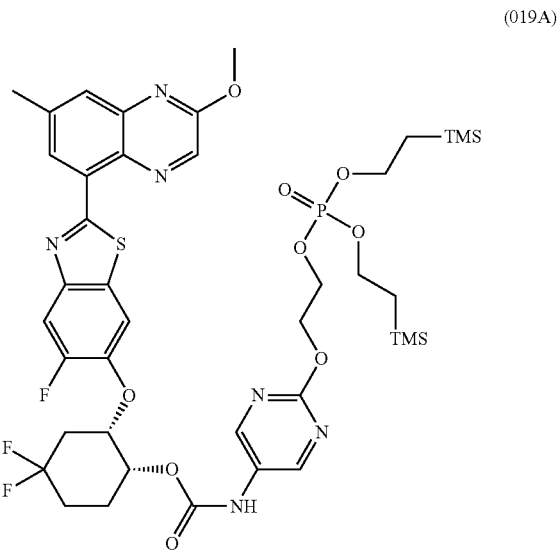 [SMILES: COc1cnc2c(-c3nc4cc(F)c(O[C@H]5CC(F)(F)CC[C@H]5OC(=O)Nc5cnc(OCCOP(=O)(OCC[Si](C)(C)C)OCC[Si](C)(C)C)nc5)cc4s3)cc(C)cc2n1]

(019A)

To a suspension solution of Example 001 (362 mg, 0.551 mmol) in anhydrous DCM (40 mL) was added bis-(2-(trimethylsilyl)ethyl) diisopropylphosphoramidite (0.416 mL, 1.654 mmol) followed by 1H-tetrazole (116 mg, 1.654 mmol) at RT. After 30 min, the reaction was cooled to 0° C. and hydrogen peroxide (0.536 mL, 5.51 mmol) was added. The reaction mixture was allowed to warm to room temperature and the solution cleared up. After 30 minutes, the reaction mixture was diluted with EtOAc, and washed with Sat. $Na_2S_2O_3$. The organic phase was dried over anhydrous $Na_2SO_4$, filtered and concentrated. The crude product was added to a silica gel (40 g) column (pre-flushed with 1% TEA/Hexane) and eluted with 0-100% EtOAc/DCM Collected fractions were evaporated to give Example 019A (301 mg, 0.321 mmol, 58.3% yield) as the product. LC-MS: method H, RT=1.40 min, MS (ESI) m/z: 937.2 (M+H)$^+$.

Example 019

To a solution of intermediate 019A (300 mg, 0.320 mmol) in DCM (5 mL) was added TFA (1 mL, 12.98 mmol). The mixture was stirred at room temperature for 10 minutes. Then the solvent was removed and the residue was purified by preparative HPLC, Method B. The collected fractions were evaporated and freeze-dried to give Example 019 (120 mg, 0.160 mmol, 49.9% yield) as a white solid. $^1$H NMR (400 MHz, DMSO-$d_6$) δ ppm 9.97 (1H, br s), 8.74 (1H, s), 8.61 (2H, br s), 8.57 (1H, d, J=1.76 Hz), 8.15 (1H, d, J=8.14 Hz), 7.97 (1H, d, J=11.66 Hz), 7.84 (1H, s), 5.35 (1H, br s), 4.79-5.03 (1H, m), 4.37 (2H, br s), 4.09 (5H, s), 3.34 (7H, br s), 2.02-2.29 (3H, m), 1.69-1.99 (1H, m); $^{19}$F NMR (376 MHz, DMSO-$d_6$) δ ppm −98.15 to −83.91 (2F, m), −133.18 (1F, s); LC-MS: method H, RT=1.07 min, MS (ESI) m/z: 736.9 (M+H)$^+$.

Example 020 rac-(cis)-4,4-difluoro-2-((5-fluoro-2-(2-methoxy-7-methylquinoxalin-5-yl)benzo[d]thiazol-6-yl)oxy)cyclohexyl (2-(2-(phosphonooxy)ethoxy)pyrimidin-5-yl)carbamate

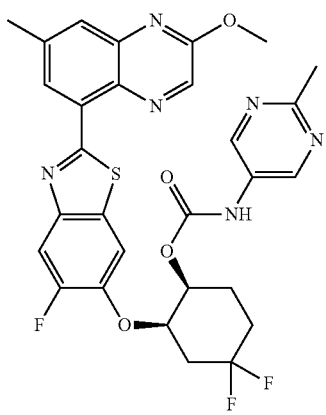

(020)

Example 020A 2-((2-amino-6-fluorothiazolo[5,4-b]pyridin-5-yl)oxy)-4,4-difluorocyclohexanone

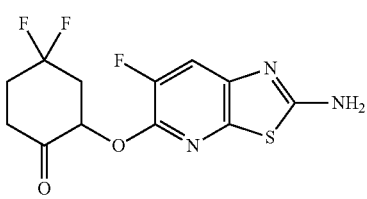

(020A)

In a round bottom flask charged with a stirring bar, Intermediate I-22 (200 mg, 0.576 mmol) was dissolved in DMF (5 mL). $K_2CO_3$ (319 mg, 2.305 mmol) was added. The mixture was stirred at room temperature for 10 minutes, then 2-chloro-4,4-difluorocyclohexanone (486 mg, 2.88 tool) was added. The mixture was stirred at 70° C. for 3 hours. After cooling to RT, the reaction was diluted by adding 40 mL of EtOAc and 20 mL of water After separation, the aq. layer was extracted by EtOAc (20 mL×2). The combined organic phases were washed with brine, dried over $Na_2SO_4$, filtered and concentrated. The residue was purified by flash chromatography (24 g silica gel, 0-100% EtOAc/DCM). Removing solvent gave Example 020A (146 mg, 0.460 mmol, 80% yield) as product. LC-MS: method H, RT=0.79 min, MS (ESI) m/z: 318.1 (M+H)$^+$.

Example 020B 2-((2-chloro-6-fluorothiazolo[5,4-b]pyridin-5-yl)oxy)-4,4-difluorocyclohexanone

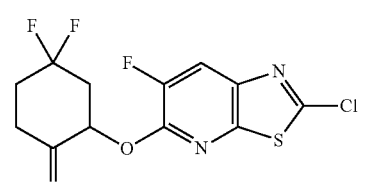

(020B)

In a round bottom flask charged with a stirring bar, copper(II) chloride (93 mg, 0.690 mmol) and tert-butyl nitrite (71.2 mg, 0.690 mmol) were dissolved in anhydrous acetonitrile (2 ml) and allowed to stir 10 minutes. Example 020A (146 mg, 0.460 mmol) was dissolved in acetonitrile (3 mL) to which the copper solution mixture was added. After stirring for 4 hours, the reaction was diluted by adding EtOAc, washed with sat. $NH_4Cl$, saturated $NaHCO_3$, then brine, dried on $Na_2SO_4$, filtered, and concentrated in vacuo. The crude product was purified by silica gel chromatography (24 g column, 0-100% EtOAc/hexane, then 0-10% MeOH/DCM). The desired fractions were collected the solvent removed to give Example 020B (63 mg, 0.187 mmol, 40.7% yield) as the product. LC-MS: method H, RT=1.07 min, MS (ESI) m/z: 337.1 (M+H)$^+$.

Example 020C rac-cis-2-((2-chloro-6-fluorothiazolo[5,4-b]pyridin-5-yl)oxy)-4,4-difluorocyclohexanol

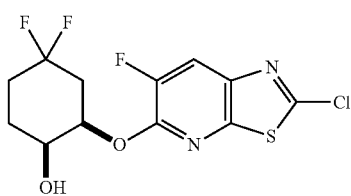

(020C)

In a round bottom flask charged with a stirring bar, Example 020B (63 mg, 0.187 mmol) was dissolved in anhydrous THF (5 ml) under N$_2$ and was cooled to −78° C. L-Selectride (0.187 ml, 0.187 mmol) was added dropwise. The mixture was stirred at −78° C. for 3 hours. Then the reaction was allowed to warm to RT, quenched by adding 5 mL of sat. NH$_4$Cl (aq.) solution, extracted by EtOAc (20 mL×3). The combined organic phases were washed with brine, dried over Na$_2$SO$_4$, filtered and concentrated to give crude Example 020C (59 mg, 0.174 mmol, 93% yield) as oil.

LC-MS: method H, RT=1.04 min, MS (ESI) m/z: 339.0 (M+H)$^+$.

Example 020D rac-cis-4,4-difluoro-2-((6-fluoro-2-(2-methoxy-7-methylquinoxalin-5-yl)thiazolo[5,4-b]pyridin-5-yl)oxy)cyclohexanol

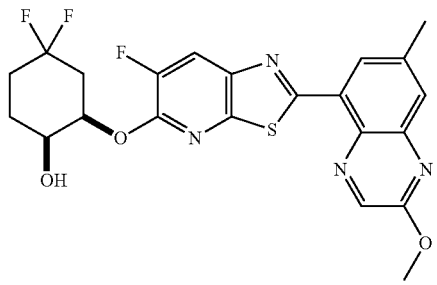

(020D)

In a vial charged with a stirring bar, Example 020C (59 mg, 0.174 mmol) was mixed with I-20 in 1,4-dioxane (2 mL). Aqueous Na$_2$CO$_3$ (0.5 mL, 2M) solution was added, followed by PdCl$_2$(dppf)-CH$_2$Cl$_2$ adduct (7.11 mg, 8.71 μmol). The mixture was stirred at 100° C. for 1 hour. After cooling to RT, the reaction was diluted by adding 20 mL of EtOAc and 10 mL of water. After separation, aqueous layer was extracted by EtOAc twice (10 mL×2). The combined organic phases were washed with brine, dried over Na$_2$SO$_4$, filtered and concentrated. The crude product was purified by silica gel chromatography (12 silica gel column, 0-100% EtOAc/hexane, hold 100% EtOAc for 5 minutes.) The desired fractions were removed the solvent to give Example 020D (29 mg, 0.061 mmol, 34.9% yield) as product. LC-MS: method H, RT=1.30 min, MS (ESI) m/z: 477.1 (M+H)$^+$.

Example 020

Example 020D (29 mg, 0.061 mmol) was dissolved in anhydrous THF (3 ml) and was treated with phosgene (0.434 ml, 0.609 mmol) at room temperature for 4 days. Then solvent was removed and the residue was dissolved in DCM (3 mL). 2-methylpyrimidin-5-amine (26.6 mg, 0.243 mmol) was added, followed by pyridine (0.025 ml, 0.304 mmol). The mixture was stirred at room temperature for 2 hours. The solvent was removed in vacuo and residue was purified on preparative HPLC with method D and dried to give Example 020 (5.5 mg, 0.008 mmol, 14.5%) as the product $^1$H NMR (500 MHz, DMSO-d$_6$) δ ppm 9.95 (1H, br s), 8.64 (2H, m), 8.56 (1H, s), 8.42 (1H, s), 8.34 (1H, d, J=10.68 Hz), 7.75 (1H, s), 5.65 (1H, m), 5.36 (1H, m), 4.04 (3H, s), 2.62 (2H, d, J=13.73 Hz), 2.57 (3H, s), 2.43 (3H, s), 2.16 (3H, m), 1.95 (1H, m.): $^{19}$F NMR (471 MHz, DMSO-d$_6$) δ ppm −88.9 (2F, m), −139.81 (1F, br s); LC-MS: method L, RT=2.483 min, MS (ESI) m/z: 612.30 (M+H)$^+$.

Example 021 rac-cis-2-((5-fluoro-2-(2-methoxy-7-methylquinoxalin-5-yl)benzo[c]thiazol-6-yl)oxy)cyclopentanol

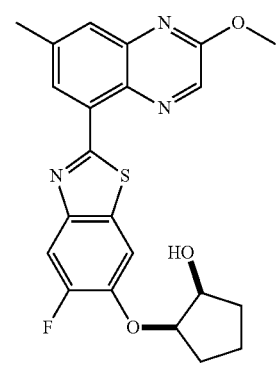

(021)

Example 021 (557 mg, 1.309 mmol, 64.0% yield) was made from I-20 (491 mg, 2,252 mmol) and I-01 (680 mg, 2.047 mmol) via the procedure described for Example 001A as a yellow solid. $^1$H NMR (400 MHz, DMSO-d$_6$) δ 8.98 (s, 1H), 8.89 (d, J=1.8 Hz, 1H), 8.56 (d, J=2.0 Hz, 1H), 8.04 (d, J=8.4 Hz, 1H), 8.00 (d, (d, J=11.7 Hz, 1H), 4.73 (d, J=5.1 Hz, 1H), 4.69 (m, 1H), 4.29-4.21 (m, 1H), 4.14 (s, 3H), 2.10-2.01 (m, 1H), 1.93-1.76 (m, 3H), 1.72 (m, 1H), 1.56 (m, 1H); $^{19}$F NMR (376 MHz, DMSO-d$_6$) δ −132.53 (s, 1F); LC-MS: method H, RT=1.21 min, MS (ESI) m/z: 426.1 (M+H)$^+$.

Example 022

(1R,2S)-2-((5-fluoro-2-(2-methoxy-7-methylqui-noxalin-5-yl)benzo[d]thiazol-6-yl)ox y)cyclopentyl (6-methoxy pyridin-3-yl)carbamate

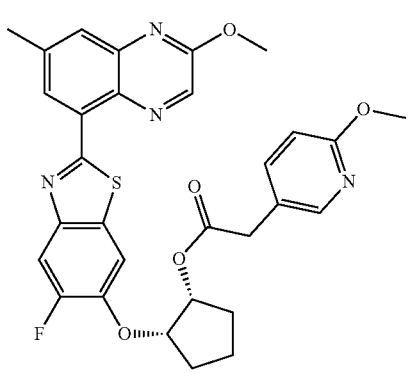

(022)

Example 022A (1R,2S)-2-((5-fluoro-2-(2-methoxy-7-methylqui-noxalin-5-yl)benzo[d]thiazol-6-yl)oxy)cyclopentan-1-ol

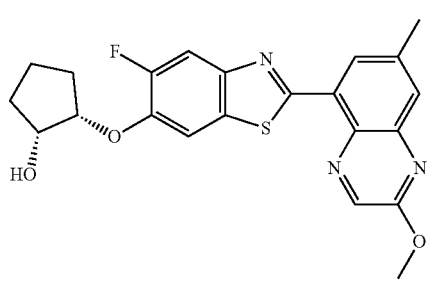

(022A)

Example 022A (185 mg, 0.435 mmol, 33.2% yield, peak 1, retention time 10.47 min) was obtained from chiral separation of Example 021 (557 mg, 1.309 mmol): Instrument: Berger Multigram II SFC; column: Chiralpak IA, 21×250 min, 5 micron: Mobile Phase: 35% EtOH/65% CO2; Flow Conditions: 45 mL/min, 150 Bar, 40° C.; Detector Wavelength: 220 nm. The assigned chirality has been verified by the chiral synthesis of this intermediate by an alternate route. Starting from (1R,2R)-2-hydroxycyclopentyl acetate, Mitsunobu reaction with I-09, followed by Suzuki cross-coupling with I-20, which concomitantly removed the acetate protecting group, provided a sample of Example 022A which was identical in all respects to that obtained by chiral separation of Example 021, including chiral HPLC retention time.

Example 022B (1R,2S)-2-((5-fluoro-2-(2-methoxy-7-methylqui-noxalin-5-yl)benzo[d]thiazol-6-yl)oxy)cyclopentyl carbonochloridate

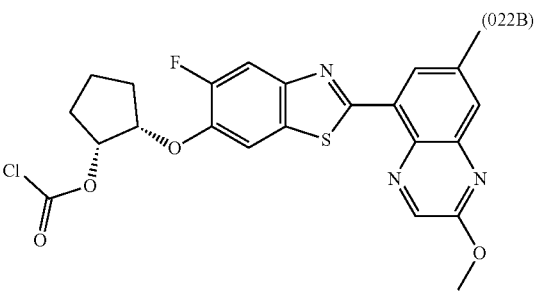 [SMILES: COc1cnc2c(-c3nc4cc(F)c(O[C@H]5CCC[C@H]5OC(=O)Cl)cc4s3)cc(C)cc2n1]

(022B)

Example 022B was made from Example 022A via the procedure described for Example 001B. LC-MS: method H, RT=1.19 min, MS (EST) m/z: 488.0 (M+H)⁺.

Example 022

Example 022 was synthesized from Example 022B via procedure described for Example 001C. $^1$H NMR (400 MHz, CDCl$_3$) δ 8.60 (d, J=1.5 Hz, 1H), 8.55 (s, 1H), 7.97 (d, J=2.9 Hz, 1H), 7.80 (d, J=11.2 Hz, 1H), 7.78-7.76 (m, 1H), 7.66 (d, J=7.7 Hz, 1H), 7.56-7.50 (m, 1H), 6.64 (d, J=8.8 Hz, 1H), 6.43 (br s, 1H), 5.25 (d, J=4.0 Hz, 1H), 5.00-4.85 (m, 1H), 4.14 (s, 3H), 3.81 (s, 3H), 2.66 (s, 3H), 216-2.06 (nm, 4H), 1.71 (d, J=7.5 Hz, 2H); $^{19}$F NMR (376 MHz, CDCl$_3$) δ −78.5 (m, 2F), −133.28 (br s, 1F); LC-MS: method H, RT=1.22 min, MS (ESI) m/z: 576.3 (M+H)⁺.

Example 023 to 038

The following additional examples have been prepared, isolated and characterized using the methods described for 022 and the examples above, from corresponding cyclic diol and aniline intermediates.

| Ex. No. | Structure | Chirality | LCMS [M + H]+ m/z | LCMS RT(Min)/ Method | NMR |
|---|---|---|---|---|---|
| 023 | 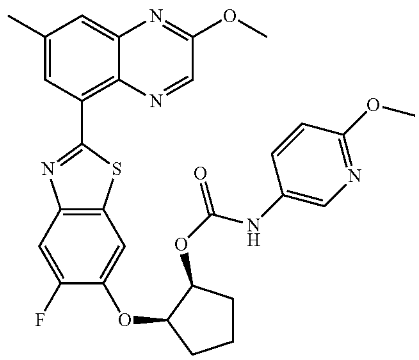 | (1S,2R) | 576.2 | 1.27/H | ¹H NMR (400 MHz, CDCl₃) δ 8.60 (d, J = 1.5 Hz, 1 H), 8.55 (s, 1 H), 7.97 (d, J = 2.9 Hz, 1 H), 7.80 (d, J = 11.2 Hz, 1 H), 7.77 (dd, J = 2.0, 0.9 Hz, 1 H), 7.66 (d, J = 8.6 Hz, 1 H), 7.55-7.50 (m, 1 H), 6.64 (d, J = 8.8 Hz, 1 H), 6.45 (br s, 1 H), 5.25 (d, J = 4.8 Hz, 1 H), 4.92 (q, J = 4.3 Hz, 1 H), 4.14 (s, 3H), 3.81 (s, 3H), 2.66 (s, 3H), 2.20-1.98 (m, 5H), 1.78-1.66 (m, 1 H); ¹⁹F NMR (376 MHz, CDCl₃) δ −133.27 (br s, 1 F) |
| 024 | 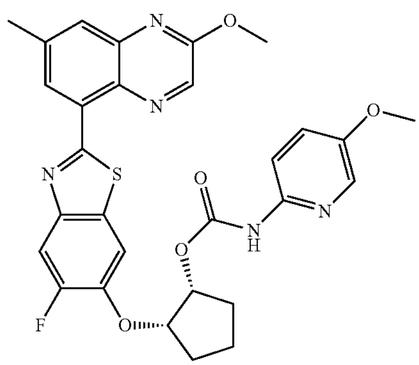 | (1R,2S) | 576.1 | 2.309/L | ¹H NMR (500 MHz, DMSO-d₆) δ ppm 9.81 (1 H, s), 8.70 (1 H, s), 8.53 (1 H, s), 7.99 (1 H, d, J = 8.24 Hz), 7.85-7.92 (2 H, m), 7.80 (1 H, s), 7.58 (1 H, d, J = 9.16 Hz), 7.35-8.09 (1 H, m), 5.23 (1 H, d, J = 4.27 Hz), 4.99 (1 H, d, J = 4.58 Hz), 4.07 (3 H, s), 3.68 (3 H, s), 2.61 (3 H, s), 2.02-2.22 (2 H, m), 1.91 (3 H, m), 1.61-1.71 (1 H, m); ¹⁹F NMR (471 MHz, DMSO-d₆) δ ppm −133.31 (1 F, br s) |
| 025 | 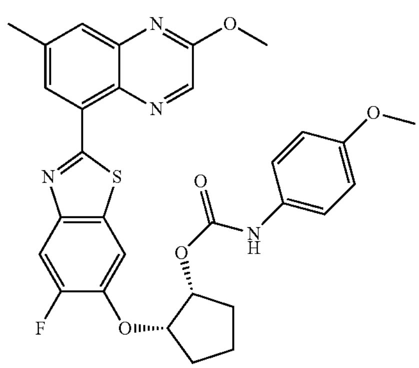 | (1R,2S) | 575.3 | 2.787/L | ¹H NMR (500 MHz, DMSO-d₆) δ ppm 9.34-9.49 (1 H, m), 8.70 (1 H, s), 8.52 (1 H, s), 7.99 (1 H, d, J = 8.24 Hz), 7.90 (1 H, d, J = 11.60 Hz), 7.80 (1 H, s), 7.26 (2 H, d, J = 8.24 Hz), 6.76 (2 H, d, J = 8.85 Hz), 5.21 (1 H, m), 4.99 (1 H, m), 4.07 (3 H, s), 3.61 (3 H, s), 2.61 (3 H, s), 2.18 (1 H, m), 2.01-2.11 (1 H, m), 1.79-1.98 (3 H, m), 1.67 (1 H, m); ¹⁹F NMR (471 MHz, DMSO-d₆) δ ppm −133.82 (1 F, s) |
| 026 | 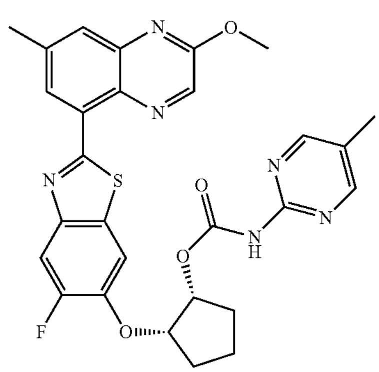 | (1R,2S) | 561.1 | 2.297/L | ¹H NMR (500 MHz, DMSO-d₆) δ ppm 10.20 (1 H, s), 8.74 (1 H, s), 8.56 (1 H, s), 8.38 (2 H, s), 8.01 (1 H, d, J = 8.24 Hz), 7.91 (1 H, d, J = 11.60 Hz), 7.83 (1 H, s), 5.17-5.32 (1 H, m), 5.00 (1 H, m), 4.09 (3 H, m), 3.34 (1 H, m), 2.63 (3 H, s), 2.18 (1 H, m), 2.09 (3 H, s), 1.85-2.00 (3 H, m), 1.69 (1 H, m); ¹⁹F NMR (471 MHz, DMSO-d₆) δ ppm −133.22 (1 F, br s) |

| Ex. No. | Structure | Chirality | LCMS [M + H]+ m/z | LCMS RT(Min)/ Method | NMR |
|---|---|---|---|---|---|
| 027 | 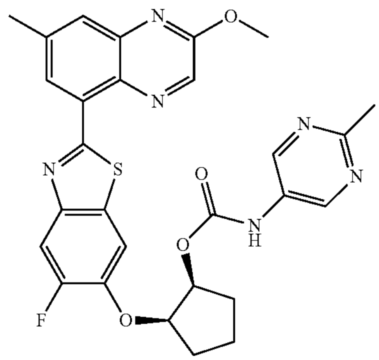 | (1S,2R) | 561.3 | 1.18/H | ¹H NMR (400 MHz, CDCl₃) δ 8.72 (s, 2H), 8.58 (d, J = 1.5 Hz, 1 H), 8.54 (s, 1 H), 7.79 (d, J = 11.2 Hz, 1 H), 7.76 (dd, J = 1.9, 1.0 Hz, 1 H), 7.51 (d, J = 7.9 Hz, 1 H), 6.74 (s, 1 H), 5.29 (d, J = 4.2 Hz, 1 H), 4.95-4.89 (m, 1 H), 4.13 (s, 3H), 2.65 (s, 3H), 2.61 (s, 3H), 2.39 (br s, 2H), 2.22-1.98 (m, 3H), 1.81-1.63 (m, 1 H); ¹⁹F NMR (376 MHz, CDCl₃) δ −133.32 (s, 1 F) |
| 028 | 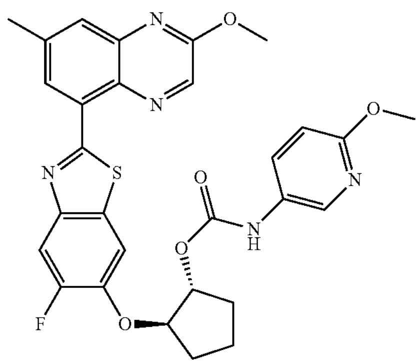 | racemic (from I-03) | 576.1 | 2.613/L | ¹H NMR (500 MHz, DMSO-d₆) δ 9.73 (br s, 1 H), 8.72 (s, 1 H), 8.56 (s, 1 H), 8.21 (br s, 1 H), 8.07 (d, J = 8.1 Hz, 1 H), 7.97 (d, J = 11.4 Hz, 1 H), 7.82 (s, 1 H), 7.78 (br s, 1 H), 6.78 (d, J = 9.1 Hz, 1 H), 5.17 (br s, 1 H), 4.94 (br s, 1 H), 4.07 (s, 3H), 3.78 (s, 3H), 2.62 (s, 3H), 2.33-2.09 (m, 2H), 1.93-1.73 (m, 4H) |
| 029 | 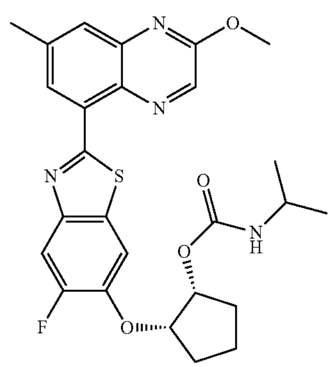 [SMILES: COc1cnc2c(-c3nc4cc(F)c(O[C@H]5CCC[C@H]5OC(=O)NC(C)C)cc4s3)cc(C)cc2n1] | (1R,2S) | 511.1 | 2.693/L | ¹H NMR (500 MHz, DMSO-d₆) δ ppm 8.71 (1 H, s), 8.55 (1 H, s), 7.88-8.00 (2 H, m), 7.81 (1 H, s), 7.02 (1 H, d, J = 7.63 Hz), 5.09 (1 H, m), 4.83-4.98 (1 H, m), 4.07 (3 H, s), 2.61 (3 H, s), 1.93-2.18 (2 H, m), 1.84 (3 H, m), 1.56-1.69 (1 H, m), 0.82-1.03 (6 H, m); ¹⁹F NMR (471 MHz, DMSO-d₆) δ ppm −133.19 (1 F, s) |
| 030 | 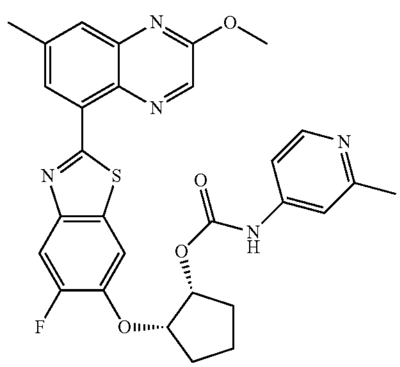 | (1R,2S) | 560.20 | 2.134/L | ¹H NMR (500 MHz, DMSO-d₆) δ ppm 11.10 (1 H, s), 8.71 (1 H, s), 8.51 (1 H, s), 8.41 (1 H, d, J = 6.71 Hz), 8.02 (1 H, d, J = 7.93 Hz), 7.89 (1 H, d, J = 11.29 Hz), 7.82 (1 H, s), 7.58-7.63 (2 H, m), 5.32 (1 H d, J = 4.88 Hz), 5.09 (1 H, d, J = 4.58 Hz), 4.08 (3 H, s), 2.61 (3 H, s), 2.47 (3 H, s), 2.24 (1 H, m), 2.12 (1 H, m), 1.87-2.03 (3 H, m), 1.71 (1 H, m); ¹⁹F NMR (471 MHz, DMSO-d₆) δ ppm −133.41 (1 F, s) |

| Ex. No. | Structure | Chirality | LCMS [M + H]+ m/z | LCMS RT(Min)/ Method | NMR |
|---|---|---|---|---|---|
| 031 | 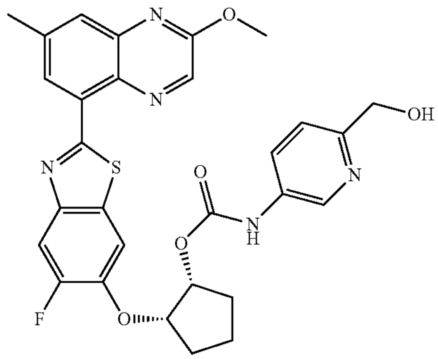 [SMILES: COc1cnc2c(-c3nc4cc(F)c(O[C@H]5CCC[C@H]5OC(=O)Nc5ccc(CO)nc5)cc4s3)cc(C)cc2n1] | (1R,2S) | 576.15 | 2.039/L | ¹H NMR (500 MHz, DMSO-d₆) δ ppm 9.76 (1 H, br s), 8.63 (1 H, s), 8.45 (1 H, s), 8.40 (1 H, br s), 7.94 (1 H, d, J = 7.93 Hz), 7.83 (1 H, d, J = 11.60 Hz), 7.67-7.77 (2 H, m), 7.25 (1 H, d, J = 8.54 Hz), 5.20 (1 H, m), 4.95 (1 H, m), 4.34 (2 H, s), 4.00 (3 H, s), 3.83 (1 H, s), 2.54 (3 H, s), 2.14 (1 H, d, J = 6.41 Hz), 1.95-2.08 (1 H, m), 1.75-1.93 (3 H, m), 1.62 (1 H, d, J = 5.80 Hz); ¹⁹F NMR (471 MHz, DMSO-d₆) δ ppm −133.51 (1 F, br s) |
| 032 | 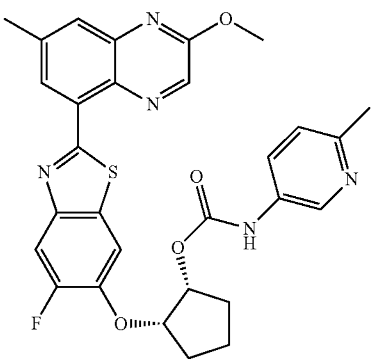 | (1R,2S) | 560.20 | 2.087/L | ¹H NMR (500 MHz, DMSO-d₆) δ ppm 10.27 (1 H, br s), 8.68 (1 H, s), 8.59 (1 H, br s), 8.48 (1 H, s), 8.00 (2 H, m), 7.86 (1 H, s), 7.79 (1 H, s), 7.53 (1 H, d, J = 8.85 Hz), 5.26 (1 H, m), 5.05 (1 H, m), 4.06 (3 H, s), 2.60 (3 H, s), 2.35 (3 H, s), 2.21 (1 H, m), 2.03-2.14 (1 H, m), 1.91 (3 H, m), 1.61-1.74 (1 H, m); ¹⁹F NMR (471 MHz, DMSO-d₆) δ ppm −133.40 (1 F, s) |
| 033 | 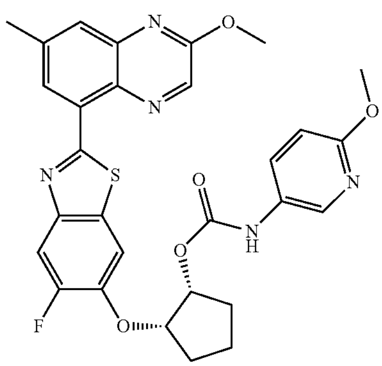 [SMILES: COc1ccc(NC(=O)O[C@@H]2CCC[C@@H]2Oc2cc3sc(-c4cc(C)cc5nc(OC)cnc45)nc3cc2F)cn1] | racemic (from I-01) | 576.3 | 1.25/H | ¹H NMR (500 MHz, DMSO-d₆) δ 9.47 (br s, 1 H), 8.59 (s, 1 H), 8.43 (s, 1 H), 8.03 (br s, 1 H), 7.89 (d, J = 8.2 Hz, 1 H), 7.83 (d, J = 11.6 Hz, 1 H), 7.72 (s, 1 H), 7.60 (d, J = 6.7 Hz, 1 H), 6.62 (d, J = 8.8 Hz, 1 H), 5.19 (m, 1 H), 4.99 (m, 1 H), 4.03 (s, 3H), 3.60 (s, 3H), 2.56 (s, 3H), 2.22-2.11 (m, 1 H), 2.11-1.99 (m, 1 H), 1.88 (m, 3H), 1.65 (m, 1 H) |
| 034 | 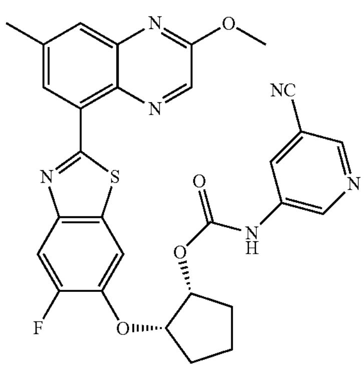 [SMILES: COc1cnc2c(-c3nc4cc(F)c(O[C@H]5CCC[C@H]5OC(=O)Nc5cncc(C#N)c5)cc4s3)cc(C)cc2n1] | (1R,2S) | 571.20 | 2.534/L | ¹H NMR (500 MHz, DMSO-d₆) δ ppm 10.18 (1 H, br s), 8.69 (2 H, d, J = 11.60 Hz), 8.49 (1 H, s), 8.43 (1 H, br s), 8.10 (1 H, br s), 7.99 (1 H, d, J = 7.93 Hz), 7.87 (1 H, d, J = 11.60 Hz), 7.79 (1 H, s), 5.26 (1 H, m), 5.07 (1 H, m), 4.06 (3 H, s), 2.60 (3 H, s), 2.20 (1 H, m), 2.09 (1 H, m), 1.81-2.01 (3 H, m), 1.68 (1 H, m); ¹⁹F NMR (471 MHz, DMSO-d₆) δ ppm −133.40 (1 F, br s) |

| Ex. No. | Structure | Chirality | LCMS [M + H]+ m/z | LCMS RT(Min)/ Method | NMR |
|---|---|---|---|---|---|
| 035 | 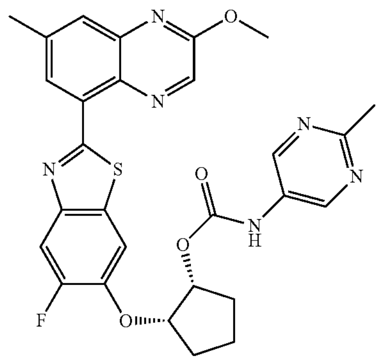 | racemic (from I-01) | 561.9 | 1.18/H | 1H NMR (400 MHz, CDCl3) δ ppm 8.67 (2 H, s), 8.60 (1 H, d, J = 1.98 Hz), 8.55 (1 H s), 7.80 (1 H, d, J = 11.22 Hz), 7.77 (1 H, s), 7.52 (1 H, d, J = 7.70 Hz), 6.47-6.64 (1 H, m), 5.28 (1 H, d, J = 4.62 Hz), 4.92 (1 H, d, J = 4.84 Hz), 4.14 (3 H, s), 2.66 (3 H s), 2.61 (3 H, s), 1.96-2.23 (3 H, m), 0.72-0.97 (3 H, m); 19F NMR (376 MHz, CDl3) δ ppm −133.35 (1 F, s) |
| 036 | 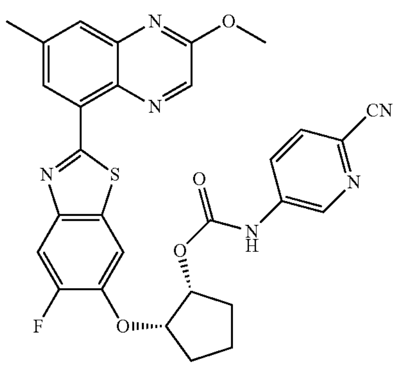 | (1R,2S) | 571.10 | 2.50/L | 1H NMR (500 MHz, DMSO-d6) δ ppm 10.25 (1 H, s), 8.63 (1 H, s), 8.55 (1 H, s), 8.44 (1 H, s), 7.87-7.95 (2 H, m), 7.83 (1 H, d, J = 11.29 Hz), 7.72-7.77 (2 H, m), 5.23 (1 H, m), 5.06 (1 H, m), 4.04 (3 H, s), 2.58 (3 H, s), 2.19 (1 H, m), 2.08 (1 H, m), 1.84-1.99 (3 H, m), 1.67 (1 H, m); 19F NMR (471 MHz, DMSO-d6) δ ppm −133.44 (1 F, s) |
| 037 | 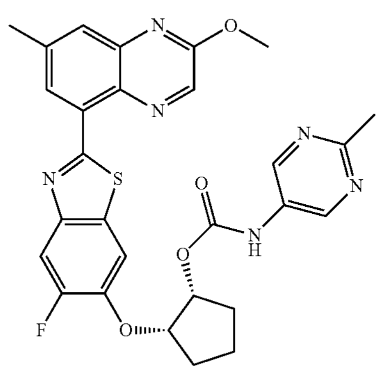 | (1R,2S) | 561.15 | 2.34/L | 1H NMR (500 MHz, DMSO-d6) δ ppm 9.89 (1 H, br s), 8.69 (1 H, s), 8.61 (2 H, s), 8.51 (1 H, s), 8.00 (1 H, d, J = 8.24 Hz), 7.89 (1 H, d, J = 11.29 Hz), 7.80 (1 H, s), 5.25 (1 H, m), 5.03 (1 H, m), 4.07 (3 H, s), 2.61 (3 H, s), 2.38 (3 H, s), 2.20 (1 H, d, J = 7.93 Hz), 2.03-2.13 (1 H, m), 1.80-2.01 (3 H, m), 1.68 (1 H, m) 19F NMR (471 MHz, DMSO-d6) δ ppm −133.52 (1 F, br s) |
| 038 | 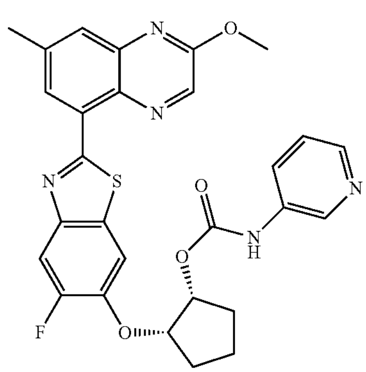 [SMILES: COc1cnc2c(-c3nc4cc(F)c(O[C@H]5CCC[C@H]5OC(=O)Nc5cccnc5)cc4s3)cc(C)cc2n1] | racemic (from I-01) | 546.15 | 2.00/L | 1H NMR (500 MHz, DMSO-d6) δ 9.82 (br s, 1 H), 8.60 (s, 1 H), 8.52 (br s, 1 H), 8.43 (s, 1 H), 8.10 (d, J = 4.3 Hz, 1 H), 7.93 (d, J = 7.9 Hz, 1 H), 7.83 (d, J = 11.3 Hz, 1 H), 7.77 (d, J = 8.5 Hz, 1 H), 7.72 (s, 1 H), 7.23 (dd, J = 8.2, 4.6 Hz, 1 H), 5.25 (d, J = 4.6 Hz, 1 H), 4.99 (d, J = 5.2 Hz, 1 H), 4.02 (s, 3H), 2.56 (s, 3H), 2.19 (d, J = 6.7 Hz, 1 H), 2.13-2.02 (m, 1 H), 1.96-1.83 (m, 3H), 1.74-1.62 (m, 1 H) |

| Ex. No. | Structure | Chirality | LCMS [M + H]+ m/z | LCMS RT(Min)/ Method | NMR |
|---|---|---|---|---|---|
| 039 | 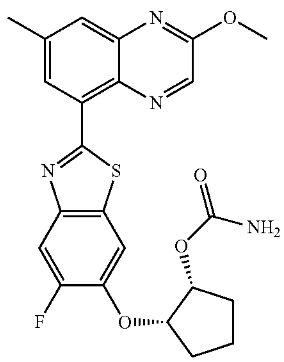 | (1R,2S) | 469.15 | 2.324/L | 1H NMR (500 MHz, DMSO-d6) δ ppm 8.65 (1 H, s), 8.49 (1 H, s), 7.84-7.93 (2 H, m), 7.76 (1 H, s), 5.88-6.88 (2 H, m), 5.04 (1 H, d, J = 4.27 Hz), 4.88 (1 H, d, J = 4.88 Hz), 4.04 (3 H, s), 2.58 (3 H, s), 2.05-2.15 (1 H, m), 1.91-2.04 (1 H, m), 1.72-1.91 (3 H, m), 1.51-1.71 (1 H, m); 19F NMR (471 MHz, DMSO-d6) δ ppm −133.24 (1 F, br. s) |

Example 040 rac-5-fluoro-2-(2-methoxy-7-methylquinoxalin-5-yl)-6-((cis-2-methoxycyclopentyl)oxy)benzo[d]thiazole

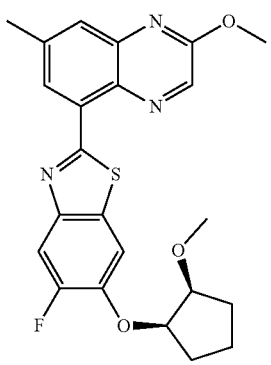

(040)

A solution of Example 021 (8.0 mg, 0.019 mmol) in acetonitrile (0.5 mL) and methyl iodide (500 μl, 8.00 mmol) was stirred in a sealed vial at 60° C. in the presence of silver oxide (350 mg, 1.510 mmol) for 3 hours. After cooling to room temperature, the reaction was diluted by adding 2 mL of DCM and the solid was removed by filtration, and the filtrate was concentrated. The residue was purified by reverse phase preparative HPLC, Method C, to obtain Example 040 (0.9 mg, 0.002 mmol, 10% yield) as the product. 1H NMR (500 MHz, DMSO-d6) δ 8.78 (s, 1H), 8.63 (s, 1H), 8.10-7.97 (m, 2H), 789 (s, 1H), 4.93 (m, 1H), 4.15 (s, 3H), 3.96 (m, 1H), 3.33 (s, 3H), 2.69 (s, 3H), 2.10 (m, 1H), 1.86 (m, 4H), 1.65 (m, 1H); LC-MS: method L, RT=2.662 min, MS (ESI) m/z: 440.15 (M+H)+.

Example 041 rac-trans-2-((5-fluoro-2-(2-methoxy-7-methylquinoxalin-5-yl)benzo[d]thiazol-6-yl)oxy)cyclopentanol

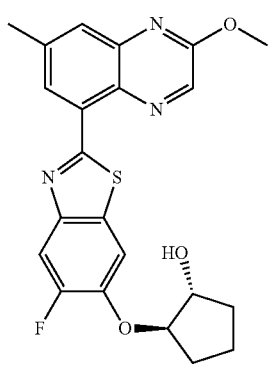

(041)

Example 041 (7.3 mg, 0.017 mmol, 18%) was made from I-03 (30.5 mg, 0.092 mmol) and I-20 (20 mg, 0.092 mmol) via the procedure described for Example 001A. 1H NMR (500 MHz, DMSO-d6) δ 8.62 (s, 1H), 8.47 (br s, 1H), 7.93-7.82 (m, 2H), 7.75 (br s, 1H), 4.59 (m, 1H), 4.14 (m, 1H), 4.04 (s, 3H), 3.65 (s, 1H), 2.58 (s, 3H), 2.24-2.13 (m, 1H), 1.98-1.86 (m, 1H), 1.81-1.63 (m, 3H), 1.57 (d, J=4.6 Hz, 11H); LC-MS: method L, RT=2.396 min, MS (ESI) m/z: 426.10 (M+H)+.

Example 042 rac-5-fluoro-2-(2-methoxy-7-methylquinoxalin-5-yl)-6-((trans-2-methoxycyclopentyl) oxy)benzo[d]thiazole

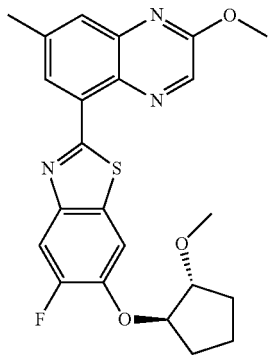

(042)

Example 042 (1.8 mg, 0.004 mmol, 24%) was made from Example 041 (7.0 mg, 0.016 mmol) by following the procedure for Example 040. $^1$H NMR (500 MHz, DMSO-$d_6$) δ 8.69 (s, 1H), 8.54 (s, 1H), 7.98-7.90 (m, 2H), 7.80 (s, 1H), 4.77 (m, 1H), 4.06 (s, 3H), 3.88 (nm, 1H), 3.29 (s, 3H), 2.61 (s, 3H), 2.15 (d, J=6.4 Hz, 1H), 1.97 (dd, J=12.8, 6.4 Hz, 1H), 1.78-1.60 (m, 4H); LC-MS: method L, RT=2.857 min, MS (ESI) m/z: 440.10 (M+H)$^+$.

Example 043 rac-trans-2-((5-fluoro-2-(7-(hydroxymethyl)-2-methoxyquinoxalin-5-yl)benzo[d]thiazol-6-yl)oxy)cyclopentanol

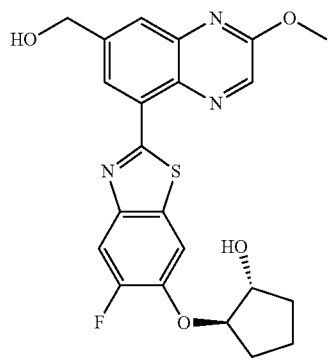

(043)

Example 043 (1.3 mg, 0.003 mmol, 11%) was made from I-03 (8.5 mg, 0.026 mmol) and I-26 (6 mg, 0.026 mmol) by following the procedure described for Example 001A. $^1$H NMR (500 MHz, DMSO-$d_6$) δ 8.74 (s, 1H), 8.71 (s, 1H), 8.02-7.88 (m, 4H), 5.74-5.58 (m, 1H), 4.81 (d, J=5.5 Hz, 3H), 4.62 (br s, 1H), 4.16 (br s, 1H), 4.08 (s, 3H), 2.02-1.84 (m, 1H), 1.83-1.61 (m, 3H), 1.58 (br s, 1H); LC-MS: method L, RT=1.78 min, MS (EST) m/z: 442.10 (M+H)$^+$.

Example 044 rac-cis-2-((5-fluoro-2-(7-(hydroxymethyl)-2-methoxyquinoxalin-5-yl)benzo[d]thiazol-6-yl)oxy)cyclopentyl pyridin-3-ylcarbamate

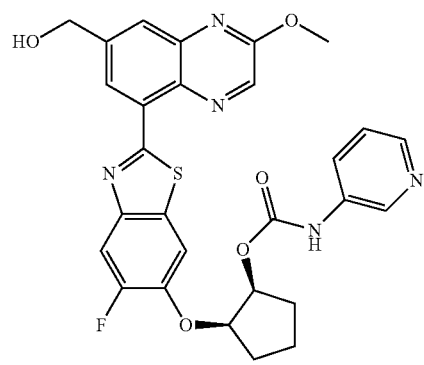

(044)

Example 044A: (1S,2R)-2-((2-chloro-5-fluorobenzo[d]thiazol-6-yl)oxy)cyclopentyl pyridin-3-ylcarbamate

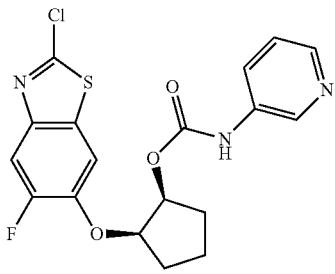

(044A)

In a round bottom flask charged with a stirring bar, I-01 (75 mg, 0.226 mmol) was dissolved in anhydrous THF (5 mL), and phosgene (1.611 mL, 2.258 mmol) was added. The mixture was stirred at room temperature overnight. On the next day, the solvent was removed on the rotary evaporator and the residue was dried on HVAC for 20 minutes. The crude chloroformate was dissolved in DCM (2 mL). DIEA (0.100 mL, 0.570 mmol) was added, followed by pyridin-3-amine (42.9 mg, 0.456 mmol). The mixture was stirred at room temperature over the weekend. On the next Monday, the reaction mixture was loaded on a silica gel column (12 g) and eluted with 0-100% EtOAc/hexane gradient. The desired fractions were collected and the solvent was removed to give Example 044A (24 mg, 0.059 mmol, 51.6% yield) as white solid. $^1$H NMR (400 MHz, CDCl$_3$) δ 8.45 (d, J=2.4 Hz, 1H), 8.32 (d, J=4.0 Hz, 1H), 782 (d, J=7.9 Hz, 1H), 7.63 (d, J=10.8 Hz, 1H), 7.36 (d, J=7.7 Hz, 1H), 7.23 (dd, J=8.4, 4.6 Hz, 1H), 6.63 (br s, 1H), 5.30-5.19 (m, 1H), 4.93-4.80 (m, 1H), 2.21-1.97 (m, 5H), 1.73 (d, J=9.2 Hz, 1H); $^{19}$F NMR (376 MHz, CDCl$_3$) δ −131.97 (br s, 1F); LC-MS: method H, RT=0.82 min, MS (ESI) m/z: 442.10 (M+H)$^+$.

Example 044

Example 044 (1.1 mg, 0.002 mmol, 11% yield) was made from Example 044A (8.4 mg, 0.021 mmol) and I-26 (4 mg, 0.015 mmol) by the procedure described for Example 001A. LC-MS: method L, RT=1.632 min, MS (ESI) m/z: 562.15 (M+H)+.

Example 045 rac-cis-2-((2-(7-cyano-2-methoxyquinoxalin-5-yl)-5-fluorobenzo[d]thiazol-6-yl)oxy)cyclopentyl (5-cyanopyridin-3-yl)carbamate

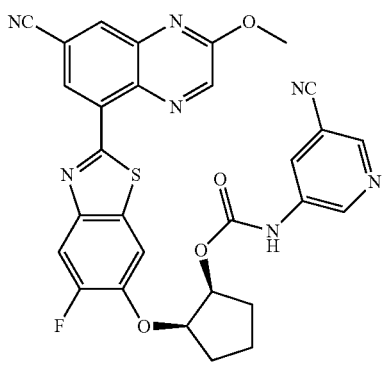

(045)

Example 045A 8-(5-fluoro-6-((cis-2-hydroxycyclopentyl)oxy)benzo[d]thiazol-2-yl)-3-methoxyquinoxaline-6-carbonitrile

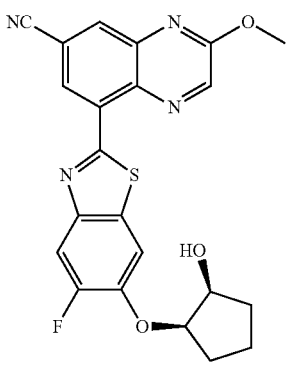

(045A)

Example 045A (21 mg, 0.046 mmol, 38.4% yield) was made from Intermediate I-01 (40 mg, 0.120 mmol) and I-25 (52.4 mg, 0.169 mmol) as a yellow solid, by following the procedure described for Example 001.1H NMR (400 MHz, DMSO-d6) δ 8.98 (s, 1H), 8.89 (d, J=1.8 Hz, 1H), 8.56 (d, J=2.0 Hz, 1H), 8.04 (d, J=8.4 Hz, 1H), 8.00 (d, J=11.7 Hz, 1H), 4.73 (d, J=5.1 Hz, 1H), 4.69 (m, 1H), 4.29-4.21 (m, 1H), 4.14 (s, 3H), 2.10-2.01 (m, 1H), 1.93-1.76 (m, 3H), 1.72 (m, 1H), 1.56 (m, 1H) 19F NMR (376 MHz, DMSO-d6): δ −132.53 (s, 1F); LC-MS: method H, RT=1.14 min, MS (ESI) m/z: 437.1 (M+H)+.

Example 045B cis-2-((2-(7-cyano-2-methoxyquinoxalin-5-yl)-5-fluorobenzo[d]thiazol-6-yl)oxy)cyclopentyl carbonochloridate

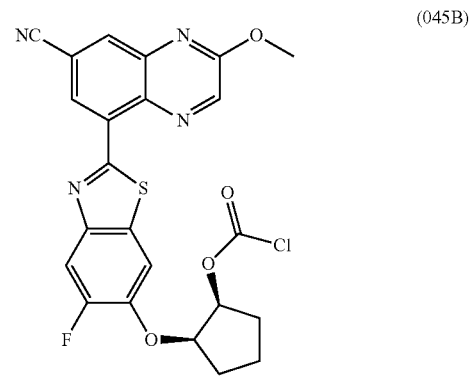 [SMILES: COc1cnc2c(-c3nc4cc(F)c(O[C@@H]5CCC[C@@H]5OC(=O)Cl)cc4s3)cc(C#N)cc2n1]

(045B)

Example 045A (20.0 mg, 0.046 mmol) in anhydrous THF (2 mL) was treated with phosgene (0.327 mL, 0.458 mmol) at room temperature for 8 hours. The solvent was removed and residue was used without purification. LC-MS: method H, RT=1.28 min, MS (ESI) m/z: 499.1 (M+H)+.

Example 045

Example 045 (2.5 mg, 0.004 mmol 17% yield) was made from Example 045B (12.5 mg, 0.025 mmol) and 5-aminonicotinonitrile (14.89 mg, 0.125 mmol) by the method described for Example 001C. 1H NMR (500 MHz, DMSO-d6) δ ppm 10.16 (1H, br s), 8.89 (1H, s), 8.75 (1H, s), 8.69 (1H, s), 8.50 (1H, s), 8.42 (1H, s), 8.07 (1H, br s), 8.02 (1H, d, J=8.24 Hz), 7.91 (1H, d, J=11.60 Hz), 5.26 (1H, m), 5.09 (1H, m), 4.11 (3H, s), 2.22 (1H, m), 2.10 (1H, m), 1.84-2.02 (3H, m), 1.69 (1H, m); 19F NMR (471 MHz, DMSO-6) δ ppm −132.73 (1F, br s); LC-MS: method L, RT=2.36 min, MS (ESI) m/z: 582.15 (M+H)+.

Example 046 rac-cis-2-((2-(7-cyano-2-methoxyquinoxalin-5-yl)-5-fluorobenzo[d]thiazol-6-yl)oxy)cyclopentyl (2-methylpyrimidin-5-yl)carbamate

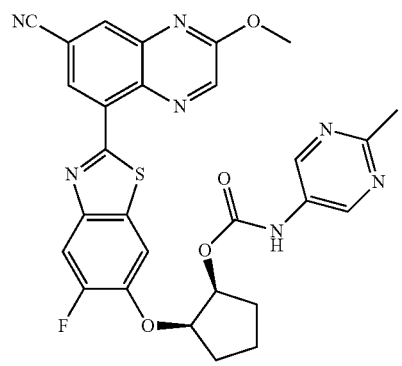

(046)

Example 046 (2.2 mg, 0.004 mmol, 15% yield) was made from Example 045B (12.47 mg, 0.025 mmol) and 2-methylpyrimidin-5-amine (13.64 mg, 0.125 mmol) by the method described for Example 001C. $^1$H NMR (500 MHz, DMSO-$d_6$) δ ppm 9.79-9.94 (1H, m), 8.89 (1H, s), 8.76 (1H, s), 8.60 (2H, s), 8.49 (1H, s), 8.02 (1H, d, J=7.93 Hz), 7.91 (1H, d, J=11.60 Hz), 5.25 (1H, m), 5.05 (1H, m), 4.10 (3H, s), 2.36 (3H, s), 2.22 (1H, d, J=6.41 Hz), 2.01-2.16 (1H, m), 178-1.99 (3H, m), 168 (1H, m); $^{19}$F NMR (471 MHz, DMSO-$d_6$) δ ppm −132.86 (1F, br s); LC-MS: method L, RT=2.151 min, MS (ESI) m/z: 572.15 (M+H)$^+$.

Example 047 methyl 5-(((((1R,2S)-2-((5-fluoro-2-(2-methoxy-7-methylquinoxalin-5-yl)benzo[d]thiazol-6-yl)oxy)cyclopentyl)oxy)carbonyl)amino)picolinate (047)

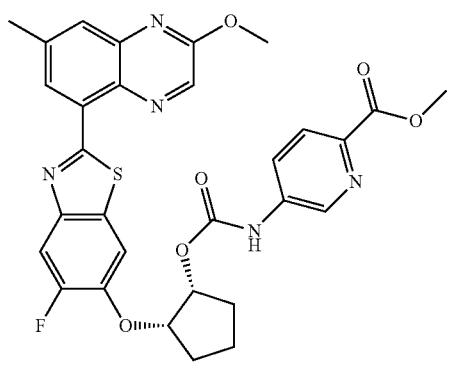

Example 047 (77.7 mg, 0.123 mmol, 85% yield) was made as a yellow solid from Example 022A (60 mg, 0.145 mmol) by the method described for Example 001. $^1$H NMR (400 MHz, DMSO-$d_6$) δ ppm 10.18 (1H, s), 8.71 (1H, s), 8.60 (1H, d, J=2.42 Hz), 8.53 (1H, s), 8.01 (1H, d, J=8.14 Hz), 7.76-7.94 (4H, m), 5.26 (1H, d, J=4.18 Hz), 5.09 (1H, d, J=4.84 Hz), 4.10 (3H, s), 3.72 (3H, s), 2.63 (3H, s), 2.17-2.29 (1H, m), 2.09 (1H, m), 1.84-2.02 (3H, m), 1.70 (1H, m); $^{19}$F NMR (376 MHz, DMSO-$d_6$) δ ppm −133.39 (1F, br s); LC-MS: method H, RT=1.17 min, MS (ESI) nit: 604.2 (M+H)$^+$.

Example 048

(1R,2S)-2-((5-fluoro-2-(2-methoxy-7-methylquinoxalin-5-yl)benzo[d]thiazol-6-yl)ox y)cyclopentyl (6-(methylcarbamoyl)pyridin-3-yl)carbamate (048)

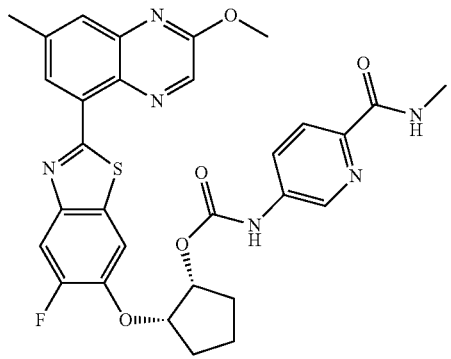

In a vial charged with a stirring bar, Example 047 (11 mg, 0.018 mmol) was dissolved in THF (0.5 mL). Methanamine (0.5 mL, 0.018 mmol) in methanol was added. The mixture was heated to 60° C. and stirred for 20 hours. On the next day, the solvent was removed and the residue was purified on the reverse phase preparative HPLC by using Method D to give Example 048 (6.9 mg, 0.011 mmol, 63% yield) as the product. $^1$H NMR (500 MHz, DMSO-) δ ppm 10.01 (1 (1H, br s), 864 (1H, s), 8.50 (1H, s), 8.47 (1H, s), 8.38 (1H, br s), 7.95 (1H, d, =7.93 Hz), 7.81-7.89 (2H, m), 7.75-7.80 (2H, m), 5.23 (1H, br s), 5.07 (1H, br s), 4.06 (3H, s), 3.16 (1H, br s), 2.67 (3H, d, J=4.27 Hz), 2.59 (3H, s), 2.19 (1H, br. m.), 2.06 (1H, d, J=12.21 Hz), 1.91 (2H, br. m.), 1.69 (1H, br. m.); $^{19}$F NMR (471 MHz, DMSO-$d_6$) δ ppm −133.48 (1F, s); LC-MS: method H, RT=1.16 min, MS (ESI) m/z: 603.1 (M+H)$^+$.

Example 049

(1R,2S)-2-((5-fluoro-2-(2-methoxy-7-methylquinoxalin-5-yl)benzo[d]thiazol-6-yl)ox y)cyclopentyl (6-carbamoylpyridin-3-yl)carbamate (049)

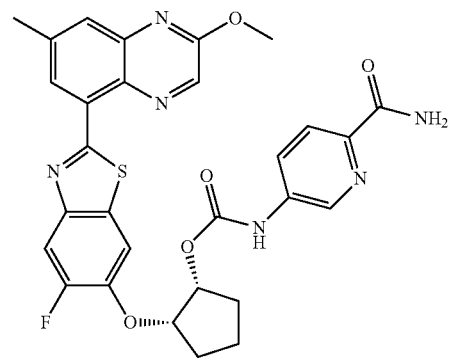

In a vial charged with a stirring bar, Example 047 (10 mg, 0.017 mmol) was dissolved in THF (0.5 mL). Ammonia (1 mL, 7.00 mmol) in methanol (7N) was added. The mixture was heated at 60° C. for 20 hours. On the next day, the solvent was removed and residue was purified on the reverse phase preparative HPLC by using Method D to give Example 049 (5.2 mg, 0.009 mmol, 53% yield) as the product. $^1$H NMR (500 MHz, DMSO-$d_6$) δ ppm 10.07 (1H, br s), 8.62 (1H, s), 8.52 (1H, s), 8.44 (1H, s), 7.93 (1H, d, J=7.93 Hz), 7.78-7.90 (4H, m), 7.76 (1H, s), 7.31 (1H, br s), 5.25 (1H, m), 5.03 (1H, m), 4.04 (3H, s), 2.57 (3H, s), 2.18 (1H, m), 1.99-2.13 (1H, m), 1.82-1.98 (2H, m), 1.67 (1H, m); $^{19}$F NMR (471 MHz, DMSO-$d_6$) δ ppm −133.48 (1F, s): LC-MS: method L, RT=2.266 min, MS (ESI) m/z: 589.2 (M+H)$^+$.

Example 050

(1R,2S)-2-((5-fluoro-2-(2-methoxy-7-methylquinoxalin-5-yl)benzo[d]thiazol-6-yl)ox y)cyclopentyl (6-(dimethylcarbamoyl)pyridin-3-yl)carbamate (050)

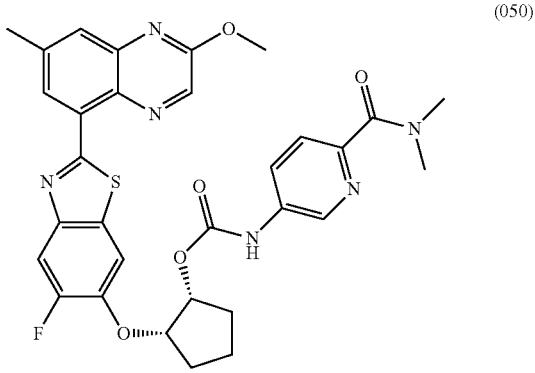

In a vial charged with a stirring bar, Example 047 (11 mg, 0.018 mmol) was dissolved in THF (0.5 mL) and dimethylamine (0.5 mL, 1.000 mmol) in MeOH. Magnesium chloride (8.68 mg, 0.091 mmol) was added and heated to 60° C. and stirred for 20 hours. On the next day, the solvent was removed and the residue was dissolved in DMF. The solid was filtered, and the crude product was purified on the reverse phase preparative HPLC by using Method D to give Example 050 (6.2 mg, 0.010 mmol, 55% yield) as the product. $^1$H NMR (500 MHz, DMSO-d) δ ppm 10.05 (1H, br s), 8.64 (1H, s), 8.50 (1H, br s), 8.46 (1H, s), 7.97 (1H, d, J=δ 8.24 Hz), 7.83-7.92 (2H, m), 7.76 (1H, s), 7.46 (1H, d, 1=8.55 Hz), 5.27 (1H, m), 5.04 (1H, nm) 4.05 (3H, s), 2.91 (3H, s), 2.83 (3H, s), 2.58 (3H, s), 2.22 (1H, m), 2.11 (1H, m), 1.84-2.02 (3H, m), 1.69 (1H, m); 19F NMR (471 MHz, DMSO-d$_6$) δ ppm −133.43 (1F, br s); LC-MS: method H, RT=1.15 min, MS (ESI) m/z: 617.2 (M+H)$^+$.

Example 051 methyl 5-(((((1R,2S)-2-((5-fluoro-2-(2-methoxy-7-methylquinoxalin-5-yl)benzo[d]thiazol-6-yl)oxy)cyclopentyl)oxy)carbonyl)amino)pyrimidine-2-carboxylate (051)

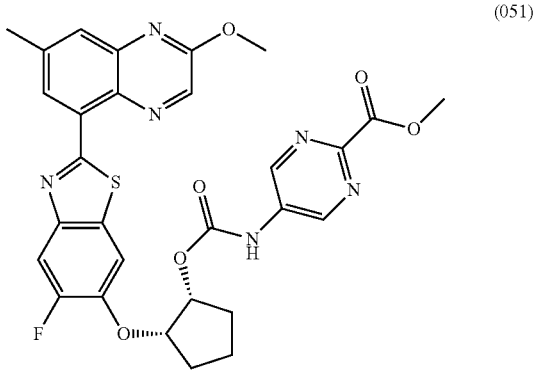

Example 051 (17 mg, 0,028 mmol, 42% yield) was made from Example 022A (28 mg, 0.066 mmol) and methyl 5-aminopyrimidine-2-carboxylate (17.07 mg, 0.111 mmol) as a yellow solid by the method described for Example 001. $^{19}$F NMR (376 MHz, CDCl$_3$) δ ppm −133.45 (1F, s); $^1$H NMR (400 MHz, CDCl$_3$) δ ppm 8.98 (2H, s), 8.55 (1H, s), 8.51 (1H, s), 7.73 (2H, s), 7.49 (1H, d, J=7.70 Hz), 7.26 (1H, br s), 5.25-5.30 (1H, m), 4.91 (1H, d, J=4.40 Hz), 4.13 (3H, s), 3.98 (3H, s), 2.64 (3H, s), 1.95-2.22 (5H, m), 1.66-1.79 (1H, nm); LC-MS: method H, RT=1.16 min, MS (ESI) m/z: 605.1 (M+H)$^+$.

Example 052

(1R,2S)-2-((5-fluoro-2-(2-methoxy-7-methylquinoxalin-5-yl)benzo[d]thiazol-6-yl)oxy)cyclopentyl (2-carbamoylpyrimidin-5-yl)carbamate (052)

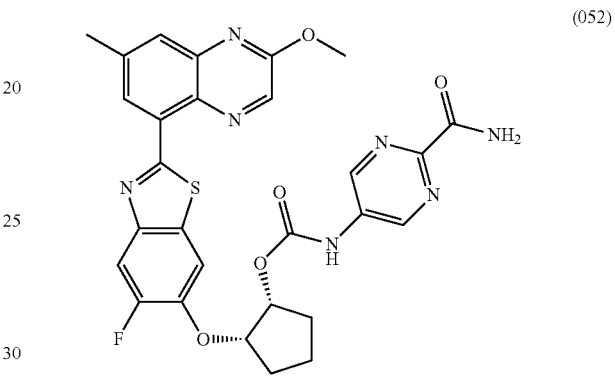

Example 052 (14.5 mg, 0.023 mmol, 95% yield) was made from Example 051 (15 mg, 0.025 mmol) by the method described for Example 049. $^1$H NMR (400 MHz, DMSO-d$_6$) δ ppm 10.27-10.48 (1H, m), 8.88 (2H, s), 8.74 (1H, s), 8.55 (1H, d, J=1.76 Hz), 8.07 (1H, d, J=8.36 Hz), 8.00 (1H, s), 7.93 (1H, d, J=11.44 Hz), 7.84 (1H, d, J=0.88 Hz), 7.60 (1H, br s), 5.32 (1H, d, J=4.18 Hz), 5.07 (1H, m), 4.09 (3H, s), 2.63 (3H, s), 2.05-2.29 (2H, m), 1.94 (3H, br s), 1.60-1.77 (1H, m); $^{19}$F NMR (376 MHz, DMSO-d$_6$) δ ppm −133.60 (1F, br s); LC-MS: method H, RT=1.09 min, MS (ESI) m/z: 590.1 (M+H)$^+$.

Example 053 rac-trans-2-((5-fluoro-2-(2-methoxy-7-methylquinoxalin-5-yl)benzo[d]thiazol-6-yl)oxy)cyclohexyl (6-methoxypyridin-3-yl)carbamate (053)

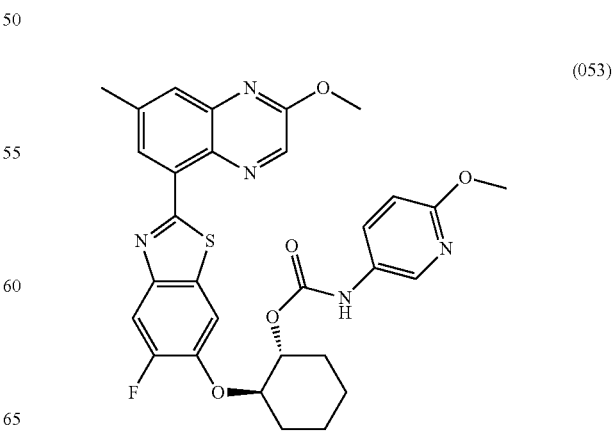

Example 053A: rac-trans-2-((2-chloro-5-fluorobenzo[d]thiazol-6-yl)oxy)cyclohexyl (6-methoxypyridin-3-yl)carbamate

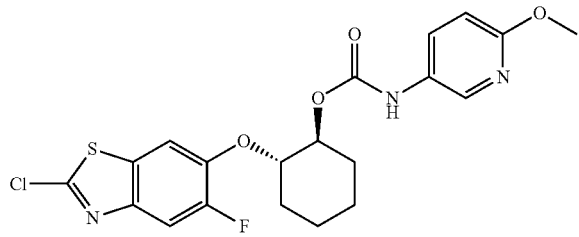

(053A)

I-18 (34 mg, 0.098 mmol) was dissolved in THF (1 mL) and was treated with phosgene (0.704 mL, 0.982 mmol) at room temperature overnight. On the next day, the solvent was removed and the residue was dissolved in anhydrous THF (1 mL), 6-methoxypyridin-3-amine (25.9 mg, 0.209 mmol) in 1 mL of THF was added, followed by adding pyridine (4.22 µl, 0.052 mmol). The mixture was stirred at room temperature for 30 minutes. Then the reaction mixture was loaded on a silica gel column (12 g) and eluted with 0-100% EtOAc/hexane gradient. The desired fractions were collected and solvent was removed to give Example 053A (19 mg, 0.042 mmol, 81% yield) as the product. LC-MS: method H, RT=1.07 min, MS (ESI) m/z: 451.8 (M+H)$^+$.

Example 053

Example 053 (9.7 mg, 0.016 mmol, 39% yield) was made from Example 053A (19 mg, 0.042 mmol) and I-20 (13.8 mg, 0.063 mmol) as a yellow solid by the method described for Example 001A. $^1$H NMR (500 MHz, DMSO-d$_6$) δ ppm 9.36-9.57 (1H, m), 8.70 (1H, s), 8.54 (1H, s), 8.14 (1H, m), 8.04 (1H, d, J=7.02 Hz), 7.90 (1H, d, J=11.29 Hz), 7.80 (1H, s), 7.70 (1H, m), 6.72 (1H, m), 4.85-4.97 (1H, m), 4.49 (1H, d, J=3.66 Hz), 4.07 (3H, s), 3.74 (3H, br s), 2.61 (3H, s), 2.20 (1H, br s), 2.06 (1H, d, J=7.32 Hz), 1.72 (2H, br s), 1.33-1.61 (4H, m); $^{19}$F NMR (471 MHz, DMSO-d$_6$) δ ppm −133.17 (1F, br s); LC-MS: method L, RT=2.616 min, MS (ESI) m/z: 590.0 (M+H)$^+$.

Example 054 rac-trans-2-((5-fluoro-2-(2-methoxy-7-methylquinoxalin-5-yl)benzo[d]thiazol-6-yl)oxy)cyclohexyl (2-methylpyrimidin-5-yl)carbamate

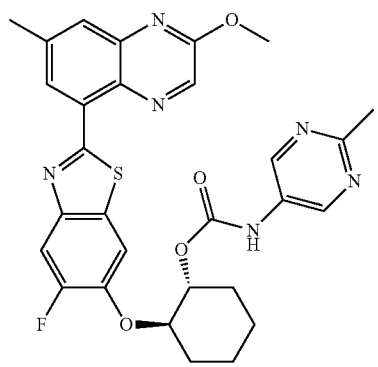

(054)

Example 054 (2.3 mg, 0.004 mmol, 9% yield) was made from I-8 by the method described for Example 053, $^1$H NMR (500 MHz, DMSO-d$_6$) δ ppm 9.83 (1H, m.), 8.72 (1H, s), 8.68 (1H, m.), 8.55 (1H, s), 8.06 (1H, d, J:=7.63 Hz), 7.91 (1H, d, J=11.60 Hz), 7.83 (1H, s), 4.87-5.07 (1H, m), 4.53 (1H, m.), 4.09 (3H, s), 2.63 (3H, s), 2.56 (3H, s), 2.25 (1H, d, J=12.82 Hz), 2.09 (1H, d, J=8.85 Hz), 1.75 (2H, m.), 1.34-1.64 (4H, min); $^{19}$F NMR (471 MHz, DMSO-d$_6$) δ ppm −133.15 (1F, br s); LC-MS: method L. RT=2.44 min, MS (ESI) m/z: 575.1 (M+H)$^+$.

Example 055 rac-cis-2-((5-fluoro-2-(2-methoxy-7-methyl quinoxalin-5-yl)benzo[d]thiazol-6-yl)oxy) cyclohexyl pyridin-3-ylcarbamate

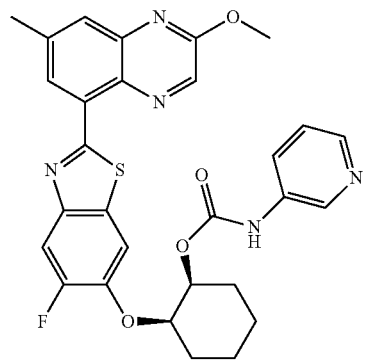

(055)

Example 055A: cis-2-((2-bromo-5-fluorobenzo[d]thiazol-6-yl)oxy)cyclohexyl Carbonochloridate

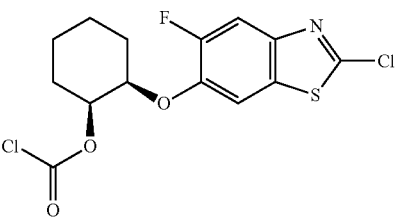

(055A)

In a round bottom flask charged with a stirring bar, I-02 (200 mg, 0.578 mmol) was suspended in anhydrous THF (5 mL) and was treated with phosgene (4.12 mL, 5.78 mmol) at room temperature overnight. On the next day, the solvent was removed on the rotary evaporator and the residue was dried on HVAC for 2 hours. The crude product was used in next step. LC-MS: method H, RT=1.20 min, MS (ESI) m/z: 364.0 (M+H)$^+$.

Example 055B: cis-2-((2-chloro-5-fluorobenzo[d]thiazol-6-yl)oxy)cyclohexyl pyridin-3-ylcarbamate

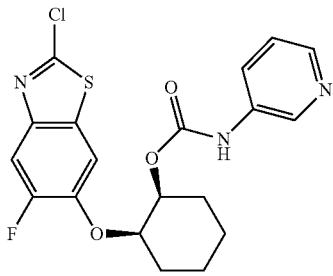
(055B)

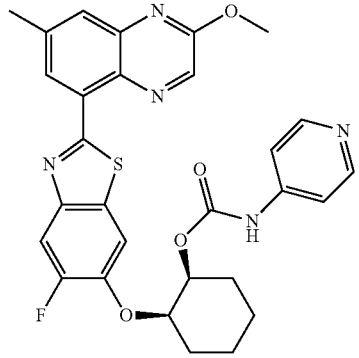
(056)

In a vial charged with a stirring bar, Example 055A (0.078 g, 0.192 mmol) was dissolved in DCM (2 mL). DIEA (0.168 mL, 0.960 mmol) was added, followed by pyridin-3-amine (0.072 g, 0.768 mmol). The mixture was stirred at room temperature overnight. On the next day, without workup, the reaction mixture was purified by silica gel chromatography (12 g silica gel column, 0-100% EtOAc/hexane gradient). Solvent was removed from the desired fractions to give Example 055B (0.037 g, 0.088 mmol, 45.7% yield) as a white solid. $^1$H NMR (400 MHz, CDCl$_3$) δ 8.47 (d, J=2.6 Hz, 1H), 8.32 (dd, J=4.7, 1.4 Hz, 1H), 7.88 (d, J=6.4 Hz, 1H), 7.66 (d, J=10.8 Hz, 1H), 7.38 (d, J=7.7 Hz, 1H), 7.26-7.22 (m, 1H), 6.62 (br s, 1H), 5.08 (d, J=9.7 Hz, 1H), 4.64 (br s, 1H), 2.31-202 (m, 2H), 1.91-1.69 (m, 4H), 1.52 (br s, 2H); $^{19}$F NMR (376 MHz, CDCl$_3$) δ -131.17 (s, 1F); LC-MS: method H, RT=0.86 min, MS (ESI) m/z: 422.1 (M+H)$^+$.

Example 055

Example 055 (11.2 mg, 0.02 mmol, 59% yield) was made from Example 055B (14.05 mg, 0.033 mmol) and I-20 (10 mg, 0.033 mmol) by the method described for Example 001A. $^1$H NMR (500 MHz, DMSO-d$_6$) δ 9.86 (br s, 1H), 8.64 (s, 1H), 8.60 (br s, 1H), 8.49 (s, 1H), 8.16 (d, J=4.3 Hz, 1H), 8.01 (d, J=8.2 Hz, 1H), 7.90 (d, J=11.6 Hz, 1H), 7.85 (d, J=7.3 Hz, 1H), 7.76 (s, 1H), 7.28 (dd, J=8.1, 4.7 Hz, 1H), 5.11 (br s, 1H), 4.82 (br s, 1H), 4.04 (s, 31H), 2.58 (s, 31H), 2.00 (d, J=8.5 i-Hz, 2H), 1.79 (br. m, 2H), 1.66 (br. m, 2H), 1.48 (br. m, 21H); $^{19}$F NMR (471 MHz, DMSO-d$_6$) δ -133.30 (br s, 1F); LC-MS: method L, RT=2.182 min, MS (ESI) m/z: 560.20 (M+H)$^+$.

Example 056 rac-cis-2-((5-fluoro-2-(2-methoxy-7-methylquinoxalin-5-yl)benzo[d]thiazol-6-yl)oxy) cyclohexyl pyridin-4-ylcarbamate Example 056 (7.8 ng, 0.014 mmol, 41% yield) was made by the method described for Example 055. $^1$H NMR (500 MHz, DMSO-d$_6$) δ 10.11 (s, 1H), 8.64 (s, 1H), 8.49 (s, 1H), 8.32 (d, J=5.2 Hz, 2H), 8.00 (d, d=8.2 Hz, 1H), 7.89 (d, J=1.6 Hz, 1H), 7.76 (s, 1H), 7.41 (d, J=5.5 Hz, 2H), 5.12 (br. m, 1H), 4.81 (br. m., 1H), 4.04 (s, 3H), 2.58 (s, 3H), 2.11-1.92 (m, 21H), 1.79 (br. m, 2H), 1.66 (br. m, 2H), 1.48 (br m, 2H); $^{19}$F NMR (471 MHz, DMSO-d$_6$) δ -133.31 (br s, 1F); LC-MS: method L, R=2.208 min, MS (ESI) m/z: 560.20 (M+H)$^+$.

Example 057 rac-cis-2-((5-fluoro-2-(2-methoxy-7-methyl quinoxalin-5-yl)benzo[d]thiazol-6-yl)oxy) cyclohexyl (6-methoxypyridin-3-yl)carbamate

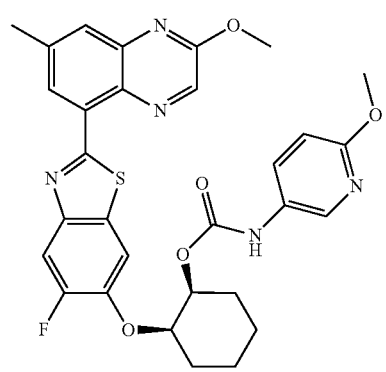
(057)

Example 057 (8.6 mg, 0.014 mmol, 42% yield) was made by the method described for Example 055. $^1$H NMR (500 MHz, CDCl$_3$) δ 8.61 (s, 1H), 8.54 (s., 1H), 8.03 (s., 1 H), 7.82 (d, J=8.0 Hz, 1H), 7.77 (s., 1H), 7.72 (s., 1H), 7.54 (s., 1H), 6.68 (s, 1H), 6.47 (s., 1H), 5.08 (m, 1H), 4.71 (m, 1H), 4.14 (s, 3H), 3.86 (s, 3H), 2.66 (s, 3H), 2.17 (m, 2H), 1.81 (m, 4H), 1.51 (m, 2H); $^{19}$F NMR (471 MHz, CDCl$_3$) δ -132.49 (s, 1F); LC-MS: method H, RT=1.30 min, MS (ESI) m/z: 590.3 (M+H)$^+$.

Example 058 cis-2-((5-fluoro-2-(2-methoxy-7-methylquinoxalin-5-yl)benzo[d]thiazol-6-yl)oxy)cyclohexyl pyridin-3-ylcarbamate (Enantiomer 1)

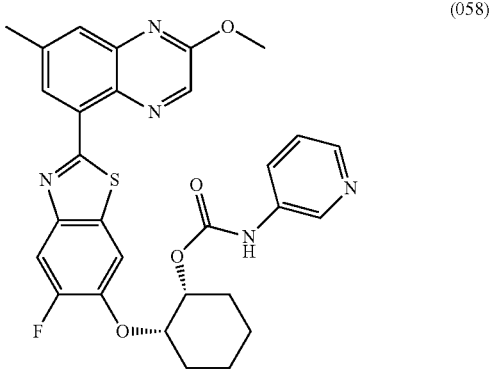 [SMILES: COc1cnc2c(-c3nc4cc(F)c(O[C@H]5CCCC[C@H]5OC(=O)Nc5cccnc5)cc4s3)cc(C)cc2n1]
(058)

Example 059 cis-2-((5-fluoro-2-(2-methoxy-7-methylquinoxalin-5-yl)benzo[d]thiazol-6-yl)oxy)cyclohexyl pyridin-3-ylcarbamate (Enantiomer 2)

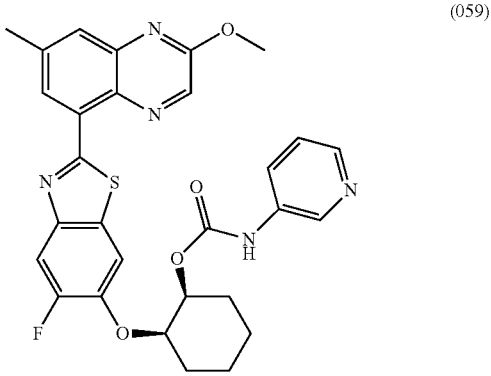 [SMILES: COc1cnc2c(-c3nc4cc(F)c(O[C@@H]5CCCC[C@@H]5OC(=O)Nc5cccnc5)cc4s3)cc(C)cc2n1]
(059)

Example 055 (10.6 mg, 0.019 mmol) was separated by chiral SFC: PIC Solution 200 SFC, Chiralpak IA column, 21×250 mm, 5 micron, 40% EtOH/60% CO2; 45 mL/min, 150 Bar, 40° C., 220 nm to yield Example 058 (peak 1, 5.1 mg, 0.009 mmol, retention time: 10.7 min, >99% ee) and Example 059 (peak 2, 4.8 mg, 0.008 mmol, retention time: 12.9 min, >99% ee) as the products.

Example 058

$^1$H NMR (400 MHz, DMSO-$d_6$) δ 9.88 (br s, 1H), 8.75 (s, 1H), 8.63 (br s, 1H), 8.59 (d, J=2.0 Hz, 1H), 8.19 (br s, 1H), 8.08 (d, J=8.6 Hz, 1H), 7.96 (d, J=11.4 Hz, 1H), 7.85 (s, 2H), 7.32-7.26 (m, 1H), 5.12 (m, 1H), 4.85 (m, 1H), 4.09 (s, 31H), 2.64 (s, 31H), 2.04 (m, 2H), 1.81 (m, 2H), 1.68 (min, 2H), 1.49 (m, 2H); $^{19}$F NMR (376 MHz, DMSO-$d_6$) δ −133.31 (s, 1F); LC-MS: method H, RT=1.07 min, MS (ESI) m/z: 560.2 (M+H)$^+$.

Example 059

$^1$H NMR (400 MHz, DMSO-$d_6$) δ 9.88 (s, 1H), 8.75 (s, 1H), 8.62 (s, 1H), 8.59 (d, J=2.0 Hz, 1H), 8.18 (d, J=4.8 Hz, 1H), 8.08 (d, J=8.4 Hz, 1H), 7.96 (d, J=11.7 Hz, 1H), 7.85 (s, 2H), 7.29 (dd, J=8.3, 4.5 Hz, 1H), 5.14 (m, 1H), 4.86 (m, 1H), 4.09 (s, 3H), 2.64 (s, 3H), 2.05 (m, 2H), 1.81 (nm, 21H), 1.70 (m, 2H), 1.51 (m, 21H); $^{19}$F NMR (376 MHz, DMSO-$d_6$) δ −133.31 (s, 1F); LC-MS: method H, RT=1.07 min, MS (ESI) m/z: 560.2 (M+H)$^+$.

Example 060 cis-2-((5-fluoro-2-(2-methoxy-7-methylquinoxalin-5-yl)benzo[d]thiazol-6-yl)oxy)cyclobutanol (Homochiral)

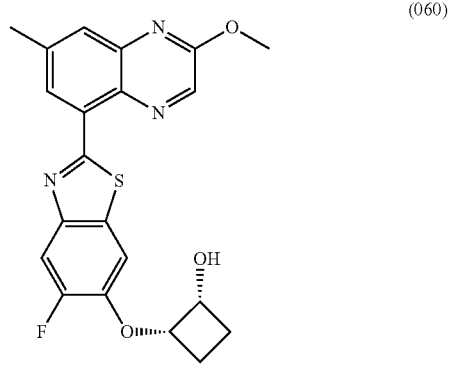
(060)

Example 60 (84 mg, 0.204 mmol, 76% yield) was made from I-09 (86 mg, 0.270 mmol) and I-20 (88 mg, 0.405 mmol) by the method described for Example 001A. $^1$H NMR (500 MHz, DMSO-$d_6$) δ 8.69 (s, 1H), 8.54 (s, 1H), 7.92 (d, J=11.6 Hz, 1H), 7.80 (s, 1H), 7.76 (d, J=8.2 Hz, 1H), 4.79 (br s, 1H), 4.53 (br s, 1H), 4.06 (s, 3H), 2.54 (s, 3H), 2.28-2.07 (m, 3H), 1.93 (m, 1H); $^{19}$F NMR (471 MHz, DMSO-$d_6$) δ −133.75 (br s, 1F); LC-MS: method H, RT=116 min, MS (ESI) m/z: 412.0 (M+H)$^+$.

Example 061 rac-cis-2-((5-fluoro-2-(2-methoxy-7-methylquinoxalin-5-yl)benzo[d]thiazol-6-yl)oxy) cyclobutyl (2-methylpyrimidin-5-yl)carbamate

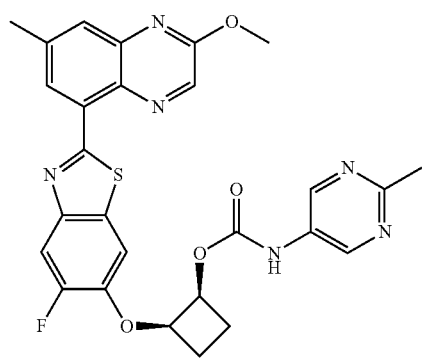
(061)

Example 061 (5.6 mg, 0.10 mmol, 35%) was made from I-07 and I-20 by the method described for Example 055. $^1$H NMR (500 MHz, DMSO-$d_6$) δ ppm 9.86-10.00 (1H, m), 8.71 (1H, s), 8.59 (2H, s), 8.53 (1H d, J=1.22 Hz), 7.92 (1H, d, J=11.60 Hz), 7.77-7.86 (2H, m), 5.44 (1H, d, J=3.66 Hz), 5.15 (1H, d, J=3.05 Hz), 4.08 (3H, s), 2.63 (3H, s), 2.39-2.45 (1H, m), 2.35 (3H, br s), 2.20-2.32 (2H, m); $^{19}$F NMR (471 MHz, DMSO-$d_6$) δ ppm −138.91 (1F, br s); LC-MS: method L, RT=2.20 min, MS (ESI) m/z: 547.30 (M+H)$^+$.

Example 062 cis-2-((5-fluoro-2-(2-methoxy-7-methylquinoxalin-5-yl)benzo[d]thiazol-6-yl)oxy)cyclobutyl (2-((R)-2-hydroxypropoxy)pyrimidin-5-yl)carbamate (Homochiral)

(062)

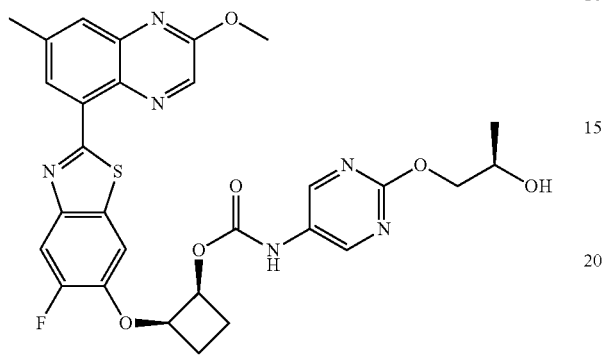

Example 062 was made from I-08 and I-31 by the method described for Example 001. $^1$H NMR (500 MHz, DMSO-$d_6$) δ ppm 9.78 (1H, br s), 8.69 (1H, s), 8.52 (1H, br s), 8.43 (2H, br s), 7.92 (1H, d, J=11.90 Hz), 7.80 (2H, br s), 5.44 (1H, br s), 5.15 (1H, br s), 4.08 (3H, s), 3.91 (1H, br s), 3.82 (2H, br s), 3.36 (1H, d, J=11.29 Hz), 2.62 (3H, s), 2.42 (1H, br s), 2.34 (1H, br s), 2.19-2.31 (2H, m), 1.04 (3H, br s); $^{19}$F NMR (471 MHz, DMSO-$d_6$) δ ppm −133.81 (1F, br s); LC-MS: method L, RT=2.19 min, MS (ESI) m/z: 607.0 (M+H)$^+$.

Example 063 to 073

The following additional examples have been prepared, isolated and characterized using the methods described for Example 001 and the examples above, from the corresponding cyclic diol and aniline intermediates.

| Ex. No. | Structure | Chirality | LCMS [M + H]$^+$ m/z | LCMS RT(Min)/ Method | NMR |
|---|---|---|---|---|---|
| 063 | 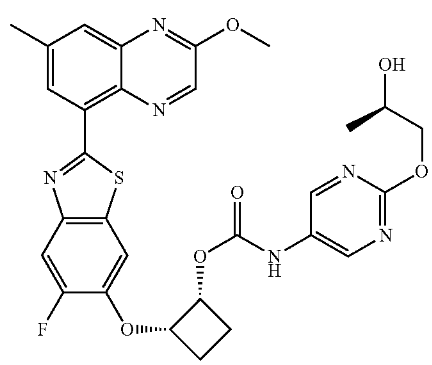 [SMILES: COc1cnc2c(-c3nc4cc(F)c(O[C@H]5CC[C@H]5OC(=O)Nc5cnc(OC[C@@H](C)O)nc5)cc4s3)cc(C)cc2n1] | homochiral (from I-09) | 607.03 | 2.20/L | $^1$H NMR (500 MHz, DMSO-$d_6$) δ ppm 9.64-9.87 (1 H, m), 8.68 (1 H, s), 8.52 (1 H, s), 8.43 (2 H, br s), 7.92 (1 H, d, J = 11.60 Hz), 7.80 (2 H, br s), 5.44 (1 H, m), 5.15 (1 H, m), 4.08 (3 H, s), 3.91 (1 H, br s), 3.80 (2 H, br s), 2.62 (3 H, s), 2.41 (1 H, br s), 2.34 (1 H, br s), 2.18-2.31 (2 H, m), 1.03 (3 H, d.); $^{19}$F NMR (471 MHz, DMSO-$d_6$) δ ppm −133.84 (1 F, s) |
| 064 | 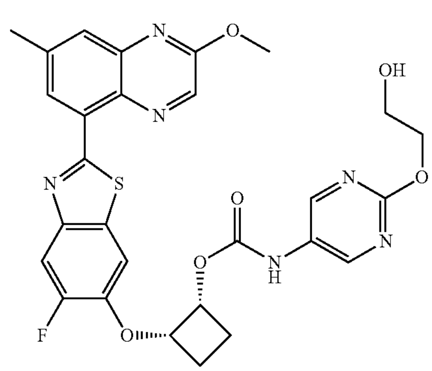 [SMILES: COc1cnc2c(-c3nc4cc(F)c(O[C@H]5CC[C@H]5OC(=O)Nc5cnc(OCCO)nc5)cc4s3)cc(C)cc2n1] | homochiral (from I-09) | 593.0 | 1.09/H | $^1$H NMR (500 MHz, DMSO-$d_6$) δ ppm 9.63-9.85 (1 H, m), 8.65 (1 H, s), 8.48 (1 H, s), 8.42 (2 H, br s), 7.89 (1 H, d, J = 11.60 Hz), 7.69-7.82 (2 H, m), 5.41 (1 H, m), 5.13 (1 H, m), 4.06 (2H, t), 4.05 (3 H, s), 3.55 (1 H, br s), 2.59 (3 H, s), 2.54 (2 H, s), 2.40 (1 H, d, J = 7.02 Hz), 2.30-2.36 (1 H, m), 2.18-2.29 (2 H, m); $^{19}$F NMR (471 MHz, DMSO-$d_6$) δ ppm −133.85 (1 F, br s) |

| Ex. No. | Structure | Chirality | LCMS [M + H]+ m/z | LCMS RT(Min)/ Method | NMR |
|---|---|---|---|---|---|
| 065 | 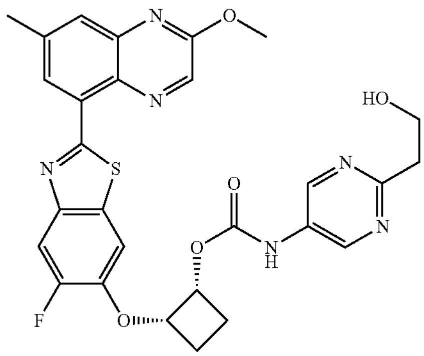 [SMILES: COc1cnc2c(-c3nc4cc(F)c(O[C@H]5CC[C@H]5OC(=O)Nc5cnc(CCO)nc5)cc4s3)cc(C)cc2n1] | homochiral (from I-09) | 577.0 | 1.06/H | ¹H NMR (500 MHz, DMSO-d₆) δ ppm 9.98 (1 H, br s), 8.66 (1 H, s), 8.62 (2 H, s), 8.48 (1 H, s), 7.89 (1 H, d, J = 11.60 Hz), 7.81 (1 H, d, J = 7.93 Hz), 7.77 (1 H, s), 5.43 (1 H, br s), 5.13 (1 H, d, J = 3.66 Hz), 4.05 (3 H, s), 3.69 (2 H, d, J= 5.80 Hz), 3.37 (1 H, br s), 2.79 (2 H, br s), 2.59 (3 H, s), 2.42 (1 H, br s), 2.33 (1 H, br s), 2.25 (2 H, d, J = 5.80 Hz); ¹⁹F NMR (471 MHz, DMSO-d₆) δ ppm −133.86 (1 F, s) |
| 066 | 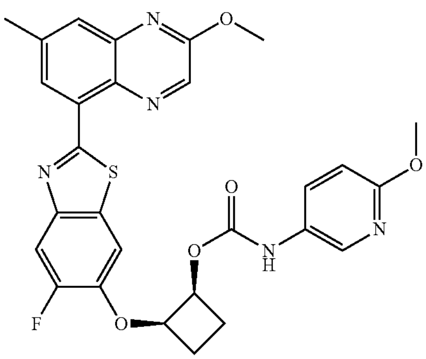 | racemic | 561.9 | 1.18/H | ¹H NMR (400 MHz, CDCl₃) δ ppm 8.51 (1 H, d, J = 1.54 Hz), 8.46 (1 H, s), 7.86 (1 H, d, J = 2.64 Hz), 7.73 (1 H, d, J = 11.44 Hz), 7.69 (1 H, d, J = 0.88 Hz), 7.54 (1 H br s), 7.31 (1 H, d, J = 7.26 Hz), 6.54 (1 H, d, J = 8.80 Hz), 6.29-6.44 (1 H, m), 5.33-5.43 (1 H, m), 4.96 (1 H, d, J = 3.96 Hz), 4.06 (3 H, s), 3.71 (3 H, br s), 2.57 (3 H, s), 2.30 (4 H, d, J = 5.28 Hz); ¹⁹F NMR (376 MHz, CDCl₃) δ ppm −134.04 (1 F, br s) |
| 067 | 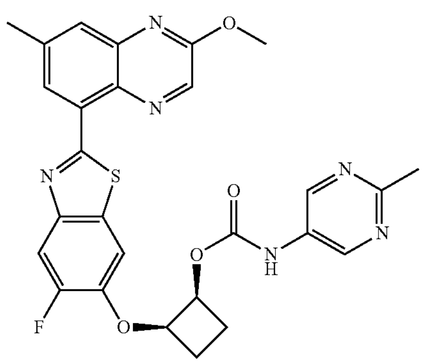 | homochiral (from I-08) | 547.30 | 2.191 | ¹H NMR (500 MHz, DMSO-d₆) δ 9.93 (br s, 1 H), 8.65 (s, 1 H), 8.57 (s, 2H), 8.47 (s, 1 H), 7.88 (d, J = 11.6 Hz, 1 H), 7.82-7.69 (m, 2H), 5.42 (br s, 1 H), 5.13 (br s, 1 H), 4.05 (s, 3H), 2.59 (s, 3H), 2.54 (s, 3H), 2.45-2.12 (m, 4H); ¹⁹F NMR (471 MHz, DMSO-d₆) δ ppm −133.88 (1 F, br s) |
| 068 | 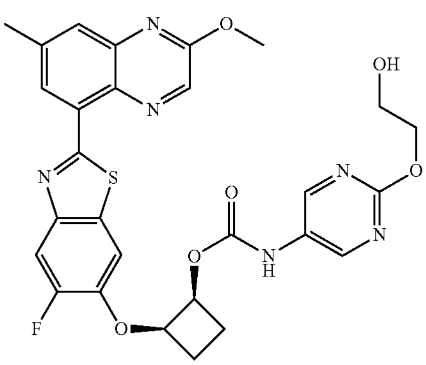 [SMILES: COc1cnc2c(-c3nc4cc(F)c(O[C@@H]5CC[C@@H]5OC(=O)Nc5cnc(OCCO)nc5)cc4s3)cc(C)cc2n1] | homochiral (from I-08) | 593.0 | 1.07/H | ¹H NMR (500 MHz, DMSO-d₆) δ ppm 9.76 (1 H, br s), 8.66 (1 H, s), 8.49 (1 H, s), 8.42 (2 H, br s), 7.90 (1 H, d, J = 11.60 Hz), 7.78 (2 H, br s), 5.42 (1 H, br s), 5.13 (1 H, br s), 4.06 (5 H, s), 3.55 (1 H, br s), 2.59 (3 H, s), 2.54 (2 H, s), 2.40 (1 H, br s), 2.32 (1 H, br s), 2.16-2.29 (2 H, m); ¹⁹F NMR (471 MHz, DMSO-d₆) δ ppm −133.83 (1 F, br s) |

-continued

| Ex. No. | Structure | Chirality | LCMS [M + H]+ m/z | LCMS RT(Min)/ Method | NMR |
|---|---|---|---|---|---|
| 069 | 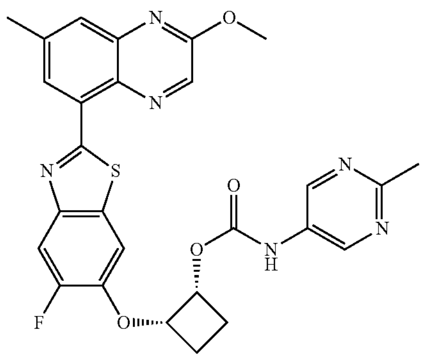 | homochiral (from I-09) | 547.3 | 2.186/L | ¹H NMR (500 MHz, DMSO-d₆) δ ppm 9.76-10.06 (1 H, m), 8.66 (1 H, s), 8.57 (2 H, s), 8.48 (1 H, s), 7.89 (1 H, d, J = 11.60 Hz), 7.71-7.82 (2 H, m), 5.42 (1 H, m), 5.14 (1 H, m), 4.05 (3 H, s), 2.59 (3 H, s), 2.54 (3 H, s), 2.14-2.45 (4 H, m); ¹⁹F NMR (471 MHz, DMSO-d₆) δ ppm −133.86 (1 F, br s) |
| 070 | 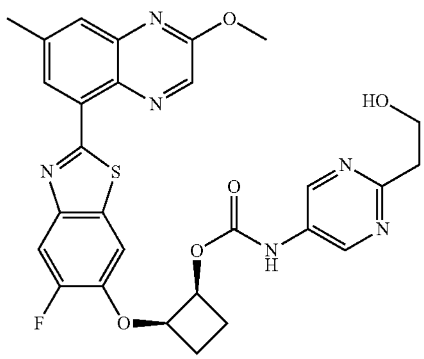 [SMILES: COc1cnc2c(-c3nc4cc(F)c(O[C@@H]5CC[C@@H]5OC(=O)Nc5cnc(CCO)nc5)cc4s3)cc(C)cc2n1] | homochiral (from I-08) | 577.2 | 2.075/L | ¹H NMR (500 MHz, DMSO-d₆) δ ppm 9.96 (1 H, br s), 8.66 (1 H, s), 8.61 (2 H, s), 8.48 (1 H, s), 7.89 (1 H, d, J = 11.60 Hz), 7.71-7.83 (2 H, m), 5.42 (1 H, m), 5.13 (1 H, m), 4.05 (3 H, s), 3.67 (2 H, d, J = 5.19 Hz), 2.77 (2 H, br s), 2.54 (3 H, s), 2.37-2.45 (1 H, m), 2.33 (1 H, m), 2.25 (2 H, d, J = 5.49 Hz); ¹⁹F NMR (471 MHz, DMSO-d₆) δ ppm −133.88 (1 F, br s) |
| 071 | 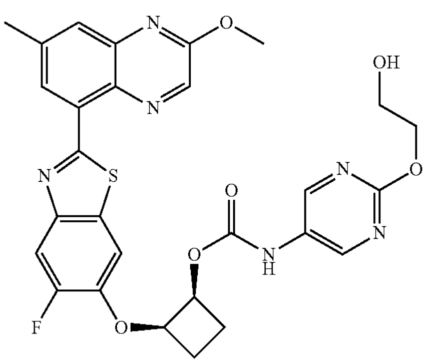 [SMILES: COc1cnc2c(-c3nc4cc(F)c(O[C@@H]5CC[C@@H]5OC(=O)Nc5cnc(OCCO)nc5)cc4s3)cc(C)cc2n1] | racemic (from I-07) | 593.5 | 2.135/L | ¹H NMR (500 MHz, DMSO-d₆) δ ppm 9.64-9.87 (1 H, m), 8.70 (1 H, s), 8.53 (1 H, s), 8.43 (2 H, br s), 7.93 (1 H, d, J = 11.60 Hz), 7.75-7.86 (2 H, m), 5.43 (1 H, d, J = 3.66 Hz), 5.14 (1 H, br s), 4.78 (1 H, br s), 4.08 (3 H, s), 4.04 (2 H, br s), 3.51-3.62 (2 H, m), 2.62 (3 H, s), 2.24 (4 H, m); ¹⁹F NMR (471 MHz, DMSO-d₆) δ ppm −133.82 (1 F, br s) |
| 072 | 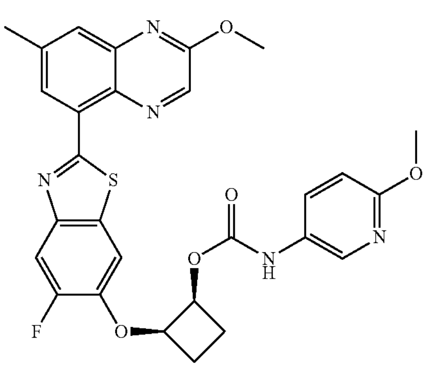 | homochiral (from I-08) | 561.9 | 1.21/H | ¹H NMR (400 MHz, CDCl₃) δ ppm 8.59 (1 H, d, J = 1.54 Hz), 8.54 (1 H, s), 7.94 (1 H, d, J = 2.42 Hz), 7.81 (1 H, d, J = 11.22 Hz), 7.76 (1 H, s), 7.57-7.68 (1 H, m), 7.34-7.46 (1 H, m), 6.61 (1 H, d, J = 8.80 Hz), 6.35-6.53 (1 H, m), 5.31-5.56 (1 H, m), 4.89-5.21 (1 H, m), 4.14 (3 H, s), 3.79 (3 H, br s), 2.65 (3 H, s), 2.38 (4 H, d, J = 4.84 Hz); ¹⁹F NMR (376 MHz, CDCl₃) δ ppm −134.03 (1 F, br s) |

| Ex. No. | Structure | Chirality | LCMS [M + H]+ m/z | LCMS RT(Min)/ Method | NMR |
|---|---|---|---|---|---|
| 073 | 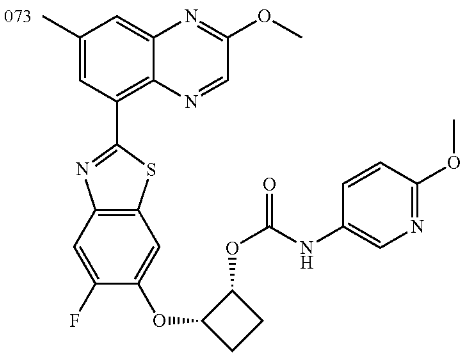 | homochiral (from I-09) | 561.9 | 1.21/H | ¹H NMR (400 MHz, CDCl₃) δ ppm 8.59 (1 H, d, J = 1.54 Hz), 8.54 (1 H, s), 7.94 (1 H, d, J = 2.64 Hz), 7.81 (1 H, d, J = 11.22 Hz), 7.76 (1 H, d, J = 0.88 Hz), 7.57-7.68 (1 H, m), 7.39 (1 H, d, J = 7.70 Hz), 6.61 (1 H, d, J = 8.80 Hz), 6.46 (1 H, br s), 5.46 (1 H, d, J = 6.82 Hz), 4.97-5.10 (1 H, m), 4.14 (3 H, s), 3.79 (3 H, br s), 2.65 (3 H, s), 2.38 (4 H, d, J = 4.84 Hz); ¹⁹F NMR (376 MHz, CDCl₃) δ ppm −134.04 (1 F, br s) |

Example 074 cis-2-((5-fluoro-2-(3-methoxy-6-methylquinolin-8-yl)benzo[d]thiazol-6-yl)oxy)cyclo butyl (2-(2-hydroxyethoxy)pyrimidin-5-yl)carbamate (Homochiral)

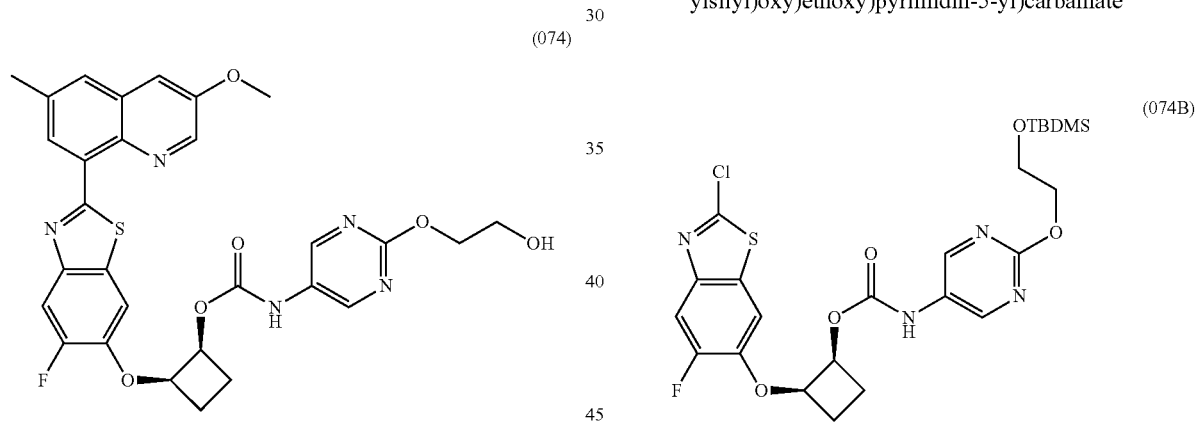

(074)

Example 074A: cis-2-((2-chloro-5-fluorobenzo[d]thiazol-6-yl)oxy)cyclobutyl Carbonochloridate

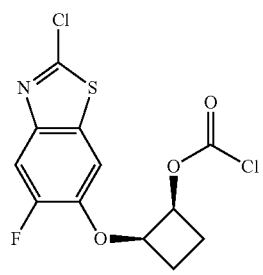

(074A)

I-08 (80 mg, 0.251 mmol) was dissolved in THF (5 mL) and was treated with phosgene (1.795 mL, 2.51 mmol) at room temperature for 18 hours. On the next day, the solvent was removed and the residue was dried on HVAC for 1 hour. The crude product was used in the next step without purification. LC-MS: method H, RT=1.09 min, MS (ESI) m/z: 336.0 (M+H)⁺.

Example 074B: cis-2-((2-chloro-5-fluorobenzo[d]thiazol-6-yl)oxy)cyclobutyl (2-(2-((tert-butyldimethylsilyl)oxy)ethoxy)pyrimidin-5-yl)carbamate (074B)

In a round bottom flask charged with a stirring bar, Intermediate I-30 (0.135 g, 0.502 mmol) was dissolved in DCM (4 mL) and mixed with pyridine (0.061 mL, 0.753 mmol). To the mixture was added Example 074A (0.084 g, 0.251 mmol) in DCM (2 mL) dropwise. The mixture was stirred at room temperature for 3 hour. Then the solvent was removed and the residue was used in the next step without purification. LC-MS: method H, RT=1.27 min, MS (EST) m/z: 569.0 (M+H)⁺.

Example 074C: cis-2-((2-chloro-5-fluorobenzo[d]thiazol-6-yl)oxy)cyclobutyl (2-(2-hydroxyethoxy)pyrimidin-5-yl)carbamate

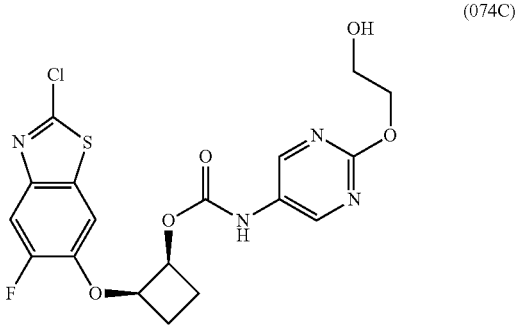 [SMILES: O=C(Nc1cnc(OCCO)nc1)O[C@H]1CC[C@H]1Oc1cc2sc(Cl)nc2cc1F]
(074C)

Example 074B (0.142 g, 0.25 mmol) was dissolved in THF (10 mL) and HCl (4M in dioxane) (1 mL, 4.00 mmol) was added. The mixture was stirred at room temperature for 1 hour. LC/MS showed partial reaction. The reaction was stirred at room temperature overnight. On the next day, the solvent was removed and the product was used without purification. LC-MS: method H, RT=0.85 min, MS (ESI) m/z: 455.0 (M+H)$^+$.

Example 074

In a vial charged with a stirring bar, Example 074A (11.37 mg, 0.025 mmol) was dissolved in 1,4-dioxane (1 mL). I-28 (11.22 mg, 0038 mmol) was added, followed by $Na_2CO_3$ (0.30 mL, 0.600 mmol) and $PdCl_2(dppf)-CH_2Cl_2$ adduct (2.042 mg, 2.500 mol). The mixture was stirred at 80° C. for 30 minutes. After cooling to RT, the reaction was diluted by EtOAc (10 mL)/$H_2O$(5 mL) After separation, the organic phase was dried on $Na_2SO_4$, filtered and concentrated. The crude product was purified by reverse phase preparative HPLC, method D to give Example 074 (5.0 mg, 0.008 mmol, 34% yield) as the product. $^1$H NMR (500 MHz, DMSO-$d_6$) δ ppm 9.69-9.87 (1H, min), 8.78 (1H, d, J=2.44 Hz), 8.58 (1H, s), 8.46 (2H, br s), 7.92 (1H, d, J=11.60 Hz), 7.86 (2H, d, J=3.05 Hz), 7.82 (1H, d, J=8.24 Hz), 5.44 (1H, br s), 5.15 (1H, br s), 4.07 (2H, br s), 3.99 (3H, s), 3.59 (1H, br s), 3.37 (2H, br s), 2.61 (3-1H, s), 2.19-2.46 (4H, nm); $^{19}$F NMR (471 MHz, DMSO-$d_6$) δ ppm −134.39 to −133.94 (1F, m); LC-MS: method H, RT=0.95 min, MS (ESI) m/z: 592.1 (M+H)$^+$.

Example 075 to 083

The following additional examples have been prepared, isolated and characterized using the methods described for Example 074 and the examples above, from corresponding cyclic diol and boronic acid/ester intermediates.

| Ex. No. | Structure | Chirality | LCMS [M + H]$^+$ m/z | LCMS RT(Min)/Method | NMR |
|---|---|---|---|---|---|
| 075 | 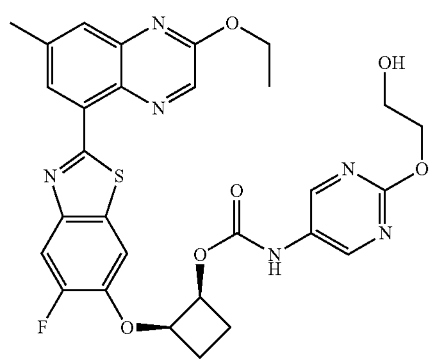 [SMILES: CCOc1cnc2c(-c3nc4cc(F)c(O[C@@H]5CC[C@@H]5OC(=O)Nc5cnc(OCCO)nc5)cc4s3)cc(C)cc2n1] | homochiral (from I-08) | 607.1 | 1.13/H | $^1$H NMR (400 MHz, CDCl$_3$) δ ppm 8.54-8.59 (1 H, m), 8.51 (1 H, s), 8.48 (2 H, s), 7.80 (1 H, d, J = 11.22 Hz), 7.73 (1 H, d, J = 0.88 Hz), 7.37 (1 H, d, J = 7.92 Hz), 6.51-6.74 (1 H, m), 5.47 (1 H, d, J = 6.38 Hz), 5.04 (1 H, d, J = 3.96 Hz), 4.58 (2 H, d, J = 7.04 Hz), 4.29-4.43 (2 H, m), 3.89 (2 H, br s), 2.64 (3 H, s), 2.27-2.56 (4 H, m), 1.51 (3 H, t, J = 7.04 Hz), 1.27 (1 H, t, J = 7.04 Hz) |
| 076 | 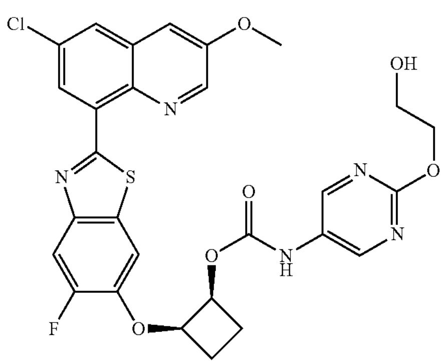 | homochiral (from I-08) | 612.0 | 1.08/H | $^1$H NMR (500 MHz, DMSO-$d_6$) δ ppm 9.74 (1 H, br s), 8.81 (1 H, d, J = 2.14 Hz), 8.55 (1 H, s), 8.40 (2 H, br s), 8.15 (1 H, s), 7.85-7.98 (2 H, m), 7.78 (1 H, d, J = 8.24 Hz), 5.41 (1 H, br s), 5.14 (1 H, br s), 3.97 (5 H, s), 3.43 (2 H, br s), 2.30-2.44 (2 H, m), 2.24 (2 H, m.); $^{19}$F NMR (471 MHz, DMSO-$d_6$) δ ppm −133.61 (1 F, s) |

| Ex. No. | Structure | Chirality | LCMS [M + H]+ m/z | LCMS RT(Min)/ Method | NMR |
|---|---|---|---|---|---|
| 077 | 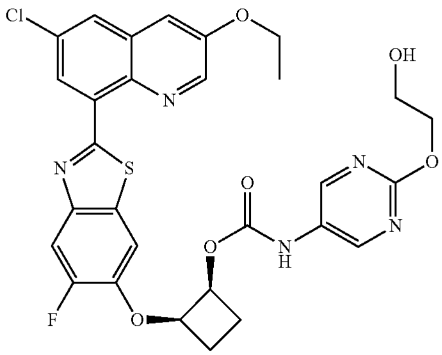 [SMILES: CCOc1cnc2c(-c3nc4cc(F)c(O[C@@H]5CC[C@@H]5OC(=O)Nc5cnc(OCCO)nc5)cc4s3)cc(Cl)cc2c1] | homochiral (from I-08) | 626.0 | 1.13/H | ¹H NMR (500 MHz, DMSO-d₆) δ ppm 9.56-9.88 (1 H, m), 8.79 (1 H, d, J = 2.44 Hz), 8.54 (1 H, s), 8.40 (2 H, br s), 8.13 (1 H, s), 7.85-7.99 (2 H, m), 7.80 (1 H, d, J = 7.93 Hz), 5.34-5.47 (1 H, m), 4.98-5.22 (1 H, m), 4.24 (2 H, q, J = 6.71 Hz), 4.00 (2 H, br s), 3.42 (3 H, d, J = 5.80 Hz), 2.30-2.44 (2 H, m), 2.17-2.30 (2 H, m), 1.44 (3 H, t, J = 6.87 Hz); ¹⁹F NMR (471 MHz, DMSO-d₆) δ ppm −133.71 (1 F, s) |
| 078 | 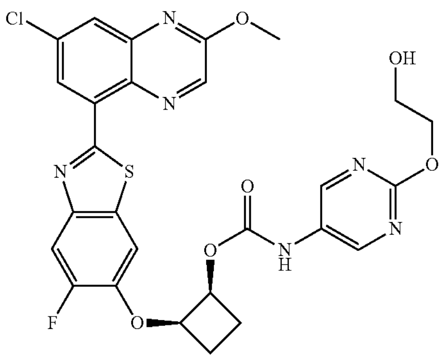 [SMILES: COc1cnc2c(-c3nc4cc(F)c(O[C@@H]5CC[C@@H]5OC(=O)Nc5cnc(OCCO)nc5)cc4s3)cc(Cl)cc2n1] | homochiral (from I-08) | 613.0 | 1.15/H | ¹H NMR (500 MHz, DMSO-d₆) δ ppm 9.71 (1 H, br s), 8.67 (1 H, s), 8.45 (1 H, s), 8.38 (2 H, br s), 7.95 (1 H, d, J = 2.14 Hz), 7.87 (1 H, d, J = 11.29 Hz), 7.73(1 H, d, J = 8.24 Hz), 5.40 (1 H, br s), 5.13 (1 H, br s), 4.05 (3 H, s), 3.98 (2 H, br s), 3.49 (2 H, s), 2.24 (4 H, br s); ¹⁹F NMR (471 MHz, DMSO-d₆) δ ppm −133.38 (1 F, br s) |
| 079 | 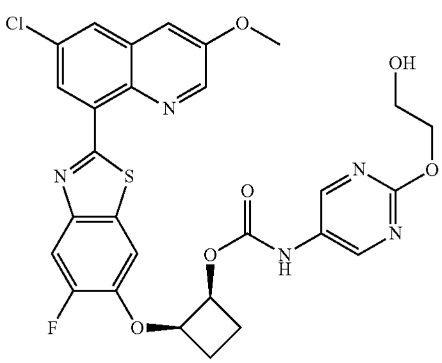 [SMILES: COc1cnc2c(-c3nc4cc(F)c(O[C@@H]5CC[C@@H]5OC(=O)Nc5cnc(OCCO)nc5)cc4s3)cc(Cl)cc2c1] | racemic (from I-07) | 612.30 | 2.16/L | ¹H NMR (500 MHz, DMSO-d₆) δ ppm 9.70-9.83 (1 H, m), 8.85 (1 H, d, J = 2.75 Hz), 8.59 (1 H, d, J = 2.14 Hz), 8.43 (2 H, br s), 8.19 (1 H, d, J = 2.44 Hz), 7.89-8.02 (2 H, m), 7.83 (1 H, d, J = 8.24 Hz), 5.44 (1 H, d, J = 3.36 Hz), 5.16 (1 H, br s), 4.79(1 H, br s), 4.03 (2 H, br s), 4.00 (3 H, s), 3.57 (1 H, br s), 2.17-2.46 (4 H, m) ¹⁹F NMR (471 MHz, DMSO-d₆) δ ppm −133.65 (1 F, br s) |
| 080 | 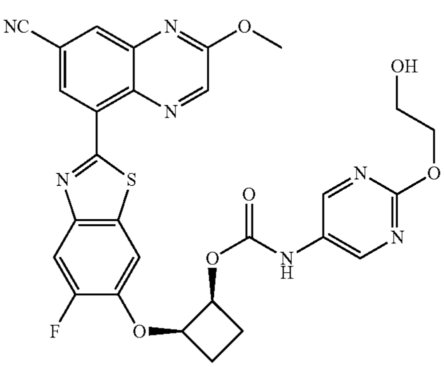 [SMILES: COc1cnc2c(-c3nc4cc(F)c(O[C@@H]5CC[C@@H]5OC(=O)Nc5cnc(OCCO)nc5)cc4s3)cc(C#N)cc2n1] | homochiral (from I-08) | 604.0 | 1.04/H | ¹H NMR (500 MHz, DMSO-d₆) δ ppm 9.74 (1 H, br s), 8.83 (1 H, s), 8.70 (1 H, s), 8.44 (1 H, s), 8.40 (2 H, br s), 7.90 (1 H, d, J = 11.29 Hz), 7.77 (1 H, d, J = 8.24 Hz), 5.42 (1 H, br s), 5.15 (1 H, br s), 4.10 (3 H, s), 4.00 (2 H, br s), 3.37-3.61 (2 H, m), 2.14-2.47 (4 H, m); ¹⁹F NMR (471 MHz, DMSO-d₆) δ ppm −133.18 (1 F, br s) |

-continued

| Ex. No. | Structure | Chirality | LCMS [M + H]+ m/z | LCMS RT(Min)/ Method | NMR |
|---|---|---|---|---|---|
| 081 | 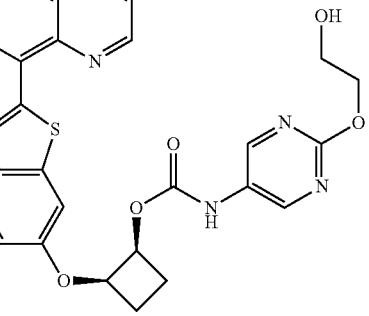 | homochiral (from I-08) | 596.0 | 1.04/H | ¹H NMR (500 MHz, DMSO-d₆) δ ppm 9.60-9.88 (1 H, m), 8.79 (1 H, br s), 8.42 (3 H, br s), 7.89-7.96 (2 H, m), 7.87 (1 H, d, J = 6.41 Hz), 7.81 (1 H, d, J = 8.24 Hz), 5.29-5.55 (1 H, m), 5.02-5.25 (1 H, m), 3.95-4.07 (5 H, m), 3.47-3.52 (3 H, m), 2.31-2.46 (2 H, m), 2.26 (2 H, m); ¹⁹F NMR (471 MHz, DMSO-d₆) δ ppm −117.45 (1 F, s), −141.88 to −135.45 (1 F, m) |
| 082 | 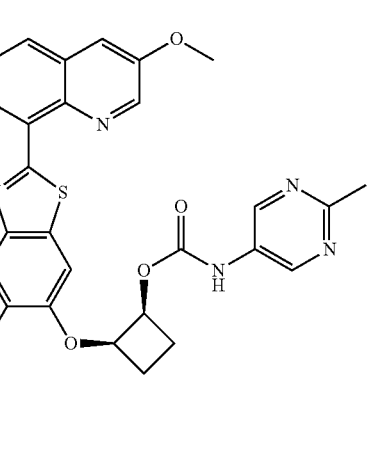 | racemic (from I-07) | 566.2 | 2.22/L | ¹H NMR (500 MHz, DMSO-d₆) δ ppm 9.70-10.00 (1 H, m), 8.85 (1 H, d, J = 2.75 Hz), 8.45-8.64 (3 H,m), 8.18 (1 H, d, J = 2.14 Hz), 7.93 (2 H, dd, J = 7.17, 4.42 Hz), 7.83 (1 H, d, J = 8.24 Hz), 5.44 (1 H, d, J = 5.49 Hz), 5.16 (1 H, d, J = 4.58 Hz), 3.99 (3 H, s), 2.30 (7 H, br s) |
| 083 | 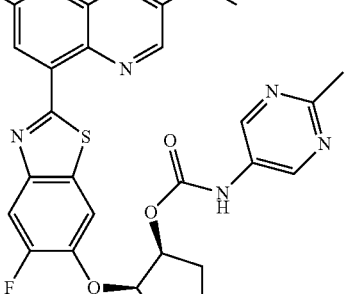 | racemic (from I-13) | 589.1 | 1.25/H | ¹H NMR (400 MHz, DMSO-d₆) δ ppm 8.75 (1 H, s), 8.63 (2 H, s), 8.56 (1 H, d, J = 1.76 Hz), 8.03 (1 H, d, J = 8.36 Hz), 7.93 (1 H, d, J = 11.44 Hz), 7.85 (1 H, s), 5.36 (1 H, s), 5.17 (1 H, s), 4.10 (3 H, s), 2.66-2.71 (1 H, m), 2.64 (3 H, s), 2.40 (3 H, s), 1.78-2.17 (4 H, m), 1.21 (3 H, s), 1.14 (3 H, s); ¹⁹F NMR (376 MHz, DMSO-d₆) δ ppm −133.61 (1 F, s) |

Example 084

(cis)-2-((5-fluoro-2-(2-methoxy-7-methylquinoxalin-5-yl)benzo[d]thiazol-6-yl)oxy)-4,4-dimethylcyclopentyl (2-methylpyrimidin-5-yl)carbamate Enantiomer 1

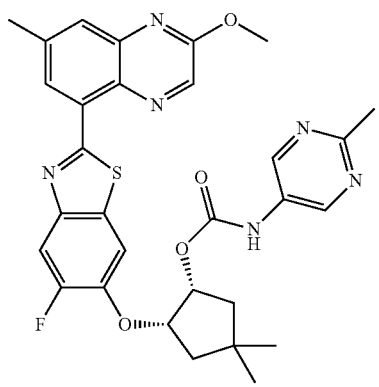

(084)

Example 085

(cis)-2-((5-fluoro-2-(2-methoxy-7-methylquinoxalin-5-yl)benzo[d]thiazol-6-yl)oxy)-4,4-dimethylcyclopentyl (2-methylpyrimidin-5-yl)carbamate Enantiomer 2

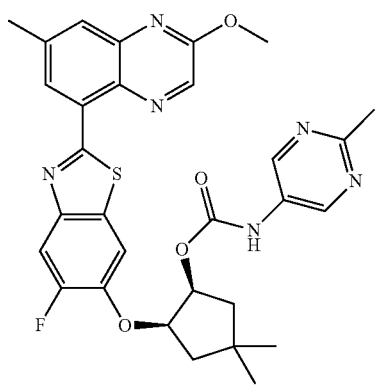

(085)

Example 083 (7 mg, 0.012 mmol) was separated by chiral SEC: Waters Berger MGII SFC, Chiralpak IB, 30×250 mm, 5 micron column; 35% MeOH/EtOH(1:1)/65% CO2, 85 mL/min, 150 Bar, 40° C., 220 nm.

The 1$^{st}$ stereoisomer to elute (retention time: 7.41 min) is Example 084: $^1$H NMR (400 MHz, CDCl$_3$) δ ppm 8.67 (2H, s), 8.59 (1H, d, J=176 Hz), 8.55 (1H, s), 7.80 (1H, d, J=11.44 Hz), 7.77 (1H, s), 7.49 (1H, d, J=7.70 Hz), 6.56 (1H, br s), 5.38 (1H, d, J=3.96 Hz), 4.95-5.03 (1H, m), 4.14 (3H, s), 2.66 (3H, s), 2.60 (3H, s), 1.94-2.13 (4H, m), 1.27 (3H, s), 1.15 (3H, s); $^{19}$F NMR (376 MHz, CDCl$_3$) δ ppm −133.34 (1F, s); LC-MS: method H, RT=1.27 min, MS (ESI) m/z: 589.2 (M+H)$^+$.

The 2nd stereoisomer to elute (retention time: 11.47 min) is Example 085: $^1$H NMR (400 MHz, CDCl$_3$) δ ppm 8.67 (2H, s), 8.59 (1H, d, J=1.76 Hz), 8.55 (1H, s), 7.79 (1H, d, J=11.44 Hz), 7.77 (1H, s), 7.48 (1H, d, J=7.70 Hz), 6.57 (1H, br s), 5.28-5.52 (1H, m), 4.99 (1H, q, J=4.77 Hz), 4.14 (3H, s), 2.65 (3H, s), 2.60 (3H, s), 1.94-2.13 (4H, nm), 1.26 (3H, s), 1.15 (3H, s); $^{19}$F NMR (376 MHz, CDCl$_3$) δ ppm −133.35 (1F, br s); LC-M method H, RT=1.27 min, MS (ESI) m/z: 589.2 (M+H)$^+$.

Example 086 rac-cis-4-((5-fluoro-2-(2-methoxy-7-methylquinoxalin-5-yl)benzo[d]thiazol-6-yl)oxy) tetrahydrofuran-3-yl (2-methylpyrimidin-5-yl)carbamate

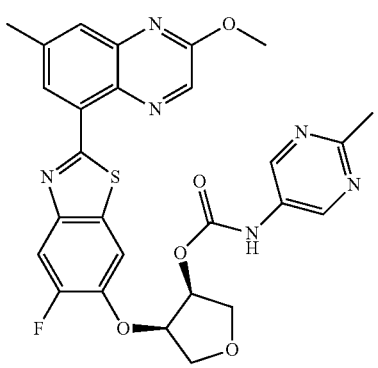

(086)

Example 086 was made from I-15 and I-20 by the method described for Example 001. $^1$H NMR (500 MHz, DMSO-d$_6$) 10.14-9.98 (m, 1H), 8.73 (s, 1H), 8.60 (s, 2H), 8.54 (d, J=1.4 Hz, 1H), 8.04 (d, J=8.3 Hz, 1H), 7.92 (d, J=11.6 Hz, 1H), 7.83 (s, 1H), 5.56 (q, J=5.2 Hz, 1H), 5.30 (d, J=5.2 Hz, 1H), 4.25 (dd, J=9.6, 5.8 Hz, 1H), 4.12 (dd, J=9.9, 5.5 Hz, 1H), 4.08 (s, 3-1H), 3.94 (ddd, J=9.8, 7.6, 4.5 Hz, 2H), 2.62 (s, 3H), 2.39 (s, 3H); LC-MS: method L, RT=1.781 min, MS (ESI) m/z: 563.15 (M+H)$^+$.

Example 087 rac-cis-4-((5-fluoro-2-(2-methoxy-7-methylquinoxalin-5-yl)benzo[d]thiazol-6-yl)oxy) tetrahydrofuran-3-yl (6-methoxypyridin-3-yl)carbamate

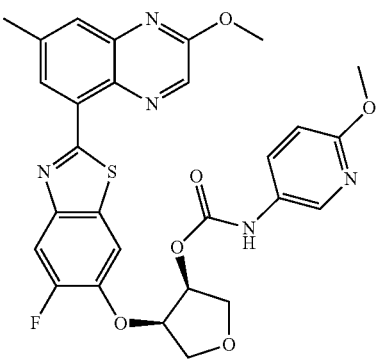

(087)

Example 087 was made from I-15 and I-20 by the method described for Example 001: $^1$H NMR (500 MHz, DMSO-d$_6$)

δ 9.68 (br s, 1H), 8.67 (s, 1H), 8.49 (s, 1H), 8.05 (br s, 1H), 7.98 (d, J=8.2 Hz, 1H), 7.89 (d, J=11.6 Hz, 1H), 7.77 (s, 1H), 7.60 (d, J=7.3 Hz, 1H), 6.64 (d, J=8.8 1-Hz, 1H), 5.52 (d, J=4.9 Hz, 1H), 5.26 (d, J=4.9 Hz, 1H), 4.24 (dd, J=9.5, 5.8 Hz, 1H), 4.11 (dd, J=9.8, 5.5 Hz, 1H), 4.05 (s, 3H), 3.92 (d, J=4.3 Hz, 2H), 3.65 (br s, 3H), 2.59 (s, 3H); LC-MS: method H, RT=1.15 min, MS (ESI) m/z: 578.3 (M+H)$^+$.

Example 088 rac-cis-3-((5-fluoro-2-(2-methoxy-7-methylquinoxalin-5-yl)benzol dithiazol-6-yl)oxy)tetrahydro-2H-pyran-4-yl (6-methoxypyridin-3-yl)carbamate

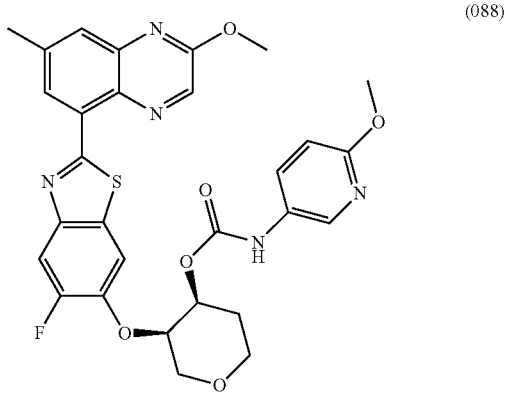 [SMILES: COc1ccc(NC(=O)O[C@H]2CCOC[C@H]2Oc2cc3sc(-c4cc(C)cc5nc(OC)cnc45)nc3cc2F)cn1]

(088)

Example 088 was made from I-16 and I-20 by the method described for Example 053: $^1$H NMR (500 MHz, DMSO-d$_6$) δ 9.57 (br s, 1H), 8.66 (s, 1H), 8.50 (s, 1H), 8.10 (br s, 1H), 8.00 (d, J=7.9 Hz, 1H), 7.94 (s, 1H) 7.91 (d, J=11.6 Hz, 1H), 7.77 (s, 1H), 765 (br s, 1H), 5.19 (d, J=8.5 Hz, 1H), 4.87 (br s, 1H), 4.05 (s, 3H), 3.89 (br s, 1H), 3.74 (d, J=11.6 Hz, 1H), 3.65-3.58 (m, 1H), 2.88 (s, 4H), 2.15 (d, J=9.8 Hz, 1H), 1.89 (d, J=10.1 Hz, 1H); LC-MS: method L, RT=2.01 min, MS (ESI) m/z: 592.05 (M+H)$^+$.

Example 089 rac-cis-3-((2-(7-cyano-2-methoxyquinoxalin-5-yl)-5-fluorobenzo[d]thiazol-6-yl)oxy)tetrahydro-2H-pyran-4-yl (6-methoxypyridin-3-yl)carbamate

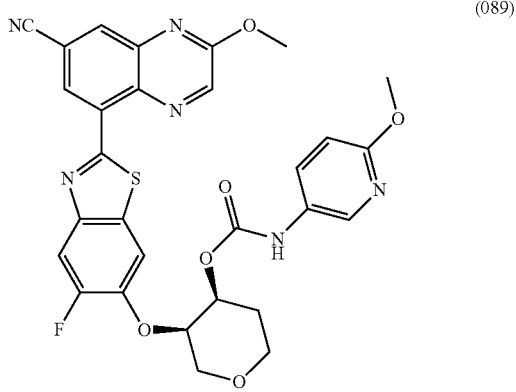 [SMILES: COc1ccc(NC(=O)O[C@H]2CCOC[C@H]2Oc2cc3sc(-c4cc(C#N)cc5nc(OC)cnc45)nc3cc2F)cn1]

(089)

Example 089 was made from I-16 and I-25 by the method described for Example 053: $^1$H NMR (400 MHz, DMSO-d$_6$) δ 8.95 (s, 1H), 8.85 (d, J=1.8 Hz, 1H), 8.55 (d, J=1.8 Hz, 1H), 8.13-8.05 (m, 2H), 8.00 (d, J=11.4 Hz, 1H), 7.65 (br s, 1H), 6.66 (d, J=8.8 Hz, 1H), 5.21 (br s, 1H), 4.92 (br s, 1H), 4.13 (s, 3H), 4.02 (br s, 1H), 3.88 (br s, 1H), 3.67 (s, 3H), 2.17 (d, J=10.1 Hz, 1H), 1.90 (d, J=8.4 Hz, 1H); $^{19}$F NMR (376 MHz, DMSO-d$_6$) δ -132.28 (br s, 1F); LC-MS: method L. RT=1.04 min, MS (ESI) m/z: 603.2 (M+H)$^+$.

Example 090 rac-trans-benzyl 3-((5-fluoro-2-(2-methoxy-7-methylquinoxalin-5-yl)benzo[d]thiazol-6-yl)oxy)-4-hydroxopyrrolidine-1-carboxylate

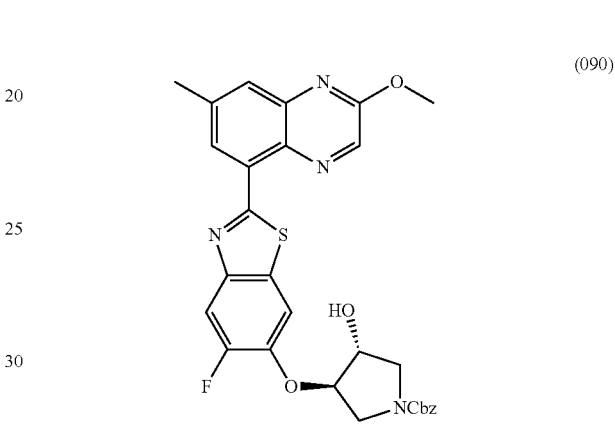

(090)

Under nitrogen atmosphere, I-27 (72 mg, 0.211 mmol) was mixed with benzyl 6-oxa-3-azabicyclo[3.1.0] hexane-3-carboxylate (185 mg, 0.844 mmol) in DMF (1 mL). Anhydrous Cs$_2$CO$_3$ (103 mg, 0.316 mmol) was added. The mixture was stirred at 80° C. for 6 hours. After cooling to room temperature, the reaction was diluted by adding 20 mL of EtOAc and 20 mL of water. After separation, the aq. layer was extracted with EtOAc (20 mL×2). The organic phases were combined and washed with brine, dried over Na$_2$SO$_4$, filtered and concentrated. The crude product was purified by silica gel chromatography (24 g silica) and eluted with 0-100% EtOAc/hexane gradient. The desired fractions were collected and solvent was removed to give Example 090 (177 mg, 0.316 mmol, 150% yield) as a yellow solid, which contains some unreacted starting material. $^1$H NMR (400 MHz, CDCl$_3$) δ ppm 8.62 (1H, d, J=176 Hz), 8.56 (1H, s), 7.84 (1H, d, J=11.44 Hz), 7.78 (1H, s), 7.49 (1H, d, J=7.70 Hz), 7.31-7.43 (5H, m), 5.18 (2H, br s), 4.78 (1H, br s), 4.58 (1H, br s), 4.14 (3H, s), 3.82-3.99 (2H, m), 3.80 (1H, s), 3.63 (1H, dd, J=19.81, 11.88 Hz), 2.66 (3H, s); $^{19}$F NMR (376 MHz, CDCl$_3$) δ ppm -140.59 to -128.86 (1F, m); LC-MS: method H, RT=1.27 min, MS (ESI) m/z: 561.1 (M+H)$^+$.

Example 091 rac-cis-tert-butyl 3-((5-fluoro-2-(2-methoxy-7-methylquinoxalin-5-yl)benzo[d]thiazol-6-yl)oxy)-4-(((2-methylpyrimidin-5-yl)carbamoyl)oxy)piperidine-1-carboxylate

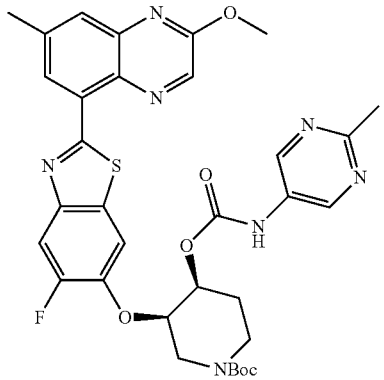

(091)

Example 091 was made from I-17 and I-20 by the method described for Example 001 ¹H NMR (500 MHz, DMSO-d₆) δ 8.72-8.68 (m, 1H), 8.67 (s, 2H), 8.52 (br s, 1H), 8.04 (d, J=6.7 Hz, 1H), 7.93 (br s, 1H), 7.78 (s, 1H), 5.15 (m, 1H), 4.94 (m, 1H), 4.33 (m, 1H), 4.05 (s, 3H), 3.32-3.20 (m, 1H), 3.06-2.96 (m, 1H), 2.59 (s, 3H), 2.54 (s, 3H), 2.14-1.98 (m, 2H), 1.93-1.81 (m, 2H), 1.00 (s, 9H); ¹⁹F NMR (471 MHz, DMSO-d₆) δ −133.36 (s, 1F); LC-MS: method L, RT=2.427 min, MS (ESI) m/z: 676.2 (M+H)⁺.

Example 092 rac-cis-tert-butyl 3-((5-fluoro-2-(2-methoxy-7-methylquinoxalin-5-yl)benzo[d]thiazol-6-yl)oxy)-4-(((6-methoxypyridin-3-yl)carbamoyl)oxy)piperidine-1-carboxylate

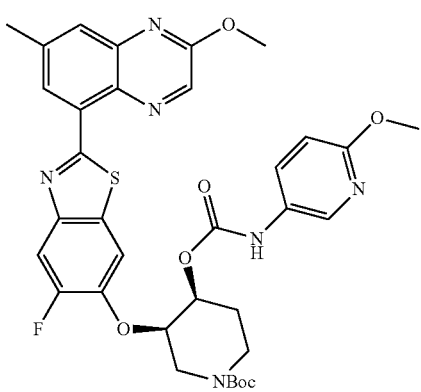

(092)

Example 092 was made from I-17 and I-20 by the method described for Example 001. ¹H NMR (500 MHz, DMSO-d₆) δ 8.70 (s, 1H), 8.55 (br s, 1H), 8.18 (br s, 1H), 8.05 (br s, 1H), 7.97 (d, J=11.6 Hz, 1H), 7.81 (s, 1H), 7.72 (br s, 1H), 6.73 (d, J=8.2 Hz, 1H), 5.14 (m, 1H), 4.94 (m, 1H), 4.35 (m, 1H), 4.07 (s, 3H), 3.74 (s, 3H), 3.27 (d, J=15.3 1-Hz, 1H), 3.09-2.94 (m, 1H), 2.61 (s, 3H), 2.07 (m, 1H), 1.88 (m, 1H), 1.40 (m, 2H), 1.02 (s., 9H); ¹⁹F NMR (471 MHz, DMSO-d₆) δ −133.30 (br s, 1F); LC-MS: method M, RT=2.677 min, MS (ESI) m/z: 691.20 (M+H)⁺.

Example 093 rac-cis-3-((5-fluoro-2-(2-methoxy-7-methylquinoxalin-5-yl)benzo[d]thiazol-6-yl)oxy) piperidin-4-yl (6-methoxypyridin-3-yl)carbamate

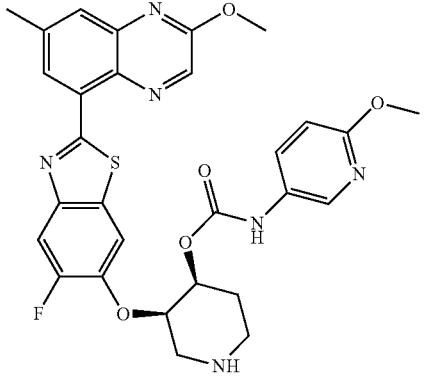

(093)

Example 092 (37 mg, 0.054 mol) was dissolved in DCM (2 mL) and was treated with TFA (500 μl, 6.49 mmol) at room temperature for 1 hour. Then the solvent was removed and the residue was purified by reverse phase preparative HPLC, method D, to afford Example 093 (2.5 mg, 0.004 mmol, 8% yield) as the product. ¹H NMR (500 MHz, DMSO-d₆) δ ppm 9.53 (1H, br s), 8.63 (1H, s), 8.48 (1H, s), 8.08 (1H, br s), 7.98 (1H, d, J=7.93 1-Hz), 7.90 (1H, d, J=11.29 Hz), 7.77 (1H, s), 7.64 (1H, br s), 6.67 (1H, d, J=885 Hz), 5.15 (1H, br s), 4.79 (1H, br s), 4.04 (4H, s), 3.24 (1H, br s), 3.05 (1H, d, J=12.51 Hz), 2.92-3.01 (1H, m), 2.81 (1H, br s), 2.54 (6H, s), 1.97-2.11 (1H, m), 1.80-1.88 (1H, m); ¹⁹F NMR (471 MHz, DMSO-d₆) δ ppm −132.44 (1F, br s); LC-MS: method L, RT=1.757 min, MS (ESI) m/z: 590.45 (M+H)⁺.

Example 094 rac-cis-1-acetyl-3-((5-fluoro-2-(2-methoxy-7-methylquinoxalin-5-yl)benzo[d]thiazol-6-yl)oxy)piperidin-4-yl (2-methylpyrimidin-5-yl)carbamate

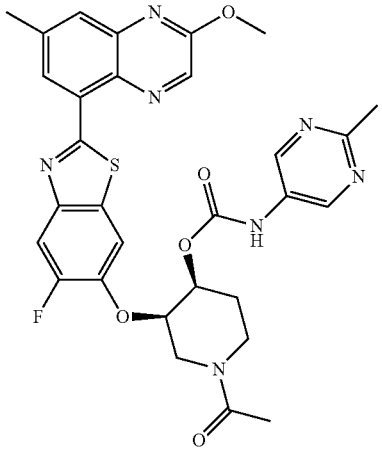

(094)

Example 094A cis-3-((5-fluoro-2-(2-methoxy-7-methylquinoxalin-5-yl)benzo[d]thiazol-6-yl)oxy)piperidin-4-yl (2-methylpyrimidin-5-yl)carbamate, TFA Salt

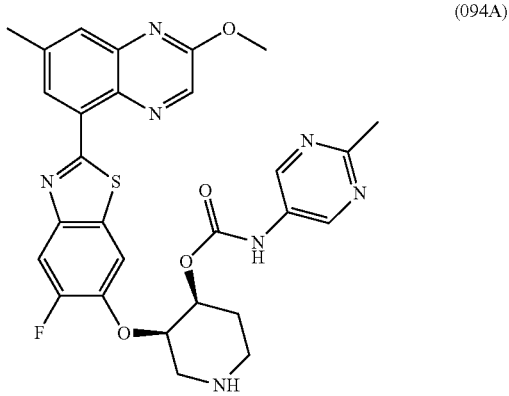
(094A)

In a round bottom flask charged with a stirring bar, Example 091 (136 mg, 0.201 mmol) was dissolved in DCM (2 mL) and treated with TFA (1 mL, 12.98 mmol) at room temperature for 30 minutes. Then the solvent was removed in vacuo and the residue was dried on HVAC for 2 hour to give crude product which was used without purification. LC-MS: method H, RT=0.85 min, MS (ESI) m/z: 576.1 (M+H)$^+$.

Example 094

In a vial charged with a stirring bar, Example 094A (35 mug, 0.051 mmol) was dissolved in THF (1 mL), and pyridine (0.012 mL, 0.152 mmol) was added, followed by Ac$_2$O (4.79 μl, 0.051 mmol). The mixture was stirred at room temperature for 1 hour. Then the solvent was removed on the rotary evaporator and the residue was purified by reverse phase preparative HPLC, method D, to give Example 094 (11.7 mg, 0.019 mmol, 37% yield) as the product. LC-MS: method L, RT=1.968 min, MS (ESI) m/z: 618.30 (M+H)$^+$.

Example 095 rac-cis-3-((5-fluoro-2-(2-methoxy-7-methyl quinoxalin-5-yl)benzo[d]thiazol-6-yl)oxy)-1-(methylsulfonyl)piperidin-4-yl (2-methylpyrimidin-5-yl)carbamate

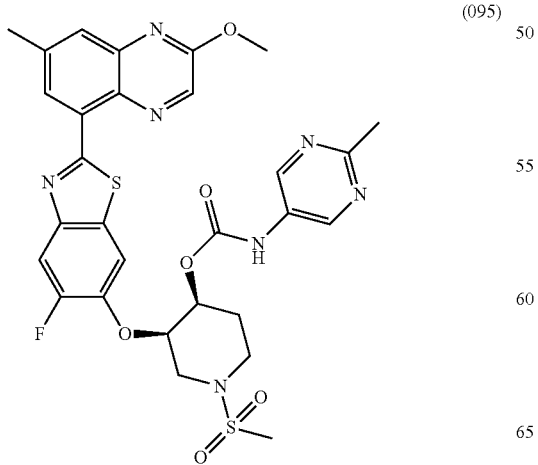
(095)

In a vial charged with a stirring bar, Example 094A (13 mg, 0.023 mmol) was suspended in DCM (1 mL), methanesulfonyl chloride (12.94 mg, 0.113 mmol) was added, followed by DIEA (0.032 mL, 0.181 mmol). The mixture was stirred at room temperature for 30 minutes. Then the solvent was removed by rotary evaporator and the residue was purified on reverse phase preparative HPLC, method D, to give Example 095 (5.2 mg, 0.008 mmol, 35% c yield) as the product. $^1$H NMR (500 MHz, DMSO-d$_6$) δ ppm 9.96 (1H, br s), 8.64 (3H, d, J=13.12 Hz), 8.49 (1H, s), 8.05 (1H, d, J=7.93 Hz), 7.92 (1H, d, J=11.29 Hz), 7.78 (1H, s), 5.17 (1H, d, J=7.32 Hz), 4.98 (1H, br s), 4.05 (3H, s), 3.69-3.83 (1H, m), 3.20-3.34 (1H, m), 2.97 (3H, s), 2.59 (3H, s), 2.39 (3H, s), 2.20 (1H, d, J=9.46 Hz), 2.01 (1H, br s), 1.03 (1H, d, J=5.80 Hz); $^{19}$F NMR (471 MHz, DMSO-d$_6$) δ ppm −132.69 (1F, br s); LC-MS: method L, RT=2.031 min, MS (ESI) m/z: 654.25 (M+H)$^+$.

Example 096 rac-cis-3-((5-fluoro-2-(2-methoxy-7-methylquinoxalin-5-yl)benzo[d]thiazol-6-yl)oxy)-1-(2,2,2-trifluoroacetyl)piperidin-4-yl (2-methylpyrimidin-5-yl)carbamate

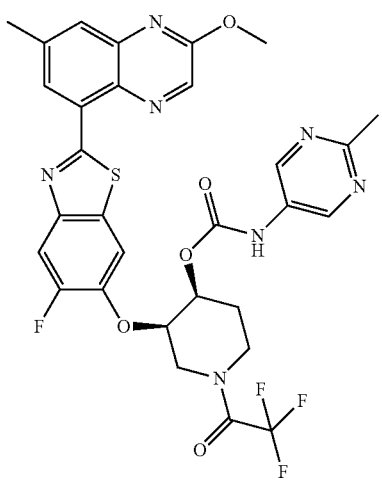
(096)

Example 096 was isolated as a side product of the reaction for making Example 095. LC-MS: method L, RT=2.272 min, MS (ESI) m/z: 672.5 (M+H)$^+$.

Example 097 rac-cis-4,4-difluoro-2-((5-fluoro-2-(2-methoxy-7-methylquinoxalin-5-yl)benzo[d]thiazol-6-yl)oxy)cyclopentyl (2-methylpyrimidin-5-yl)carbamate)

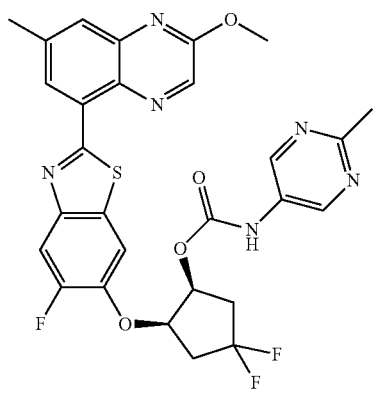

(097)

Example 097 was made from I-10 and I-20 by the method described for Example 053. $^1$H NMR (400 MHz, DMSO-d$_6$) δ ppm 10.02 (1H, br s), 8.75 (1H, s), 8.63 (2H, s), 8.56 (1H, d, J=1.76 Hz), 8.09 (1H, d, J=8.14 Hz), 7.96 (1H, d, J=11.66 Hz), 7.85 (1H, s), 5.53 (1H, d, J=4.40 Hz), 5.32 (1H, d, J=4.62 Hz), 4.10 (3H, s), 2.82-2.99 (1H, m), 2.71-2.81 (1H, m), 2.64 (3H, s), 2.54-2.62 (2H, m), 2.39 (3H, s); $^{19}$F NMR (376 MHz, DMSO-d$_6$) δ ppm −85.28 to −78.90 (2F, m), −133.42 (1F, s); LC-MS: method H, RT=1.13 min, MS (ESI) m/z: 597.0 (M+H)$^+$.

Example 098 rac-cis-2-((2-(6-chloro-3-methoxyquinolin-8-yl)-5-fluorobenzo[d]thiazol-6-yl)oxy)-4,4-difluorocyclopentyl (2-methylpyrimidin-5-yl)carbamate

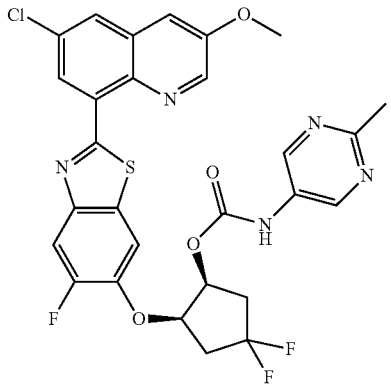

(098)

Example 098 was made from I-10 and Intermediate I-29 by the method described for Example 053. $^1$H NMR (500 MHz, DMSO-d$_6$) δ 8.88-8.83 (m, 1H), 8.74 (br s, 2H), 8.62-8.55 (m, 1H), 8.17 (d, J=1.8 Hz, 1H), 8.09 (d, J=8.2 Hz, 1H), 8.00 (d, J=11.3 Hz, 1H), 7.92 (d, J=2.7 Hz, 1H), 5.37 (br s, 1H), 5.17 (br s, 1H), 3.98 (s, 3H), 2.98-2.80 (m, 2H), 2.52 (s, 3H), 2.41-2.27 (m, 1H), 2.25-2.12 (m, 1H); $^{19}$F NMR (471 MHz, DMSO-d$_6$) δ −82.56 to −84.40 (m, 2F), −133.53 (s, 1F); LC-MS: method L, RT=2.442 min, MS (ESI) m/z: 616.20 (M+H)$^+$.

Example 099

(cis)-4,4-difluoro-2-((5-fluoro-2-(2-methoxy-7-methylquinoxalin-5-yl)benzo[d]thiazol-6-yl)oxy)cyclopentyl (2-methylpyrimidin-5-yl)carbamate (Homochiral)

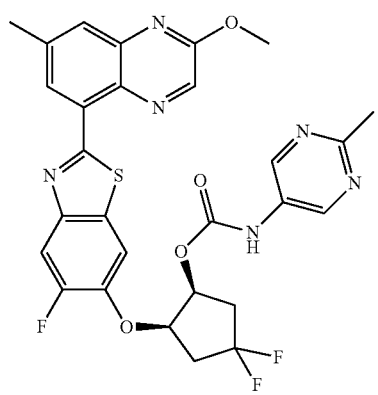

(099)

Example 099 was made from I-12 and I-20 by the method described for Example 053. $^1$H NMR (500 MHz, DMSO-d$_6$) δ 9.98 (br s, 1H), 8.65 (s, 1H), 8.58 (s, 2H), 8.47 (s, 1H), 8.00 (d, J=8.2 Hz, 1H), 7.89 (d, J=11.6 Hz, 1H), 7.78 (s 1H), 5.49 (br s, 1H), 5.32 (br s, 1H), 4.06 (s, 3H), 2.98-2.68 (m, 2H), 2.63 (m, 2H), 2.60 (s, 3H), 2.33 (s, 3H); $^{19}$F NMR (471 MHz, DMSO-d$_6$) δ −81.18 to −85.01 (m, 2F), −133.36 (s., 1F); LC-MS: method L. RT=2.271 min, MS (ESI) m/z: 597.10 (M+H)$^+$.

Example 100

(cis)-4,4-difluoro-2-((5-fluoro-2-(2-methoxy-7-methylquinoxalin-5-yl)benzo[d]thiazol-6-yl)oxy)cyclopentyl (2-methylpyrimidin-5-yl)carbamate (Homochiral

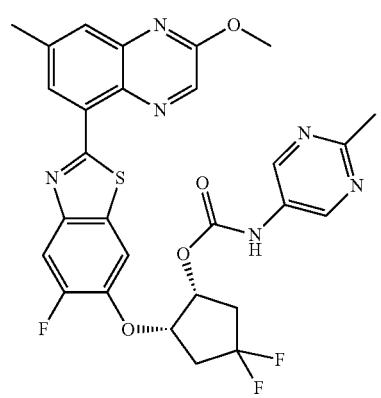

(100)

Example 099 was made from I-11 and I-20 by the method described for Example 053. ¹H NMR (500 MHz, DMSO-$d_6$) δ ppm 9.95 (1H, br s), 8.64 (1H, s), 8.56 (2H, s), 8.46 (1H, s), 7.99 (1H, d, J=7.93 Hz), 7.87 (1H, d, J=11.60 Hz), 7.77 (1H, s), 5.39-5.55 (1H, m), 5.30 (1H, br s), 4.04 (3H, s), 2.85 (1H, d, J=16.48 Hz), 2.66-2.78 (1H, m), 2.58 (2H, m), 2.54 (3H, s), 2.32 (3H, s); ¹⁹F NMR (471 MHz, DMSO-$d_6$) S ppm −84.29 to −81.53 (2F, m), −133.53 to −133.25 (1F, s); LC-MS: method L, RT=2.270 min, MS (ESI) m/z: 597.0 (M+H)⁺.

Example 101

(cis)-4,4-difluoro-2-((5-fluoro-2-(3-methoxy-6-methylquinolin-8-yl)benzo[d]thiazol-6-yl)oxy)cyclopentyl (2-(2-hydroxyethoxy)pyrimidin-5-yl)carbamate (Homochiral)

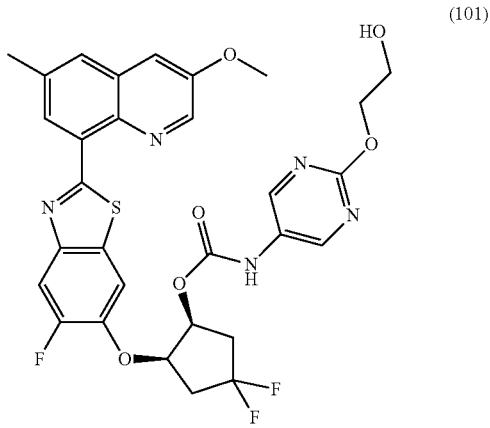 [SMILES: COc1cnc2c(-c3nc4cc(F)c(O[C@@H]5CC(F)(F)C[C@@H]5OC(=O)Nc5cnc(OCCO)nc5)cc4s3)cc(C)cc2c1]

(101)

Example 101 was made from I-12, 1-20 and Intermediate I-30 by the method described for Example 053, ¹H NMR (500 MHz, DMSO-$d_6$) δ 9.85 (br s, 1H), 8.67 (s, 1H), 8.50 (s, 1H), 8.47 (br s, 2H), 8.03 (d, J=7.9 Hz, 1H), 7.92 (d, J 11.6 Hz, 1H), 7.79 (s, 1H), 5.49 (m, 1H), 5.30 (m, 1H), 4.10 (m, 2H), 4.06 (s, 3H), 3.58 (m, 2H), 2.95-2.67 (m, 2H), 2.60 (m, 2H), 2.54 (s, 3H); LC-MS: method L, RT=2.19 min, MS (ESI) m/Z: 643.0 (M+H)⁺.

Example 102

(cis)-4,4-difluoro-2-((5-fluoro-2-(3-m ethoxy-6-methylquinolin-8-yl)benzo[d]thiazol-6-yl)oxy)cyclopentyl (2-(2-hydroxyethoxy)pyrimidin-5-yl)carbamate Homochiral

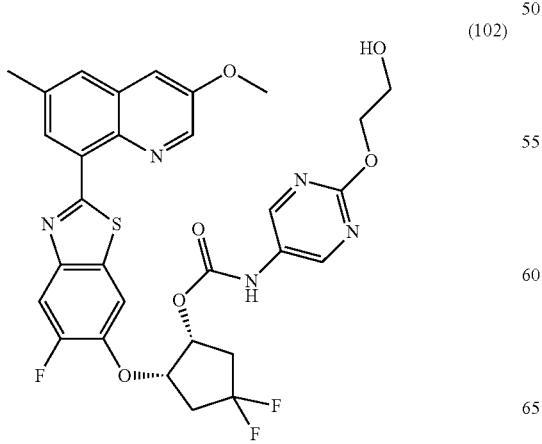

(102)

Example 102 was made from I-11, 1-20 and Intermediate I-30 by the method described for Example 053. ¹H NMR (500 MHz, DMSO-$d_6$) δ 9.82 (br s, 1H), 8.63 (s, 1H), 8.46 (m, 3H), 7.99 (d, J=8.2 Hz, 1H), 7.89 (d, J=11.3 Hz, 1H), 7.76 (s, 1H), 5.48 (m, 1H), 5.29 (m, 1H), 4.06 (m, 2H), 4.04 (s, 3H), 3.51 (m, 2H), 2.95-2.65 (m, 2H), 2.63-2.59 (nm, 2H), 2.58 (s, 3H); ¹⁹F NMR (471 MHz, DMSO-$d_6$) δ −81.43 to −84.12 (m, 2F), −133.23 (s, 1F); LC-MS: method L, RT=2.20 min, MS (ESI) m/z: 665.0 (M+Na)⁺.

Example 103 rac-cis-5-((5-fluoro-2-(2-methoxy-7-methyl)quinoxalin-5-yl)benzo[d]thiazol-6-yl)oxy)-2,2-dimethylcyclopentanol

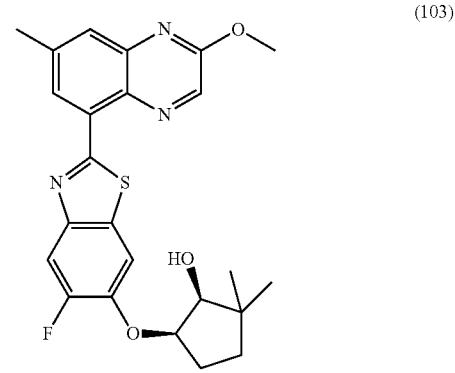

(103)

Example 103 was made from I-14 and I-20 by the method described for Example 001A. ¹H NMR (500 MHz, DMSO-$d_6$) δ ppm 8.70 (1H, s), 8.55 (1H, s), 7.88-7.97 (2H, m), 7.80 (1H, s), 4.87 (1H, d, J=6.71 Hz), 4.68 (1H, d, J=5.80 Hz), 4.07 (3H, s), 3.73 (1H, t, J=5.34 Hz), 2.61 (3H, s), 2.19 (1H, d, J=7.93 Hz), 1.80 (1H, d, J=5.19 Hz), 1.59-1.72 (1H, m), 1.37 (1H, dd, J=12.66, 6.56 Hz), 1.03 (6H, d, J=2.44 Hz); LC-MS: method M, RT=2.716 min, MS (ESI) m/z: 454.20 (M+H)⁺.

Example 104 rac-cis-5-((5-fluoro-2-(2-methoxy-7-methylquinoxalin-5-yl)benzo[d]thiazol-6-yl)oxy)-2,2-dimethylcyclopentyl (2-methylpyrimidin-5-yl)carbamate

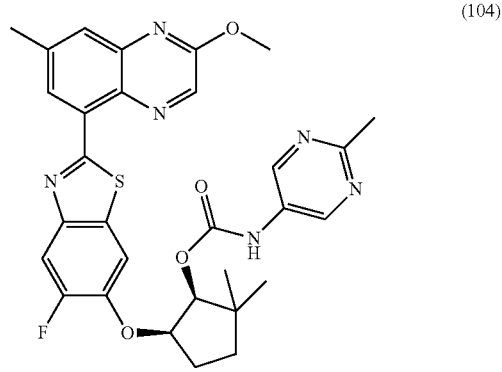

(104)

Example 104 (10.8 mg, 0.017 mmol, 32% yield) was made from Example 103 (28 mg, 0.054 mmol) via the procedure described for Example 055. $^1$H NMR (500 MHz, DMSO-$d_6$) δ ppm 9.84 (1H, br s), 8.63 (1H, s), 8.58 (2H, br s), 8.45 (1H, s), 7.91 (1H, d, J=7.93 Hz), 7.81 (1H, d, J=11.60 Hz), 7.74 (1H, s), 5.14 (1H, d, J=6.41 Hz), 4.83 (1H, br s), 4.02 (3H, s), 2.56 (3H, s), 2.46 (3H, br s), 2.37 (2H, d, J=5.80 Hz), 1.86 (1H, br s), 1.73 (1H, br s), 1.44-1.56 (1H, m), 1.05-1.15 (6H, m); $^{19}$F NMR (471 MHz, DMSO-$d_6$) δ ppm −133.68 (1F, br s); LC-MS: method L, RT=2.521 min, MS (ESI) m/z: 589.20 (M+H)+.

What is claimed is:

1. A compound of formula (I) to (IV):

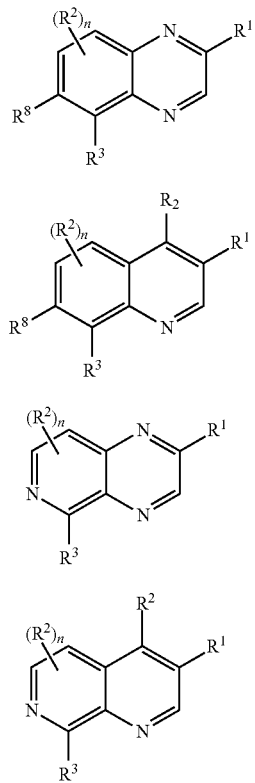

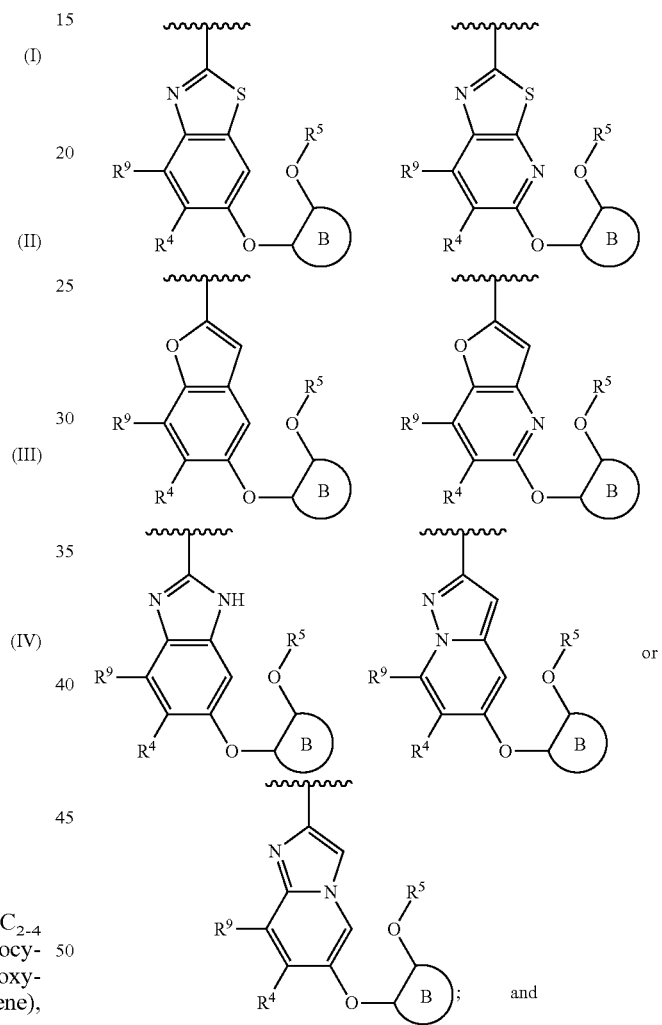

stereoisomer, or salt thereof; wherein:

$R^1$ is F, Cl, —OH, $C_{1-4}$ alkyl, $C_{1-4}$ fluoroalkyl, $C_{2-4}$ alkenyl, $C_{2-4}$ alkynyl, $C_{3-7}$ cycloalkyl, $C_{3-7}$ fluorocycloalkyl, $C_{1-4}$ alkoxy, $C_{1-4}$ fluoroalkoxy, $C_{2-4}$ hydroxyalkoxy, $C_{3-6}$ cycloalkoxy, ($C_{1-3}$ alkoxy)-($C_{1-3}$ alkylene), ($C_{1-3}$ alkoxy)-($C_{1-3}$ fluoroalkylene), ($C_{1-3}$ fluoroalkoxy)-($C_{1-3}$ fluoroalkylene), ($C_{1-3}$ deuteroalkoxy)-($C_{1-3}$ deuteroalkylene), ($C_{1-3}$ fluoroalkoxy)-($C_{1-3}$ alkylene), —(CH$_2$)$_n$O(phenyl), —(CH$_2$)$_n$NR$^a$R$^a$, —C(O)O($C_{1-6}$ alkyl), —C(O)NR$^a$R$^a$, —C(O)NR$^b$R$^b$, —NH$_2$, —NH($C_{16}$ alkyl), —N($C_{1-6}$ alkyl)$_2$, —NH($C_{1-6}$ hydroxyalkyl), azetidinyl, pyrrolidinyl, furanyl, pyranyl, piperidinyl, morpholinyl, piperazinyl, —S(O)$_2$($C_{1-3}$ alkyl), —S(O)$_2$NR$^a$R$^a$, $C_{1-3}$ alkylthio, or $C_{1-3}$ fluoroalkylthio;

R$_2$, at each occurrence, is independently H, F, Cl, Br, —OH, —CN, $C_{1-4}$ alkyl, $C_{1-4}$ fluoroalkyl, $C_{1-4}$ hydroxyalkyl, $C_{1-3}$ aminoalkyl, $C_{2-4}$ alkenyl, $C_{2-4}$ alkynyl, $C_{3-7}$ cycloalkyl, $C_{3-7}$ fluorocycloalkyl, $C_{1-6}$ alkoxy, $C_{1-3}$ fluoroalkoxy, $C_{1-3}$ alkylthio, $C_{1-3}$ fluoroalkylthio, ($C_{1-3}$ alkoxy)-($C_{1-3}$ alkylene), ($C_{1-3}$ fluoroalkoxy)-($C_{1-3}$ alkylene), —C(O)NH$_2$, —C(O)NH($C_{1-6}$ alkyl), —C(O)N($C_{1-6}$ alkyl)$_2$, —C(O)O($C_{1-6}$ alkyl), —C(O)NH(CH$_2$CH$_2$O($C_{1-3}$ alkyl)), —C(O)NR$^b$R$^b$, —C(O)(piperidinyl), —CH(OH)($C_{3-6}$ cycloalkyl), —CH(OH)(phenyl), —CH(OH)(pyridyl), —S(O)$_2$($C_{1-3}$ alkyl), —S(O)$_2$NR$^a$R$^a$, or a cyclic group selected from phenyl, 5- to 6-membered heteroaryl, and 5- to 7-membered heterocyclyl, wherein said cyclic group is substituted with zero to 5 substituents independently selected from F, Cl, hydroxy, $C_{1-4}$ alkyl, $C_{1-4}$ fluoroalkyl, $C_{1-3}$ alkoxy, $C_{1-3}$ fluoroalkoxy, cyclopropyl, and —CN;

$R^3$ is:

$R^4$ is H, F, Cl, hydroxy, $C_{1-4}$ alkyl, $C_{1-4}$ fluoroalkyl, $C_{1-4}$ hydroxyalkyl, $C_{1-3}$ alkoxy, $C_{1-3}$ fluoroalkoxy, $C_{1-3}$ alkylthio, cyclopropyl, or —CN;

Ring B, along with the two carbon atoms through which it is attached, is a 3 to 7 membered cycloalkyl, or a 5 to 7 membered heterocycle having 1 nitrogen, oxygen, or sulphur atom, wherein the cycloalkyl and heterocycle are substituted with 0-4 R$^d$;

$R^5$ is H, or C(O)NR$^a$R$^6$;

$R^6$ is H, $C_{1-4}$ alkyl, phenyl, or a 5 or 6 membered heteroaryl, containing 1 to 3 nitrogen atoms and 0-1 oxygen or sulphur atoms, the phenyl or heteroaryl being substituted with 0-2 R$^7$;

$R^7$ is CN, hydroxy, $NR^aR^a$, halogen, $C_{1-4}$ alkyl, $C_{1-4}$fluoroalkyl, $C_{1-4}$-hydroxyalkyl, $C_{1-4}$-hydroxyfluoroalkyl, $C(O)R^a$, $C(O)OR^a$, $C(O)NR^aR^c$, $S(O)_2NR^aR^c$, and $S(O)_2R^a$, —O—$C_{1-4}$ alkyl, —S—$C_{1-4}$alkyl, —O—$C_{1-4}$-hydroxyalkyl, —O—$C_{1-4}$-aminoalkyl, —O—$C_{1-4}$-hydroxyfluoroalkyl, O—$C_{1-4}$ fluoroalkyl, O—$PO_3^{-2}$, —$C_{1-4}$ alkyl-O—$PO_3^{-2}$, —$C_{1-4}$ fluoroalkyl-O—$PO_3^{-2}$, —O—$C_{1-4}$alkyl-O—$PO_3^{-2}$, —O—$C_{1-4}$ fluoroalkyl-O—$PO_3^{-2}$, —N($R^a$)—$C_{1-4}$hydroxyalkyl, or —N($R^a$)—$C_{1-4}$hydroxyfluoroalkyl;

$R^8$ is H, F, Cl, or $CH_3$;

$R^9$ is H, CN, hydroxyl, $C_{1-4}$ alkyl, $C_{1-4}$ fluoroalkyl, cyclopropyl, or halogen;

$R^a$ is H, $C_{1-4}$alkyl, or $C_{1-4}$fluoroalkyl;

two $R^b$ along with the nitrogen atom to which they are attached form a 4- to 7-membered heterocyclo ring, having 1 to 2 nitrogen atoms and 0-1 oxygen or sulfur atoms;

$R^c$ is H, $C_{1-4}$alkyl, or $C_{1-4}$hydroxyalkyl;

$R^d$ is F, Cl, hydroxy, $C_{1-4}$ alkyl, $C_{1-4}$ fluoroalkyl, $C_{1-4}$ hydroxyalkyl, $C_{1-3}$ alkoxy, $C_{1-3}$ fluoroalkoxy, $C_{1-3}$ alkylthio, cyclopropyl, —CN, $C(O)R^a$, $C(O)OR^a$, $C(O)NR^aR^c$, $S(O)_2NR^aR^c$, or $S(O)_2R^a$; and n is 1 to 3.

2. A compound of claim 1, stereoisomer or salt thereof, wherein $R^1$ is methyl, methoxy, ethoxy, $OCHF_2$, or —$CH_2OCH_3$;

$R^2$ is F, Cl, CN, methyl, hydroxymethyl, methoxy, or difluoromethyl;

$R^3$ is

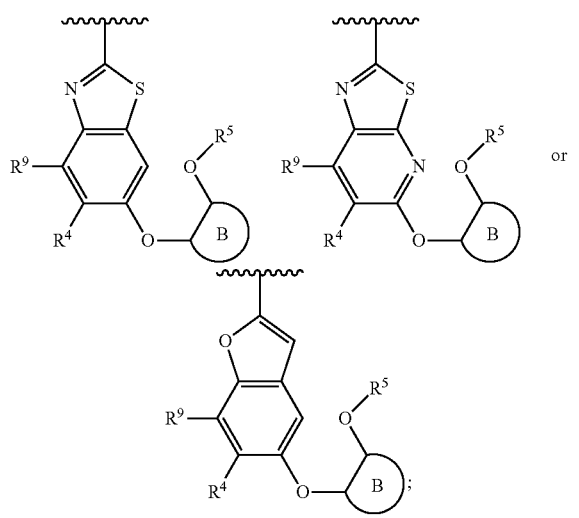

$R^4$ is H or F;

Ring B, along with the two carbon atoms through which it is attached, is cyclobutyl, cyclopentyl, cyclohexyl, tetrahydrofuranyl, pyrrolidinyl, tetrahydropyranyl, or piperadinyl, each of these being substituted with 0-3 $R^d$;

$R^5$ is $C(O)NHR^6$;

$R^6$ is phenyl, pyridinyl, pyrimidinyl, pyridazinyl, or pyrazinyl, each of these being substituted with 0-2 $R^7$;

$R^7$ is F, Cl, CN, hydroxy, $C_{1-4}$alkyl, $C_{1-4}$fluoroalkyl $C_{1-4}$-hydroxyalkyl, $C(O)R^a$, $C(O)NR^aR^c$, —O—$C_{1-4}$alkyl, —S—$C_{1-4}$alkyl, —O—$C_{1-4}$-hydroxyalkyl, O—$C_{1-4}$fluoroalkyl, —O—$PO_3^{-2}$, —$C_{1-4}$ alkyl-O—$PO_3^{-2}$, or —O—$C_{1-4}$alkyl-O—$PO_3^{-2}$;

$R^8$ is H or F;

$R^9$ is H, F, Cl, $CH_3$, or $CHF_2$;

$R^a$ is H, or $C_{1-4}$alkyl;

$R^c$ is H, $C_{1-4}$alkyl, $C_{1-4}$hydroxyalkyl; and $R^d$ is F, $C_{1-4}$ alkyl, $C(O)O$—$C_{1-4}$alkyl, $C_{1-4}$ fluoroalkyl, $C_{1-3}$ alkoxy, or $C_{1-3}$ fluoroalkoxy.

3. A compound of claim 2, stereoisomer or salt thereof, wherein $R^1$ is methoxy, or ethoxy;

$R^2$ is F, Cl, CN, or methyl;

$R^3$ is

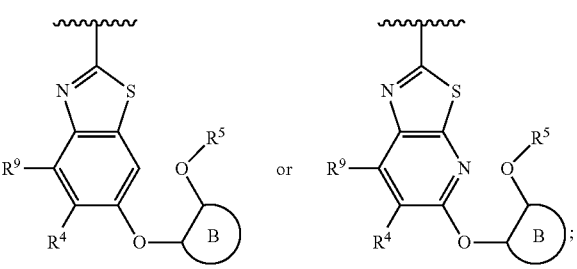

$R^4$ is H or F;

Ring B, along with the two carbon atoms through which it is attached, is a cyclobutyl, cyclopentyl, or cyclohexyl, each of these being substituted with 0-2 $R^d$;

$R^5$ is $C(O)NHR^6$;

$R^6$ is pyridinyl, or pyrimidinyl, each of these being substituted with 0-2 $R^7$;

$R^7$ is F, Cl, CN, hydroxy, methyl, $CF_3$, $CHF_2$, $CH_2OH$, $CH_2CH_2OH$, —$OCH_2CH_2OH$, —$OCH_3$, —$OCF_3$—$OCHF_2$, —$CH_2CH(CH_3)OH$, —O—$CH_2CH(CH_3)$ OH, —O—$PO_3^{-2}$, $CH_2O$—$PO_3^{-2}$, $CH_2CH_2O$—$PO_3^{-2}$, —$OCH_2CH_2O$—$PO_3^{-2}$, $CH_2CH(CH_3)O$—$PO_3^{-2}$, or —O—$CH_2CH(CH_3)O$—$PO_3^{-2}$;

$R^8$ is H or F;

$R^9$ is H; and $R^d$ is F, or methyl.

4. A compound of claim 3, stereoisomer or salt thereof, wherein $R^3$ is

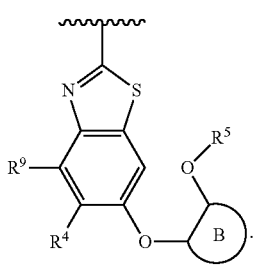

5. A compound of claim 4, stereoisomer or salt thereof, wherein the compound is of formula (I)

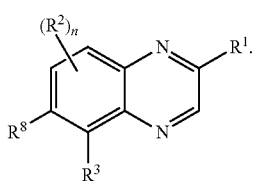
(I)
6. A compound of claim 1, stereoisomer or salt thereof, wherein the compound is of formula
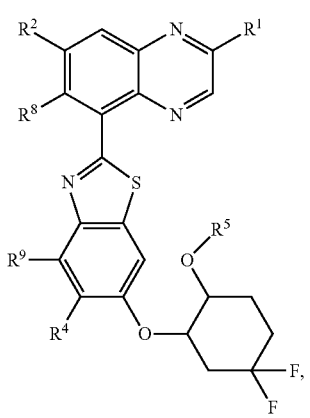
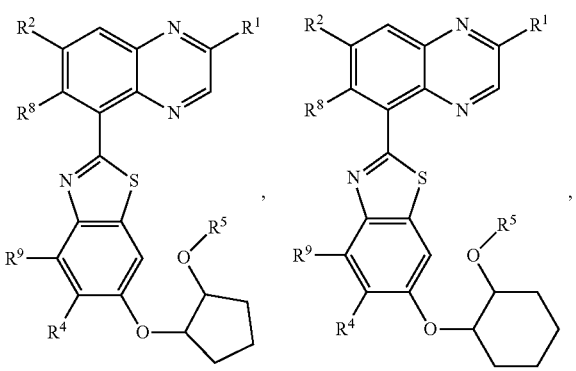
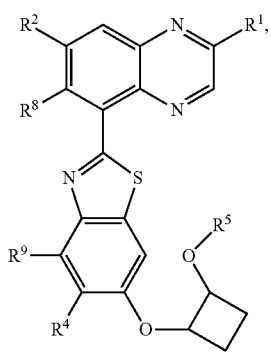
-continued
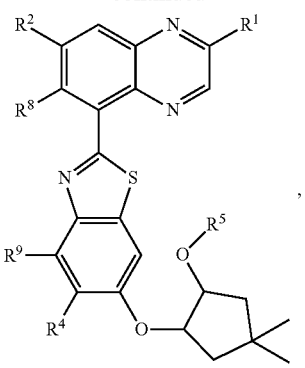
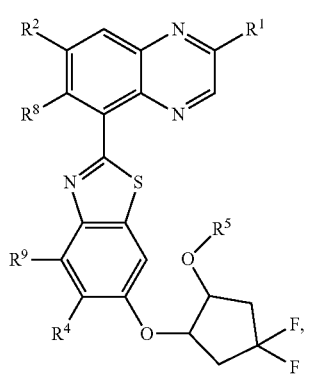
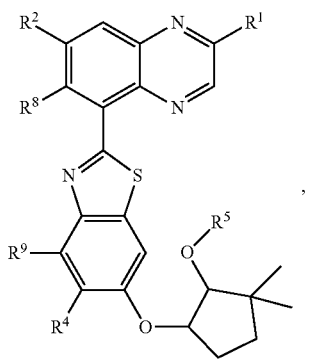
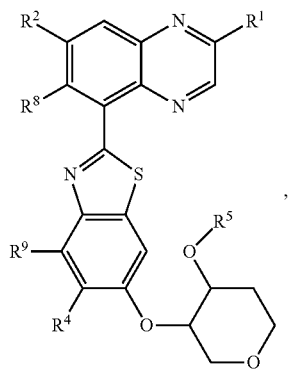

-continued

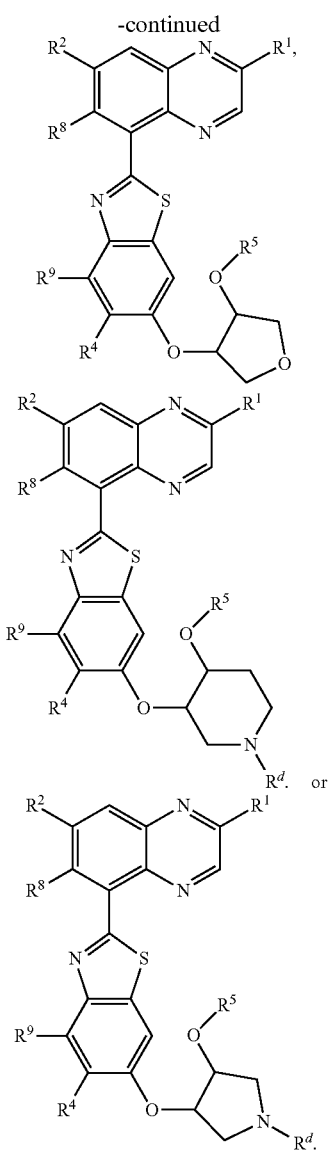

7. The compound of claim 6, stereoisomer or salt thereof, wherein

R¹ is methoxy, or ethoxy;

R² is F, Cl, CN, or methyl;

R⁴ is F;

R⁵ is C(O)NHR⁶;

R⁶ is pyridinyl, or pyrimidinyl, each of these being substituted with 0-2 R⁷;

R⁷ is F, Cl, CN, hydroxy, methyl, CF₃, CHF₂, CH₂OH, CH₂CH₂OH, —OCH₂CH₂OH, —OCH₃, —OCF₃— OCHF₂, —CH₂CH(CH₃)OH, or —O—CH₂CH(CH₃)OH;

R⁸ is H;

R⁹ is H; and

R$^d$ is H, methyl, or C(O)O—C₁₋₄alkyl.

8. The compound of claim 5, stereoisomer or salt thereof, wherein

R³ is

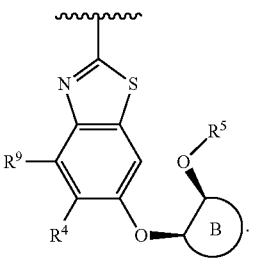

9. A compound of claim 8, stereoisomer or salt thereof, wherein

R⁷ is F, Cl, CN, hydroxy, methyl, CF₃, CHF₂, CH₂OH, CH₂CH₂OH, —OCH₂CH₂OH, —OCH₃, —OCF₃— OCHF₂, —CH₂CH(CH₃)OH, or —O—CH₂CH(CH₃)OH.

10. The compound according to claim 1 stereoisomer or salt thereof, wherein said compound is selected from

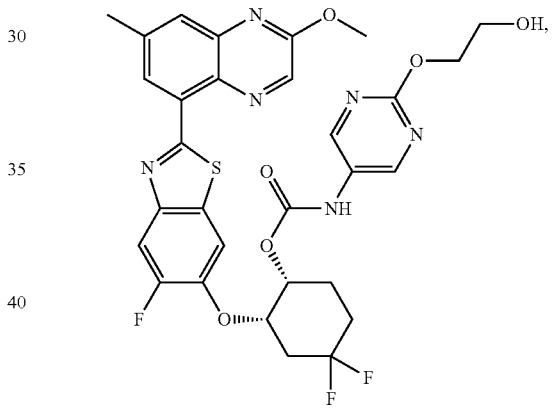

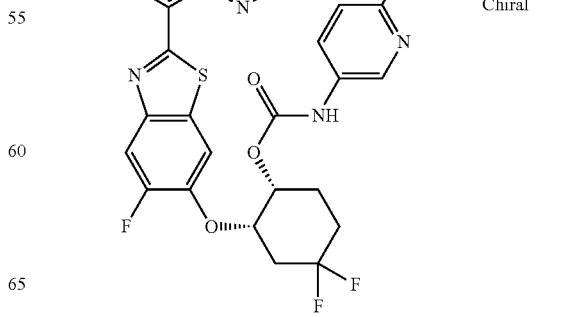

167
-continued
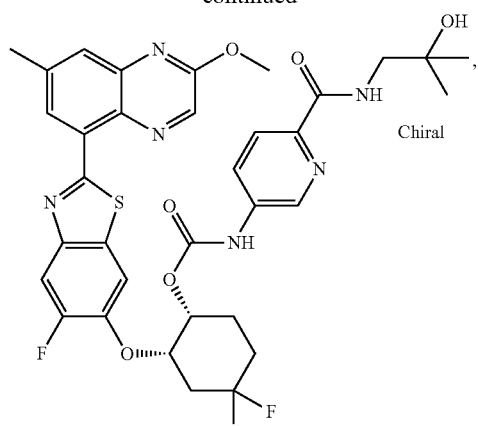
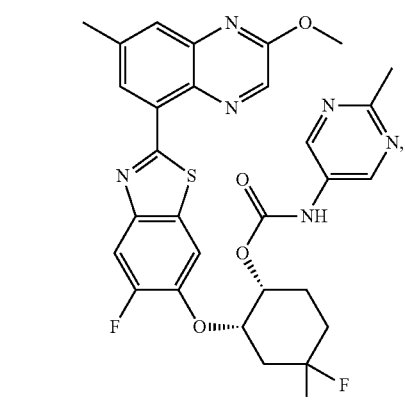
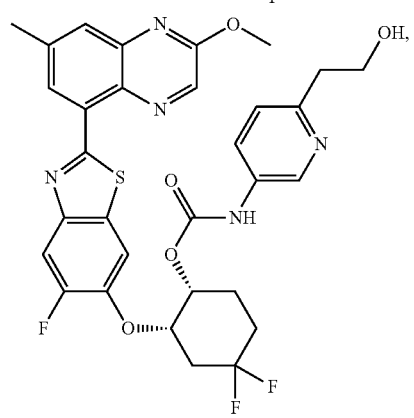
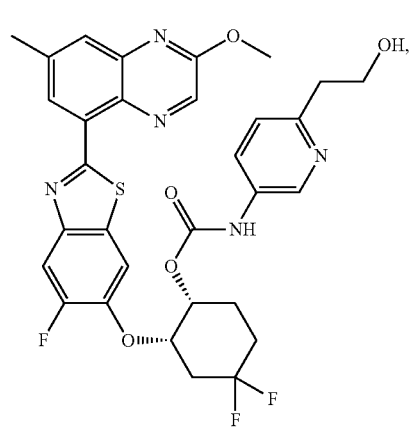
168
-continued
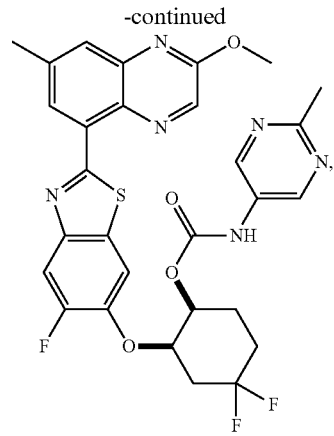
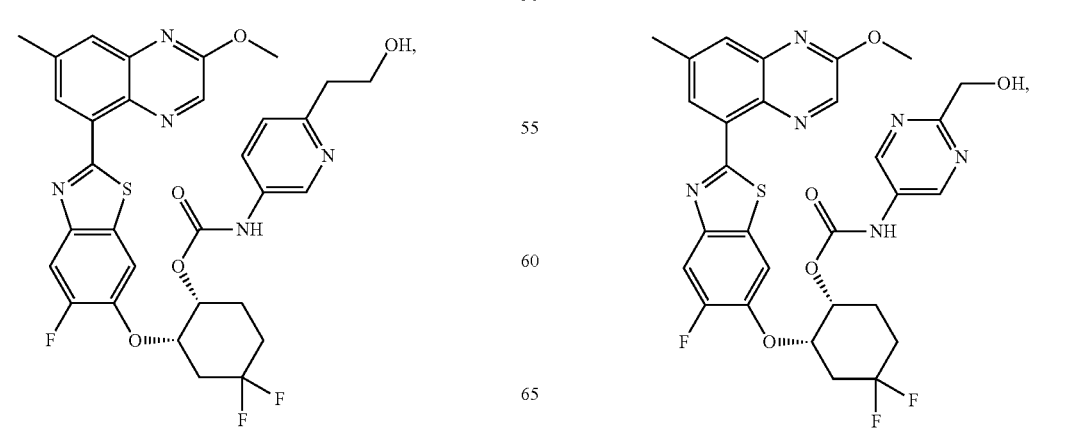
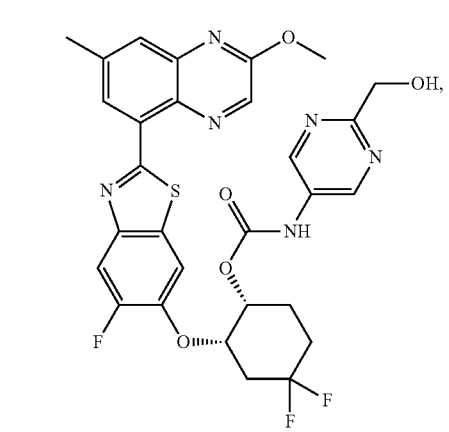

169
-continued
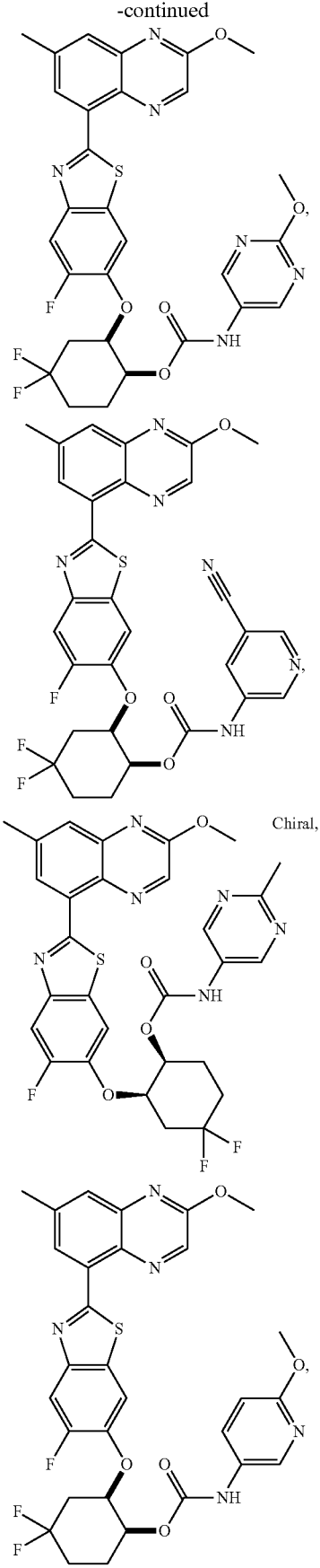
170
-continued
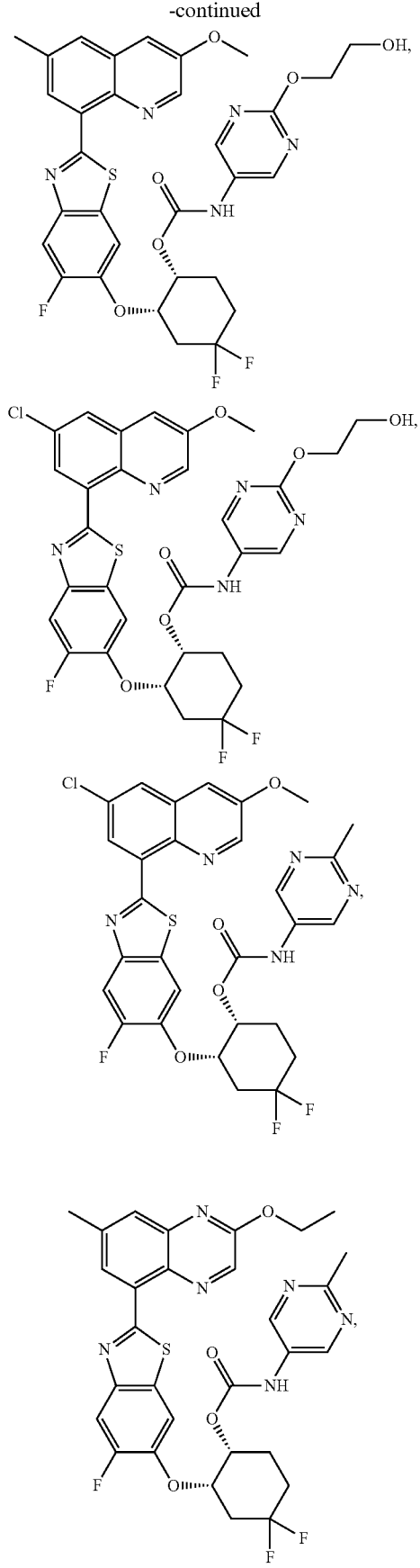

-continued
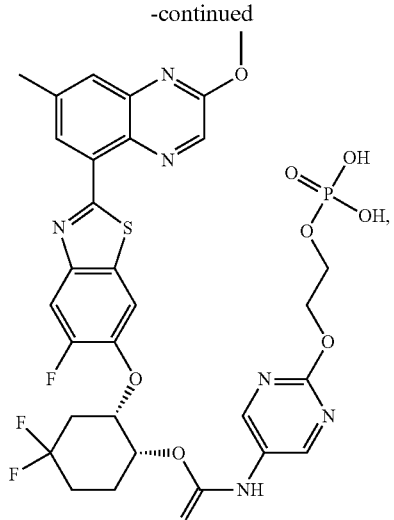
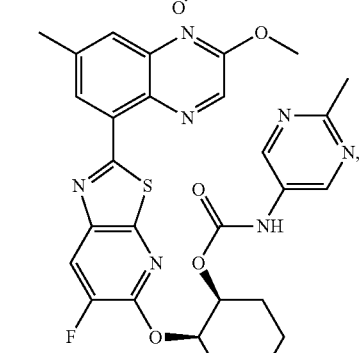
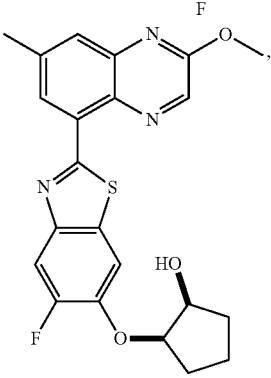
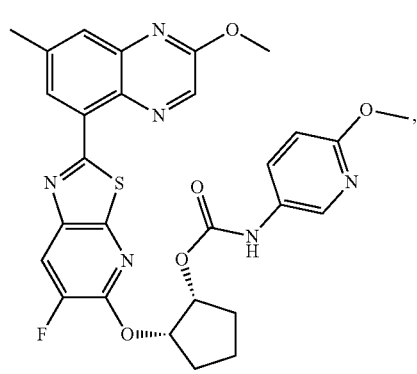
-continued
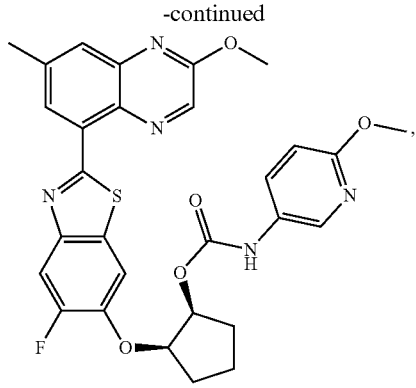
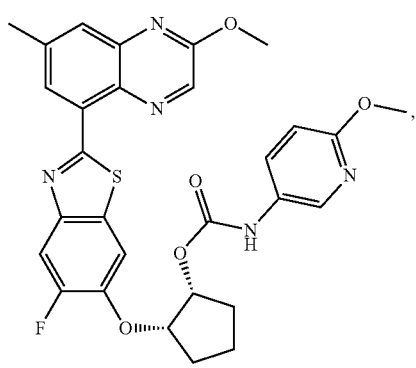
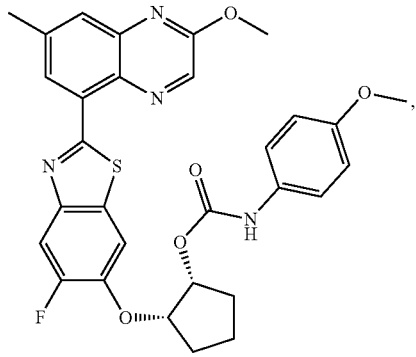
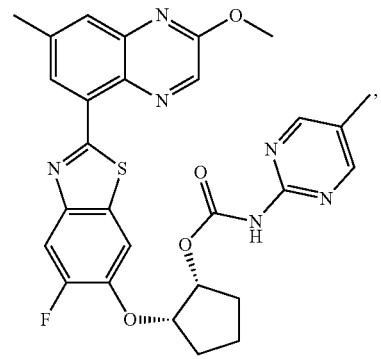

173
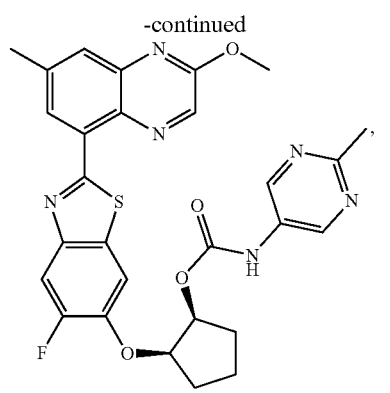
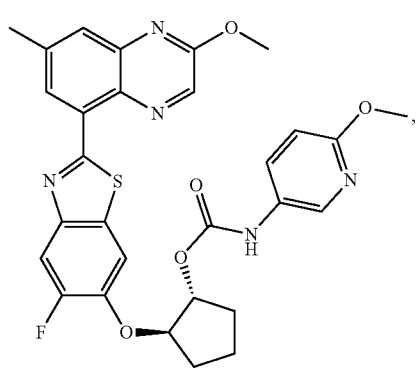
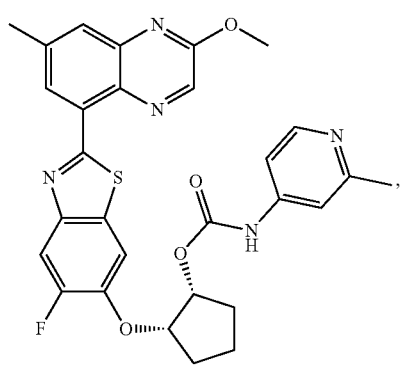
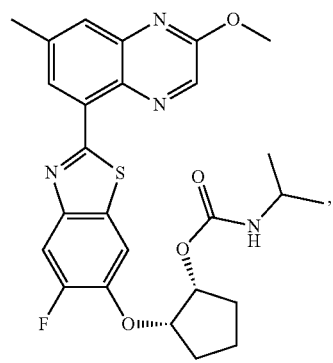
174
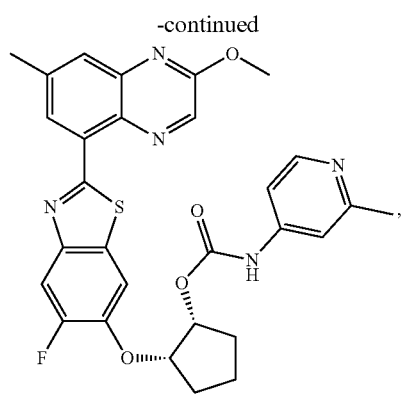
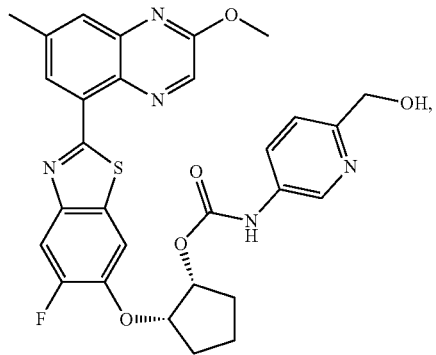
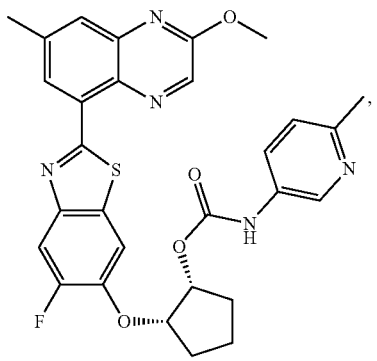
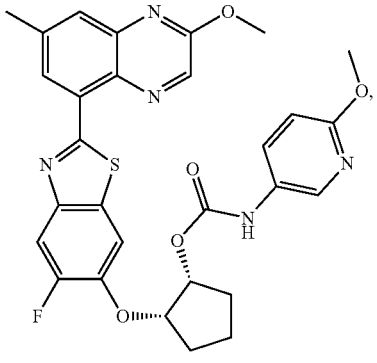

175
-continued
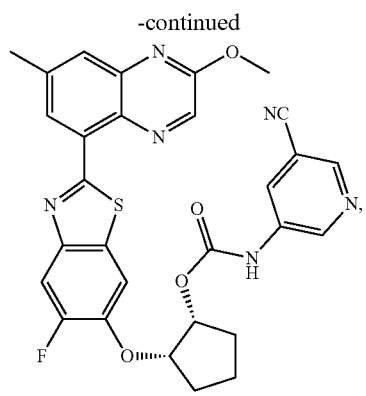
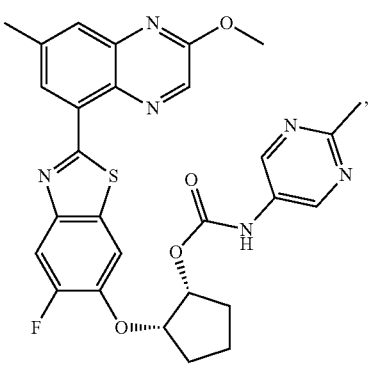
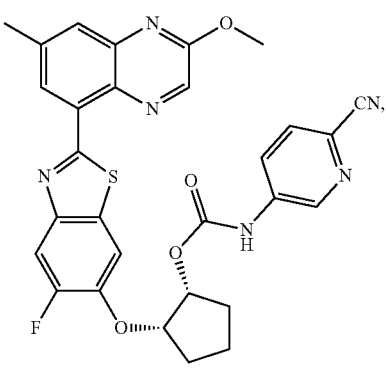
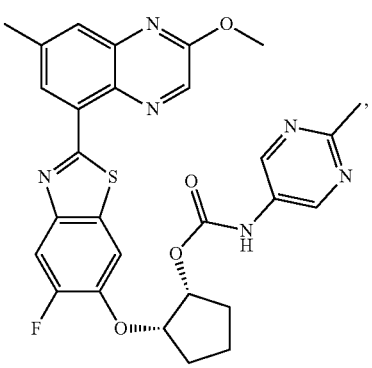
176
-continued
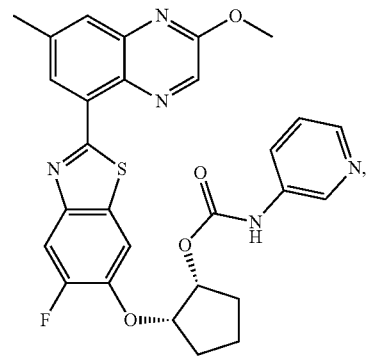
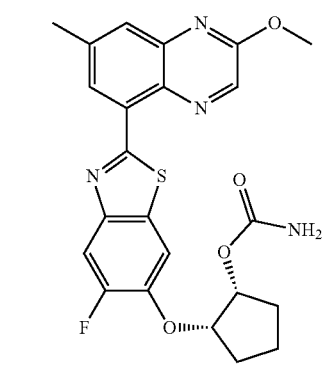
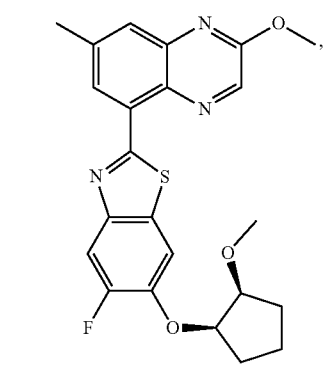
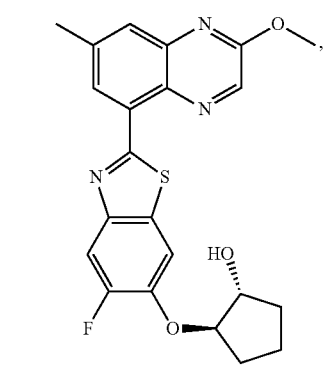

177
-continued
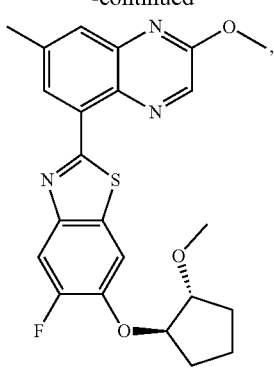
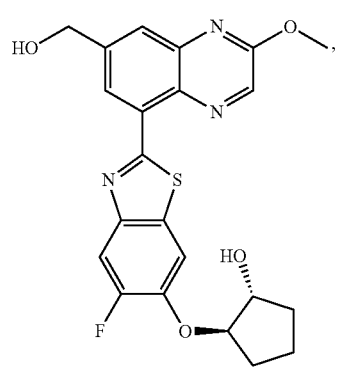
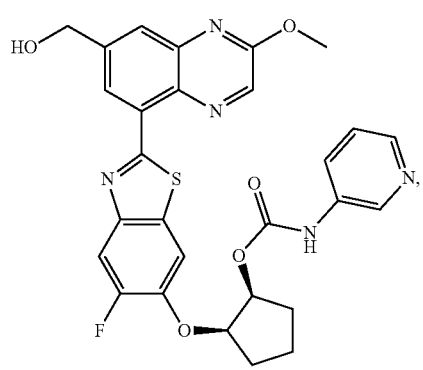
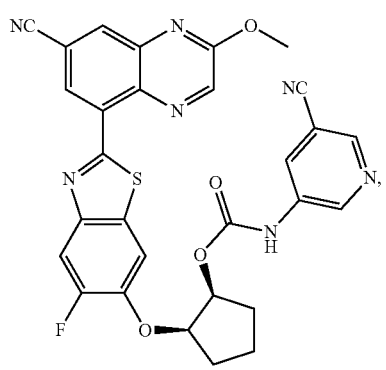
178
-continued
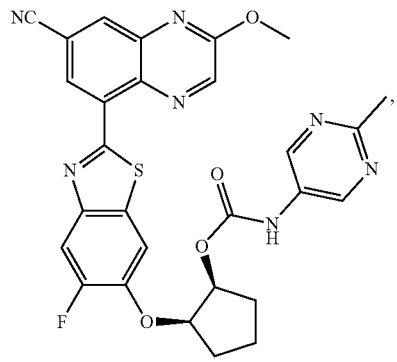
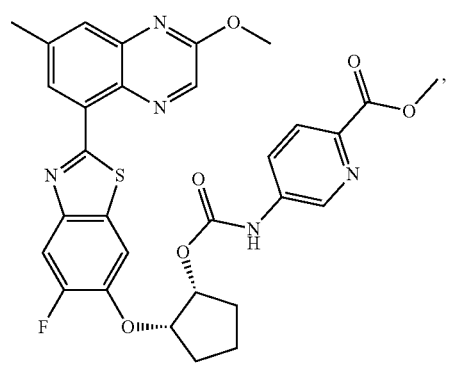
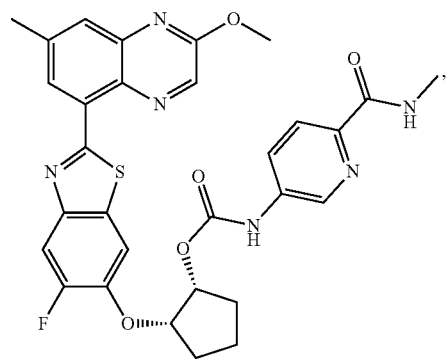
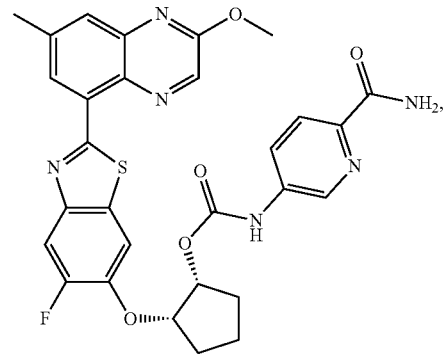

179
-continued
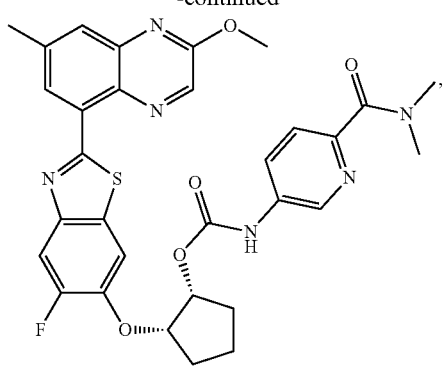
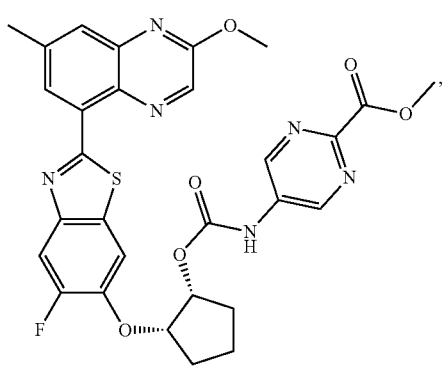
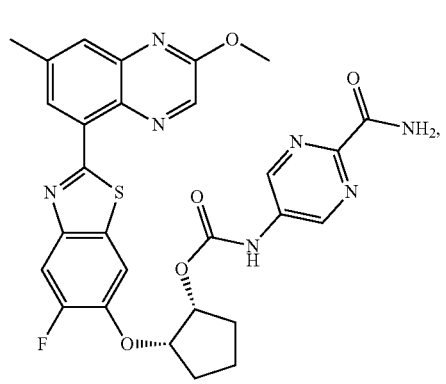
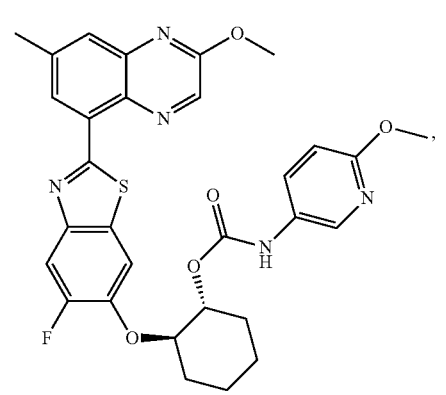
180
-continued
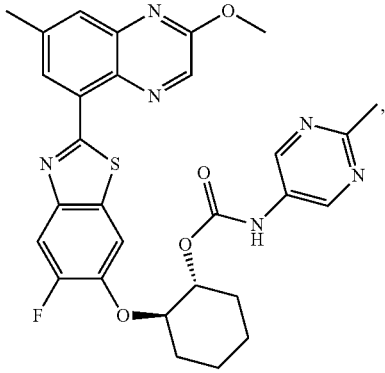
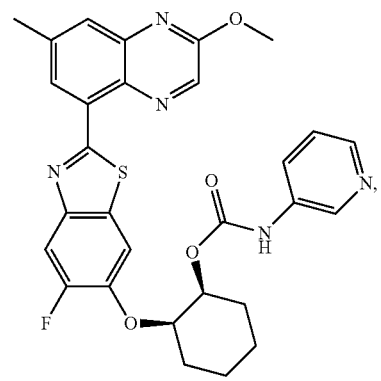
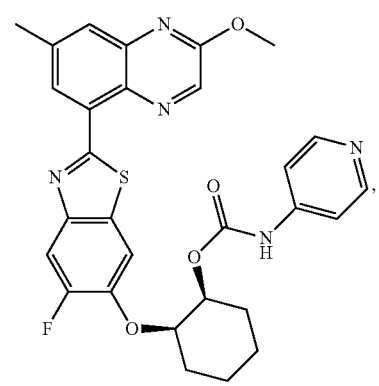
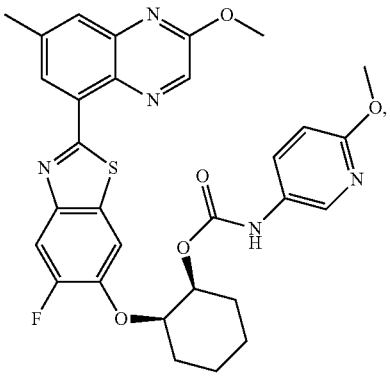

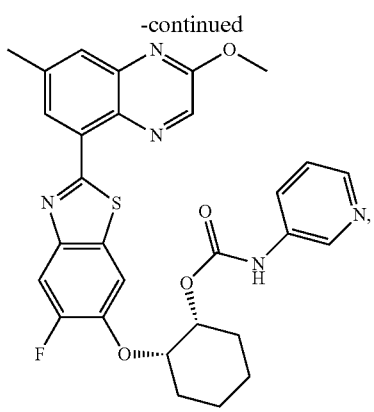
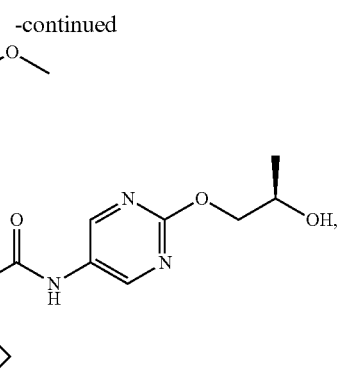
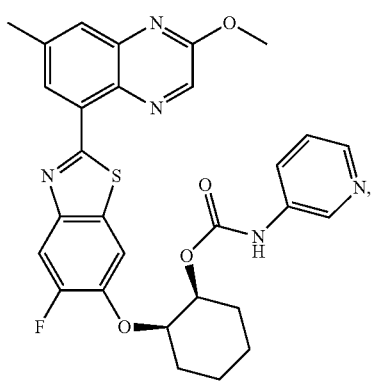
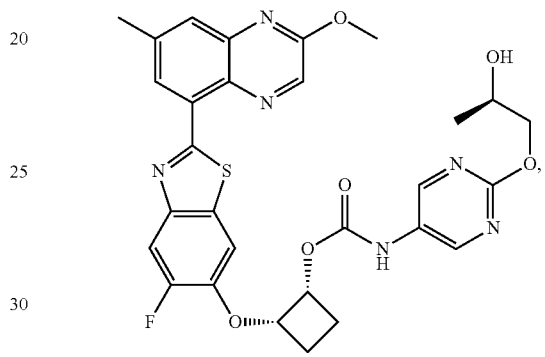
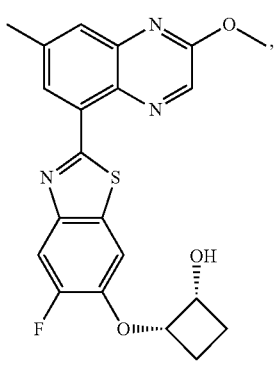
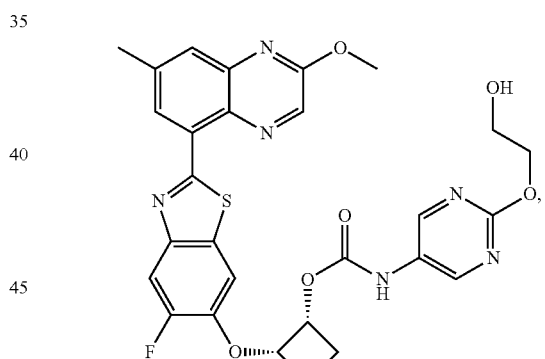
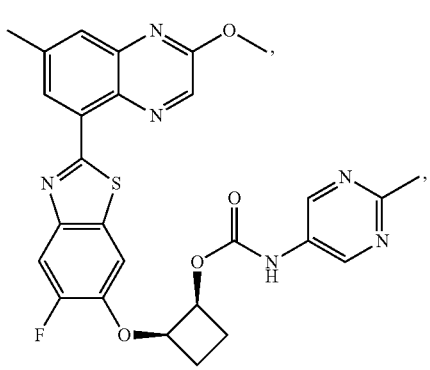
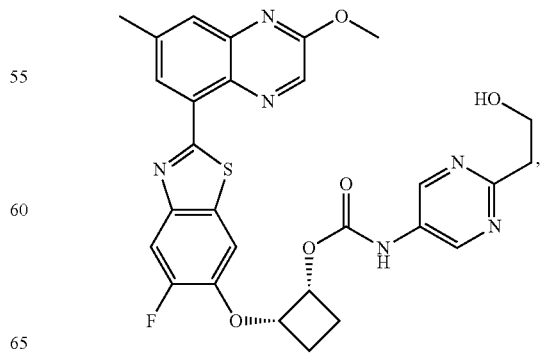

183
-continued
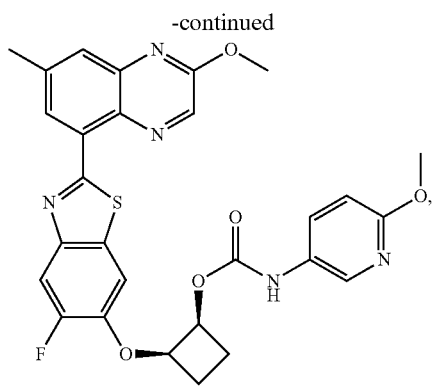
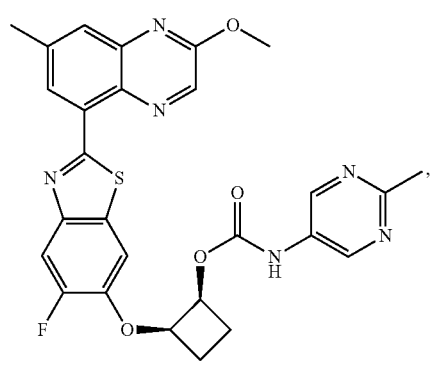
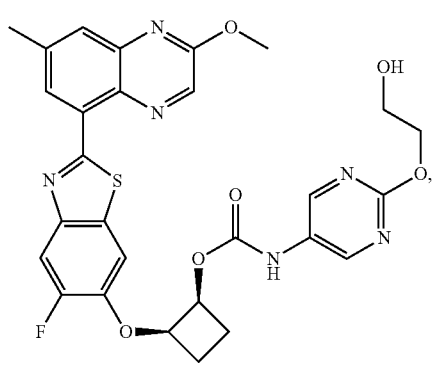
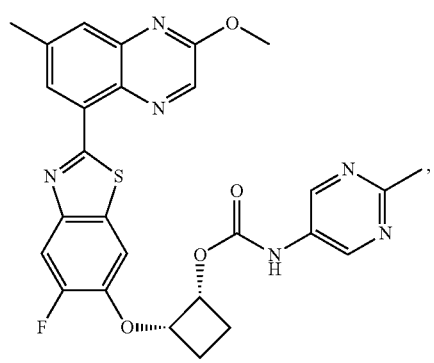
184
-continued
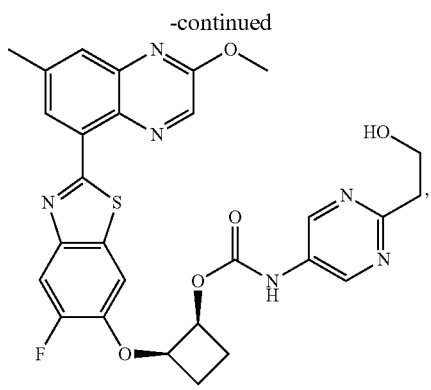
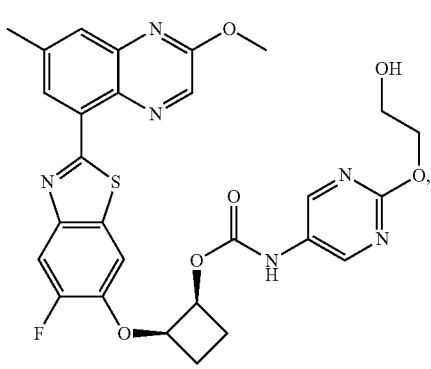
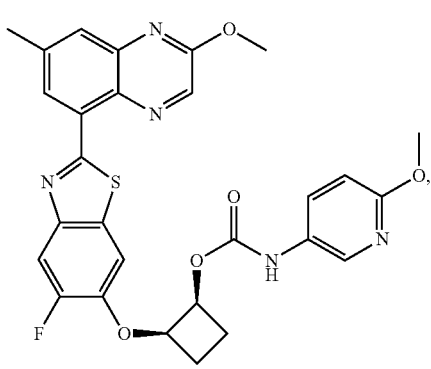
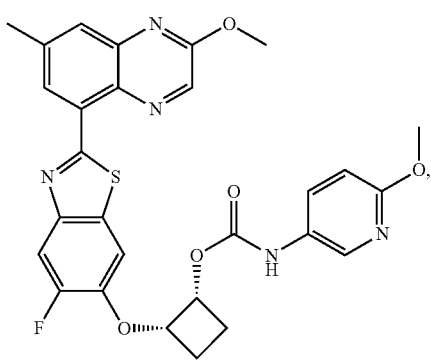

185
-continued
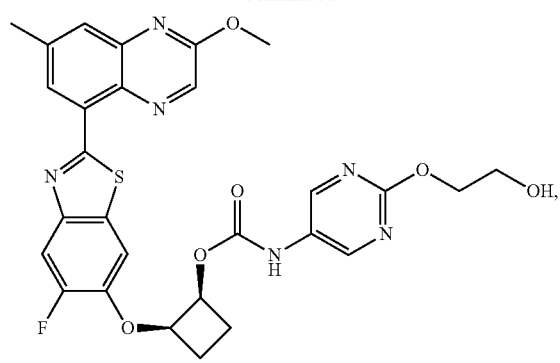
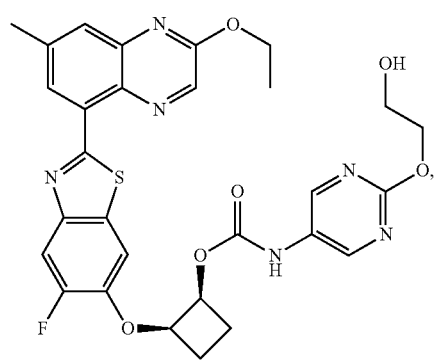
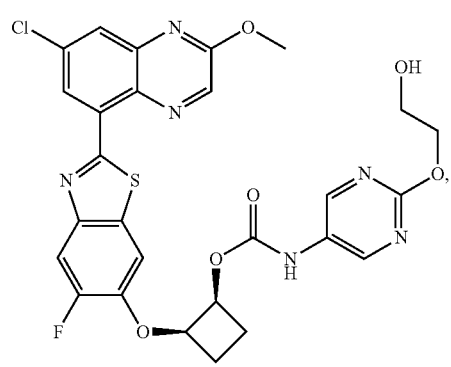
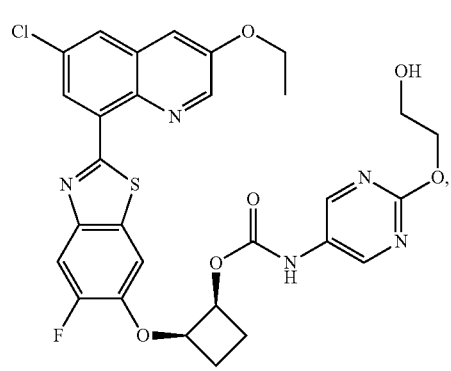
186
-continued
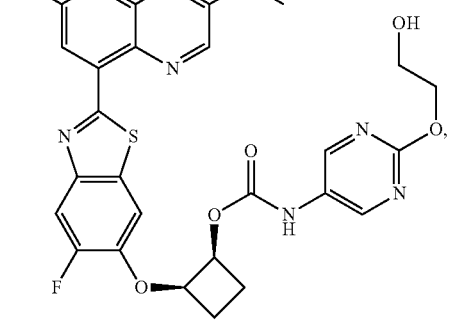
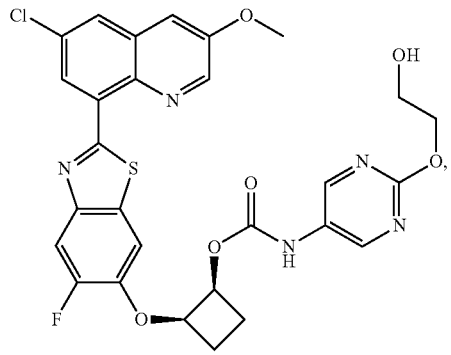
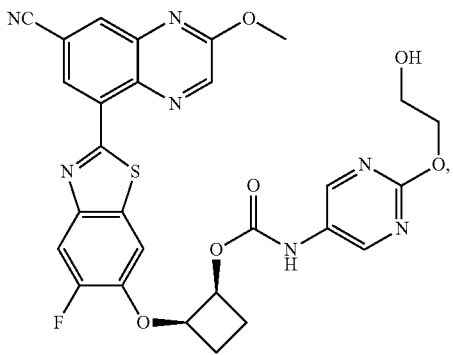
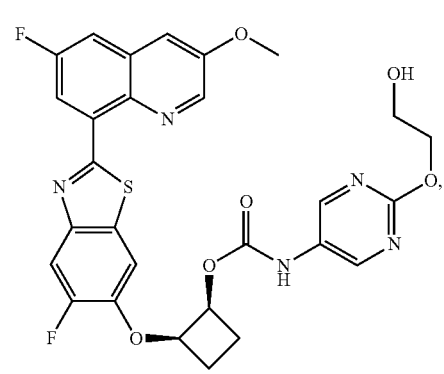

187
-continued
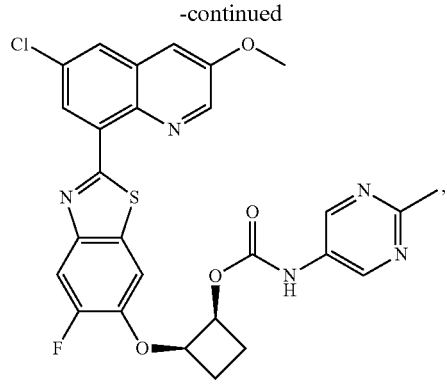
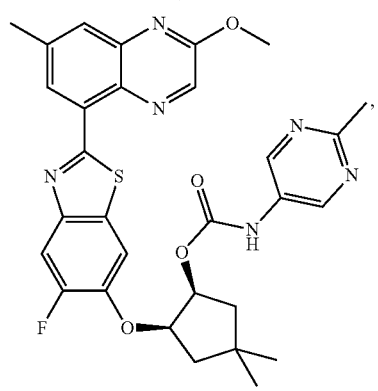
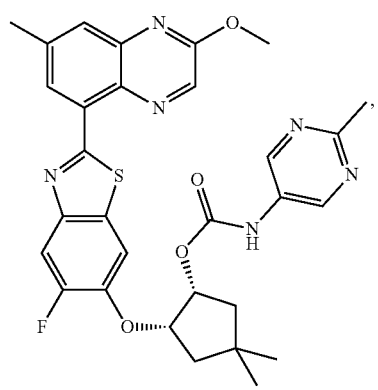
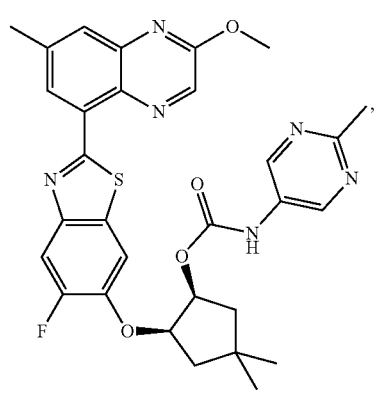
188
-continued
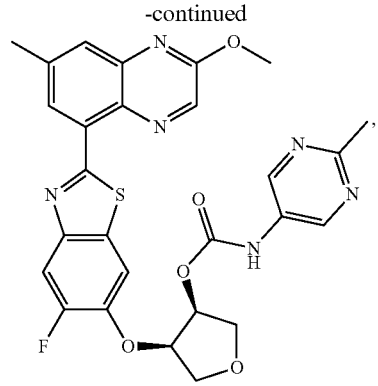
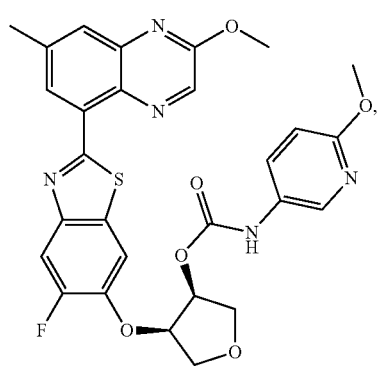
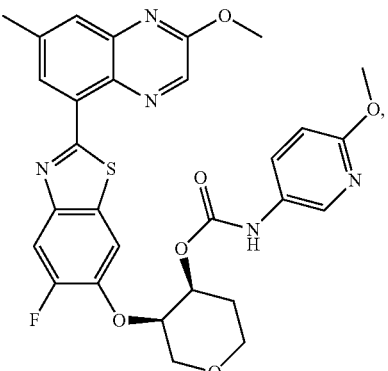
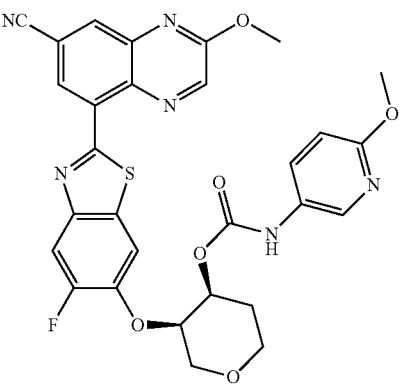

189
-continued
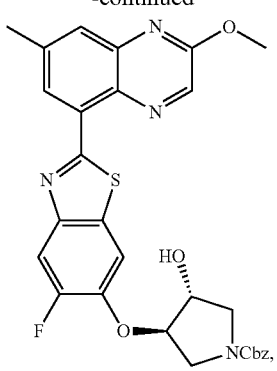
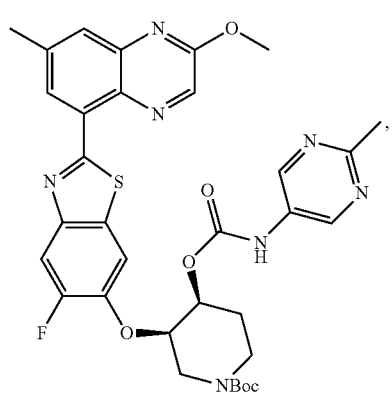
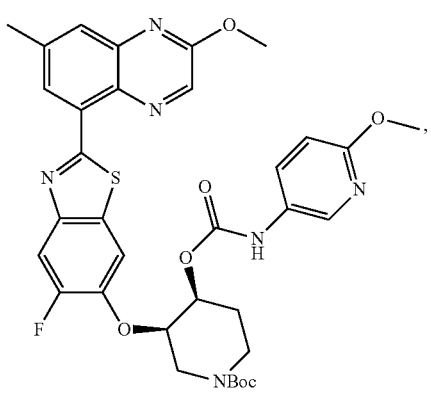
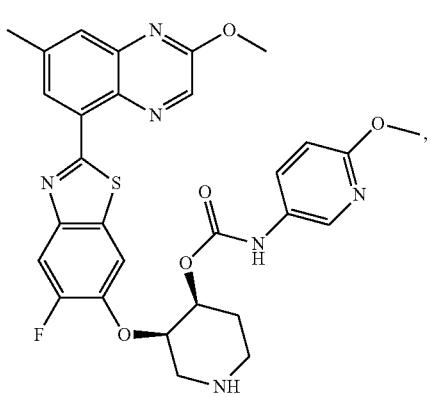
190
-continued
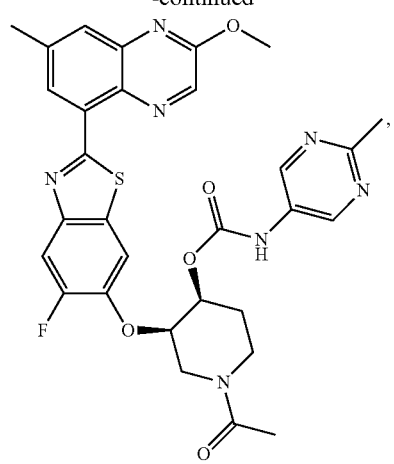
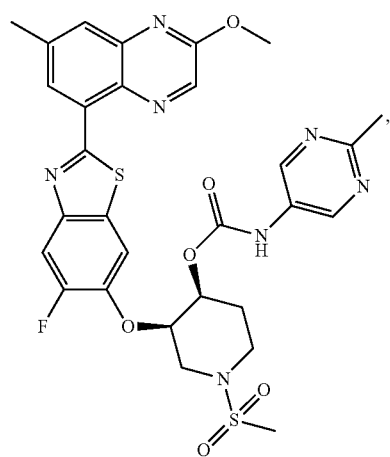
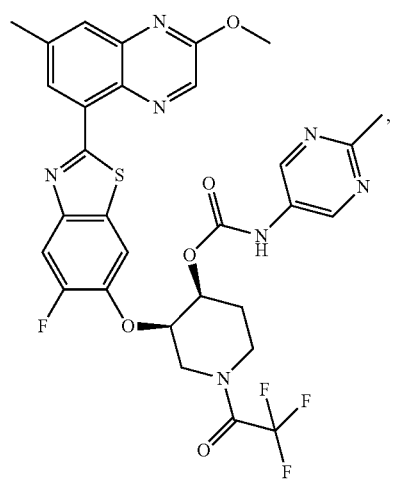

191
-continued
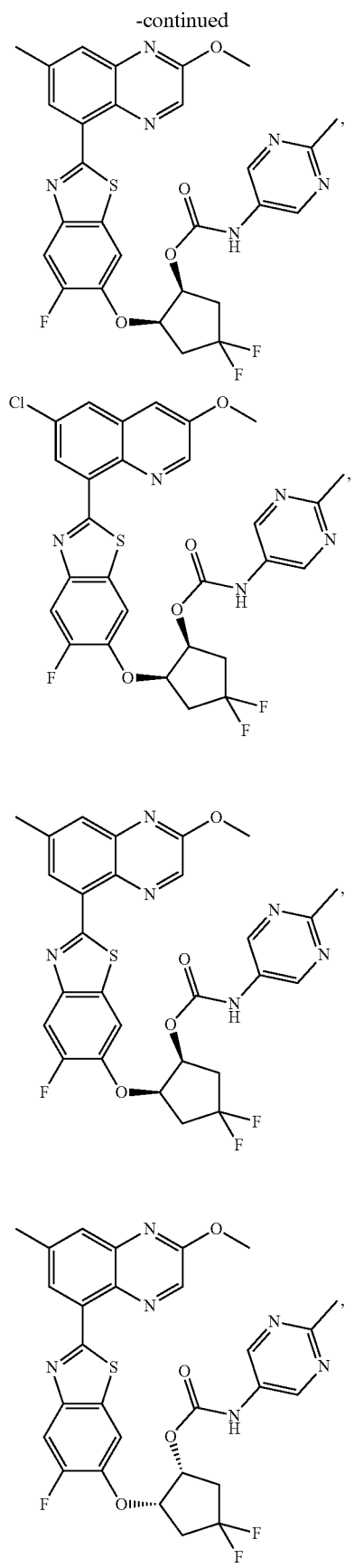
192
-continued
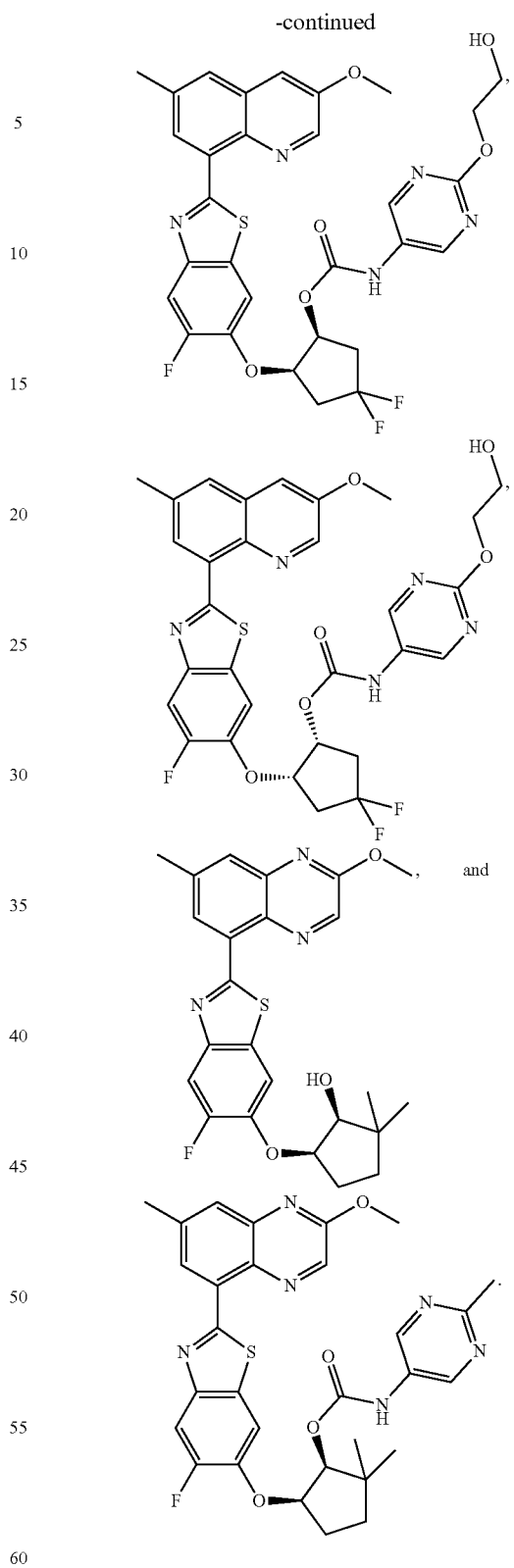
11. A pharmaceutical composition, which comprises a pharmaceutically acceptable carrier and a compound according to claim 1 or a pharmaceutically acceptable salt thereof, alone or in combination with another therapeutic agent.
12. A method for the treatment of a thromboembolic disorder or the primary prophylaxis of a thromboembolic disorder, which comprises the steps of administering to a patient in need thereof a therapeutically effective amount of a compound according to claim 1 or a pharmaceutically acceptable salt thereof, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

13. The method according to claim 12 wherein the thromboembolic disorder is selected from the group consisting of unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, and procedures in which blood is exposed to an artificial surface that promotes thrombosis.

14. A method of inhibiting or preventing platelet aggregation, which comprises the step of administering to a subject in need thereof a therapeutically effective amount of a compound according to claim 1 or a salt thereof.

\* \* \* \* \*

UNITED STATES PATENT AND TRADEMARK OFFICE
CERTIFICATE OF CORRECTION

PATENT NO. : 10,730,868 B2
APPLICATION NO. : 16/317218
DATED : August 4, 2020
INVENTOR(S) : Fu et al.

It is certified that error appears in the above-identified patent and that said Letters Patent is hereby corrected as shown below:

In the Claims

Column 159, Line 58, Claim 1, delete "—NH($C_{16}$ alkyl)," and insert -- —NH($C_{1-6}$ alkyl), --, therefor.

Column 161, Line 58, Claim 2, delete "piperadinyl," and insert -- piperidinyl, --, therefor.

Column 165, Line 15-30, Claim 6, delete " 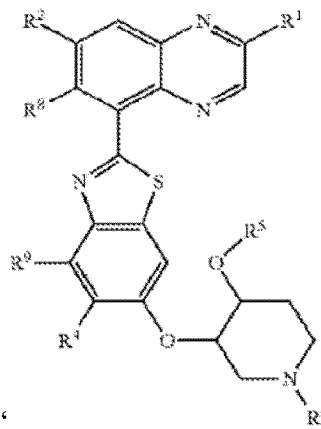 " and insert

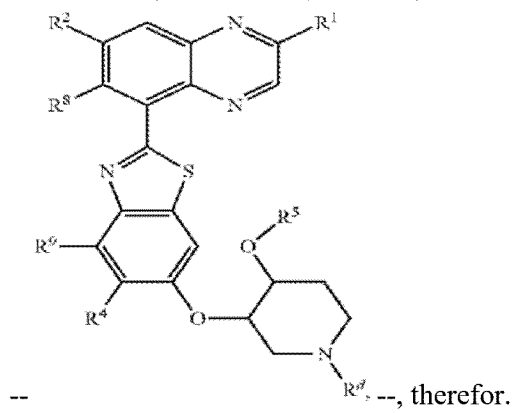

-- , therefor.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,730,868 B2

Column 185, Line 1-15, Claim 10, delete " 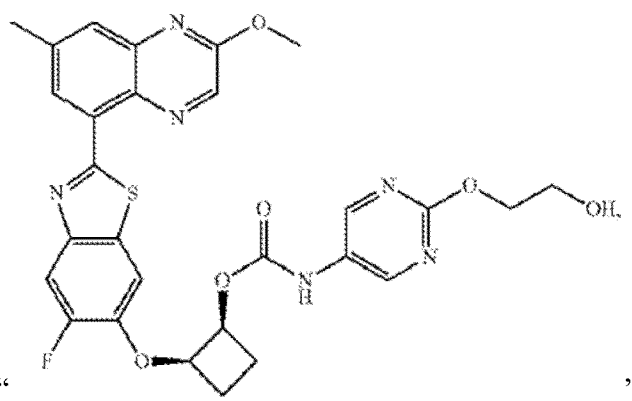 " and insert -- 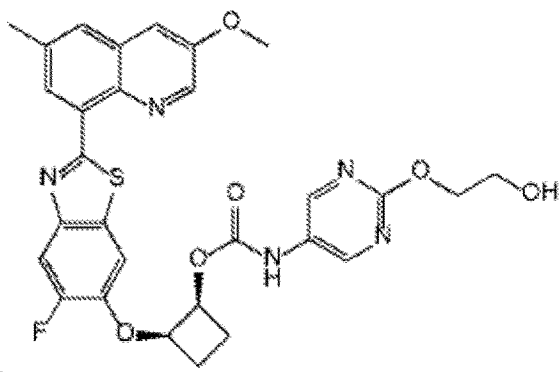 --, therefor.